US009725522B2

(12) United States Patent
Bouche et al.

(10) Patent No.: US 9,725,522 B2
(45) Date of Patent: *Aug. 8, 2017

(54) PULMONARY ADMINISTRATION OF IMMUNOGLOBULIN SINGLE VARIABLE DOMAINS AND CONSTRUCTS THEREOF

(71) Applicant: Ablynx N.V., Zwijnaarde (BE)

(72) Inventors: Marie-Paule Lucienne Armanda Bouche, Gentbrugge (BE); Peter Vanlandschoot, Bellem (BE); Erwin Sablon, Merchtem (BE); Erik Depla, Destelbergen (BE); Stefan De Buck, Buesserach (CH); Xavier Saelens, Leper (BE); Bert Schepens, Drongen (BE); Karen Silence, Overijse (BE); Mark Vaeck, Hofstade (BE); Paul M. P. Van Bergen En Henegouwen, Utrecht (NL); Hans De Haard, Oudelande (NL)

(73) Assignee: Ablynx N.V., Zwijnaarde (BE)

( * ) Notice: Subject to any disclaimer, the term of this patent is extended or adjusted under 35 U.S.C. 154(b) by 0 days.

This patent is subject to a terminal disclaimer.

(21) Appl. No.: 15/063,961

(22) Filed: Mar. 8, 2016

(65) Prior Publication Data

US 2016/0280799 A1 Sep. 29, 2016

Related U.S. Application Data

(60) Division of application No. 13/761,554, filed on Feb. 7, 2013, now Pat. No. 9,320,792, which is a
(Continued)

(30) Foreign Application Priority Data

Jan. 10, 2003 (EP) .................................... 03447005
Jun. 23, 2003 (WO) ................. PCT/EP2003/006581
Jul. 8, 2003 (WO) ................. PCT/EP2003/007313

(51) Int. Cl.
*A61K 39/395* (2006.01)
*C07K 16/42* (2006.01)
*C07K 16/18* (2006.01)
*C07K 16/24* (2006.01)
*C07K 16/28* (2006.01)
*C07K 16/36* (2006.01)
(Continued)

(52) U.S. Cl.
CPC ........ *C07K 16/4291* (2013.01); *A61K 39/395* (2013.01); *C07K 16/1027* (2013.01); *C07K 16/18* (2013.01); *C07K 16/241* (2013.01); *C07K 16/244* (2013.01); *C07K 16/249* (2013.01); *C07K 16/2863* (2013.01); *C07K 16/2875* (2013.01); *C07K 16/36* (2013.01); *C07K 16/40* (2013.01); *C07K 16/468* (2013.01); *A61K 2039/505* (2013.01); *A61K 2039/54* (2013.01); *A61K 2039/542* (2013.01); *A61K 2039/544* (2013.01); *A61M 11/005* (2013.01); *A61M 15/0065* (2013.01); *C07K 2317/22* (2013.01); *C07K 2317/24* (2013.01); *C07K 2317/31* (2013.01); *C07K 2317/565* (2013.01); *C07K 2317/569* (2013.01); *C07K 2317/62* (2013.01); *C07K 2317/626* (2013.01); *C07K 2317/73* (2013.01); *C07K 2317/76* (2013.01); *C07K 2317/77* (2013.01); *C07K 2319/00* (2013.01); *C07K 2319/31* (2013.01)

(58) Field of Classification Search
None
See application file for complete search history.

(56) References Cited

U.S. PATENT DOCUMENTS

| 4,405,306 A | 9/1983 | Pritchard et al. |
| 5,091,513 A | 2/1992 | Huston et al. |
| 5,196,193 A | 3/1993 | Carroll |
| 5,487,890 A | 1/1996 | Taylor et al. |
| 5,637,038 A | 6/1997 | Davis |

(Continued)

FOREIGN PATENT DOCUMENTS

| BE | WO 03035694 A2 * | 5/2003 | ............. C07K 16/18 |
| EP | 0 288 088 A2 | 10/1988 | |

(Continued)

OTHER PUBLICATIONS

Janeway et al., Immunobiology, third edition, Garland Press, 1997, pp. 2:2-2:5, 3:1-3:11, and 11:11.*

(Continued)

*Primary Examiner* — Michael Szperka
(74) *Attorney, Agent, or Firm* — Wolf, Greenfield & Sacks, P.C.

(57) ABSTRACT

In one aspect, the invention relates to a method suitable for administering protein therapeutic molecules orally, sublingually, topically, intravenously, subcutaneously, nasally, vaginally, rectally or by inhalation so as to avoid inactivation, by using VHH polypeptides derived from Camelidae antibodies. The invention further relates to the said therapeutic molecules. The invention further a method for delivering therapeutic molecules to the interior of cells. The invention further relates to anti-IgE therapeutic molecules.

In one aspect, the present invention relates to a method wherein an immunoglobulin single variable domain (such as a Nanobody) and/or construct thereof are absorbed in pulmonary tissue. More particularly, the invention provides systemic delivery of an immunoglobulin single variable domain and/or construct thereof via the pulmonary route.

7 Claims, 44 Drawing Sheets

Related U.S. Application Data continuation-in-part of application No. 12/487,684, filed on Jun. 19, 2009, now Pat. No. 9,243,065, which is a continuation of application No. 10/534,292, filed as application No. PCT/BE03/00190 on Nov. 7, 2003, now abandoned, said application No. 13/761,554 is a continuation-in-part of application No. 13/143,736, filed as application No. PCT/EP2010/050414 on Jan. 14, 2010, now abandoned.

(60) Provisional application No. 60/425,073, filed on Nov. 8, 2002, provisional application No. 60/425,063, filed on Nov. 8, 2002, provisional application No. 61/251,879, filed on Oct. 15, 2009, provisional application No. 61/144,586, filed on Jan. 14, 2009.

(51) Int. Cl.
  *C07K 16/40* (2006.01)
  *C07K 16/10* (2006.01)
  *C07K 16/46* (2006.01)
  *A61K 39/00* (2006.01)
  *A61M 11/00* (2006.01)
  *A61M 15/00* (2006.01)

(56) References Cited

U.S. PATENT DOCUMENTS

| | | |
|---|---|---|
| 5,644,034 A | 7/1997 | Rathjen et al. |
| 5,656,273 A | 8/1997 | Amiri et al. |
| 5,672,347 A | 9/1997 | Aggarwal et al. |
| 5,837,243 A | 11/1998 | Deo et al. |
| 5,843,440 A | 12/1998 | Pouletty et al. |
| 5,891,996 A | 4/1999 | Mateo de Acosta del Rio et al. |
| 5,942,602 A | 8/1999 | Wels et al. |
| 5,976,532 A | 11/1999 | Coller et al. |
| 5,994,511 A | 11/1999 | Lowman et al. |
| 6,066,718 A | 5/2000 | Hardman et al. |
| 6,251,393 B1 | 6/2001 | Handin |
| 6,419,934 B1 | 7/2002 | Tobinick |
| 6,504,013 B1 | 1/2003 | Lawton et al. |
| 6,670,453 B2 | 12/2003 | Frenken et al. |
| 6,759,518 B1 | 7/2004 | Kontermann et al. |
| 6,838,254 B1 | 1/2005 | Hamers et al. |
| 6,902,734 B2 | 6/2005 | Giles-Komar et al. |
| 7,084,257 B2 | 8/2006 | Deshpande et al. |
| 7,300,655 B2 | 11/2007 | Hansen et al. |
| 7,368,111 B2 | 5/2008 | Thompson et al. |
| 7,589,180 B2 | 9/2009 | Old et al. |
| 7,598,350 B2 | 10/2009 | Liu et al. |
| 7,807,162 B2 * | 10/2010 | Silence ............... A61K 38/36 424/133.1 |
| 7,822,540 B2 | 10/2010 | Fukaya et al. |
| 7,897,151 B2 | 3/2011 | Morsey et al. |
| 8,097,251 B2 * | 1/2012 | Muyldermans ......... C07K 16/18 424/133.1 |
| 8,188,223 B2 | 5/2012 | Beirnaert et al. |
| 8,217,140 B2 | 7/2012 | Revets |
| 8,372,398 B2 * | 2/2013 | Silence ............... A61K 38/36 424/133.1 |
| 8,703,131 B2 | 4/2014 | Beirnaert et al. |
| 9,028,816 B2 * | 5/2015 | Silence ............... A61K 38/166 424/133.1 |
| 9,243,065 B2 * | 1/2016 | Silence ............... C07K 16/241 |
| 9,320,792 B2 * | 4/2016 | Bouche ............... A61K 39/395 |
| 9,371,381 B2 * | 6/2016 | Silence ............... C07K 16/241 |
| 2001/0024647 A1 | 9/2001 | Handin |
| 2002/0001587 A1 | 1/2002 | Erickson et al. |
| 2002/0009453 A1 | 1/2002 | Haurum et al. |
| 2002/0028204 A1 | 3/2002 | Nagano et al. |
| 2002/0052479 A1 | 5/2002 | Anderson et al. |
| 2002/0054878 A1 | 5/2002 | Lowe et al. |
| 2002/0058033 A1 | 5/2002 | Raisch et al. |
| 2002/0076404 A1 | 6/2002 | Chang |
| 2002/0132275 A1 | 9/2002 | Fidler et al. |
| 2002/0165387 A1 | 11/2002 | Anderson et al. |
| 2003/0088074 A1 | 5/2003 | Hamers et al. |
| 2003/0092892 A1 | 5/2003 | Frenken et al. |
| 2003/0118592 A1 | 6/2003 | Ledbetter et al. |
| 2004/0063912 A1 * | 4/2004 | Blumberg ............ A61K 9/0073 530/351 |
| 2004/0180046 A1 | 9/2004 | Himawan |
| 2004/0197326 A1 | 10/2004 | Fick et al. |
| 2004/0219643 A1 | 11/2004 | Winter et al. |
| 2004/0253638 A1 | 12/2004 | Casterman et al. |
| 2005/0054001 A1 | 3/2005 | Muyldermans et al. |
| 2006/0034833 A1 | 2/2006 | Beirnaert |
| 2006/0034845 A1 | 2/2006 | Silence et al. |
| 2006/0115470 A1 | 6/2006 | Silence et al. |
| 2006/0228355 A1 | 10/2006 | Laeremans et al. |
| 2007/0031424 A1 | 2/2007 | Muyldermans |
| 2007/0077249 A1 | 4/2007 | Silence et al. |
| 2007/0178082 A1 | 8/2007 | Silence et al. |
| 2007/0237769 A1 | 10/2007 | Silence et al. |
| 2007/0264253 A1 | 11/2007 | Liu et al. |
| 2009/0022721 A1 | 1/2009 | Silence et al. |
| 2009/0238829 A1 | 9/2009 | Silence et al. |
| 2009/0324512 A1 | 12/2009 | Silence et al. |
| 2010/0003248 A1 | 1/2010 | Silence et al. |
| 2010/0003249 A1 | 1/2010 | Silence et al. |
| 2010/0003253 A1 | 1/2010 | Laeremans et al. |
| 2010/0021459 A1 | 1/2010 | Silence et al. |
| 2010/0040613 A1 | 2/2010 | Silence et al. |
| 2011/0027281 A1 | 2/2011 | Silence et al. |
| 2011/0123529 A1 | 5/2011 | Laeremans et al. |
| 2011/0178277 A1 | 7/2011 | Silence et al. |
| 2011/0184145 A1 | 7/2011 | Silence et al. |
| 2011/0184150 A1 | 7/2011 | Silence et al. |
| 2011/0184151 A1 | 7/2011 | Laeremans et al. |
| 2012/0202977 A1 | 8/2012 | Silence et al. |
| 2012/0251540 A1 | 10/2012 | Silence et al. |
| 2013/0136744 A1 | 5/2013 | Bouche et al. |
| 2015/0064182 A1 | 3/2015 | Silence et al. |
| 2015/0110782 A1 | 4/2015 | Silence et al. |

FOREIGN PATENT DOCUMENTS

| | | | |
|---|---|---|---|
| EP | 0 366 043 A1 | 5/1990 | |
| EP | 0 368 684 A1 | 5/1990 | |
| EP | 0 476 226 A1 | 3/1992 | |
| EP | 0 584 421 A1 | 3/1994 | |
| EP | 0 589 840 A1 | 3/1994 | |
| EP | 0 614 984 A2 | 9/1994 | |
| EP | 0 952 218 A2 | 10/1999 | |
| EP | 0 954 978 A1 | 11/1999 | |
| EP | 1 002 861 A1 | 5/2000 | |
| EP | 1 118 669 A1 | 7/2001 | |
| EP | 1 134 231 A1 | 9/2001 | |
| EP | 1 517 921 | 3/2005 | |
| GB | 0115841.9 | 6/2001 | |
| GB | 0230202.4 | 12/2002 | |
| IT | WO 9834645 A1 * | 8/1998 | ........ A61K 47/48415 |
| JP | 62175426 A | 8/1987 | |
| JP | 01-268645 | 10/1989 | |
| JP | H11-503918 | 4/1999 | |
| WO | WO 89/06138 A1 | 7/1989 | |
| WO | WO 90/05144 A1 | 5/1990 | |
| WO | WO 90/10707 A1 | 9/1990 | |
| WO | WO 91/01743 A1 | 2/1991 | |
| WO | WO 91/02078 A1 | 2/1991 | |
| WO | WO 91/04054 A1 | 4/1991 | |
| WO | WO 92/01787 A1 | 2/1992 | |
| WO | WO 92/16142 A1 | 10/1992 | |
| WO | WO 93/04173 A1 | 3/1993 | |
| WO | WO 94/04678 A1 | 3/1994 | |
| WO | WO 94/12531 A1 | 6/1994 | |
| WO | WO 95/10302 A1 | 4/1995 | |
| WO | WO 95/17673 A1 | 6/1995 | |
| WO | WO 96/32478 A1 | 10/1996 | |
| WO | WO 96/34096 A1 | 10/1996 | |
| WO | WO 96/34103 A1 | 10/1996 | |
| WO | WO 96/40210 A1 | 12/1996 | |
| WO | WO 97/10846 A1 | 3/1997 | |

(56) References Cited

FOREIGN PATENT DOCUMENTS

| WO | WO 97/17207 A1 | 5/1997 |
|---|---|---|
| WO | WO 97/29131 A1 | 8/1997 |
| WO | WO 98/34645 A1 | 8/1998 |
| WO | WO 98/40469 A1 | 9/1998 |
| WO | WO 99/02078 A1 | 1/1999 |
| WO | WO 99/09055 A2 | 2/1999 |
| WO | WO 99/23221 A2 | 5/1999 |
| WO | WO 99/46300 A1 | 9/1999 |
| WO | WO 99/64069 A1 | 12/1999 |
| WO | WO 00/29004 A1 | 5/2000 |
| WO | WO 00/29442 A1 | 5/2000 |
| WO | WO 00/40262 A1 | 7/2000 |
| WO | WO 00/56772 A2 | 9/2000 |
| WO | WO 00/65057 A1 | 11/2000 |
| WO | WO 01/19871 A2 | 3/2001 |
| WO | WO 01/45746 A2 | 6/2001 |
| WO | WO 01/58956 A2 | 8/2001 |
| WO | WO 01/89567 A1 | 11/2001 |
| WO | WO 02/12502 A2 | 2/2002 |
| WO | WO 02/48193 A2 | 6/2002 |
| WO | WO 02/051351 A1 | 7/2002 |
| WO | WO 02/057445 A1 | 7/2002 |
| WO | WO 02/078598 A2 | 10/2002 |
| WO | WO 02/079781 A1 | 10/2002 |
| WO | WO 02/080967 A1 | 10/2002 |
| WO | WO 02/081649 A2 | 10/2002 |
| WO | WO 03/002609 A2 | 1/2003 |
| WO | WO 03/035694 A2 | 5/2003 |
| WO | WO 03/077834 A2 | 9/2003 |
| WO | WO 2004/003019 A2 | 1/2004 |
| WO | WO 2004/041862 A2 | 5/2004 |
| WO | WO 2004/041863 A2 | 5/2004 |
| WO | WO 2004/041865 A2 | 5/2004 |
| WO | WO 2004/041867 A2 | 5/2004 |
| WO | WO 2004/081026 A2 | 9/2004 |
| WO | WO 2006/056306 A2 | 6/2006 |
| WO | WO 2006/059108 A2 | 6/2006 |
| WO | WO 2007/066109 A1 | 6/2007 |
| WO | WO 2009/074634 A2 | 6/2009 |

OTHER PUBLICATIONS

Annex to Summons to Attend Oral Proceedings dated May 7, 2009.
Annex to the Decision Revoking European Patent No. EP 1 517 921—Grounds for the Decision to Revoke European Patent No. EP 1 517 921 filed Apr. 8, 2010.
Annex to the Decision Revoking European Patent No. EP 1 517 921—Opposition. Apr. 8, 2010.
Annex to the Decision Revoking European Patent No. EP 1 517 921. Apr. 8, 2010.
Applicant's Remarks for Reply to Written Opinion filed Apr. 28, 2006.
Auxiliary Request 1 filed by patentee on Jul. 30, 2010.
Auxiliary Request 2 filed by patentee on Jul. 30, 2010.
Auxiliary Request 3 filed by patentee on Jul. 30, 2010.
Decision Revoking European Patent No. EP 1 517 921. Letter dated Apr. 8, 2010.
Filing of a New Opposition in EP 1 517 921. Filed on Mar. 6, 2007.
Letter of Opponent dated Apr. 15, 2008 in opposition to EP 1 517 921 and in response to Patentee's Letter of Oct. 30, 2007.
Letter of Opponent dated May 28, 2008 in opposition to EP 1 517 921 and in response to Patentee's Letter of Oct. 30, 2007.
Letter of opponent regarding the opposition procedure filed in the opposition to EP 1 517 921 on Mar. 30, 2009.
Letter of Opponent regarding the Opposition Procedure in EP 1 517 921 dated Sep. 25, 2009.
Letter of Opponent regarding the Opposition Procedure in EP 1 517 921 filed by opponent. Dec. 10, 2009.
Letter of Patentee dated Oct. 13, 2008 in EP 1 517 921.
Letter of Patentee regarding the Opposition Procedure for EP 1 517 921 filed May 19, 2009.
Main Request filed by Patentee on Jul. 30, 2010.
Notice of Opposition in EP 1 517 921. Filed on Mar. 6, 2007.
Official Action concerning European application No. 03 775 004.9 dated Jan. 22, 2007.
Official Action concerning European application No. 03 776 677 dated Jun. 5, 2009.
Official Action concerning European application No. 06 006 277 dated May 29, 2009.
Reply of the patent proprietor to the notices of opposition dated Oct. 30, 2007.
Response to Patentee's Grounds of Appeal, dated Feb. 25, 2011.
Statement of Grounds of Appeal filed by patentee on Jul. 30, 2010.
Summary of telephone consultation in European Application No. 06 006 277.5, submitted in EP 1 517 921 on Sep. 25, 2009.
Third party observations in the Opposition Proceedings concerning European patent EP 1 517 921 in the name of Domantis Limited. Barcelona. Sep. 1, 2009.
Third party observations in the Opposition Proceedings concerning European patent EP 1 517 921 in the name of Domantis Limited. Munich. Jun. 17, 2009.
Third party observations in the Opposition Proceedings concerning European patent EP 1 517 921 in the name of Domantis Limited. Munich. Nov. 28, 2008.
Third party observations in the Opposition Proceedings concerning European patent EP 1 517 921 in the name of Domantis Limited. Paris. Sep. 4, 2009.
[No Author Listed] Domain antibodies. http://www.domantis.com/domain.htm. Accessed on Oct. 28, 2009.
[No Author Listed] Domantis and Peptech announce outstanding pre-clinical results for their anti-tnf domain antibody in rheumatoid arthritis. Last accessed on May 25, 2012 at http://web.archive.org/web/20030907213244/http://www.domantis.com/press_pf.asp?id=27.
[No Author Listed] Immunochemistry. Nankodo Co., Ltd., Jul. 15, 1983 (1st ed.), pp. 35-36.
[No Author Listed] Letter from D. Young & Co. regarding EP 1 558 650 Third Party Observations dated Sep. 12, 2007.
[No Author Listed] Letters from D. Young & Co. regarding opposition to EP 0656946 dated May 18, 2007 and Jun. 5, 2007.
[No Author Listed] Omalizumab: anti-IgE monoclonal antibody E25, E25, humanised anti-IgE MAb, IGE 025, monoclonal antibody E25, Olizumab, Xolair, rhuMAb-E25. BioDrugs. 2002;16(5):380-6.
[No Author Listed] Patentee's Letter regarding EP 05076402.6 dated Sep. 25, 2006.
[No Author Listed] Patentee's Letter regarding EP03776677.1 dated Dec. 23, 2005.
[No Author Listed] The Gale Encyclopedia of Medicine. Olenderf et al., eds. 1999;1:419.
Adams et al., Generating improved single-chain Fv molecules for tumor targeting. J Immunol Methods. Dec. 10, 1999;231(1-2):249-60.
Adriouch et al., Probing the expression and function of the P2X7 purinoceptor with antibodies raised by genetic immunization. Cell Immunol. Jul.-Aug. 2005;236(1-2):72-7. Epub Sep. 12, 2005.
Amagai, Autoimmunity against desmosomal cadherins in pemphigus. J Dermatol Sci. Jun. 1999;20(2):92-102. Review.
Arbabi Ghahroudi et al., Selection and identification of single domain antibody fragments from camel heavy-chain antibodies. FEBS Lett. Sep. 15, 1997;414(3):521-6.
Baniyash et al., Inhibition of IgE binding to mast cells and basophils by monoclonal antibodies to murine IgE. Eur J Immunol. Sep. 1984;14(9):799-807.
Barrios et al., Length of the antibody heavy chain complementarity determining region 3 as a specificity-determining factor. J Mol Recognit. Jul.-Aug. 2004;17(4):332-8.
Bass et al., Molecular basis of age-dependent gastric inactivation of rhesus rotavirus in the mouse. J Clin Invest. Jun. 1992;89(6):1741-5.
Becerril et al., Toward selection of internalizing antibodies from phage libraries. Biochem Biophys Res Commun. Feb. 16, 1999;255(2):386-93.
Bins et al., A rapid and potent DNA vaccination strategy defined by in vivo monitoring of antigen expression. Nat Med. Aug. 2005;11(8):899-904. Epub Jun. 19, 2005.

(56) References Cited

OTHER PUBLICATIONS

Bins et al., In vivo antigen stability affects DNA vaccine immunogenicity. J Immunol. Aug. 15, 2007;179(4):2126-33.
Birkett, Chapter 3: Half-life. In Pharmacokinetics Made Easy. 2004:16-24.
Bogdan et al., Epidermal growth factor receptor signaling. Curr Biol. Apr. 17, 2001;11(8):R292-5.
Boulougouris et al., Epidermal growth factor receptor structure, regulation, mitogenic signalling and effects of activation. Anticancer Res. Jul.-Aug. 2001;21(4A):2769-75.
Cataldo et al., Matrix metalloproteinase-9 deficiency impairs cellular infiltration and bronchial hyperresponsiveness during allergen-induced airway inflammation. Am J Pathol. Aug. 2002;161(2):491-8.
Chang, The pharmacological basis of anti-IgE therapy. Nat Biotechnol. Feb. 2000;18(2):157-62.
Chen et al., TTD: Therapeutic Target Database. Nucleic Acids Res. Jan. 1, 2002;30(1):412-5.
Cheong et al., Affinity enhancement of bispecific antibody against two different epitopes in the same antigen. Biochem Biophys Res Commun. Dec. 31, 1990;173(3):795-800.
Chuang et al., Pharmaceutical strategies utilizing recombinant human serum albumin. Pharm Res. May 2002;19(5):569-77.
Cochran et al., Domain-level antibody epitope mapping through yeast surface display of epidermal growth factor receptor fragments. J Immunol Methods. Apr. 2004;287(1-2):147-58.
Colman, Effects of amino acid sequence changes on antibody-antigen interactions. Res Immunol. Jan. 1994;145(1):33-6.
Connelly, Fully human domain antibody therapeutics: the best of both worlds. Innovations in Pharmaceutical Technology. 2005;42-5.
Conrath et al., Beta-lactamase inhibitors derived from single-domain antibody fragments elicited in the camelidae. Antimicrob Agents Chemother. Oct. 2001;45(10):2807-12.
Conrath et al., Camel single-domain antibodies as modular building units in bispecific and bivalent antibody constructs. J Biol Chem. Mar. 9, 2001;276(10):7346-50.
Cortez-Retamozo et al., Efficient tumor targeting by single-domain antibody fragments of camels. Int J Cancer. Mar. 20, 2002;98(3):456-62.
Crombet-Ramos et al., Antiproliferative, antiangiogenic and proapoptotic activity of h-R3: A humanized anti-EGFR antibody. Int J Cancer. Oct. 20, 2002;101(6):567-75.
Crowe et al., Recombinant human respiratory syncytial virus (RSV) monoclonal antibody Fab is effective therapeutically when introduced directly into the lungs of RSV-infected mice. Proc Natl Acad Sci U S A. Feb. 15, 1994;91(4):1386-90.
D'Haens et al., Endoscopic and histological healing with infliximab anti-tumor necrosis factor antibodies in Crohn's disease: A European multicenter trial. Gastroenterology. May 1999;116(5):1029-34.
Davies et al., 'Camelising' human antibody fragments: NMR studies on VH domains. FEBS Lett. Feb. 21, 1994;339(3):285-90.
Davies et al., Antibody VH domains as small recognition units. Biotechnology (N Y). May 1995;13(5):475-9.
Davies et al., Single antibody domains as small recognition units: design and in vitro antigen selection of camelized, human VH domains with improved protein stability. Protein Eng. Jun. 1996;9(6):531-7.
Davis et al., 508.1 Anatomy of the Glomerulus. Nelson Textbook of Pediatrics, 18th edition, 2007. Part XXII—Nephrology, Section 1—Glomerular Disease:2163.
Declaration of Dr. Felix Kratz, Feb. 21, 2011.
Declaration of Professor Per-Åke Nygren, Feb. 22, 2011.
Declaration of Professor Roland E. Kontermann. Filed in opposition to EP 1517921. Dec. 3, 2009.
Dennis et al., Albumin binding as a general strategy for improving the pharmacokinetics of proteins. J Biol Chem. Sep. 20, 2002;277(38):35035-43. Epub Jul. 15, 2002.

Desmyter et al., Antigen specificity and high affinity binding provided by one single loop of a camel single-domain antibody. J Biol Chem. Jul. 13, 2001;276(28):26285-90. Epub May 7, 2001.
Desmyter et al., Three camelid VHH domains in complex with porcine pancreatic alpha-amylase. Inhibition and versatility of binding topology. J Biol Chem. Jun. 28, 2002;277(26):23645-50. Epub Apr. 17, 2002.
Dolk et al., Isolation of llama antibody fragments for prevention of dandruff by phage display in shampoo. Appl Environ Microbiol. Jan. 2005;71(1):442-50.
Drejer et al., Receptor binding and tyrosine kinase activation by insulin analogues with extreme affinities studied in human hepatoma HepG2 cells. Diabetes. Nov. 1991;40(11):1488-95.
Dubnovitsky et al., Expression, refolding, and ferritin-binding activity of the isolated VL-domain of monoclonal antibody F11. Biochemistry (Mosc). Sep. 2000;65(9):1011-8.
Ebina et al., Passive immunizations of suckling mice and infants with bovine colostrum containing antibodies to human rotavirus. J Med Virol. Oct. 1992;38(2):117-23.
Fahrner et al., Industrial purification of pharmaceutical antibodies: development, operation, and validation of chromatography processes. Biotechnol Genet Eng Rev. 2001;18:301-27.
Fahy et al., Effect of aerosolized anti-IgE (E25) on airway responses to inhaled allergen in asthmatic subjects. Am J Respir Crit Care Med. Sep. 1999;160(3):1023-7.
Fan et al., Three-dimensional structure of an Fv from a human IgM immunoglobulin. J Mol Biol. Nov. 5, 1992;228(1):188-207.
Fendly et al., Murine monoclonal antibodies defining neutralizing epitopes on tumor necrosis factor. Hybridoma. Aug. 1987;6(4):359-70.
Frenken et al., Isolation of antigen specific llama VHH antibody fragments and their high level secretion by *accharomyces cerevisiae*. J Biotechnol. Feb. 28, 2000;78(1):11-21.
Guarino et al., Oral immunoglobulins for treatment of acute rotaviral gastroenteritis. Pediatrics. Jan. 1994;93(1):12-6.
Haber et al., Extensive degradation of antibody by pepsin. Biochemistry. Jul. 1967;6(7):1974-80.
Hamada et al., Localization of carcinoembryonic antigen in medullary thyroid carcinoma by immunofluorescent techniques. Br J Cancer. Nov. 1977;36(5):572-6.
Hamilton-Wessler et al., Mechanism of protracted metabolic effects of fatty acid acylated insulin, NN304, in dogs: retention of NN304 by albumin. Diabetologia. Oct. 1999;42(10):1254-63.
Harmsen et al., *Escherichia coli* F4 fimbriae specific llama single-domain antibody fragments effectively inhibit bacterial adhesion in vitro but poorly protect against diarrhoea. Vet Microbiol. Nov. 30, 2005;111(1-2):89-98. Epub Oct. 10, 2005.
Harmsen et al., Llama heavy-chain V regions consist of at least four distinct subfamilies revealing novel sequence features. Mol Immunol. Aug. 2000;37(10):579-90.
Harmsen et al., Prolonged in vivo residence times of llama single-domain antibody fragments in pigs by binding to porcine immunoglobulins. Vaccine. Sep. 30, 2005;23(41):4926-34.
Harmsen et al., Selection and optimization of proteolytically stable llama single-domain antibody fragments for oral immunotherapy. Appl Microbiol Biotechnol. Sep. 2006;72(3):544-51. Epub Feb. 1, 2006.
Heitner et al., Selection of cell binding and internalizing epidermal growth factor receptor antibodies from a phage display library. J Immunol Methods. Feb. 1, 2001;248(1-2):17-30.
Heusser et al., New concepts of IgE regulation. Int Arch Allergy Appl Immunol. 1991;94(1-4):87-90.
Hey et al., Artificial, non-antibody binding proteins for pharmaceutical and industrial applications. Trends Biotechnol. Oct. 2005;23(10):514-22.
Hoefman et al., Pre-clinical intravenous serum pharmacokinetics of albumin binding and non-half-life extended Nanobodies® ⁂ . Antibodies. 2015;4(3):141-156.
Holliger et al., Retargeting serum immunoglobulin with bispecific diabodies. Nat Biotechnol. Jul. 1997;15(7):632-6.

(56) References Cited

OTHER PUBLICATIONS

Holm et al., Functional mapping and single chain construction of the anti-cytokeratin 8 monoclonal antibody TS1. Mol Immunol. Feb. 2007;44(6):1075-84. Epub Sep. 20, 2006.
Holt et al., Domain antibodies: proteins for therapy. Trends Biotechnol. Nov. 2003;21(11):484-90.
Hoogenboom, Mix and match: building manifold binding sites. Nat Biotechnol. Feb. 1997;15(2):125-6.
Hori et al., Effect of orally administered enterotoxigenic Escherichia coli K99-specific monoclonal antibody to neonatal calves. Journal of the Japan Veterinary Medical Association. 1989;42(6):411-16. Abstract Only.
Hulme et al., The measurement of renal permeability using labelled marcromolecules. Proc R Soc Med. Jun. 1966;59(6):509-12.
Janeway et al., Immunobiology. 3rd Edition. 1997. Garland Press. 11:11.
Janeway et al., Immunobiology. 3rd Edition. 1997. Garland Press. 2:2-2:5; 3.1-3.11; 11.1.
Janeway et al., Immunobiology. 3rd Edition. 1997. Garland Press. 3:1-3:11.
Janeway et al., Immunobiology: the immune system in health and disease. Third ed., New York: Garland Pub, 1997:2:19-2:20.
Kang et al., Anti-EGFR monoclonal antibody Cetuximab binds the EGFR variant III receptor and internalizes phosphorylated receptor on the cell surface. Eur. J. Cancer. 38:S149.
Kilpatrick et al., Gene gun delivered DNA-based immunizations mediate rapid production of murine monoclonal antibodies to the Flt-3 receptor. Hybridoma. Dec. 1998;17(6):569-76.
King, Applications and Engineering of Monoclonal Antibodies. Taylor and Francis Ltd, 1998:40-50.
Knudsen et al., Potent derivatives of glucagon-like peptide-1 with pharmacokinetic properties suitable for once daily administration. J Med Chem. May 4, 2000;43(9):1664-9.
Koch-Nolte et al., Single domain antibodies from llama effectively and specifically block T cell ecto-ADP-ribosyltransferase ART2.2 in vivo. FASEB J. Nov. 2007;21(13):3490-8. Epub Jun. 15, 2007.
Kolbinger et al., Humanization of a mouse anti-human IgE antibody: a potential therapeutic for IgE-mediated allergies. Protein Eng. Nov. 1993;6(8):971-80.
Kontermann, Strategies for extended serum half-life of protein therapeutics. Curr Opin Biotechnol. Dec. 2011;22(6):868-76. doi:10.1016/j.copbio.2011.06.012. Epub Aug. 20, 2011.
Koumenis et al., Modulating pharmacokinetics of an anti-interleukin-8 F(ab")(2) by amine-specific PEGylation with preserved bioactivity. Int J Pharm. Mar. 30, 2000;198(1):83-95.
Krüger et al., Therapeutic effect of llama derived VHH fragments against Streptococcus mutans on the development of dental caries. Appl Microbiol Biotechnol. Oct. 2006;72(4):732-7. Epub Apr. 25, 2006.
Kuo et al., Topical antibody delivery systems produce sustained levels in mucosal tissue and blood. Nat Biotechnol. Feb. 1998;16(2):163-7.
Kurtzhals et al., Albumin binding and time action of acylated insulins in various species. J Pharm Sci. Mar. 1996;85(3):304-8.
Kurtzhals et al., Albumin binding of insulins acylated with fatty acids: characterization of the ligand-protein interaction and correlation between binding affinity and timing of the insulin effect in vivo. Biochem J. Dec. 15, 1995;312 ( Pt 3):725-31.
Lauwereys et al., Potent enzyme inhibitors derived from dromedary heavy-chain antibodies. EMBO J. Jul. 1, 1998;17(13):3512-20.
Lederman et al., A single amino acid substitution in a common African allele of the CD4 molecule ablates binding of the monoclonal antibody, OKT4. Mol Immunol. Nov. 1991;28(11):1171-81.
Lewis et al., Immunoglobulin complementarity-determining region grafting by recombinant polymerase chain reaction to generate humanised monoclonal antibodies. Gene. May 30, 1991;101(2):297-302.
Lorimer et al., Mutant epidermal growth factor receptors as targets for cancer therapy. Curr Cancer Drug Targets. Jun. 2002;2(2):91-102. Review.
Losonsky et al., Oral administration of human serum immunoglobulin in immunodeficient patients with viral gastroenteritis. A pharmacokinetic and functional analysis. J Clin Invest. Dec. 1985;76(6):2362-7.
Maccallum et al., Antibody-antigen interactions: contact analysis and binding site topography. J Mol Biol. Oct. 11, 1996;262(5):732-45.
Macewan, TNF ligands and receptors—a matter of life and death. Br J Pharmacol. Feb. 2002;135(4):855-75.
Mallender et al., Construction, expression, and activity of a bivalent bispecific single-chain antibody. J Biol Chem. Jan. 7, 1994;269(1):199-206.
Mamot et al., Epidermal growth factor receptor (EGFR)-targeted immunoliposomes mediate specific and efficient drug delivery to EGFR- and EGFRvIII-overexpressing tumor cells. Cancer Res. Jun. 15, 2003;63(12):3154-61.
Mauri et al., Prevention of arthritis by interleukin 10-producing B cells. J Exp Med. Feb. 17, 2003;197(4):489-501.
Melamed et al., Benefit of oral immune globulin therapy in patients with immunodeficiency and chronic diarrhea. J Pediatr. Sep. 1991;119(3):486-9.
Mitri et al., Inhaled insulin—what went wrong. Nat Clin Pract Endocrinol Metab. Jan. 2009;5(1):24-5. doi: 10.1038/ncpendmet1007. Epub Nov. 4, 2008.
Miyajima et al., Rat monoclonal anti-murine IgE antibody removes IgE molecules already bound to mast cells or basophilic leukemia cells, resulting in the inhibition of systemic anaphylaxis and passive cutaneous anaphylaxis. Int Arch Allergy Immunol. May 2002;128(1):24-32.
Moghal et al., Multiple positive and negative regulators of signaling by the EGF-receptor. Curr Opin Cell Biol. Apr. 1999;11(2):190-6.
Morelli et al., Oral administration of anti-doxorubicin monoclonal antibody prevents chemotherapy-induced gastrointestinal toxicity in mice. Cancer Res. May 1, 1996;56(9):2082-5.
Murthy et al., Combination therapy of pentoxifylline and TNFalpha monoclonal antibody in dextran sulphate-induced mouse colitis. Aliment Pharmacol Ther. Feb. 1999;13(2):251-60.
Muruganandam et al., Selection of phage-displayed llama single-domain antibodies that transmigrate across human blood-brain barrier endothelium. FASEB J. Feb. 2002;16(2):240-2. Epub Dec. 28, 2001.
Muyldermans et al., Recognition of antigens by single-domain antibody fragments: the superfluous luxury of paired domains. Trends Biochem Sci. Apr. 2001;26(4):230-5.
Muyldermans et al., Unique single-domain antigen binding fragments derived from naturally occurring camel heavy-chain antibodies. J Mol Recognit. Mar.-Apr. 1999;12(2):131-40.
Muyldermans, Single domain camel antibodies: current status. J Biotechnol. Jun. 2001;74(4):277-302.
Myers et al., Acylation of human insulin with palmitic acid extends the time action of human insulin in diabetic dogs. Diabetes. Apr. 1997;46(4):637-42.
Nagatomi et al., [Absorption of the antibody formation to anticartilage-antiparathyroid antibodies administered into the rectum (author's transl)]. Nihon Yakurigaku Zasshi. Aug. 1981;78(2):109-15. Japanese.
Nagatomi et al., Antigen-binding activity and allergenicity of heterologous gamma-globulin absorbed from the rectum. Int Arch Allergy Appl Immunol. 1980;63(3):340-3.
Nielsen et al., Carcino-embryonic antigen (CEA) in gastric adenocarcinomas. Morphologic patterns and their relationship to a histogenetic classification. Acta Pathol Microbiol Immunol Scand A. Nov. 1982;90(6):393-6. Abstract only.
Nilsson et al., Affinity fusion strategies for detection, purification, and immobilization of recombinant proteins. Protein Expr Purif. Oct. 1997;11(1):1-16. Review.
Nuttall et al., Immunoglobulin VH domains and beyond: design and selection of single-domain binding and targeting reagents. Curr Pharm Biotechnol. Nov. 2000;1(3):253-63.
Nygren et al., In vivo stabilization of a human recombinant CD4 derivative by fusion to a serum-albumin-binding receptor. Vaccines. 1991;91:363-8.

(56) References Cited

OTHER PUBLICATIONS

Osborn et al., Pharmacokinetic and pharmacodynamic studies of a human serum albumin-interferon-alpha fusion protein in cynomolgus monkeys. J Pharmacol Exp Ther. Nov. 2002;303(2):540-8.
Pant et al., Lactobacilli expressing variable domain of llama heavy-chain antibody fragments (lactobodies) confer protection against rotavirus-induced diarrhea. J Infect Dis. Dec. 1, 2006;194(11):1580-8. Epub Oct. 23, 2006.
Pant et al., Lactobacilli producing bispecific llama-derived anti-rotavirus proteins in vivo for rotavirus-induced diarrhea. Future Microbiol. May 2011;6(5):583-93.
Patton, Breathing life into protein drugs. Nat Biotechnol. Feb. 1998;16(2):141-3.
Paul, Fv structure and diversity in three dimensions. Fundamental immunology, 3rd Edition, 1993:292-295.
Poul et al., Selection of tumor-specific internalizing human antibodies from phage libraries. J Mol Biol. Sep. 1, 2000;301(5):1149-61.
Presta et al., Generation of a humanized, high affinity anti-tissue factor antibody for use as a novel antithrombotic therapeutic. Thromb Haemost. Mar. 2001;85(3):379-89.
Prince et al., Effectiveness of topically administered neutralizing antibodies in experimental immunotherapy of respiratory syncytial virus infection in cotton rats. J Virol. Jun. 1987;61(6):1851-4.
Prince et al., Mechanism of antibody-mediated viral clearance in immunotherapy of respiratory syncytial virus infection of cotton rats. J Virol. Jun. 1990;64(6):3091-2.
Queen et al., A humanized antibody that binds to the interleukin 2 receptor. Proc Natl Acad Sci U S A. Dec. 1989;86(24):10029-33.
Radomsky et al., Controlled vaginal delivery of antibodies in the mouse. Biol Reprod. Jul. 1992;47(1):133-40.
Reeck et al., "Homology" in proteins and nucleic acids: a terminology muddle and a way out of it. Cell. Aug. 28, 1987;50(5):667.
Reilly et al., Oral delivery of antibodies. Future pharmacokinetic trends. Clin Pharmacokinet. Apr. 1997;32(4):313-23.
Reiter et al., An antibody single-domain phage display library of a native heavy chain variable region: isolation of functional single-domain VH molecules with a unique interface. Mol Biol. Jul. 16, 1999;290(3):685-98.
Reiter et al., Engineering antibody Fv fragments for cancer detection and therapy: disulfide-stabilized Fv fragments. Nat Biotechnol. Oct. 1996;14(10):1239-45.
Rheinnecker et al., Multivalent antibody fragments with high functional affinity for a tumor-associated carbohydrate antigen. J Immunol. Oct. 1, 1996;157(7):2989-97.
Riechmann et al., Reshaping human antibodies for therapy. Nature. Mar. 24, 1988;332(6162):323-7.
Riechmann et al., Single domain antibodies: comparison of camel VH and camelised human VH domains. J Immunol Methods. Dec. 10, 1999;231(1-2):25-38.
Riechmann, Rearrangement of the former VL interface in the solution structure of a camelised, single antibody VH domain. J Mol Biol. Jun. 28, 1996;259(5):957-69.
Riemer et al., Matching of trastuzumab (Herceptin) epitope mimics onto the surface of Her-2/neu—a new method of epitope definition. Mol Immunol. May 2005;42(9):1121-4. Epub Jan. 8, 2005.
Roovers et al., Efficient inhibition of EGFR signaling and of tumour growth by antagonistic anti-EFGR Nanobodies. Cancer Immunol Immunother. 2007;56(3):303-317.
Rosenberg, Effects of protein aggregates: an immunologic perspective. AAPS J. Aug. 4, 2006;8(3):E501-7.
Rote et al., Antithrombotic effects of DMP 728, a platelet GPIIb/IIIa receptor antagonist, in a canine model of arterial thrombosis. J Cardiovasc Pharmacol. Apr. 1994;23(4):681-9.
Rudikoff et al., Single amino acid substitution altering antigen-binding specificity. Proc Natl Acad Sci U S A. Mar. 1982;79(6):1979-83.

Saelman et al., Platelet adhesion to collagen types I through VIII under conditions of stasis and flow is mediated by GPIa/IIa (alpha 2 beta 1-integrin). Blood. Mar. 1, 1994;83(5):1244-50.
Saerens et al., Identification of a universal VHH framework to graft non-canonical antigen-binding loops of camel single-domain antibodies. J Mol Biol. Sep. 23, 2005;352(3):597-607.
Saltzman et al., Long-term vaginal antibody delivery: delivery systems and biodistribution. Biotechnol Bioeng. Feb. 5, 2000;67(3):253-64. Erratum in: Biotechnol Bioeng Nov. 20, 2001;75(4):494.
Scheurich et al., Quantification and characterization of high-affinity membrane receptors for tumor necrosis factor on human leukemic cell lines. Int J Cancer. Jul. 15, 1986;38(1):127-33.
Schlaeppi et al., Characterization of a new potent, in vivo neutralizing monoclonal antibody to human vascular endothelial growth factor. J Cancer Res Clin Oncol. 1999;125(6):336-42.
Shalaby et al., The involvement of human tumor necrosis factors-alpha and -beta in the mixed lymphocyte reaction. J Immunol. Jul. 15, 1988;141(2):499-503.
Sherman et al., Protection of calves against fatal enteric colibacillosis by orally administered *Escherichia coli* K99-specific monoclonal antibody. Infect Immun. Nov. 1983;42(2):653-8.
Shimamoto et al., Inhibition of Helicobacter pylori infection by orally administered yolk-derived anti-Helicobacter pylori antibody. Database Biosis Bioscience Information Service, Philadelphia, PA, US. May 2002.
Silacci et al., Design, construction, and characterization of a large synthetic human antibody phage display library. Proteomics. Jun. 2005;5(9):2340-50.
Skurkovich et al., Treatment of corneal transplant rejection in humans with anti-interferon-gamma antibodies. Am J Ophthalmol Jun. 2002;133(6):829-30.
Smith et al., Prolonged in vivo residence times of antibody fragments associated with albumin. Bioconjug Chem. Sep.-Oct. 2001;12(5):750-6.
Stadler et al., Biological activities of anti-IgE antibodies. Int Arch Allergy Immunol. 1993;102(2):121-6.
Ståhl et al., The use of gene fusions to protein A and protein G in immunology and biotechnology. Pathol Biol (Paris). Jan. 1997;45(1):66-76.
Stancovski et al., Mechanistic aspects of the opposing effects of monoclonal antibodies to the ERBB2 receptor on tumor growth. Proc Natl Acad Sci U S A. Oct. 1, 1991;88(19):8691-5.
Strohl, Fusion proteins for half-life extension of biologics as a strategy to make biobetters. BioDrugs. Aug. 2015;29(4):215-39. doi:10.1007/s40259-015-0133-6.
Sunada et al., Monoclonal antibody against epidermal growth factor receptor is internalized without stimulating receptor phosphorylation. Proc Natl Acad Sci U S A. Jun. 1986;83(11):3825-9.
Syed et al., Potent antithrombin activity and delayed clearance from the circulation characterize recombinant hirudin genetically fused to albumin. Blood. May 1, 1997;89(9):3243-52.
Tanha et al., Optimal design features of camelized human single-domain antibody libraries. J Biol Chem. Jul. 6, 2001;276(27):24774-80. Epub May 2, 2001.
Tanha et al., Selection by phage display of llama conventional V(H) fragments with heavy chain antibody V(H)H properties. J Immunol Methods. May 1, 2002;263(1-2):97-109.
Teitelbaum et al., A mAb recognizing a surface antigen of Mycobacterium tuberculosis enhances host survival. Proc Natl Acad Sci U S A. Dec. 22, 1998;95(26):15688-93.
Terskikh et al., "Peptabody": a new type of high avidity binding protein. Proc Natl Acad Sci U S A. Mar. 4, 1997;94(5):1663-8.
Thiel et al., Penetration of engineered antibody fragments into the eye. Clin Exp Immunol. Apr. 2002;128(1):67-74.
Tijink et al., Improved tumor targeting of anti-epidermal growth factor receptor Nanobodies through albumin binding: taking advantage of modular Nanobody technology. Mol Cancer Ther. Aug. 2008;7(8):2288-97.

(56) References Cited

OTHER PUBLICATIONS

Tsaltas et al., Demonstration of monoclonal anti-carcinoembryonic antigen (CEA) antibody internalization by electron microscopy, western blotting and radioimmunoassay. Anticancer Res. Nov.-Dec. 1992;12(6B):2133-42. Abstract only.

Valle et al., Infliximab. Expert Opin Pharmacother. Jun. 2001;2(6):1015-25. Review.

Van Den Beucken et al., Building novel binding ligands to B7.1 and B7.2 based on human antibody single variable light chain domains. J Mol Biol. Jul. 13, 2001;310(3):591-601.

Van Der Linden et al., Induction of immune responses and molecular cloning of the heavy chain antibody repertoire of Lama glama. J Immunol Methods. Jun. 23, 2000;240(1-2):185-95.

Van Der Vaart et al., Reduction in morbidity of rotavirus induced diarrhoea in mice by yeast produced monovalent llama-derived antibody fragments. Vaccine. May 8, 2006;24(19):4130-7. Epub Mar. 7, 2006.

Vickers, A vaccine against Alzheimer's disease: developments to date. Drugs Aging. 2002;19(7):487-94.

Waldmann et al., The renal handling of low molecular weight proteins. II. Disorders of serum protein catabolism in patients with tubular proteinuria, the nephrotic syndrome, or uremia. J Clin Invest. Aug. 1972;51(8):2162-74.

Ward et al., Binding activities of a repertoire of single immunoglobulin variable domains secreted from *Escherichia coli*. Nature. Oct. 12, 1989;341(6242):544-6.

Weir et al., Formatting antibody fragments to mediate specific therapeutic functions. Biochem Soc Trans. Aug. 2002;30(4):512-6.

Wesolowski et al., Single domain antibodies: promising experimental and therapeutic tools in infection and immunity. Med Microbiol Immunol. Aug. 2009;198(3):157-74. Epub Jun. 16, 2009.

Wilkstrand et al., Monoclonal antibodies against EGFRvIII are tumor specific and react with breast and lung carcinomas and malignant gliomas. Cancer Res. Jul. 15, 1995;55(14):3140-8.

Winkler et al., Changing the antigen binding specificity by single point mutations of an anti-p24 (HIV-1) antibody. J Immunol. Oct. 15, 2000;165(8):4505-14.

Witte et al., Monoclonal antibodies targeting the VEGF receptor-2 (Flk1/KDR) as an anti-angiogenic therapeutic strategy. Cancer Metastasis Rev. Jun. 1998;17(2):155-61.

Worledge et al., Oral administration of avian tumor necrosis factor antibodies effectively treats experimental colitis in rats. Dig Dis Sci. Dec. 2000;45(12):2298-305.

Zhu et al., Inhibition of tumor growth and metastasis by targeting tumor-associated angiogenesis with antagonists to the receptors of vascular endothelial growth factor. Invest New Drugs. 1999;17(3):195-212.

Wang et al., Binding of serum albumin on tumor cells and characterization of the albumin binding protein. J Biochem. May 1994;115(5):898-903.

\* cited by examiner

```
                                  <    FR1                   >  CDR1   <   FR2      >  CDR2
(SEQ ID N° 126)   1.35    EVQLVESGGGLVQPGGSLRLSCAASGFIFS  SHYMS  WFRQAPGKEREFVA  AITSSSRTYYTESVKG
(SEQ ID N° 112)   3.14    AVQLVESGGGLVQPGGSLRLSCAASGFTFS  SHYMS  WFRQAPGKEREFVA  AITSSSRIYYTESVKG
(SEQ ID N° 113)   2.04    QVKLEESGGGLVQPGDSLRLSCAASGFTFS  SHYMS  WFRQAPGKEREFVA  AITSSSRIYYTESVKG
(SEQ ID N° 127)   1.4     EVQLVESGGGLVQAGGSLRLSCAASGRTFS  NYVMG  WFRQAPGKERDFVV  GIGRSGGDNTYYADSVKG
(SEQ ID N° 114)   Ia9     QVQLVESGGGLVQAGGSLRLSCAASGRTFS  NYVMG  WFRQAPGKERDFVV  GIGRSGGDNTYYADSVKG
(SEQ ID N° 128)   2.26    EVQLVESGGGLVQAGGSLRLSCAASGRSFS  SYAMA  WFRQAPGKEREFVA  AISWGGGSTYYAVSVKG
(SEQ ID N° 129)   IIIa6   EVQLVESGGGLVQAGGSLRLSCAASGRSFS  SYAMA  WFRQAPGKEREFVA  AISWGGGSTYYAVSVKG
(SEQ ID N° 115)   Ia26    QVQLQESGGGSVQAGGSLRLSCAATGRGFS  RYAMG  WFRQAPCQDREFVA  TLSWTNSTDYADSVKG
(SEQ ID N° 130)   IIIa42  EVQLVESGGGSVQAGGSLRLSCAASGRSFS  TYAMG  WFRQAPGQDREFVA  TISWTDSTDYADSVKG
(SEQ ID N° 116)   Ia33    QVQLQESGGGSVQAGGSLRLSCTASGRRFS  TYAVG  WFRQAPGQDREFVA  TLSWTNSTDYADSVKG
(SEQ ID N° 117)   3.1     EVQLVESGGGSVQAGGSLRLSCTASGRRFS  TYAVG  WFRQAPGQDREFVA  TISWINSTDYADSVKG
(SEQ ID N° 131)   Ia1     QVQLQESGGGLVQAGGSLLLSCAASGRTFS  SYANG  WFRQAPGKEREFVA  AINWGGGSTYADSVKG
(SEQ ID N° 118)   Ia21    QVQLQESGGGLVQAGGSLLLSCAASGRTFS  SYAMG  WFRQAPGKERDFVA  AINWSGGSTYADSVKG
(SEQ ID N° 119)   II1a3   QVQLQESGGGLVQAGGSLLLSCAASGRTFS  SYAMG  WFRQAPGKEREFVA  AINWSGGSTYADSVKG
(SEQ ID N° 132)   1.9     QVQLQESGGGLVQAGGSLRLSCAASGRTFS  SYVMG  WFRQAPGKEREFVG  AINWGGGRTYYADSVKG
(SEQ ID N° 133)   1.34    QVQLQESGGGLVQAGGSLRLSCAASGRTFS  KYAMG  WFRQAPGKEREFVS  AISWSGGSTYYADSVKG
(SEQ ID N° 134)   Ia10    QVQLQESGGGLVQAGGSLRLSCAASGRTFS  KYAMG  WFRQAPGKEREFVS  AISWSGGSTYYADSVKG
(SEQ ID N° 135)   7.6     QVQLQESGGGLVQAGGSLRLSCAASGHFS   NYAMG  WFRQAPGKEREFVA  AINWGGGNTYYADSVKG
(SEQ ID N° 136)   3.34    QVQLQESGGGLVQAGGSLRLSCAASGRTFS  SYAIG  WFRQAPGKEREFVA  AISWGGGSNTYYADSVKG
(SEQ ID N° 137)   1.38    QVQLQDSGGGLVQAGGSLRLSCAASGRSFG  SYAMG  WFRQAPGKEREFVA  AISWSGGSTYYADSLRG
(SEQ ID N° 138)   3.32    QVQLQESGGGLVQAGGSLRLSCAASGRTFS  SYAMG  WFRQAPGGEREFVA  AISWRGTSTYYGDSASG
(SEQ ID N° 139)   4.43    QVQLQESGGGLVQAGGSLRLSCAASGRTFS  DYAMG  WFRQAPGLEREFVA  AISWRGTGTYYGDSASG
(SEQ ID N° 140)   Ia15    QVQLQDSGGGLVQAGGSLRLSCAASGGTFS  SYAMG  WFRQAPGKEREFVS  AIGLNTYYADSVKG
(SEQ ID N° 141)   Ia7     QVQLQESGGGLVQTGGSLRLSCAASGGTFS  TYAIG  WFRQAPGKEREFVA  AISRGGSTYYADSVKG
(SEQ ID N° 142)   3.39    QVQLQESGGGLVQTGGSLRLSCAASGRYIM G       WFRQAPGKEREFVA  GISRSGASTAYADSVKD
(SEQ ID N° 143)   3.40    QVKLEESGGGLVQAGGSLRLSCSASGLTFS NYAMA  WFRQAFGKEREFVA  TISDRGGMRHYLDSVKE
(SEQ ID N° 120)   4.22    QVKLEESGGGLVQAGGSLRLSCAASGGIFS  INAMG  WYRQAPGKQRELVA  RITGCGTGITGAVGTNYADSVKG
(SEQ ID N° 121)   4.11    QVKLEESGGGLVQAGGSLRLSCAASGRSFS  SITNG  WFRQAPGKERQFVS  AINSWGNRYYADSVKG
(SEQ ID N° 122)   4.21    EVQLVESGGGLVQAGGSLRLSCAVSGRTFS  SMG    WFRQAPGKEREFVA  TINLSGDRTDYADSVKG
(SEQ ID N° 123)   IIIa5   EVQLVESGGGLVQAGGSLRLSCTASGRTFS  SYANG  WFRQTPGKEREFVA  AITTSGGSTYYADSVKG
(SEQ ID N° 124)   3.18    EVQLVESGGGLVQPGGSLRLSCVASGFTSA DYAMS  WVRQAPGKGLQWVS  SISYNGGTYYAESMKG
```

Figure 9 - 1

```
        <   FR3                          >.CDR3                         <   FR4   >
1.33    RFTISRDNAKNTVYLQMNSLKSEDTAVYYCAA  DRTFYGSTWSKYDY                RGQGTQVTVSS
3.14    RFTISRDNAKNTVYLQMNSLKSEDTAVYYCAA  DRTFYGSTWSKYDY                RGQGTQVTVSS
2.34    RFTISRDNAKNTVYLQMDSLKSEDTAVYYCAA  DRTFYGSTNSKYDY                RGQGTQVTVSS
1.4     RFTISWDNAKNTMYLQMNSLKPEDTAVYYCAA  STYSRDTIFTKWANYNY             WGQGTQVTVSS
Ia9     RFTISWDNAKNTMYLQMNSLKPEDTAVYYCAA  STYSRDTIFTKNARYNY             WGQGTQVTVSS
2.20    RFTISRDNAKNTVYLQMNSLKPEDTARYYCAA  DRTFHSSAYGEYEY                WGQGTQVTVSS
IIIa6   RFTISRDNAKNTVYLQMNSLKPEDTARYYCAA  DRTFHSSAYGEYEY                WGQGTQVTVSS
Ia26    RFAISRDNAKNTAYLQMNSLKPEDTAVYYCAA  DKWASSIRSIDYDY                WGQGIQVTVSS
IIIa42  RFTISRDNAKNTGYLQMNSLKPEDTAVYYCAA  DRWASSRRNVDYDY                WGQGTQVTVSS
Ia33    RFTISRDNAKNTGYLQMNSLKPEDTSVYYCAA  DKWSSSRRSVDYDY                WGQGTQVTVSS
3.1     RFTISRDNAKNTGYLQMNSLKPEDTSVYYCAA  DKWSSSRRSVDYDY                WGQGTQVTVSS
Ia1     RFTISRDNTKNTVYLQMNSLKPEDTAAFYCAA  TYNPYSRDHYFPRMTTSYDY          WGQGTQVTVSS
Ia21    RFTISKDNIKNTVYLQMNSLKPEDTAAFYCAA  TYNPYSRDHYFPRMTTSYDY          WGQGTQVTVSS
IIIa3   RFTISRDNTKNTVYLQMNSLKPEDTAAFYCAA  TYNPYSRDHYFPRMTTSYDY          WGQGTQVTVSS
1.9     RFTISSDNAKNTLYLQMNSLKPEDTAVYYCAA  SRIIYSYVHYVNPGEYDY            WGQGTQVTVSS
1.34    RFTISRDNAKNTVYLQVNSLKPEDTAVYYCAA  TYLVDVWAVEVPIRPYEYDY          WGQGTQVTVSS
Ia10    RFTISRDNAKNTVYLQVNSLKPEDTAVYYCAA  TYLVDVWAVEVPIRPYRYDY          WGQGTQVSVSS
2.6     RFTISRDNAKNTVYLQMNSLKPEDTAVYYCAA  SEWGGSEYDEDYDY                WGQGTQVTVSS
3.34    RFTISRDNAKNTVYLQMNSLKPEDTAVYYCAA  GEVSNSDYAYEYDY                WGQGTQVTVSS
1.38    RFTISRDNAKNTVYLQMNSLKPEDTALYYCAA  GLRPSFNYNHER-SYDY             WGQGTQVTVSS
3.32    RFTISRDNAKNTVYLQMNSLKPEDTAVYYCAA  GSHSDYAPDYDY                  WGQGTQVTVSS
4.43    RFTISRDNAKNTVYLQMNSLKPEDTAVYYCAA  GSHSDYAPDYDY                  WGQGTQVTVSS
Ia15    RFTISRDNAKNTVYLQMNSLKPEDTAVYYCAA  RTSGVVGGTPKRYDY               WGQGTQVTVSS
Ia7     RFTISRDNAKNTVYLEMNSLKPEDTAVYYCAA  REGVALGLRNDANY                WGQGTQVTVSS
3.39    RFTISRDSALNTVYLQMNSLKAEDTAVYFCAA  ALAIRLGIPRGSTEYEY             WGQGTQVTVSS
3.40    RFTISRDNAKNTVYLQMNSLKPDDTAVYYCAA  DLMYGVDPRYDY                  WGRGTQVTVSS
```

Figure 9 - 2

Pulmonary delivered Nanobodies are stable in the lung for at least 24 hrs post-administration ∇ Exposure in BALF after intra-tracheal administration for at least 24 hrs

Figure 24 peris competing with fetuin binding to HA-bio

[Bar chart, OD490 axis 0–0.45, samples: 202-C2, 202-F3, 202-D5, 202-E5, 202-B7, 202-E7, 202-C8, 202-D8, 202-F8, 202-E11, HA-bio+strep]

Figure 25

Nanobody-mediated inhibition of the H5 HA interaction with fetuin

[Bar chart, OD490 axis 0–1.2, legend: 5 µg/ml, 0.5 µg/ml; samples: 203-B1, 203-H1, 203-B2, 203-E12, 203-H9, 203-B12, 203-A9, 203-D9, 202-C8, 189-E2, HA-bio, streptavidin]

Figure 36e
Scaled Residuals for bodyweight
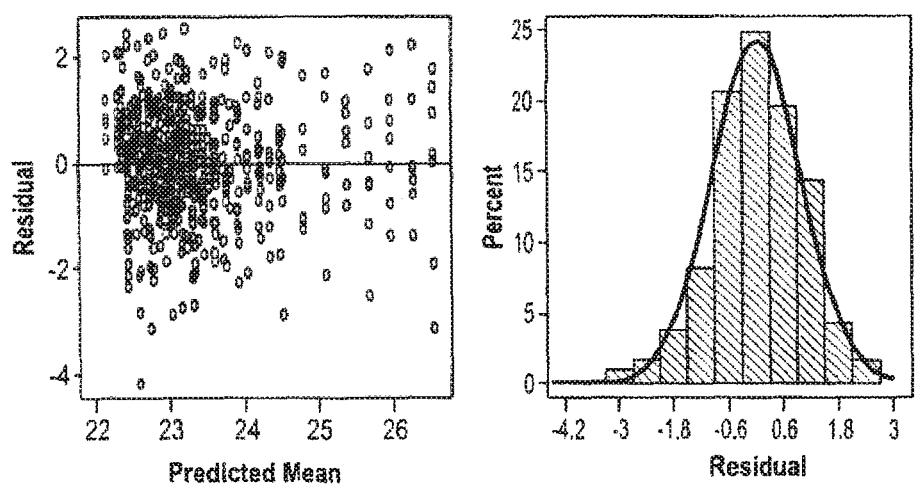
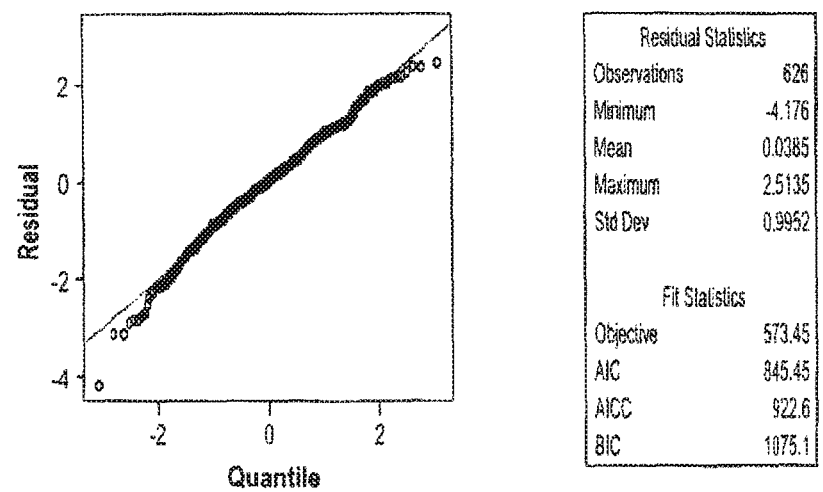

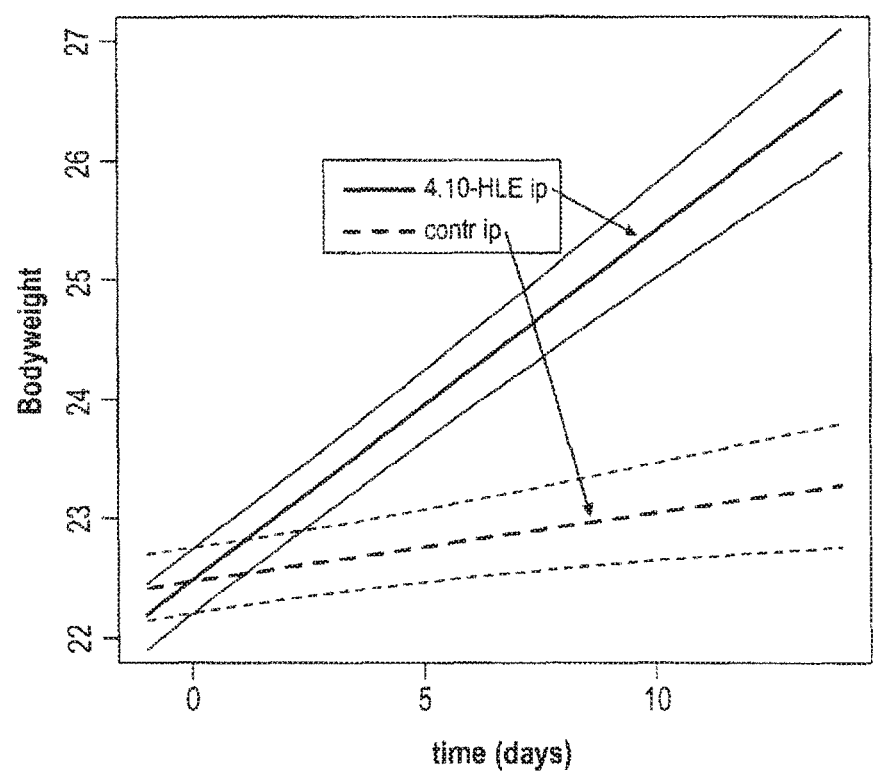

PULMONARY ADMINISTRATION OF IMMUNOGLOBULIN SINGLE VARIABLE DOMAINS AND CONSTRUCTS THEREOF

RELATED APPLICATIONS

This application is a divisional of U.S. patent application Ser. No. 13/761,554, filed Feb. 7, 2013, which is a continuation-in-part application of U.S. patent application Ser. No. 12/487,684, filed Jun. 19, 2009, which is a continuation of U.S. application Ser. No. 10/534,292, filed May 9, 2005, which is a national stage filing under 35 U.S.C. §371 of international application PCT/BE03/00190, filed Nov. 7, 2003, which was published under PCT Article 21(2) in English, which claims priority to international application PCT/EP03/06581, filed Jun. 23, 2003, and international application PCT/EP03/07313, filed Jul. 8, 2003, and also claims the benefit under 35 U.S.C. 119(e) of U.S. provisional application Ser. No. 60/425,073, filed Nov. 8, 2002, and U.S. provisional application Ser. No. 60/425,063, filed Nov. 8, 2002, the disclosures of which are incorporated by reference herein in their entireties.

U.S. patent application Ser. No. 13/761,554 is also a continuation-in-part application of U.S. patent application Ser. No. 13/143,736, filed Sep. 2, 2011, which is a national stage filing under 35 U.S.C. §371 of international application PCT/EP2010/050414, filed Jan. 14, 2010, which was published under PCT Article 21(2) in English, and claims the benefit under 35 U.S.C. §119(e) of U.S. provisional application Ser. No. 61/144,586, filed Jan. 14, 2009, and of U.S. provisional application Ser. No. 61/251,879, filed Oct. 15, 2009, the disclosures of which are incorporated by reference herein in their entireties.

FIELD OF THE INVENTION

The present invention relates to a method wherein an immunoglobulin single variable domain (such as a Nanobody) and/or construct thereof are absorbed in pulmonary tissue. More particularly, the invention provides systemic delivery of an immunoglobulin single variable domain and/or construct thereof via the pulmonary route.

BACKGROUND

Polypeptide therapeutics and in particular antibody-based therapeutics have significant potential as drugs because they have exquisite specificity to their target and a low inherent toxicity. However, they have one important drawback: these are complex, large molecules and therefore relatively unstable, and they are sensitive to breakdown by proteases. Because the degradation they undergo during passage through, for instance, the gastrointestinal tract, administration of conventional antibodies and their derived fragments or single-chain formats (e.g. scFv's) is not very effective. This means that conventional antibody drugs cannot be administered orally, sublingually, topically, nasally, vaginally, rectally or by inhalation because they are not resistant to the low pH at these sites, the action of proteases at these sites and in the blood and/or because of their large size. They have to be administered by injection (intravenously, subcutaneously, etc.) to overcome some of these problems. Administration by injection is therefore the most frequently used method of administration although the method has many disadvantages, for example: (a) poor tolerance by patients, especially when treating chronic disorder; (b) a consequent risk of poor compliance with the dosage when the drug is not a 'life saver'; (c) difficulty of carrying out self-administration by the patient; (d) possible non-availability of suitable surroundings for carrying out the procedure in an aseptic manner; (e) requires specialist training in order to use a hypodermic syringe or needle correctly and safely. A method for the delivery of therapeutic polypeptides which avoids the need for injection has not only cost/time savings, but would also be more convenient and more comfortable for the subject.

In most animal cells, a specialised pathway is present for uptake of specific macromolecules from the extracellular fluid. The macromolecules that bind to specific cell-surface receptors are internalized, a process called receptor-mediated endocytosis. Receptor internalization is based on the principle of regulation of signal transduction by a process called sequestration, whereby bound agonistic (i.e. receptor activation) ligands are recovered from the cell surface in complex with the receptor. For many applications it is necessary to deliver effector molecules across the cell membrane and into the cytosol. This can be achieved by taking advantage of such internalizing receptors. Antibodies have been described that internalize upon binding to internalizing receptors. However, they have important drawbacks: these antibodies are complex, large molecules and therefore relatively unstable, and they are sensitive to breakdown by proteases. Moreover, the domains of such antibodies are held together by disulphide bonds that dissociate in the reducing environment of the cytoplasm leading to a substantial loss of binding activity. Therefore, they cannot be used to target intracellular proteins.

Another process that relies on internalisation is the efficient induction of an immune response. In particular, a T-cell response depends heavily on efficient presentation of certain epitopes to the T cells by antigen presenting cells (APCs). In the case of a protein antigen this means that the APC has to take up the protein, internally process it (this is cleaving it) and express certain peptide fragments on its surface in association with MHC (major histocompatibility complex) or HLA molecules. One major and critical event in this process is the efficient uptake of the protein antigen by its APC. Techniques which can enhance antigen uptake by APCs enables an immune response to be elicited against antigens which naturally elicit a weak or no immune response. Therefore, a technique which can boost an immune response against antigenic antigens, naturally weak or non-immunogenic antigens has important implications for vaccination programs.

IgE plays a major role in allergic disease by causing the release of histamine and other inflammatory mediatord from mast cells. A mainstay of treatment of allergic disease, including asthma, is allergen avoidance and treatment of symptoms. Presently, the most effective treatments of allergic diseases are directed towards a regulation of the inflammatory process with corticosteroids. A more direct approach without the negative effects of corticosteroids consists in regulating the allergic process at the level of the initiator of the allergic inflammation, IgE, via an anti-IgE.

The concept of using anti-IgE antibodies as a treatment for allergy has been widely disclosed in the scientific literature. A few representative examples are as follows. Baniyash and Eshhar (European Journal of Immunology 14:799-807 (1984)) demonstrated that an anti-IgE monoclonal antibody could specifically block passive cutaneous anaphylaxis reaction when injected intradermally before challenging with the antigen; U.S. Pat. No. 4,714,759 discloses a product and process for treating allergy, using an antibody specific for IgE; and Rup and Kahn (International Archives Allergy and Applied Immunology, 89:387-393 (1989) discuss the prevention of the development of allergic responses with monoclonal antibodies which block mast cell-IgE sensitization.

Anti-IgE antibodies which block the binding of IgE to its receptor on basophils and which fail to bind to IgE bound to the receptor, thereby avoiding histamine release are disclosed, for example, by Rup and Kahn (supra), by Baniyash et al. (Molecular Immunology 25:705-711, 1988), and by Hook et al. (Federation of American Societies for Experimental Biology, 71st Annual Meeting, Abstract #6008, 1987).

Antagonists of IgE in the form of receptors, anti-IgE antibodies, binding factors, or fragments thereof have been disclosed in the art. For example, U.S. Pat. No. 4,962,035 discloses DNA encoding the alpha-subunit of the mast cell IgE receptor or an IgE binding fragment thereof. Hook et al. (Federation Proceedings Vol. 40, No. 3, Abstract #4177) disclose monoclonal antibodies, of which one type is anti-idiotypic, a second type binds to common IgE determinants, and a third type is directed towards determinants hidden when IgE is on the basophil surface.

U.S. Pat. No. 4,940,782 discloses monoclonal antibodies which react with free IgE and thereby inhibit IgE binding to mast cells, and react with IgE when it is bound to the B-cell FcE receptor, but do not bind with IgE when it is bound to the mast cell FcE receptor, nor block the binding of IgE to the B-cell receptor.

U.S. Pat. No. 4,946,788 discloses a purified IgE binding factor and fragments thereof, and monoclonal antibodies which react with IgE binding factor and lymphocyte cellular receptors for IgE, and derivatives thereof.

U.S. Pat. No. 5,091,313 discloses antigenic epitopes associated with the extracellular segment of the domain which anchors immunoglobulins to the B cell membrane. The epitopes recognized are present on IgE-bearing B cells but not basophils or in the secreted, soluble form of IgE. U.S. Pat. No. 5,252,467 discloses a method for producing antibodies specific for such antigenic epitopes. U.S. Pat. No. 5,231,026 discloses DNA encoding murine-human antibodies specific for such antigenic epitopes.

U.S. Pat. No. 4,714,759 discloses an immunotoxin in the form of an antibody or an antibody fragment coupled to a toxin to treat allergy.

Presta et al. (J. Immunol. 151:2623-2632 (1993)) disclose a humanized anti-IgE antibody that prevents the binding of free IgE to FceRI but does not bind to FceRI-bound IgE. Copending WO93/04173 discloses polypeptides which bind differentially to the high- and low-affinity IgE receptors.

U.S. Pat. No. 5,428,133 discloses anti-IgE antibodies as a therapy for allergy, especially antibodies which bind to IgE on B cells, but not IgE on basophils. This publication mentions the possibility of treating asthma with such antibodies. U.S. Pat. No. 5,422,258 discloses a method for making such antibodies.

EP0841946 discloses methods for treating allergic asthma using IgE antagonists.

TECHNOLOGICAL BACKGROUND

Inhalation is an attractive delivery route to administer pulmonary local-acting agents in respiratory diseases (i.e. asthma, infections). Its use is also being adopted for the delivery of systemic-acting therapeutics whether they are small molecules or macromolecules (A. J. Bitonti and J. A. Dumont. Pulmonary administration of therapeutic proteins using an immunoglobulin transport pathway. Adv. Drug Deliv. Rev. 58:1106-1118 (2006).). As a hallmark of success, the first inhaled insulin powder, Exubera®, has recently been approved in Europe and US for the treatment of adult patients with type 1 or type 2 diabetes (L. Fabbri. Pulmonary safety of inhaled insulins: a review of the current data. Curr. Med. Res. Opin. 22 (Suppl 3) 21-28 (2006).).

For example, the systemic delivery of a conventional antibody, Cetuximab, a chimeric conventional antibody targeting the epidermal growth factor receptor (EGFR), is described in Maillet et al. (Maillet et al. Pharmaceutical Research, Vol. 25, No. 6, June 2008). Cetuximab was nebulized using three types of delivery devices and the immunological and pharmacological properties of cetuximab were evaluated. It was found that the conventional antibody aggregates and although they conclude that the antibody resists to physical constraints of nebulization as it remains biologically active, it is thought that the aggregated IgG will be lost for systemic uptake.

Furthermore, inhaled immunoglobulin single variable domain for local pulmonary delivery has been suggested for therapeutic use in lung diseases (see e.g. WO2007049017). However, the lung as a portal of entry for systemic drug delivery of immunoglobulin single variable domain and in particular Nanobodies and construct thereof has never been described in any details. Most immunoglobulin single variable domains for use as a biotherapeutic are still only developed as an intravenous injection delivery form. The use of these intravenous injection delivery forms is associated often with low patient compliance and high costs (application of injection often only by medical staff) in clinical practice. To improve compliance and a cost effect application, the development of non-invasive, easy to use delivery strategies such as pulmonary absorption of pharmaceuticals in particular biopharmaceuticals, e.g. such as immunoglobulin single variable domain, is clearly a medical need.

AIMS OF THE INVENTION

The aim of the invention is to provide a method of administering protein therapeutic molecules orally, sublingually, topically, nasally, vaginally, rectally, intravenously, subcutaneously or by inhalation which overcomes the problems of the prior art. It is a further aim to provide said therapeutic molecules.

Another aim of the invention is to provide a method for delivering therapeutic substances to the interior of cells via internalizing receptors without receptor activation.

It is further aim of the invention to provide a therapeutic agent for the treatment of allergies.

It is a further aim of the invention to provide therapeutic nanobodies.

SUMMARY OF THE INVENTION

One embodiment of the present invention is a polypeptide construct comprising at least one single domain antibody directed against IgE.

Another embodiment of the present invention is a polypeptide construct as described above wherein at least one single domain antibody is a Camelidae VHH.

Another embodiment of the present invention is a polypeptide construct as described above wherein at least one single domain antibody corresponds to a sequence represented by any of SEQ ID NOs: 1 to 11.

Another embodiment of the present invention is a polypeptide construct as described above, wherein the number of anti-IgE single domain antibodies is at least two.

Another embodiment of the present invention is a polypeptide construct as described above, wherein at least one single domain antibody is a humanized Camelidae VHH.

Another embodiment of the present invention is a polypeptide construct as described above, wherein a single domain antibody is an homologous sequence, a functional portion, or a functional portion of an homologous sequence of the full length single domain antibody.

Another embodiment of the present invention is a polypeptide construct as described above, wherein the polypeptide construct is an homologous sequence, a functional portion, or a functional portion of an homologous sequence of the full length polypeptide construct.

Another embodiment of the present invention is a nucleic acid encoding a polypeptide construct as described above.

Another embodiment of the present invention is a polypeptide construct as described above for treating and/or preventing and/or alleviating disorders relating to inflammatory processes.

Another embodiment of the present invention is a use of a polypeptide construct as described above for the preparation of a medicament for treating and/or preventing and/or alleviating disorders relating to inflammatory reactions.

Another embodiment of the present invention is a method for delivering an anti-target compound to a subject for the treatment of a disorder without being inactivated by administering thereto a polypeptide construct comprising one or more single domain antibodies directed against said target.

Another embodiment of the present invention is a method as described above wherein said target is located in the gut system, and said a polypeptide construct is delivered orally.

Another embodiment of the present invention is a method as described above wherein said target is located in vaginal and/or rectal tract, and said a polypeptide construct is delivered to the vaginal and/or rectal tract.

Another embodiment of the present invention is a method as described above wherein said target is located in nose, upper respiratory tract and/or lung, and said a polypeptide construct is delivered to nose, upper respiratory tract and/or lung.

Another embodiment of the present invention is a method as described above wherein said target is located in intestinal mucosa, and said a polypeptide construct is delivered orally.

Another embodiment of the present invention is a method as described above wherein said target is located in the tissues beneath the tongue, and said a polypeptide construct is delivered to the tissues beneath the tongue.

Another embodiment of the present invention is a method as described above wherein said target is located in the skin, and said a polypeptide construct is delivered topically.

Another embodiment of the present invention is a method as described above wherein said target is in, or accessible via the blood, and said a polypeptide construct is delivered orally, to the vaginal and/or rectal tract, nasally, by inhalation though the mouth or nose, to the tissues beneath the tongue, or topically.

Another embodiment of the present invention is a polypeptide construct comprising at least one single domain antibody directed against a target, for use in treating, preventing and/or alleviating the symptoms of disorders which are susceptible to modulation by an anti-target therapeutic compound that is able pass through the gastric environment without being inactivated.

Another embodiment of the present invention is a polypeptide construct comprising at least one single domain antibody directed against a target for use in treating, preventing and/or alleviating the symptoms of disorders which are susceptible to modulation by an anti-target therapeutic compound that is able pass through the wall of the intestinal mucosa without being inactivated Another embodiment of the present invention is a polypeptide construct comprising at least one single domain antibody directed against a target for use in treating, preventing and/or alleviating the symptoms of disorders which are susceptible to modulation by an anti-target therapeutic compound that is able pass through the wall of the nose, upper respiratory tract and/or lung without being inactivated Another embodiment of the present invention is a polypeptide construct comprising at least one single domain antibody directed against a target for use in treating, preventing and/or alleviating the symptoms of disorders which are susceptible to modulation by an anti-target therapeutic compound that is able pass through the wall of virginal and/or rectal tract without being inactivated Another embodiment of the present invention is a polypeptide construct comprising at least one single domain antibody directed against a target for use in treating, preventing and/or alleviating the symptoms of disorders which are susceptible to modulation by a therapeutic compound that is able pass through the tissues beneath the tongue without being inactivated Another embodiment of the present invention is a polypeptide construct comprising at least one single domain antibody directed against a target for use in treating, preventing and/or alleviating the symptoms of disorders which are susceptible to modulation by a therapeutic compound that is able pass through the skin without being inactivated Another embodiment of the present invention is a method as described above or polypeptide construct as described above, wherein said target is TNF-alpha and the disorder is inflammation.

Another embodiment of the present invention is a method or polypeptide as described above, wherein a single domain antibody corresponds to a sequence represented by any of SEQ ID NOs: 12 to 14.

Another embodiment of the present invention is a method as described above or polypeptide construct as described above, wherein said target is CEA and the disorder colon cancer.

Another embodiment of the present invention is a method as described above or polypeptide construct as described above, wherein said target is EGFR and the disorder is any of head, neck, lung and colon cancer.

Another embodiment of the present invention is a method or polypeptide construct as described above, wherein a single domain antibody corresponds to a sequence represented by any of SEQ ID NOs: 23 to 44

Another embodiment of the present invention is a method as described above or polypeptide construct as described above, wherein said target is antigen of *Helicobacter pylori* and the disorder is any of indigestion, gastritis.

Another embodiment of the present invention is a method as described above or polypeptide construct as described above, wherein said target is antigen of *Mycobacterium tuberculosis* and the disorder is tuberculosis.

Another embodiment of the present invention is a method as described above or polypeptide construct as described above, wherein said target is antigen of influenza virus and the disorder is flu.

Another embodiment of the present invention is a method as described above or polypeptide construct as described above, wherein said target is antigen of IgE and the disorder is allergic response.

Another embodiment of the present invention is a method or polypeptide construct as described above, wherein a single domain antibody corresponds to a sequence represented by any of SEQ ID NOs: 1 to 11

Another embodiment of the present invention is a method as described above or polypeptide construct as described above, wherein said target is antigen of MMP and the disorder is cancer.

Another embodiment of the present invention is a method or polypeptide construct as described above, wherein a single domain antibody corresponds to a sequence represented by any of SEQ ID NOs: 15 to 22

Another embodiment of the present invention is a method as described above or polypeptide construct as described above, wherein said target is antigen of IFN-gamma and the disorder is any of cancer, transplant rejection, auto immune disorder.

Another embodiment of the present invention is a method or polypeptide construct as described above, wherein a single domain antibody corresponds to a sequence represented by any of SEQ ID NOs: 45 to 70

Another embodiment of the present invention is a method as described above or polypeptide construct as described above wherein said target is any of antigen of *Helicobacter pylori*, antigen of *Mycobacterium tuberculosis*, antigen of influenza virus.

Another embodiment of the present invention is a polypeptide construct comprising at least one single domain antibody directed against an internalising cellular receptor, and at least one single domain antibody directed against a therapeutic target.

Another embodiment of the present invention is a polypeptide construct comprising at least one single domain antibody directed against an internalising cellular receptor, and at least one therapeutic polypeptide or agent.

Another embodiment of the present invention is a polypeptide construct as described above wherein said internalising cellular receptor is Epidermal Growth Factor receptor.

Another embodiment of the present invention is a polypeptide as described above wherein a single domain antibody directed against an internalising cellular receptor corresponds to a sequence represented by SEQ ID NO: 23 to 44.

Another embodiment of the present invention is a polypeptide construct as described above wherein said internalising cellular receptor is any of LDL receptor, FGF2r, ErbB2r, transferring receptor, PDGr, VEGr, or PsmAr.

Another embodiment of the present invention is a polypeptide construct as described above wherein a single domain antibody directed against a therapeutic target, is directed against PDK1.

Another embodiment of the present invention is a polypeptide construct as described above use in treating cancer Another embodiment of the present invention is a polypeptide construct as described above wherein a single domain antibody directed against a therapeutic target is directed against any of GSK1, Bad, caspase and Forkhead.

Another embodiment of the present invention is a polypeptide construct as described above use in treating cancer.

Another embodiment of the present invention is a method for delivering an anti-target therapeutic compound to the interior of a cell comprising administering to a subject a polypeptide construct as described above.

Another embodiment of the present invention is a method for delivering an anti-target therapeutic compound to the interior of a cell without being inactivated comprising administering to a subject a polypeptide construct as described above.

Another embodiment of the present invention is a method as described above wherein said cell is located in the gut system, and said a polypeptide construct is delivered orally.

Another embodiment of the present invention is a method as described above wherein said cell is located in vaginal and/or rectal tract, and said a polypeptide construct is delivered to the vaginal and/or rectal tract.

Another embodiment of the present invention is a method as described above wherein said cell is located in nose, upper respiratory tract and/or lung, and said a polypeptide construct is delivered to nose, upper respiratory tract and/or lung.

Another embodiment of the present invention is a method as described above wherein said cell is located in intestinal mucosa, and said a polypeptide construct is delivered orally.

Another embodiment of the present invention is a method as described above wherein said cell is located in the tissues beneath the tongue, and said a polypeptide construct is delivered to the tissues beneath the tongue.

Another embodiment of the present invention is a method as described above wherein said cell is located in the skin, and said a polypeptide construct is delivered topically.

Another embodiment of the present invention is a method as described above wherein said cell is in, or accessible via the blood, and said a polypeptide construct is delivered orally, to the vaginal and/or rectal tract, nasally, by inhalation though the mouth or nose, to the tissues beneath the tongue, or topically.

Another embodiment of the present invention is a polypeptide construct as described above, or a method as described above, wherein the single domain antibodies are humanized Camelidae VHHs.

Another embodiment of the present invention is a polypeptide construct as described above, or a method as described above, wherein said single domain antibody is an homologous sequence, a functional portion, or a functional portion of an homologous sequence of the full length single domain antibody.

Another embodiment of the present invention is a polypeptide construct as described above or a method as described above, wherein the polypeptide construct is an homologous sequence, a functional portion, or a functional portion of an homologous sequence of the full length polypeptide construct.

Another embodiment of the present invention is a polypeptide construct as described above or a method as described above wherein said single domain antibodies are Camelidae VHHs.

Another embodiment of the present invention is a nucleic acid capable of encoding a polypeptide construct as described above.

Another embodiment of the present invention is a composition comprising a polypeptide construct as defined above, together with a pharmaceutical carrier.

The systemic exposure of immunoglobulin single variable domains such as a Nanobody and/or constructs thereof is often short as they are cleared from the systemic circulation rapidly. For example the in vivo half-life of a monovalent Nanobody is about 45 minutes in mouse (Expert Opinion on Biological Therapy, Volume 5, Number 1, 1 Jan. 2005, pp. 111-124(14). EP 1'517'921 proposes a strategy to prolong systemic exposure by making a construct that comprises an immunoglobulin variable domain against an antigen and an immunoglobulin variable domain against a serum protein with increased half-life. However, there is a clear need for alternative and/or improved strategies to prolong the half-life of immunoglobulin single variable domains.

The generation of immunoglobulin variable domains, such as Nanobodies, has been described extensively in various publications, among which WO 94/04678, Hamers-Casterman et al. Nature. 1993 Jun. 3; 363(6428):446-8 and S. Muyldermans (J Biotechnol. 2001 June; 74(4):277-302 Review) can be exemplified. In these methods, camelids such as lamas are immunized with the target antigen in order to induce an immune response against said target antigen. The repertoire of Nanobodies obtained from said immunization is further screened for Nanobodies that bind the target antigen.

Currently, the art provides no method to systemically deliver immunoglobulin single variable domains and/or constructs thereof (e.g. such as Nanobodies and/or constructs thereof) via pulmonary tissue absorption in an effective amount. WO2007049017 describes an immunoglobulin single variable domain that was administered to the lungs but not delivered systemically in substantial amounts.

It is the objective of the present invention to overcome these shortcomings of the art. In particular it is an objective of the present invention to provide a method for delivering immunoglobulin single variable domains and/or constructs thereof to a mammal, e.g. a human. Furthermore, the methods described herein provide a sustained delivery of said immunoglobulin single variable domains.

The herein mentioned problems are overcome by the present invention. It has been found that administration of immunoglobulin single variable domains and/or constructs thereof can result in a sustained release of said immunoglobulin single variable domains and/or constructs thereof to the systemic circulation in an effective amount i.e. an amount that can have a prophylactic and/or therapeutic effect.

The present invention relates to the following.

A method for providing to the systemic circulation of a mammal an effective amount of an immunoglobulin single variable domain and/or construct thereof that can bind to and/or have affinity for at least one antigen; wherein the method comprises the step of:
  a) administering the immunoglobulin single variable domain and/or construct thereof to the pulmonary tissue of said mammal.

In a preferred method, the administration in said above mentioned method is performed by inhaling said immunoglobulin single variable domain and/or construct thereof in an aerosol cloud.

In one embodiment of the invention, the immunoglobulin single variable domain is a light chain variable domain sequence (e.g. a $V_L$-sequence), or heavy chain variable domain sequence (e.g. a $V_H$-sequence); more specifically, the immunoglobulin single variable domain can be a heavy chain variable domain sequence that is derived from a conventional four-chain antibody or heavy chain variable domain sequence that is derived from a heavy chain antibody.

According to the invention, the immunoglobulin single variable domain can be a domain antibody, or an amino acid sequence that is suitable for use as a domain antibody, a single domain antibody, or an amino acid sequence that is suitable for use as single domain antibody, a "dAb", or an amino acid sequence that is suitable for use as a dAb, or a Nanobody, including but not limited to a $V_{HH}$ sequence, and preferably is a Nanobody.

According to the invention, the construct comprising at least one immunoglobulin single variable domain can be a construct or polypeptide designed from the above mentioned sequences.

In a preferred method the immunoglobulin single variable domain and/or construct thereof of above mentioned method is a Nanobody and/or a construct thereof. In a further similar preferred method, i.e. when using a Nanobody and/or a construct thereof, the method includes effective local pulmonary delivery of said Nanobody and/or a construct thereof.

According to the invention, inhaling of the aerosol cloud can be performed by an inhaler device. The device should generate from a formulation comprising the immunoglobulin single variable domain and/or construct thereof an aerosol cloud of the desired particle size (distribution) at the appropriate moment of the mammal's inhalation cycle, containing the right dose of the immunoglobulin single variable domain and/or construct thereof ("Pulmonary Drug Delivery", Edited by Karoline Bechtold-Peters, Henrik Luessen, 2007, ISBN 978-3-87193-322-6, page 125).

The invention also relates to uses, formulations and devices suitable in the performance of the methods of the invention.

BRIEF DESCRIPTION OF FIGURES

FIG. 9: Amino acid alignment of 31 clones identified by the epitope specific elution selection procedure

FIG. 24: Competition of periplasmic fractions of the invention with fetuin for binding to the hemagglutinin.

FIG. 25: Competition of purified nanobodies with fetuin for binding to the hemagglutinin

(FIG. 34A) Nanobody construct 4.10-Alb1 in circulation after i.p. and i.t. administration; (FIG. 34B) leptin levels before and after i.t. Nanobody construct 4.10-Alb1 administration; (FIG. 34C) leptin levels before and after i.p. Nanobody construct 4.10-Alb1 administration (FIG. 35A) Nanobody constructs 4.10-Alb1 and IL6R202 were detected in blood following each i.t. or i.p. inoculation; (FIG. 35B) Leptin levels after injection of 4.10-Alb1 and IL6R202 control; (FIG. 35C) Leptin levels after i.t. administration of 4.10-Alb1 and IL6R202 control.

FIGS. 36A-36G: Increase in body weight following i.t. administration of 4 increasing amounts of 4.10 Nanobodies. (FIG. 36A) increase in body weight with 4.10-Alb1 (also referred to as "4.10") via i.p. injections; (FIG. 36B) no increase in body weight with IL6R202 via i.p. injection; (FIG. 36C) increase in body weight with 4.10-Alb1 (also referred to as "4.10") via i.t. administration; (FIG. 36D) no increase in body weight with IL6R202 via i.t. administration; (FIG. 36E) mixed model is a good model for the bodyweight levels; (FIG. 36F) & (FIG. 36G) bodyweight model with corresponding confidence bands (4.10-HLE intratrach=4.10-Alb1 i.t. administration; contr intratrach=IL6R202 i.t. administration; 4.10-HLE ip=4.10-Alb1 i.p. injection; contr. Ip=IL6R202 i.p. injection).

DETAILED DESCRIPTION OF THE INVENTION

Figure 1:
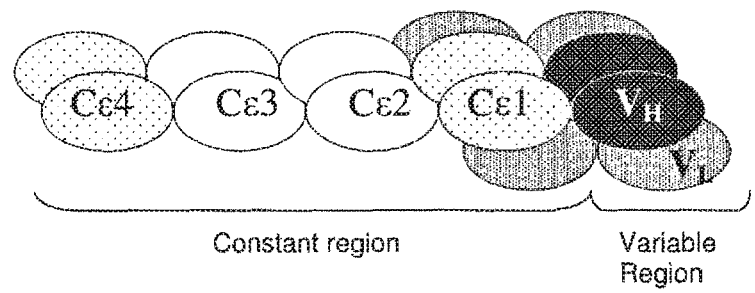
FIG. 1: Schematic illustrating the regions of IgE

The present invention relates to a polypeptide construct comprising one or more single domain antibodies directed to one or more target molecule(s), each in a suitable dosage form either directly or as part of a composition containing an ingredient which facilitates delivery.

The invention further relates to polypeptide constructs comprising one or more single domain antibodies, for administration to a subject by non-invasive methods, such as orally, sublingually, topically, nasally, vaginally, rectally or by inhalation. Such non-invasive routes of delivery unexpectedly provide an effective means to conveniently deliver therapeutic compounds The present invention also relates to constructs comprising one or more single domain antibodies, for administration to a subject by normal invasive methods such as intravenously and subcutaneously.

The invention further relates to a method for delivering therapeutic peptides comprises the steps of administering a polypeptide construct comprising one or more single domain antibodies orally, sublingually, topically, intravenously, subcutaneously, nasally, vaginally, rectally or by inhalation to a subject.

The invention further relates to polypeptide constructs comprising anti-IgE single domain antibodies.

Single domain antibodies are antibodies whose complementary determining regions are part of a single domain polypeptide. Examples include, but are not limited to, heavy chain antibodies, antibodies naturally devoid of light chains, single domain antibodies derived from conventional 4-chain antibodies, engineered antibodies and single domain scaffolds other than those derived from antibodies. Single domain antibodies may be any of the art, or any future single domain antibodies. Single domain antibodies may be derived from any species including, but not limited to mouse, human, camel, llama, goat, rabbit, bovine. According to one aspect of the invention, a single domain antibody as used herein is a naturally occurring single domain antibody known as heavy chain antibody devoid of light chains. Such single domain antibodies are disclosed in WO 9404678 for example. For clarity reasons, this variable domain derived from a heavy chain antibody naturally devoid of light chain is known herein as a VHH or nanobody to distinguish it from the conventional VH of four chain immunoglobulins. Such a VHH molecule can be derived from antibodies raised in Camelidae species, for example in camel, llama, dromedary, alpaca and guanaco. Other species besides Camelidae may produce heavy chain antibodies naturally devoid of light chain; such VHHs are within the scope of the invention.

VHHs, according to the present invention, and as known to the skilled addressee are heavy chain variable domains derived from immunoglobulins naturally devoid of light chains such as those derived from Camelidae as described in WO 94/04678 (and referred to hereinafter as VHH domains or nanobodies). VHH molecules are about 10× smaller than IgG molecules. They are single polypeptides and very stable, resisting extreme pH and temperature conditions. Moreover, they are resistant to the action of proteases which is not the case for conventional antibodies. Furthermore, in vitro expression of VHHs produces high yield, properly folded functional VHHs. In addition, antibodies generated in Camelids will recognize epitopes other than those recognised by antibodies generated in vitro through the use of antibody libraries or via immunisation of mammals other than Camelids (WO 9749805). As such, anti-albumin VHH's may interact in a more efficient way with serum albumin which is known to be a carrier protein. As a carrier protein some of the epitopes of serum albumin may be inaccessible by bound proteins, peptides and small chemical compounds. Since VHH's are known to bind into 'unusual' or non-conventional epitopes such as cavities (WO 97/49805), the affinity of such VHH's to circulating albumin may be increased.

The present invention further relates to a polypeptide construct, wherein a single domain antibody is a VHH directed against a target, wherein the VHH belongs to a class having human-like sequences. The class is characterised in that the VHHs carry an amino acid from the group consisting of glycine, alanine, valine, leucine, isoleucine, proline, phenylalanine, tyrosine, tryptophan, methionine, serine, threonine, asparagine, or glutamine at position 45, such as, for example, L45 according to the Kabat numbering. A VHH sequence represented by SEQ ID NO: 15 which binds to MMP-12, belongs to this human-like class of VHH polypeptides. As such, peptides belonging to this class show a high amino acid sequence homology to human VH framework regions and said peptides might be administered to a human directly without expectation of an unwanted immune response therefrom, and without the burden of further humanisation.

Another human-like class of Camelidae single domain antibodies represented by sequences 68 which binds to IFN gamma, have been described in WO03035694 and contain the hydrophobic FR2 residues typically found in conventional antibodies of human origin or from other species, but compensating this loss in hydrophilicity by the charged arginine residue on position 103 that substitutes the conserved tryptophan residue present in VH from conventional antibodies. As such, peptides belonging to these two classes show a high amino acid sequence homology to human VH framework regions and said peptides might be administered to a human directly without expectation of an unwanted immune response therefrom, and without the burden of further humanisation.

Any of the VHHs as used by the invention may be of the traditional class or of the classes of human-like Camelidae antibodies. Said antibodies may be directed against whole target or a fragment thereof, or a fragment of a homologous sequence thereof. These polypeptides include the full length Camelidae antibodies, namely Fc and VHH domains, chimeric versions of heavy chain Camelidae antibodies with a human Fc domain.

Targets of the invention are any which are of pharmaceutical interest. Examples are provided here of several targets, and are not intended to limit the invention thereto. Examples of targets include, TNF-alpha, IgE, IFN-gamma, MMP-12, EGFR, CEA, *H. pylori*, TB, influenza. A single domain antibody directed against a target means a single domain antibody that is capable of binding to said target with an affinity of better than $10^{-6}$ M.

Targets may also be fragments of said targets. Thus a target is also a fragment of said target, capable of eliciting an immune response. A target is also a fragment of said target, capable of binding to a single domain antibody raised against the full length target.

A fragment as used herein refers to less than 100% of the sequence (e.g., 99%, 90%, 80%, 70%, 60%, 50%, 40%, 30%, 20%, 10% etc.), but comprising 5, 6, 7, 8, 9, 10, 12, 13, 14, 15, 16, 17, 18, 19, 20, 21, 22, 23, 24, 25 or more amino acids. A fragment is of sufficient length such that the interaction of interest is maintained with affinity of $1 \times 10^{-6}$ M or better.

A fragment as used herein also refers to optional insertions, deletions and substitutions of one or more amino acids which do not substantially alter the ability of the target to bind to a single domain antibody raised against the wild-type target. The number of amino acid insertions deletions or substitutions is preferably up to 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69 or 70 amino acids.

One embodiment of the present invention is a polypeptide construct as disclosed herein, wherein the number of single domain antibodies directed to a target is two or more. Such multivalent polypeptide constructs have the advantage of unusually high functional affinity for the target, displaying much higher than expected inhibitory properties compared to their monovalent counterparts.

Multivalent polypeptide constructs have functional affinities that are several orders of magnitude higher than polypeptide constructs which are monovalent. The inventors have found that the functional affinities of these multivalent polypeptides are much higher than those reported in the prior art for bivalent and multivalent antibodies. Surprisingly, the multivalent polypeptide constructs of the present invention linked to each other directly or via a short linker sequence show the high functional affinities expected theoretically with multivalent conventional four-chain antibodies.

The inventors have found that such large increased functional activities can be detected preferably with antigens composed of multidomain and multimeric proteins, either in straight binding assays or in functional assays, e.g. animal model of chronic colitis.

A multivalent anti-target polypeptide as used herein refers to a polypeptide comprising two or more anti-target polypeptides which have been covalently linked. The anti-target polypeptides may be identical in sequence or may be different in sequence, but are directed against the same target or antigen. Depending on the number of anti-target polypeptides linked, a multivalent anti-target polypeptide may be bivalent (2 anti-target polypeptides), trivalent (3 anti-target polypeptides), tetravalent (4 anti-target polypeptides) or have a higher valency molecules.

An example of a multivalent polypeptide construct of the invention, comprising more than one anti-TNF-alpha VHHs is described in Example 7.

The single domain antibodies may be joined to form any of the polypeptide constructs disclosed herein comprising more than one single domain antibody using methods known in the art or any future method. They may be joined non-covalently (e.g. using streptavidin/biotin combination, antibody/tag combination) or covalently. They may be fused by chemical cross-linking by reacting amino acid residues with an organic derivatising agent such as described by Blattler et al, Biochemistry 24, 1517-1524; EP294703. Alternatively, the single domain antibody may be fused genetically at the DNA level i.e. a polynucleotide construct formed which encodes the complete polypeptide construct comprising one or more anti-target single domain antibodies. A method for producing bivalent or multivalent VHH polypeptide constructs is disclosed in PCT patent application WO 96/34103. One way of joining VHH antibodies is via the genetic route by linking a VHH antibody coding sequences either directly or via a peptide linker. For example, the C-terminal end of the VHH antibody may be linked to the N-terminal end of the next single domain antibody.

This linking mode can be extended in order to link additional single domain antibodies for the construction and production of tri-, tetra-, etc. functional constructs.

According to one aspect of the present invention, the single domain antibodies are linked to each other via a peptide linker sequence. Such linker sequence may be a naturally occurring sequence or a non-naturally occurring sequence. The linker sequence is expected to be non-immunogenic in the subject to which the multivalent anti-target polypeptide is administered. The linker sequence may provide sufficient flexibility to the multivalent anti-target polypeptide, at the same time being resistant to proteolytic degradation. A non-limiting example of a linker sequences is one that can be derived from the hinge region of VHHs described in WO 96/34103.

The polypeptide constructs disclosed herein may be made by the skilled artisan according to methods known in the art or any future method. For example, VHHs may be obtained using methods known in the art such as by immunising a camel and obtaining hybridomas therefrom, or by cloning a library of single domain antibodies using molecular biology techniques known in the art and subsequent selection by using phage display.

According to an aspect of the invention a polypeptide construct may be a homologous sequence of a full-length polypeptide construct. According to another aspect of the invention, a polypeptide construct may be a functional portion of a full-length polypeptide construct. According to another aspect of the invention, a polypeptide construct may be a homologous sequence of a full length polypeptide construct. According to another aspect of the invention, a polypeptide construct may be a functional portion of a homologous sequence of a full length polypeptide construct. According to an aspect of the invention a polypeptide construct may comprise a sequence of a polypeptide construct.

According to an aspect of the invention a single domain antibody used to form a polypeptide construct may be a complete single domain antibody (e.g. a VHH) or a homologous sequence thereof. According to another aspect of the invention, a single domain antibody used to form the polypeptide construct may be a functional portion of a complete single domain antibody. According to another aspect of the invention, a single domain antibody used to form the polypeptide construct may be a homologous sequence of a complete single domain antibody. According to another aspect of the invention, a single domain antibody used to form the polypeptide construct may be a functional portion of a homologous sequence of a complete single domain antibody.

As used herein, a homologous sequence of the present invention may comprise additions, deletions or substitutions of one or more amino acids, which do not substantially alter the functional characteristics of the polypeptides of the invention. The number of amino acid deletions or substitutions is preferably up to 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69 or 70 amino acids.

A homologous sequence according to the present invention may be a sequence of an anti-target polypeptide modified by the addition, deletion or substitution of amino acids, said modification not substantially altering the functional characteristics compared with the unmodified polypeptide.

A homologous sequence of the present invention may be a polypeptide which has been humanised. The humanisation of antibodies of the new class of VHHs would further reduce the possibility of unwanted immunological reaction in a human individual upon administration.

A homologous sequence according to the present invention may be a sequence which exists in other Camelidae species such as, for example, camel, llama, dromedary, alpaca, guanaco etc.

Where homologous sequence indicates sequence identity, it means a sequence which presents a high sequence identity (more than 70%, 75%, 80%, 85%, 90%, 95% or 98% sequence identity) with the parent sequence and is preferably characterised by similar properties of the parent sequence, namely affinity, said identity calculated using known methods.

Alternatively, a homologous sequence may also be any amino acid sequence resulting from allowed substitutions at any number of positions of the parent sequence according to the formula below:
Ser substituted by Ser, Thr, Gly, and Asn;
Arg substituted by one of Arg, His, Gln, Lys, and Glu;
Leu substituted by one of Leu, Ile, Phe, Tyr, Met, and Val;
Pro substituted by one of Pro, Gly, Ala, and Thr;
Thr substituted by one of Thr, Pro, Ser, Ala, Gly, His, and Gln;
Ala substituted by one of Ala, Gly, Thr, and Pro;
Val substituted by one of Val, Met, Tyr, Phe, Ile, and Leu;
Gly substituted by one of Gly, Ala, Thr, Pro, and Ser;
Ile substituted by one of Ile, Met, Tyr, Phe, Val, and Leu;
Phe substituted by one of Phe, Trp, Met, Tyr, Ile, Val, and Leu;
Tyr substituted by one of Tyr, Trp, Met, Phe, Ile, Val, and Leu;
His substituted by one of His, Glu, Lys, Gln, Thr, and Arg;
Gln substituted by one of Gln, Glu, Lys, Asn, His, Thr, and Arg;
Asn substituted by one of Asn, Glu, Asp, Gln, and Ser;
Lys substituted by one of Lys, Glu, Gln, His, and Arg;
Asp substituted by one of Asp, Glu, and Asn;
Glu substituted by one of Glu, Asp, Lys, Asn, Gln, His, and Arg;
Met substituted by one of Met, Phe, Ile, Val, Leu, and Tyr.

A homologous nucleotide sequence according to the present invention may refer to nucleotide sequences of more than 50, 100, 200, 300, 400, 500, 600, 800 or 1000 nucleotides able to hybridize to the reverse-complement of the nucleotide sequence capable of encoding the patent sequence, under stringent hybridisation conditions (such as the ones described by Sambrook et al., Molecular Cloning, Laboratory Manuel, Cold Spring, Harbor Laboratory press, New York).

As used herein, a functional portion refers to a sequence of a single domain antibody that is of sufficient size such that the interaction of interest is maintained with affinity of $1 \times 10^{-6}$ M or better.

Alternatively, a functional portion comprises a partial deletion of the complete amino acid sequence and still maintains the binding site(s) and protein domain(s) necessary for the binding of and interaction with its target.

As used herein, a functional portion refers to less than 100% of the complete sequence (e.g., 99%, 90%, 80%, 70%, 60%, 50%, 40%, 30%, 20%, 10%, 5%, 1% etc.), but comprising 5 or more amino acids or 15 or more nucleotides.

Anti-IgE Single Domain Antibodies

One aspect of the present invention relates to therapeutic compounds which are suitable for alleviating the symptoms, for the treatment and prevention of allergies. Said therapeutic compounds interact with IgE, and modulate the cascade of immunological responses that is responsible for an allergic response.

Another aspect of the present invention relates to the use of anti-IgE single domain antibodies (e.g. VHHs) in the preparation of topical ophthalmic compositions for the treatment of an ocular allergic disorder (Example 2). Given the ease of production and the low cost using bacterial or yeast expression systems for VHHs, for example, compared to production of conventional antibodies in mammalian cells, the economics of preparing such compositions using VHHs of the invention are much more favourable then for conventional antibodies.

Ocular penetration and consequently ocular efficacy is highly unexpected with conventional antibodies and derived fragments given their large size. The polypeptide constructs of the invention however are expected to be highly efficient given their high potency, stability combined with a low molecular weight. Therefore, applications for such indications other than topical can be envisaged with polypeptide constructs of the invention.

One embodiment of the present invention is a polypeptide construct comprising one or more single domain antibodies directed against IgE.

Another embodiment of the present invention is a polypeptide construct comprising one or more single domain antibodies directed against IgE, wherein a single domain antibody corresponds to a sequence represented by any of SEQ ID NOs: 1 to 11. Said sequences are derived from Camelidae VHHs.

The present invention also relates to the finding that a polypeptide construct comprising one or more single domain antibodies directed against IgE and further comprising one or more single domain antibodies directed against one or more serum proteins of a subject, surprisingly has significantly prolonged half-life in the circulation of said subject compared with the half-life of the anti-IgE single domain antibody when not part of said construct. Furthermore, such polypeptide constructs were found to exhibit the same favourable properties of VHHs such as high stability remaining intact in mice, extreme pH resistance, high temperature stability and high target affinity.

Another embodiment of the present invention is a polypeptide construct comprising one or more single domain antibodies directed against IgE further comprising one or more single domain antibodies directed against one or more serum proteins.

The serum protein may be any suitable protein found in the serum of subject, or fragment thereof. In one aspect of the invention, the serum protein is serum albumin, serum immunoglobulins, thyroxine-binding protein, transferrin, or fibrinogen. Depending on the intended use such as the required half-life for effective treatment and/or compartmentalisation of the target antigen, the VHH-partner can be directed to one of the above serum proteins.

One aspect of the invention, is a polypeptide construct comprising one or more single domain antibodies directed against IgE, further comprising an anti-serum albumin single domain antibody corresponding to a sequence represented by any of SEQ ID NO: 71 to 84.

Delivery of Polypeptide Constructs

The aspect of the invention relating to the delivery of polypeptide constructs of the invention is not limited to a polypeptide construct comprising anti-IgE single domain antibodies disclosed herein, but, as shown below, is applicable to any target. The polypeptide constructs may comprise single domain antibodies directed against more than one target, optionally with the variations described above.

One embodiment of the present invention is a polypeptide construct comprising at least one single domain antibody directed against a target for use in treating, preventing and/or alleviating the symptoms of disorders susceptible to modulation by an anti-target therapeutic compound that is able pass through the gastric environment without being inactivated.

As known by persons skilled in the art, once in possession of said polypeptide construct, formulation technology may be applied to release a maximum amount of VHHs in the right location (in the stomach, in the colon, etc.). This method of delivery is important for treating, prevent and/or alleviate the symptoms of disorder whose targets that are located in the gut system.

An aspect of the invention is a method for treating, preventing and/or alleviating the symptoms of a disorder susceptible to modulation by a therapeutic compound that is able pass through the gastric environment without being inactivated, by orally administering to a subject a polypeptide construct comprising one or more single domain antibodies specific for antigen related to the disorder.

Another embodiment of the present invention is a use of a polypeptide construct as disclosed herein for the preparation of a medicament for treating, preventing and/or alleviating the symptoms of disorders susceptible to modulation by an anti-target therapeutic compound that is able pass through the gastric environment without being inactivated.

An aspect of the invention is a method for delivering an anti-target therapeutic compound to the gut system without being inactivated, by orally administering to a subject a polypeptide construct comprising one or more single domain antibodies directed against said target.

An aspect of the invention is a method for delivering an anti-target therapeutic compound to the bloodstream of a subject without being inactivated, by orally administering to a subject a polypeptide construct comprising one or more single domain antibodies directed against said target.

Another embodiment of the present invention is a polypeptide construct comprising at least one single domain antibody directed against a target herein for use in treating, preventing and/or alleviating the symptoms of disorders susceptible to modulation by an anti-target therapeutic compound to the vaginal and/or rectal tract.

In a non-limiting example, a formulation according to the invention comprises a polypeptide construct as disclosed herein comprising one or more VHHs directed against one or more targets in the form of a gel, cream, suppository, film, or in the form of a sponge or as a vaginal ring that slowly releases the active ingredient over time (such formulations are described in EP 707473, EP 684814, U.S. Pat. No. 5,629,001).

An aspect of the invention is a method for treating, preventing and/or alleviating the symptoms of disorders susceptible to modulation by a therapeutic compound to the vaginal and/or rectal tract, by vaginally and/or rectally administering to a subject a polypeptide construct comprising one or more single domain antibodies specific for antigen related to the disorder.

Another embodiment of the present invention is a use of a polypeptide construct as disclosed herein for the preparation of a medicament for treating, preventing and/or alleviating the symptoms of disorders susceptible to modulation by an anti-target therapeutic compound to the vaginal and/or rectal tract without being inactivated.

An aspect of the invention is a method for delivering an anti-target therapeutic compound to the vaginal and/or rectal tract without being inactivated, by administering to the vaginal and/or rectal tract of a subject a polypeptide construct comprising one or more single domain antibodies directed against said target.

An aspect of the invention is a method for delivering an anti-target therapeutic compound to the bloodstream of a subject without being inactivated, by administering to the vaginal and/or rectal tract of a subject a polypeptide construct comprising one or more single domain antibodies directed against said target.

Another embodiment of the present invention is a polypeptide construct comprising at least one single domain antibody directed against a target comprising at least one single domain antibody directed against a target, for use in treating, preventing and/or alleviating the symptoms of disorders susceptible to modulation by an anti-target therapeutic compound to the nose, upper respiratory tract and/or lung.

In a non-limiting example, a formulation according to the invention, comprises a polypeptide construct as disclosed herein directed against one or more targets in the form of a nasal spray (e.g. an aerosol) or inhaler. Since the construct is small, it can reach its target much more effectively than therapeutic IgG molecules.

An aspect of the invention is a method for treating, preventing and/or alleviating the symptoms of disorders susceptible to modulation by a therapeutic compound to the upper respiratory tract and lung, by administering to a subject a polypeptide construct as disclosed herein wherein one or more single domain antibodies are specific for an antigen related to the disorder, by inhalation through the mouth or nose.

Another aspect of the invention is a dispersible VHH composition, in particular dry powder dispersible VHH compositions, such as those described in U.S. Pat. No. 6,514,496. These dry powder compositions comprise a plurality of discrete dry particles with an average particle size in the range of 0.4-10 μm. Such powders are capable of being readily dispersed in an inhalation device. VHH's are particularly suited for such composition as lyophilized material can be readily dissolved (in the lung subsequent to being inhaled) due to its high solubilisation capacity (Muyldermans, S., Reviews in Molecular Biotechnology, 74, 277-303, (2001)). Alternatively, such lyophilized VHH formulations can be reconstituted with a diluent to generate a stable reconstituted formulation suitable for subcutaneous administration. For example, anti-IgE antibody formulations (Example 1; U.S. Pat. No. 6,267,958, EP 841946) have been prepared which are useful for treating allergic asthma.

Another embodiment of the present invention is a use of a polypeptide construct as disclosed herein for the preparation of a medicament for treating, preventing and/or alleviating the symptoms of disorders susceptible to modulation by an anti-target therapeutic compound to to the nose, upper respiratory tract and/or lung without being inactivated.

An aspect of the invention is a method for delivering an anti-target therapeutic compound to the nose, upper respiratory tract and lung, by administering to the nose, upper respiratory tract and/or lung of a subject a polypeptide construct comprising one or more single domain antibodies directed against said target.

An aspect of the invention is a method for delivering an anti-target therapeutic compound to the nose, upper respiratory tract and/or lung without being inactivated, by administering to the nose, upper respiratory tract and/or lung of a subject a polypeptide construct comprising one or more single domain antibodies directed against said target.

An aspect of the invention is a method for delivering an anti-target therapeutic compound to the bloodstream of a subject without being inactivated by administering to the nose, upper respiratory tract and/or lung of a subject a polypeptide construct comprising one or more single domain antibodies directed against said target.

One embodiment of the present invention is a polypeptide construct comprising at least one single domain antibody directed against a target for use in treating, preventing and/or alleviating the symptoms of disorders wherein the permeability of the intestinal mucosa is increased. Because of their small size, a polypeptide construct as disclosed herein can pass through the intestinal mucosa and reach the bloodstream more efficiently in subjects suffering from disorders which cause an increase in the permeability of the intestinal mucosa, for example Crohn's disease.

An aspect of the invention is a method for treating, preventing and/or alleviating the symptoms of disorders wherein the permeability of the intestinal mucosa is increased, by orally administering to a subject a polypeptide construct as disclosed herein comprising one or more single domain antibodies specific for an antigen related to the disorder.

This process can be even further enhanced by an additional aspect of the present invention—the use of active transport carriers. In this aspect of the invention, VHH is fused to a carrier that enhances the transfer through the intestinal wall into the bloodstream. In a non-limiting example, this "carrier" is a second VHH which is fused to the therapeutic VHH. Such fusion constructs made using methods known in the art. The "carrier" VHH binds specifically to a receptor on the intestinal wall which induces an active transfer through the wall.

Another embodiment of the present invention is a use of a polypeptide construct as disclosed herein for the preparation of a medicament for treating, preventing and/or alleviating the symptoms of disorders susceptible to modulation by an anti-target therapeutic compound to the intestinal mucosa, wherein said disorder increases the permeability of the intestinal mucosa.

An aspect of the invention is a method for delivering an anti-target therapeutic compound to the intestinal mucosa without being inactivated, by administering orally to a subject a polypeptide construct comprising one or more single domain antibodies directed against said target.

An aspect of the invention is a method for delivering an anti-target therapeutic compound to the bloodstream of a subject without being inactivated, by administering orally to a subject a polypeptide construct comprising one or more single domain antibodies directed against said target.

One embodiment of the present invention is a polypeptide construct comprising at least one single domain antibody directed against a target for use in treating, preventing and/or alleviating the symptoms of disorders susceptible to modulation by an anti-target therapeutic compound that is able pass through the tissues beneath the tongue effectively. A formulation of said polypeptide construct as disclosed herein, for example, a tablet, spray, drop is placed under the tongue and adsorbed through the mucus membranes into the capillary network under the tongue.

An aspect of the invention is a method for treating, preventing and/or alleviating the symptoms of disorders susceptible to modulation by a therapeutic compound that is able pass through the tissues beneath the tongue effectively, by sublingually administering to a subject a VHH specific for an antigen related to the disorder.

Another embodiment of the present invention is a use of a polypeptide construct as disclosed herein for the preparation of a medicament for treating, preventing and/or alleviating the symptoms of disorders susceptible to modulation by an anti-target therapeutic compound that is able to pass through the tissues beneath the tongue.

An aspect of the invention is a method for delivering an anti-target therapeutic compound to the tissues beneath the tongue without being inactivated, by administering orally to a subject a polypeptide construct comprising one or more single domain antibodies directed against said target.

An aspect of the invention is a method for delivering an anti-target therapeutic compound to the bloodstream of a subject without being inactivated, by administering orally to a subject a polypeptide construct comprising one or more single domain antibodies directed against said target.

One embodiment of the present invention is a polypeptide construct comprising at least one single domain antibody for use in treating, preventing and/or alleviating the symptoms of disorders susceptible to modulation by an anti-target therapeutic compound that is able pass through the skin effectively. A formulation of said polypeptide construct, for example, a cream, film, spray, drop, patch, is placed on the skin and passes through.

An aspect of the invention is a method for treating, preventing and/or alleviating the symptoms of disorders susceptible to modulation by a therapeutic compound that is able pass through the skin effectively, by topically administering to a subject a polypeptide construct as disclosed herein comprising one or more single domain antibodies specific for an antigen related to the disorder.

Another aspect of the invention is the use of a polypeptide construct as disclosed herein as a topical ophthalmic composition for the treatment of ocular disorder, such as allergic disorders, which method comprises the topical administration of an ophthalmic composition comprising polypeptide construct as disclosed herein, said construct comprising one or more anti-IgE VHH (Example 1, Example 2).

Another aspect of the present invention is a use of a polypeptide construct as disclosed herein for the preparation of a medicament for treating, preventing and/or alleviating the symptoms of disorders susceptible to modulation by an anti-target therapeutic compound that is able pass through the skin effectively.

An aspect of the invention is a method for delivering an anti-target therapeutic compound to the skin without being inactivated, by administering topically to a subject a polypeptide construct comprising one or more single domain antibodies directed against said target.

An aspect of the invention is a method for delivering an anti-target therapeutic compound to the bloodstream of a subject, by administering topically to a subject a polypeptide construct comprising one or more single domain antibodies directed against said target.

A non-limiting example of a therapeutic target against which a polypeptide construct of the invention may be used is TNF, which is involved in inflammatory processes. The blocking of TNF action can have an anti-inflammatory effect, which is highly desirable in certain disease states such as, for example, Crohn's disease. Current therapy consists of intravenous administration of anti-TNF antibodies. Our Examples (Example 4) demonstrate VHHs according to the invention which bind TNF and moreover, block its binding to the TNF receptor. Oral delivery of these anti-TNF polypeptide constructs results in the delivery of such molecules in an active form in the colon at sites that are affected by the disorder. These sites are highly inflamed and contain TNF-producing cells. These anti-TNF polypeptide constructs can neutralise the TNF locally, avoiding distribution throughout the whole body and thus limiting negative side-effects. Genetically modified microorganisms such as *Micrococcus lactis* are able to secrete antibody fragments (U.S. Pat. No. 6,190,662, WO 0023471). Such modified microorganisms can be used as vehicles for local production and delivery of antibody fragments in the intestine. By using a strain which produces a TNF neutralizing antibody fragment, inflammatory bowel disorder could be treated. Another aspect of the invention is a polypeptide construct comprising at least one single domain antibody specific for TNF-alpha for use in the treatment, prevention and/or alleviation of disorders relating to inflammatory processes, wherein said polypeptide construct is administered orally, sublingually, topically, intravenously, subcutaneously, nasally, vaginally, rectally or by inhalation. Another aspect of the invention is a method of treating, preventing and/or alleviating disorders relating to inflammatory processes, comprising administering to a subject a polypeptide construct comprising at least one single domain antibody directed against for example TNF-alpha orally, sublingually, topically, intravenously, subcutaneously, nasally, vaginally, rectally or by inhalation.

According to one aspect of the invention, a polypeptide construct of the invention comprises at least one single domain antibody directed against TNF-alpha, said single domain antibody corresponding to a sequence represented by any of SEQ ID NOs: 12 to 14. Said sequences are anti-TNF-alpha Camelidae VHHs.

Further non-limiting examples of therapeutic targets against which a polypeptide construct of the invention may be used are certain colon cancer specific antigens, such as, for example, CEA or EGF receptors. In one aspect of the invention, therapeutic VHHs against colon cancer antigens are linked to or provided with one more tumor destroying reagents such as for example, a chemical compound or a radioactive compound.

As stated above a colon cancer specific antigen according to the invention is epidermal growth factor receptor (EGFR) which is an essential mediator of cell division in mammalian cells and is a recognised cellular oncogene. After the binding of EGF to its receptor (EGFR), a signaling cascade is initiated resulting in cell development. The EGFR is also involved in human tumorigenesis as it is overexpressed on cells associated with epithelial malignancies located in sites such as the head, neck, lung, colon. Another aspect of the invention is a polypeptide construct comprising at least one single domain antibody directed against EGFR for use in the treatment, prevention and/or alleviation of disorders relating to EGFR-mediated cancer, wherein said VHH is administered orally, sublingually, topically, nasally, intravenously, subcutaneously, vaginally, rectally or by inhalation (Examples 25 to 31). Another aspect of the invention is a method of treating, preventing and/or alleviating disorders relating to EGFR-mediated cancer, comprising administering to a subject a polypeptide construct comprising at least one single domain antibody directed against EGFR orally, sublingually, topically, intravenously, subcutaneously, nasally, vaginally, rectally or by inhalation.

According to one aspect of the invention, a polypeptide construct of the invention comprises at least one single domain antibody directed against EGFR, said single domain antibody corresponding to a sequence represented by any of SEQ ID NOs: 23 to 44. Said sequences are anti-EGRF Camelidae VHHs.

As stated above another colon cancer specific antigen according to the invention is carcinoembryonic antigen (CEA), a recognized tumor marker. Another aspect of the invention is a polypeptide construct comprising one or more single domain antibodies specific for CEA for use in the treatment, prevention and/or alleviation of disorders relating to CEA-mediated cancer, wherein said polypeptide is administered orally, sublingually, topically, intravenously, subcutaneously, nasally, vaginally, rectally or by inhalation. Another aspect of the invention is a method of treating, preventing and/or alleviating disorders relating to CEA-mediated cancer, comprising administering to a subject a polypeptide construct comprising at least one single domain antibody directed against CEA, orally, sublingually, topically, intravenously, subcutaneously, nasally, vaginally, rectally or by inhalation. A few VHHs specific for this glycoprotein have been isolated by selection on solid-phase coated with CEA out of a dedicated library obtained after immunization of a dromedary. By using FACS analysis it appeared that only two fragments recognized the cell-bound antigen. One of the VHHs that recognised the native structure, has been used to construct a fusion protein with β-lactamase. The functionality of the purified fusion protein was tested in vitro in a prodrug converting cytotoxicity assay. In addition the immunoconjugate was tested in vivo in a tumor-targeting biodistribution study.

A non-limiting example of a therapeutic target against which a polypeptide construct of the invention may be used is *Helicobacter pylori*, which is a bacterium that lives in the mucus which coats the lining of the human stomach and duodenum. The normal human stomach has a very thin layer of mucus that coats the whole of its inside surface. This mucus has a protective role, acting as a barrier between the acid in the stomach and the sensitive stomach wall. *H. pylori* acts as an irritant to the lining of the stomach, and this causes inflammation of the stomach (gastritis). In one embodiment of the invention is a polypeptide construct comprising at least one single domain antibody directed against *H. pylori*, said construct and inhibits the enzymatic function of urease. Since single domain antibodies, in particular VHHs have the specific characteristic to occupy enzymatic sites, selected VHHs would inhibit the enzymatic activity and neutralize the virulence of a *H. pylori* infection. In another aspect of the invention is a polypeptide construct comprising at least one single domain antibody directed against *H. pylori*, said construct inhibiting the adhesion of the bacteria to the stomach wall so preventing irritation of the stomach wall and gastritis. One aspect of the invention is a polypeptide construct comprising one or more single domain antibodies directed against *Helicobacter pylori* for use in the treatment, prevention and/or alleviation of disorders relating to irritation of the stomach wall and gastritis, wherein said polypeptide construct is administered orally, sublingually, topically, intravenously, subcutaneously, nasally, vaginally, rectally or by inhalation, but preferably orally. Another aspect of the invention is a method of treating, preventing and/or alleviating disorders relating to irritation of the stomach wall and gastritis, comprising administering to a subject a polypeptide construct comprising one or more single domain antibodies directed against *Helicobacter pylori*, orally, sublingually, topically, intravenously, subcutaneously, nasally, vaginally, rectally or by inhalation, but preferably orally.

Another non-limiting example of a therapeutic target against which the VHH of the invention may be used is Hepatitis E, which is a viral disorder transmitted via the fecal/oral route. Symptoms increase with age and include abdominal pain, anorexia, dark urine, fever, hepatomegaly, jaundice, malaise, nausea, and vomiting. The overall fatality rate is 1-3%, but 15-25% in pregnant women. Once encountered, most patients develop a neutralizing IgG response which gives life-long protection Neutralizing VHH molecules have the advantage over conventional IgG molecules because they may be administered orally. Since most infections with hepatitis E occur in North-Africa, Central-Africa, Asia and Central-America, oral administration is a significant advantage, since medical logistics are less developed in those countries. One aspect of the invention is one or more VHHs specific for HEV capsid protein (56 kDa) for use in the treatment, prevention and/or alleviation of disorders relating hepatitis E, wherein said VHH is administered orally, sublingually, topically, intravenously, subcutaneously, nasally, vaginally, rectally or by inhalation. Another aspect of the invention is a method of treating, preventing and/or alleviating disorders relating to hepatitis E, comprising administering to a subject said VHH orally, sublingually, topically, intravenously, subcutaneously, nasally, vaginally, rectally or by inhalation."

Other non-limiting examples of therapeutic targets against which a polypeptide construct of the invention may be used are micro-organisms induce respiratory disorders such as the TB bacterium and influenza virus. TB or tuberculosis, is a disorder caused by bacteria called *Mycobacterium tuberculosis*. The bacteria can attack any part of the body, but they usually attack the lungs. Influenza is a viral disorder that causes 'flu'. Influenza viruses are also present in the lung. One aspect of the invention is a polypeptide construct comprising at least one single domain antibody directed against *Mycobacterium tuberculosis* epitope for use in the treatment, prevention and/or alleviation of disorders relating TB, wherein said polypeptide construct is administered orally, sublingually, topically, intravenously, subcutaneously, nasally, vaginally, rectally or by inhalation. Another aspect of the invention is a method of treating, preventing and/or alleviating disorders relating to TB, comprising administering to a subject said polypeptide construct orally, sublingually, topically, intravenously, subcutaneously, nasally, vaginally, rectally or by inhalation. Another aspect of the invention is a polypeptide construct comprising at least one single domain antibody directed against an influenza virus epitope for use in the treatment, prevention and/or alleviation of disorders relating flu, wherein said polypeptide construct is administered orally, sublingually, topically, intravenously, subcutaneously, nasally, vaginally, rectally or by inhalation. Another aspect of the invention is a method of treating, preventing and/or alleviating disorders relating to flu, comprising administering to a subject said polypeptide construct orally, sublingually, topically, intravenously, subcutaneously, nasally, vaginally, rectally or by inhalation.

Another non-limiting example of a therapeutic target against which a polypeptide of the invention may be used is IgE in relation to allergies. During their lifetime, subjects may develop an allergic response to harmless parasites (e.g. *Dermatophagoides pteronyssinus*, house dust mite) or substances (clumps, plastics, metals). This results in the induction of IgE molecules that initiate a cascade of immunological responses. One aspect of the present invention is a polypeptide construct comprising at least one single domain antibody directed against IgE, said polypeptide preventing the interaction of IgE with their receptor(s) on mast cells and basophils. As such they prevent the initiation of the immunological cascade, an allergic reaction. Since IgE molecules are present in the bloodstream, it is within the scope of the invention to fuse the VHH one or more active transport carriers in order to reach their target. Another aspect of the invention is a polypeptide construct comprising at least one single domain antibody directed against an IgE epitope for use in the treatment, prevention and/or alleviation of disorders relating to allergies, wherein said polypeptide construct is administered orally, sublingually, topically, nasally, vaginally, rectally or by inhalation. Another aspect of the invention is a method of treating, preventing and/or alleviating disorders relating to allergies, comprising administering to a subject said polypeptide construct orally, sublingually, topically, intravenously, subcutaneously, nasally, vaginally, rectally or by inhalation.

According to one aspect of the invention, a polypeptide construct of the invention comprises at least one single domain antibody directed against IgE, said single domain antibody corresponding to a sequence represented by any of SEQ ID NOs: 1 to 11. Said sequences are anti-IgE Camelidae VHHs.

Another non-limiting example of a therapeutic target against which a polypeptide construct of the invention may be used is human macrophage elastase (MMP-12), which is a member of the family of matrix metalloproteases (MMPs). These enzymes play an important role in normal and inflammatory processes contributing to tissue remodeling and destruction. MMPs play besides proper extracellular matrix remodeling also an important role in diverse disease states such as cancer and inflammation. Macrophage elastase or MMP-12 has a large specificity pocket and broad substrate specificity. It plays a role in several disorders owing to excessive protein degradation of extracellular proteins (e.g. lung damage in smoke induced emphysema. Churg et al, A. 2003) or increased matrix degradation (e.g. higher MMP-12 enzymatic activity in obesity, Chavey et al, 2003). Other clinical indications include coeliac disorder and dermatitis herpetiformis (Salmela et al, 2001), glomerulo nephritis (Kaneko et al, 2003), esophageal squamous cell carcinoma (Ding et al, 2002) and skin cancer (Kerkela et al, 2000).

MMP-12 is secreted into the extracellular space by lung alveolar macrophages and dysregulation of MMP-12 is a possible reason for degradation of the alveolar membrane leading to lung emphysema. Target substrates of MMP-12 include extracellular matrix proteins such as elastin, fibronectin and laminin, but also al-antitrypsin and tissue factor protease inhibitor. One aspect of the invention is a polypeptide construct comprising at least one single domain antibody directed against MMP-12 for use in the treatment, prevention and/or alleviation of disorders relating to inflammatory processes, wherein said polypeptide construct is administered orally, sublingually, topically, nasally, vaginally, rectally or by inhalation. Another aspect of the invention is a method of treating, preventing and/or alleviating disorders relating to inflammatory processes, comprising administering to a subject said polypeptide construct orally, sublingually, topically, intravenously, subcutaneously, nasally, vaginally, rectally or by inhalation.

Another aspect of this invention consists of (1) VHH's that specifically bind to a metalloproteinase and are not degraded by a metalloproteinase, (2) VHH's which inhibit the proteolytic activity of one or more metalloproteinase and (3) inhibitory VHH's which are highly specific for one MMP (e.g. MMP-12 specific antagonist), unlike none-specific chemical inhibitors (e.g. batimastat, merimastat . . . )

According to one aspect of the invention, a polypeptide construct of the invention comprises at least one single domain antibody directed against human MMP-12, said single domain antibody corresponding to a sequence represented by any of SEQ ID NOs: 15 to 22. Said sequences are anti-MMP-12 Camelidae VHHs.

Another non-limiting example of a therapeutic target against which a polypeptide construct of the invention may be used is IFN-gamma, which is secreted by some T cells. In addition to its anti-viral activity, IFN gamma stimulates natural killer (NK) cells and T helper 1 (Th1) cells, and activates macrophages and stimulates the expression of MHC molecules on the surface of cells. Hence, IFN gamma generally serves to enhance many aspects of immune function, and is a candidate for treatment of disease states where the immune system is over-active (e.g. Crohn's disease), e.g., autoimmune disorders and organ plant rejection. One aspect of the invention is a polypeptide construct comprising at least one single domain antibody directed against IFN-gamma for use in the treatment, prevention and/or alleviation of disorders relating to the immune response, wherein said polypeptide construct is administered orally, sublingually, topically, intravenously, subcutaneously, nasally, vaginally, rectally or by inhalation. Another aspect of the invention is a method of treating, preventing and/or alleviating disorders relating to the immune response, comprising administering to a subject said polypeptide construct orally, sublingually, topically, intravenously, subcutaneously, nasally, vaginally, rectally or by inhalation. In other embodiments of the present invention polypeptide constructs that neutralize IFN gamma are used to treat patients with psoriasis.

According to one aspect of the invention, a polypeptide construct of the invention comprises at least one single domain antibody directed against IFN-gamma, said single domain antibody corresponding to a sequence represented by any of SEQ ID NOs: 45 to 70. Said sequences are anti-IFN-gamma Camelidae VHHs.

The invention also relates to a method of identifying single domain antibodies (e.g. VHHs) harbouring specific sequences which facilitates the delivery or transport of the anti-target single domain antibodies across human or animal tissues (as described in U.S. Pat. No. 6,361,938), including without limitation GIT epithelial layers, alveolar cells, endothelial of the blood-brain barrier, vascular smooth muscle cells, vascular endothelial cells, renal epithelial cells, M cells of the Peyers Patch, and hepatocytes. Furthermore, delivery systems could be used in conjunction with the VHH's of the invention, comprising nanoparticles, microparticles, liposomes, micelles, cyclodextrines. Only small (<600 daltons) and hydrophobic (Partridge et al, Adv. Drug Delivery Reviews, 15, 5-36 (1995)) molecules can easily pass the blood-brain barrier, severely limiting the development of novel brain drugs which can be used without the use of invasive neurosurgical procedures.

Delivering Polypeptide Constructs to the Interior of Cells

Another aspect of the present invention is a method and molecules for delivering therapeutic polypeptides and/or agents to the inside of cells. A further aspect of the invention is a method and molecules for delivering antigens to the inside of antigen presenting cells, and thereby eliciting a powerful immune response thereto. A still further aspect of the invention is to provide a method and molecules for delivery of therapeutic polypeptides and/or agents across natural barriers such as the blood-brain barrier, lung-blood barrier.

One aspect of the invention is a polypeptide construct comprising one or more single domain antibodies directed against a target and comprising one or more single domain antibodies directed against an internalising cellular receptor, wherein said polypeptide construct internalises upon binding to said receptor.

The targets inside cells may affect the functioning of said cell, or binding thereto may lead to a change in the phenotype of the cell itself by itself. This can be for example, cell death, effects on cell cycling or cell growth or interference with intracellular signaling pathways (see, for example, Poul M A et al, J Mol Biol, 2000, 301, 1149-1161).

Figure 12:
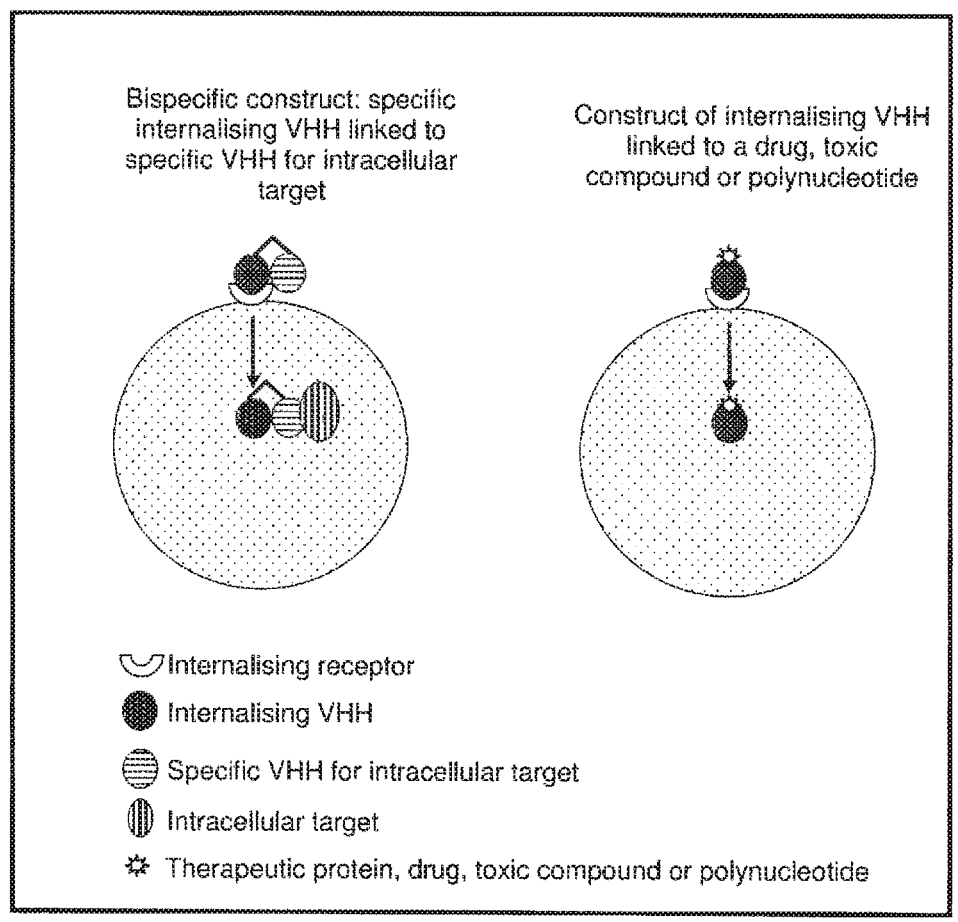
FIG. 12: Schematic illustrating a use of VHHs directed towards internalising receptors to deliver therapeutic protein, toxic compound, drug or polynucleotide.

One embodiment of the present invention is a polypeptide construct comprising one or more single domain antibodies specific for an internalising cellular receptor, wherein said construct internalises upon binding to said receptor, wherein the polypeptide construct comprises a therapeutic polypeptide or agent which is covalently or non-covalently linked thereto. Said therapeutic polypeptide or agent has one or more targets which acts intracellularly. See, for example, FIG. 12. Said therapeutic polypeptides may harbour specific sequences which target the polypeptide to specific compartments in the cell, comprising vesicles, organelles and other cytoplasmic structures, membrane-bound structures, the nucleus.

An internalising receptor according to the invention is a receptor displayed on the surface of a cell which upon binding to a ligand, mediates the internalisation of said ligand into the cytoplasm of the cell. Internalising receptors according to the invention include, but are not limited to, LDL receptors, EGFr, FGF2r, ErbB2r, transferrin receptor, PDGFr, VEGFr, PsmAr or antigen presenting cell internalising receptors.

One embodiment of the present invention is a polypeptide construct comprising one or more single domain antibodies specific for an internalising cellular receptor as disclosed herein, further comprising an antigen.

One embodiment of the present invention is a polypeptide construct comprising one or more single domain antibodies specific for an internalising cellular receptor as disclosed herein, wherein said receptor is an internalising receptor on an antigen presenting cell (APC). Preferably the receptor is highly specific for APCs and not present or is present in lower amounts on other cell types.

Another embodiment of the invention is a polypeptide construct comprising one or more anti-receptor single domain antibodies and an antigen. Thus by linking an antigen to a VHH directed towards an internalising receptor on an APC, antigen uptake by APC is not determined by the passive interaction between APC and antigen, but by the "active" binding between VHH and said receptor. This not only makes the process more efficient, but also more reproducible and not dependent on the antigen structure which causes great variability in the T-cell activation from antigen to antigen.

After internalization, the complex is digested by the APC and pieces of the antigen can be exposed on the surface in association with MHC/HLA and elicit a more powerful immune response.

Another embodiment of the present invention is a method for immunising a subject against an antigen comprising administering to a subject in need thereof a polypeptide construct comprising at least one single domain antibody directed against an antigen present on an APC, wherein said single domain antibody further comprises the antigen of interest.

One embodiment of the present invention is a polypeptide construct comprising one or more single domain antibodies specific for an internalising cellular receptor as disclosed herein, wherein said receptor is EGFR. In general internalization of receptors occurs upon binding of the agonistic ligand in a process called sequestration. In order to ensure that extracellular signals are translated into intracellular signals of appropriate magnitude and specificity, the signalling cascades are tightly regulated via the process of sequestration, whereby receptors are physically removed from the cell surface by internalization to a cytosolic compartment (Carman. C. V. and Benovic, J. L. Current Opinion in Neurobiology 1998, 8: 335-344). This implies that only agonistic ligands or antibodies indeed are expected to internalize via such receptors. In terms of therapeutic use it is not a desired effect that the antibody first triggers proliferation of the tumor cells, before it can deliver a toxic payload to the interior of the cell.

Some of internalising receptors are over-expressed on certain cells, such as the epidermal growth factor receptor (EGFR) or ErBb2 receptor on tumor cells. Epidermal growth factor (EGF) is an essential mediator of cell division in mammalian cells and is a recognized cellular oncogene and is therefore an appropriate target for anti-receptor therapy. After the binding of EGF to its receptor (EGFR), a signaling cascade is initiated resulting in cell development. The EGFR is involved in human tumorigenesis as it is overexpressed on cells of many epithelial malignancies such as head, neck, lung, colon. VHH that are internalised upon binding to one of these receptors can be used to deliver molecules inside the cell.

One embodiment of the present invention a polypeptide construct comprising one or more single domain antibodies directed against EGFR, wherein a single domain antibody corresponds to a sequence represented by any of SEQ ID NOs: 23 to 44. Surprisingly, one of the single domain antibodies, did not activate the EGFR, despite the fact that it was internalized efficiently. Such types of antibodies are preferred for therapeutic applications, since these can deliver toxic payloads into cells without stimulating its proliferation.

Another embodiment of the present invention is a polypeptide construct construct comprising one or more single domain antibodies directed against for EGFR, wherein said anti-EGFR single domain antibody does not activate the EGFR. Said polypeptide construct may be used for the delivery of a therapeutic agents and/or polypeptides into a cell, as mentioned herein, without stimulating the EGFR.

Another embodiment of the present is a polypeptide construct comprising one or more single domain antibodies directed against for EGFR, wherein said anti-EGFR single domain antibody does not activate the EGFR and corresponds to a sequence represented by SEQ ID NO: 31.

Another embodiment of the present invention is a polypeptide construct comprising at least one single domain antibody directed against an internalising cellular receptor, wherein said construct internalises upon binding to said receptor, and further comprising one or more single domain antibodies directed against an intracellular target, said single domain antibodies covalently or non-covalently linked. This multispecific polypeptide construct may be used in the treatment, prevention and/or alleviation of disorders, according to the target of the non-receptor specific single domain antibody. This target can be, for example, a kinase such as PDK1. PDK1 is over-expressed in breast tumor cells. It activates Akt by phosphorylating T308 in the activation loop. A number of downstream substrates of Akt play a direct role in promoting cell survival. These include GSK3. Bad, caspase-9 and Forkhead.

One embodiment of the present invention is a polypeptide construct comprising a single domain antibody directed against an internalising cellular receptor, wherein said construct internalises upon binding to said receptor, and further comprising one or more single domain antibodies directed against any of PDK1, GSK1, Bad, caspase-9 and Forkhead. Another aspect of the invention the use of said construct for treating cancer. Another aspect of the invention is said construct for the preparation of a medicament for treating cancer.

Another embodiment of the present invention is a polypeptide construct comprising at least one single domain antibody directed against an internalising cellular receptor, wherein said construct internalises upon binding to said receptor, wherein the construct further comprises a drug or a toxic compound covalently or non-covalently linked thereto. One example of a toxic compound is a compound that is only active intracellularly due to reducing environment (e.g. an enzyme recombinantly modified with additional cysteins resulting in inactive enzyme, but active in reducing environment). Another example of a toxic compound is a one that is specifically toxic only to a particular cell-type. An example of a toxic compound or a drug is a compound activated by a ligand present inside the cell and leading to the phenotype of interest. Other examples include prodrugs, small organic molecules. One aspect of the invention the use of said construct in the treatment of disorder requiring administration of the same. Another aspect of the invention is said construct for the preparation of a medicament for the treatment of disorder requiring administration of the same.

Another embodiment of the present invention is a polypeptide construct comprising at least one single domain antibody directed against an internalising cellular receptor, wherein said construct internalises upon binding to said receptor, and wherein a filamentous phage expresses said construct on its surface. Said construct may be attached to the tip of the phage. In one aspect of the invention, construct-phage assembly can be used to package and deliver DNA to the cell for use as a gene therapy vector. According to the invention, the phage may carry DNA in additional to that encoding said construct, for use therapeutically. According to the invention, the phage may carry a gene encoding a therapeutic polypeptide controlled by a promoter for the expression of said gene inside the cell. An example of said promoter includes, but is not limited to, the CMV promoter (Kassner et al, Biochem Biophys Res Commun, 1999, 264: 921-928). Phage have distinct advantages over existing gene therapy vectors because they are simple, economical to produce at high titer, have no intrinsic tropism for mammalian cells, and are relatively simple to genetically modify and evolve (Larocca D et al, Curr. Pharm. Biotechnol, 2002: 3: 45-57).

Another embodiment of the present invention is a polypeptide construct as disclosed herein, wherein said single domain antibody is a peptide derived from a VHH specific for an internalising cellular receptor. Said VHH peptide may bind their antigen almost only through the peptide. Internalising VHHs may be prepared from a peptide library which is screened for internalising properties. It is an aspect of the invention that these VHH peptides can be added as a tag to therapeutic polypeptides or agents, for intracellular uptake. The VHH peptide, may, for example, be used to transport a therapeutic VHH into a cell. In one embodiment of the invention, the VHH peptide is the CDR3. In another one embodiment of the invention, the VHH peptide is any other CDR.

Another embodiment of the present invention is a method of selecting for VHHs specific for an internalising cellular receptor, wherein said VHH internalise upon binding to said receptor, comprising panning receptor-displaying cells with a phage library (naïve or immune) of VHH, and selecting for internalising VHH by recovering the endocytosed phage from within the cell. The invention includes a selection method which uses cell lines that overexpress a receptor or cell lines transfected with a receptor gene to allow the easy selection of phage antibodies binding to the receptor. This avoids the need for protein expression and purification, speeding up significantly the generation of internalizing VHH.

Another embodiment of the present invention is a method for delivering a therapeutic polypeptide, agent or antigen for uptake by cellular internalisation by covalently or non-covalently attaching thereto a polypeptide construct comprising at least one single domain antibody specific for an internalising cellular receptor, wherein said construct internalises upon binding to said receptor.

The VHHs according to the invention may be used to treat, prevent and/or alleviate symptoms of disorders requiring the administration of the same.

Another embodiment of the present invention is a method for delivering a therapeutic polypeptide or agent that interacts with intracellular targets molecules comprising administering to a subject in need thereof one or more VHHs specific for an internalising cellular receptor, wherein said VHH internalise upon binding to said receptor, wherein said VHH is fused to said polypeptide or agent.

Another embodiment of the present invention is a method for delivering a therapeutic polypeptide, agent or antigen across a natural barrier by covalently or non-covalently attaching thereto a polypeptide construct comprising at least one single domain antibody directed against an internalising cellular receptor, wherein said construct internalises upon binding to said receptor. According to the invention, a natural barrier includes, but is not limited to, the blood-brain, lung-blood, gut-blood, vaginal-blood, rectal-blood and nasal-blood barriers.

For example, a peptide construct delivered via the upper respiratory tract and lung can be used for transport of therapeutic polypeptides or agents from the lung lumen to the blood. The construct binds specifically to a receptor present on the mucosal surface (bronchial epithelial cells) resulting in transport, via cellular internalisation, of the therapeutic polypeptides or agents specific for bloodstream targets from the lung lumen to the blood. In another example, a therapeutic polypeptide or agent is linked to a polypeptide construct comprising at least one single domain antibody directed against an internalising cellular receptor present on the intestinal wall into the bloodstream. Said construct induces a transfer through the wall, via cellular internalization, of said therapeutic polypeptide or agent.

Another embodiment of the present invention is a VHH specific for an internalising cellular receptor, wherein said VHH internalises upon binding to said receptor, said VHH is covalently or non-covalently attached to a therapeutic polypeptide or agent, and said VHH crosses a natural barrier.

Another embodiment of the present invention is a method for delivering a therapeutic polypeptide, agent or antigen for uptake at a local by covalently or non-covalently attaching it to a VHH specific for an internalising cellular receptor, wherein said VHH internalises upon binding to said receptor. A local area, according to the invention, includes, but is not limited to, the brain, lung, gut, vaginal, rectal and nasal areas.

One embodiment of the present invention is a polypeptide construct comprising at least one single domain antibody directed against a target for use in treating, preventing and/or alleviating the symptoms of disorders susceptible to modulation by an anti-target therapeutic compound that is able pass through the gastric environment without being inactivated.

As known by persons skilled in the art, once in possession of said polypeptide construct, formulation technology may be applied to release a maximum amount of VHHs in the right location (in the stomach, in the colon, etc.). This method of delivery is important for treating, prevent and/or alleviate the symptoms of disorder whose targets that are located in the gut system.

An aspect of the invention is a method for treating, preventing and/or alleviating the symptoms of a disorder susceptible to modulation by a therapeutic compound that is able pass through the gastric environment without being inactivated, by orally administering to a subject a polypeptide construct comprising one or more single domain antibodies specific for antigen related to the disorder.

Another embodiment of the present invention is a use of a polypeptide construct as disclosed herein for the preparation of a medicament for treating, preventing and/or alleviating the symptoms of disorders susceptible to modulation by an anti-target therapeutic compound that is able pass through the gastric environment without being inactivated.

An aspect of the invention is a method for delivering an anti-target therapeutic compound to the gut system without being inactivated, by orally administering to a subject a polypeptide construct comprising one or more single domain antibodies directed against said target.

An aspect of the invention is a method for delivering an anti-target therapeutic compound to the bloodstream of a subject without being inactivated, by orally administering to a subject a polypeptide construct comprising one or more single domain antibodies directed against said target.

Another embodiment of the present invention is a polypeptide construct comprising at least one single domain antibody directed against a target for use in treating, preventing and/or alleviating the symptoms of disorders susceptible to modulation by an anti-target therapeutic compound delivered to the vaginal and/or rectal tract.

In a non-limiting example, a formulation according to the invention comprises a polypeptide construct as disclosed herein comprising one or more VHHs directed against one or more targets in the form of a gel, cream, suppository, film, or in the form of a sponge or as a vaginal ring that slowly releases the active ingredient over time (such formulations are described in EP 707473, EP 684814, U.S. Pat. No. 5,629,001).

An aspect of the invention is a method for treating, preventing and/or alleviating the symptoms of disorders susceptible to modulation by an anti-target therapeutic compound delivered to the vaginal and/or rectal tract, by vaginally and/or rectally administering to a subject a polypeptide construct comprising one or more single domain antibodies directed against said target.

Another embodiment of the present invention is a use of a polypeptide construct as disclosed herein for the preparation of a medicament for treating, preventing and/or alleviating the symptoms of disorders susceptible to modulation by an anti-target therapeutic compound delivered to the vaginal and/or rectal tract without being inactivated.

An aspect of the invention is a method for delivering an anti-target therapeutic compound to the vaginal and/or rectal tract without being inactivated, by administering to the vaginal and/or rectal tract of a subject a polypeptide construct comprising one or more single domain antibodies directed against said target.

An aspect of the invention is a method for delivering an anti-target therapeutic compound to the bloodstream of a subject without being inactivated, by administering to the vaginal and/or rectal tract of a subject a polypeptide construct comprising one or more single domain antibodies directed against said target.

Another embodiment of the present invention is a polypeptide construct comprising at least one single domain antibody directed against a target comprising at least one single domain antibody directed against a target, for use in treating, preventing and/or alleviating the symptoms of disorders susceptible to modulation by an anti-target therapeutic compound delivered to the nose, upper respiratory tract and/or lung.

In a non-limiting example, a formulation according to the invention, comprises a polypeptide construct as disclosed herein directed against one or more targets in the form of a nasal spray (e.g. an aerosol) or inhaler. Since the construct is small, it can reach its target much more effectively than therapeutic IgG molecules.

An aspect of the invention is a method for treating, preventing and/or alleviating the symptoms of disorders susceptible to modulation by an anti-target therapeutic delivered to the nose, upper respiratory tract and lung, by administering to a subject a polypeptide construct as disclosed herein wherein one or more single domain antibodies are specific for an antigen related to the disorder, by inhalation through the mouth or nose.

Another aspect of the invention is a dispersible VHH composition, in particular dry powder dispersible VHH compositions, such as those described in U.S. Pat. No. 6,514,496. These dry powder compositions comprise a plurality of discrete dry particles with an average particle size in the range of 0.4-10 mm. Such powders are capable of being readily dispersed in an inhalation device. VHH's are particularly suited for such composition as lyophilized material can be readily dissolved (in the lung subsequent to being inhaled) due to its high solubilisation capacity (Muyldermans, S., Reviews in Molecular Biotechnology, 74, 277-303, (2001)). Alternatively, such lyophilized VHH formulations can be reconstituted with a diluent to generate a stable reconstituted formulation suitable for subcutaneous administration. For example, anti-IgE antibody formulations (Example 1; U.S. Pat. No. 6,267,958, EP 841946) have been prepared which are useful for treating allergic asthma.

Another embodiment of the present invention is a use of a polypeptide construct as disclosed herein for the preparation of a medicament for treating, preventing and/or alleviating the symptoms of disorders susceptible to modulation by an anti-target therapeutic compound delivered to the nose, upper respiratory tract and/or lung without being inactivated.

An aspect of the invention is a method for delivering an anti-target therapeutic compound to the nose, upper respiratory tract and lung, by administering to the nose, upper respiratory tract and/or lung of a subject a polypeptide construct comprising one or more single domain antibodies directed against said target.

An aspect of the invention is a method for delivering an anti-target therapeutic compound to the nose, upper respiratory tract and/or lung without being inactivated, by administering to the nose, upper respiratory tract and/or lung of a subject a polypeptide construct comprising one or more single domain antibodies directed against said target.

An aspect of the invention is a method for delivering an anti-target therapeutic compound to the bloodstream of a subject without being inactivated by administering to the nose, upper respiratory tract and/or lung of a subject a polypeptide construct comprising one or more single domain antibodies directed against said target.

One embodiment of the present invention is a polypeptide construct as disclosed herein for use in treating, preventing and/or alleviating the symptoms of disorders susceptible to modulation by an anti-target therapeutic compound delivered to the intestinal mucosa, wherein said disorder increases the permeability of the intestinal mucosa. Because of their small size, a polypeptide construct as disclosed herein can pass through the intestinal mucosa and reach the bloodstream more efficiently in subjects suffering from disorders which cause an increase in the permeability of the intestinal mucosa, for example, Crohn's disease.

An aspect of the invention is a method for treating, preventing and/or alleviating the symptoms of disorders susceptible to modulation by an anti-target therapeutic compound delivered to the intestinal mucosa, wherein said disorder increases the permeability of the intestinal mucosa, by orally administering to a subject a polypeptide construct as disclosed herein.

Another embodiment of the present invention is a use of a polypeptide construct as disclosed herein for the preparation of a medicament for treating, preventing and/or alleviating the symptoms of disorders susceptible to modulation by an anti-target therapeutic compound delivered to the intestinal mucosa, wherein said disorder increases the permeability of the intestinal mucosa.

An aspect of the invention is a method for delivering an anti-target therapeutic compound to the intestinal mucosa without being inactivated, by administering orally to a subject a polypeptide construct of the invention.

An aspect of the invention is a method for delivering an anti-target therapeutic compound to the bloodstream of a subject without being inactivated, by administering orally to a subject a polypeptide construct of the invention.

This process can be even further enhanced by an additional aspect of the present invention—the use of active transport carriers. In this aspect of the invention, a polypeptide construct as described herein is fused to a carrier that enhances the transfer through the intestinal wall into the bloodstream. In a non-limiting example, this "carrier" is a VHH which is fused to said polypeptide. Such fusion constructs made using methods known in the art. The "carrier" VHH binds specifically to a receptor on the intestinal wall which induces an active transfer through the wall.

One embodiment of the present invention is a polypeptide construct comprising at least one single domain antibody directed against a target for use in treating, preventing and/or alleviating the symptoms of disorders susceptible to modulation by an anti-target therapeutic compound that is able pass through the tissues beneath the tongue effectively. A formulation of said polypeptide construct as disclosed herein, for example, a tablet, spray, drop is placed under the tongue and adsorbed through the mucus membranes into the capillary network under the tongue.

An aspect of the invention is a method for treating, preventing and/or alleviating the symptoms of disorders susceptible to modulation by a therapeutic compound that is able pass through the tissues beneath the tongue effectively, by sublingually administering to a subject a VHH specific for an antigen related to the disorder.

Another embodiment of the present invention is a use of a polypeptide construct as disclosed herein for the preparation of a medicament for treating, preventing and/or alleviating the symptoms of disorders susceptible to modulation by an anti-target therapeutic compound that is able to pass through the tissues beneath the tongue.

An aspect of the invention is a method for delivering an anti-target therapeutic compound to the tissues beneath the tongue without being inactivated, by administering orally to a subject a polypeptide construct comprising one or more single domain antibodies directed against said target.

An aspect of the invention is a method for delivering an anti-target therapeutic compound to the bloodstream of a subject without being inactivated, by administering orally to a subject a polypeptide construct comprising one or more single domain antibodies directed against said target.

One embodiment of the present invention is a polypeptide construct comprising at least one single domain antibody for use in treating, preventing and/or alleviating the symptoms of disorders susceptible to modulation by an anti-target therapeutic compound that is able pass through the skin effectively. A formulation of said polypeptide construct, for example, a cream, film, spray, drop, patch, is placed on the skin and passes through.

An aspect of the invention is a method for treating, preventing and/or alleviating the symptoms of disorders susceptible to modulation by a therapeutic compound that is able pass through the skin effectively, by topically administering to a subject a polypeptide construct as disclosed herein comprising one or more single domain antibodies specific for an antigen related to the disorder.

Another aspect of the invention is the use of a polypeptide construct as disclosed herein as a topical ophthalmic composition for the treatment of ocular disorder, such as allergic disorders, which method comprises the topical administration of an ophthalmic composition comprising polypeptide construct as disclosed herein, said construct comprising one or more anti-IgE VHH (Example 1, Example 2).

Another embodiment of the present invention is a use of a polypeptide construct as disclosed herein for the preparation of a medicament for treating, preventing and/or alleviating the symptoms of disorders susceptible to modulation by an anti-target therapeutic compound that is able pass through the skin effectively.

An aspect of the invention is a method for delivering an anti-target therapeutic compound to the skin without being inactivated, by administering topically to a subject a polypeptide construct comprising one or more single domain antibodies directed against said target.

An aspect of the invention is a method for delivering an anti-target therapeutic compound to the bloodstream of a subject, by administering topically to a subject a polypeptide construct comprising one or more single domain antibodies directed against said target.

Another aspect of the present invention is a method to determine which single domain antibodies (e.g. VHHs) molecules cross a natural barrier into the bloodstream upon administration using, for example, oral, nasal, lung, skin. In a non-limiting example, the method comprises administering a naïve, synthetic or immune single domain antibody phage library to a small animal such as a mouse. At different time points after administration, blood is retrieved to rescue phages that have been actively transferred to the bloodstream. Additionally, after administration, organs can be isolated and bound phages can be stripped off. A non-limiting example of a receptor for active transport from the lung lumen to the bloodstream is the Fc receptor N (FcRn). The method of the invention thus identifies single domain antibodies which are not only actively transported to the blood, but are also able to target specific organs. The method may identify which VHH are transported across the gut and into the blood; across the tongue (or beneath) and into the blood; across the skin and into the blood etc.

One aspect of the invention are the single domain antibodies obtained by using said method. According to the invention, said single domain antibody may be used as a single domain antibody in a polypeptide construct of the invention. Said construct, further comprising another single domain antibody, a therapeutic agent, or polypeptide carrier directed against a target accessible via or in the blood may be administered by the route most efficient for said single domain antibody.

In general, "therapeutically effective amount", "therapeutically effective dose" and "effective amount" means the amount needed to achieve the desired result or results (such as for instance modulating IFN-gamma binding; treating or preventing inflammation). One of ordinary skills in the art will recognize that the potency and, therefore, an "effective amount" can vary for the various compounds that modulate ligand-target binding, such as for instance IFN-gamma binding used in the invention. One skilled in the art can readily assess the potency of the compound.

As used herein, the term "compound" refers to a polypeptide construct of the present invention, or a nucleic acid capable of encoding said polypeptide construct.

By "pharmaceutically acceptable" is meant a material that is not biologically or otherwise undesirable, i.e., the material may be administered to an individual along with the compound without causing any undesirable biological effects or interacting in a deleterious manner with any of the other components of the pharmaceutical composition in which it is contained.

The polypeptide constructs of the present invention are useful for treating or preventing conditions in a subject and comprises administering a pharmaceutically effective amount of a compound or composition.

The polypeptide constructs as disclosed here in are useful for treating or preventing conditions in a subject and comprises administering a pharmaceutically effective amount of a compound combination with another, such as, for example, doxorubicin.

The present invention is not limited to the administration of formulations comprising a single compound of the invention. It is within the scope of the invention to provide combination treatments wherein a formulation is administered to a patient in need thereof that comprises more than one compound of the invention.

A compound useful in the present invention can be formulated as pharmaceutical compositions and administered to a mammalian host, such as a human patient or a domestic animal in a variety of forms adapted to the chosen route of administration, i.e., parenterally, intravenously, intramuscularly, subcutaneously, to the vaginal and/or rectal tract, nasally, by inhalation though the mouth or nose, to the tissues beneath the tongue, or topically.

A compound of the present invention can also be administered using gene therapy methods of delivery. See, e.g., U.S. Pat. No. 5,399,346, which is incorporated by reference in its entirety. Using a gene therapy method of delivery, primary cells transfected with the gene for the compound of the present invention can additionally be transfected with tissue specific promoters to target specific organs, tissue, grafts, tumors, or cells.

Thus, the present compound may be administered in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form must be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compound may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, hydroxyalkyls or glycols or water-alcohol/glycol blends, in which the present compound can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compound to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compound can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compound(s) in a liquid composition, such as a lotion, will be from about 0.1-25 wt-%, preferably from about 0.5-10 wt-%. The concentration in a semi-solid or solid composition such as a gel or a powder will be about 0.1-5 wt-%, preferably about 0.5-2.5 wt-%.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician. Also the dosage of the compound varies depending on the target cell, tumor, tissue, graft, or organ.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

An administration regimen could include long-term, daily treatment. By "long-term" is meant at least two weeks and preferably, several weeks, months, or years of duration. Necessary modifications in this dosage range may be determined by one of ordinary skill in the art using only routine experimentation given the teachings herein. See Remington's Pharmaceutical Sciences (Martin, E. W., ed. 4), Mack Publishing Co., Easton, Pa. The dosage can also be adjusted by the individual physician in the event of any complication.

The present invention encompasses, but is not limited to, the subject matter of the appended claims and preferred aspects as described herein.

A) DEFINITIONS

Unless indicated or defined otherwise, all terms used have their usual meaning in the art, which will be clear to the skilled person. Reference is for example made to the standard handbooks, such as Sambrook et al, "Molecular Cloning: A Laboratory Manual" (2nd. Ed.), Vols. 1-3, Cold Spring Harbor Laboratory Press (1989); F. Ausubel et al, eds., "Current protocols in molecular biology", Green Publishing and Wiley Interscience, New York (1987); Lewin, "Genes II", John Wiley & Sons, New York, N.Y., (1985); Old et al., "Principles of Gene Manipulation: An Introduction to Genetic Engineering", 2nd edition. University of California Press, Berkeley, Calif. (1981); Roitt et al., "Immunology" (6th. Ed.), Mosby/Elsevier, Edinburgh (2001); Roitt et al., Roitt's Essential Immunology, $10^{th}$ Ed. Blackwell Publishing, UK (2001); and Janeway et al., "Immunobiology" (6th Ed.), Garland Science Publishing/Churchill Livingstone, New York (2005), as well as to the general background art cited herein;

Unless indicated otherwise, the term "immunoglobulin single variable domain"—whether used herein to refer to e.g. a Nanobody or to a dAb—is used as a general term to include both the full-size Nanobody or dAb, as well as functional fragments thereof. The terms antigen-binding molecules or antigen-binding protein are used interchangeably with immunoglobulin single variable domain and/or constructs thereof, and include Nanobodies and their constructs. In one embodiment of the invention, the immunoglobulin single variable domain are light chain variable domain sequences (e.g. a $V_L$-sequence), or heavy chain variable domain sequences (e.g. a $V_H$-sequence); more specifically, the immunoglobulin single variable domains can be heavy chain variable domain sequences that are derived from a conventional four-chain antibody or heavy chain variable domain sequences that are derived from a heavy chain antibody. According to the invention, the immunoglobulin single variable domains can be domain antibodies, or amino acid sequences that are suitable for use as domain antibodies, single domain antibodies, or amino acid sequences that are suitable for use as single domain antibodies, "dAbs", or amino acid sequences that are suitable for use as dAbs, or Nanobodies, including but not limited to humanized $V_{HH}$ sequences, affinity matured $V_{HH}$ sequences, chemically stabilized and/or $V_{HH}$ sequences with improved solubilisation and preferably are Nanobodies. The immunoglobulin single variable domains provided by the invention are preferably in essentially isolated form (as defined herein), or form part of a construct, protein or polypeptide of the invention (as defined herein), which may comprise or essentially consist of one or more amino acid sequences of the invention and which may optionally further comprise one or more further amino acid sequences (all optionally linked via one or more suitable linkers). For example, and without limitation, the one or more amino acid sequences of the invention may be used as a binding unit in such a construct, protein or polypeptide, which may optionally contain one or more further amino acid sequences that can serve as a binding unit (i.e. against one or more other antigens than cell associated antigens), so as to provide a monovalent, multivalent or multispecific construct of the invention, respectively, all as described herein. Such a construct may also be in essentially isolated form (as defined herein).

The invention includes immunoglobulin single variable domains of different origin, comprising mouse, rat, rabbit, donkey, human and camelid immunoglobulin sequences. The invention also includes fully human, humanized or chimeric immunoglobulin sequences. For example, the invention comprises camelid immunoglobulin sequences and humanized camelid immunoglobulin sequences, or camelized domain antibodies, e.g. camelized dAb as described by WO 94/04678). Moreover, the invention comprises fused immunoglobulin sequences, e.g. forming a multivalent and/or multispecific construct (for multivalent and multispecific polypeptides containing one or more $V_{HH}$ domains and their preparation, reference is also made to Conrath et al., J. Biol. Chem., Vol. 276, 10. 7346-7350, 2001, as well as to for example WO 96/34103 and WO 99/23221), and immunoglobulin single variable domains comprising tags or other functional moieties, e.g. toxins, labels, radiochemicals, etc., which are derivable from the immunoglobulin single variable domains of the present invention.

The amino acid sequence and structure of an immunoglobulin single variable domains, in particular a Nanobody can be considered—without however being limited thereto—to be comprised of four framework regions or "FR's", which are referred to in the art and herein as "Framework region 1" or "FR1"; as "Framework region 2" or "FR2"; as "Framework region 3" or "FR3"; and as "Framework region 4" or "FR4", respectively; which framework regions are interrupted by three complementary determining regions or "CDR's", which are referred to in the art as "Complementarity Determining Region 1" or "CDR1"; as "Complementarity Determining Region 2" or "CDR2"; and as "Complementarity Determining Region 3" or "CDR3", respectively.

The total number of amino acid residues in a Nanobody can be in the region of 110-120, is preferably 112-115, and is most preferably 113. It should however be noted that parts, fragments, analogs or derivatives (as further described herein) of a Nanobody are not particularly limited as to their length and/or size, as long as such parts, fragments, analogs or derivatives meet the further requirements outlined herein and are also preferably suitable for the purposes described herein.

As used herein, the term a sequence to the "immunoglobulin single variable domain" may refer to both the nucleic acid sequences coding for said immunoglobulin molecule, and the immunoglobulin polypeptide per se. Any more limiting meaning will be apparent from the particular context.

All these molecules are also referred to as "agent(s) of the invention", which is synonymous with "immunoglobulin single variable domain(s) and/or construct(s) thereof" of the invention.

In addition, the term "sequence" as used herein (for example in terms like "immunoglobulin single variable domain sequence", "Nanobody sequence", "$V_{HH}$ sequence" or "polypeptide sequence"), should generally be understood to include both the relevant amino acid sequence as well as nucleic acid sequences or nucleotide sequences encoding the same, unless the context requires a more limited interpretation.

Unless indicated otherwise, all methods, steps, techniques and manipulations that are not specifically described in detail can be performed and have been performed in a manner known per se, as will be clear to the skilled person. Reference is for example again made to the standard handbooks and the general background art mentioned herein and to the further references cited therein; as well as to for example the following review "Pulmonary Drug Delivery" (Bechtold-Peters and Luessen, eds., referenced supra), which describe techniques for pulmonary drug delivery of biopharmaceuticals such as the agent(s) of the invention.

In a specific and preferred aspect, the immunoglobulin single variable domains are Nanobodies against, and in particular Nanobodies against druggable antigen from a mammal, and especially Nanobodies against human druggable antigen; as well as construct(s) comprising at least one such Nanobody.

In particular, the invention provides Nanobodies against druggable antigen, and constructs comprising the same, that have improved therapeutic and/or pharmacological properties and/or other advantageous properties (such as, for example, improved ease of preparation and/or reduced costs of goods), compared to conventional antibodies against druggable antigen or fragments thereof, compared to constructs that could be based on such conventional antibodies or antibody fragments (such as Fab' fragments, F(ab')$_2$ fragments, ScFv constructs, "diabodies" and other multispecific constructs (see for example the review by Holliger and Hudson, Nat Biotechnol. 2005 September; 23(9):1126-36)), and also compared to the so-called "dAb's" or similar (single) domain antibodies that may be derived from variable domains of conventional antibodies. These improved and advantageous properties will become clear from the further description herein, and for example include, without limitation, one or more of:

increased affinity and/or avidity for druggable antigen, either in a monovalent format, in a multivalent format (for example in a bivalent format) and/or in a multispecific format (for example one of the multispecific formats described herein below);

better suitability for formatting in a multivalent format (for example in a bivalent format);

better suitability for formatting in a multispecific format (for example one of the multispecific formats described herein below);

improved suitability or susceptibility for "humanizing" substitutions;

less immunogenicity, either in a monovalent format, in a multivalent format (for example in a bivalent format) and/or in a multispecific format (for example one of the multispecific formats described herein below);

increased stability, either in a monovalent format, in a multivalent format (for example in a bivalent format) and/or in a multispecific format (for example one of the multispecific formats described herein below);

increased specificity towards druggable antigen, either in a monovalent format, in a multivalent format (for example in a bivalent format) and/or in a multispecific format (for example one of the multispecific formats described herein below);

decreased or where desired increased cross-reactivity with druggable antigen from different species;

and/or one or more other improved properties desirable for pharmaceutical use (including prophylactic use and/or therapeutic use) and/or for diagnostic use (including but not limited to use for imaging purposes), either in a monovalent format, in a multivalent format (for example in a bivalent format) and/or in a multispecific format (for example one of the multispecific formats described herein below).

As generally described herein for the agent of the invention, the Nanobodies and construct thereof of the invention are preferably in essentially isolated form (as defined herein), wherein the constructs may comprise or essentially consist of one or more Nanobodies of the invention and which may optionally further comprise one or more further amino acid sequences (all optionally linked via one or more suitable linkers). For example, and without limitation, the Nanobody of the invention may be used as a binding unit in such a construct, which may optionally contain one or more further Nanobodies that can serve as a binding unit (i.e. against one or more other druggable antigens), so as to provide a monovalent, multivalent or multispecific construct of the invention, respectively, all as described herein. In particular, such a construct may comprise or essentially consist of one or more Nanobodies of the invention and optionally one or more (other) Nanobodies (i.e. directed against other druggable antigens), all optionally linked via one or more suitable linkers, so as to provide a monovalent, multivalent or multispecific Nanobody constructs, respectively, as further described herein. Such proteins or polypeptides may also be in essentially isolated form (as defined herein).

In a Nanobody of the invention, the binding site for binding against a druggable antigen is preferably formed by the CDR sequences. Optionally, a Nanobody of the invention may also, and in addition to the at least one binding site for binding against druggable antigen, contain one or more further binding sites for binding against other antigens. For methods and positions for introducing such second binding sites, reference is for example made to Keck and Huston, Biophysical Journal, 71, October 1996, 2002-2011; EP 0 640 130; and WO 06/07260.

As generally described herein for the amino acid sequences of the invention, when a Nanobody of the invention (or a polypeptide of the invention comprising the same) is intended for administration to a subject (for example for therapeutic, prophylactic and/or diagnostic purpose as described herein), it is preferably directed against a human druggable antigen; whereas for veterinary purposes, it is preferably directed against a druggable antigen from the species to be treated. Also, as with the amino acid sequences of the invention, a Nanobody of the invention may or may not be cross-reactive (i.e. directed against druggable antigen from two or more species of mammal, such as against human druggable antigen and druggable antigen from at least one of the species of mammal mentioned herein).

Also, again as generally described herein for the agents of the invention, the Nanobodies of the invention may generally be directed against any antigenic determinant, epitope, part, domain, subunit or confirmation of a druggable antigen.

As already described herein, the amino acid sequence and structure of a Nanobody can be considered—without however being limited thereto—to be comprised of four framework regions or "FR's" (or sometimes also referred to as "FW's"), which are referred to in the art and herein as "Framework region 1" or "FR1"; as "Framework region 2" or "FR2"; as "Framework region 3" or "FR3"; and as "Framework region 4" or "FR4", respectively; which framework regions are interrupted by three complementary determining regions or "CDR's", which are referred to in the art as "Complementarity Determining Region 1" or "CDR1"; as "Complementarity Determining Region 2" or "CDR2"; and as "Complementarity Determining Region 3" or "CDR3", respectively. Some preferred framework sequences and CDR's (and combinations thereof) that are present in the Nanobodies of the invention are as e.g. described on page 146ff of WO2008/074839.

According to a non-limiting but preferred aspect of the invention, (the CDR sequences present in) the Nanobodies of the invention are such that:

the Nanobodies can bind to a druggable antigen with a dissociation constant ($K_D$) of $10^{-5}$ to $10^{-12}$ moles/liter or less, and preferably $10^{-7}$ to $10^{-12}$ moles/liter or less and more preferably $10^{-8}$ to $10^{-12}$ moles/liter (i.e. with an association constant ($K_A$) of $10^5$ to $10^{12}$ liter/moles or more, and preferably $10^7$ to $10^{12}$ liter/moles or more and more preferably $10^8$ to $10^{12}$ liter/moles);

and/or such that:

the Nanobodies can bind to a druggable antigen with a $k_{on}$-rate of between $10^2$ $M^{-1}s^{-1}$ to about $10^7$ $M^{-1}s^{-1}$ preferably between $10^3$ $M^{-1}s^{-1}$ and $10^7$ $M^{-1}s^{-1}$, more preferably between $10^4$ $M^{-1}s^{-1}$ and $10^7$ $M^{-1}s^{-1}$, such as between $10^5$ $M^{-1}s^{-1}$ and $10^7$ $M^{-1}s^{-1}$;

and/or such that they:

the Nanobodies can bind to a druggable antigen with a $k_{off}$ rate between 1 $s^{-1}$ ($t_{1/2}$=0.69 s) and $10^{-6}$ $s^{-1}$ (providing a near irreversible complex with a $t_{1/2}$ of multiple days), preferably between $10^{-2}$ $s^{-1}$ and $10^{-6}$ $s^{-1}$, more preferably between $10^{-3}$ $s^{-1}$ and $10^{-6}$ $s^{-1}$, such as between $10^{-4}$ $s^{-1}$ and $10^{-6}$ $s^{-1}$.

Preferably, (the CDR sequences present in) the Nanobodies of the invention are such that: a monovalent Nanobody of the invention (or a polypeptide that contains only one Nanobody of the invention) is preferably such that it will bind to druggable antigen with an affinity less than 500 nM, preferably less than 200 nM, more preferably less than 10 nM, such as less than 500 pM.

The affinity of the Nanobody of the invention against druggable antigen can be determined in a manner known per se, for example using the general techniques for measuring $K_D$, $K_A$, $k_{off}$ or $k_{on}$ mentioned herein, as well as some of the specific assays described herein.

Some preferred IC50 values for binding of the Nanobodies of the invention (and of polypeptides comprising the same) to druggable antigen will become clear from the further description and examples herein.

The invention relates to immunoglobulin single variable domains and/or constructs thereof that can bind to and/or have affinity for an antigen as defined herein. In the context of the present invention, "binding to and/or having affinity for" a certain antigen has the usual meaning in the art as understood e.g. in the context of antibodies and their respective antigens.

In particular embodiments of the invention, the term "binds to and/or having affinity for" means that the immunoglobulin single variable domain and/or construct thereof specifically interacts with an antigen, and is used interchangeably with immunoglobulin single variable domains and/or constructs thereof "against" the said antigen.

The term "specificity" refers to the number of different types of antigens or antigenic determinants to which a particular immunoglobulin single variable domains and/or constructs thereof (such as a Nanobody or other agent of the invention) can bind. The specificity of an antigen-binding protein can be determined based on affinity and/or avidity. The affinity, represented by the equilibrium constant for the dissociation of an antigen with an antigen-binding protein ($K_D$), is a measure for the binding strength between an antigenic determinant and an antigen-binding site on the antigen-binding protein: the lesser the value of the $K_D$, the stronger the binding strength between an antigenic determinant and the antigen-binding molecule (alternatively, the affinity can also be expressed as the affinity constant ($K_A$), which is $1/K_D$). As will be clear to the skilled person (for example on the basis of the further disclosure herein), affinity can be determined in a manner known per se, depending on the specific antigen of interest. Avidity is the measure of the strength of binding between an antigen-binding molecule (such as a Nanobody or other agent of the invention) and the pertinent antigen. Avidity is related to both the affinity between an antigenic determinant and its antigen binding site on the antigen-binding molecule and the number of pertinent binding sites present on the antigen-binding molecule.

Typically, immunoglobulin single variable domains and/or constructs thereof of the present invention (such as the Nanobodies and/or other agents of the invention) will bind to their antigen with a dissociation constant ($K_D$) of $10^{-5}$ to $10^{-12}$ moles/liter or less, and preferably $10^{-7}$ to $10^{-12}$ moles/liter or less and more preferably $10^{-8}$ to $10^{-12}$ moles/liter (i.e. with an association constant ($K_A$) of $10^5$ to $10^{12}$ liter/moles or more, and preferably $10^7$ to $10^{12}$ liter/moles or more and more preferably $10^8$ to $10^{12}$ liter/moles); and/or bind to antigens as e.g. defined herein with a $k_{on}$-rate of between $10^2$ $M^{-1}s^{-1}$ to about $10^7$ $M^{-1}s^{-1}$, preferably between $10^3$ $M^{-1}s^{-1}$ and $10^7$ $M^{-1}s^{-1}$, more preferably between $10^4$ $M^{-1}s^{-1}$ and $10^7$ $M^{-1}s^{-1}$, such as between $10^5$ $M^{-1}s^{-1}$ and $10^7$ $M^{-1}s^{-1}$;

and/or bind to the antigens as e.g. defined herein with a $k_{off}$ rate between 1 $s^{-1}$ ($t_{1/2}$=0.69 s) and $10^{-6}$ $s^{-1}$ (providing a near irreversible complex with a $t_{1/2}$ of multiple days), preferably between $10^{-2}$ $s^{-1}$ and $10^{-6}$ $s^{-1}$, more preferably between $10^{-3}$ $s^{-1}$ and $10^{-6}$ $s^{-1}$, such as between $10^{-4}$ $s^{-1}$ and $10^{-6}$ $s^{-1}$.

Any $K_D$ value greater than $10^{-4}$ mol/liter (or any $K_A$ value lower than $10^4$ $M^{-1}$) liters/mol is generally considered to indicate non-specific binding.

Preferably, a monovalent immunoglobulin single variable domain of the invention will bind to the desired antigen with an affinity less than 500 nM, preferably less than 200 nM, more preferably less than 10 nM, such as less than 500 pM.

Specific binding of an antigen-binding protein to an antigen or antigenic determinant can be determined in any suitable manner known per se, including, for example, Scatchard analysis and/or competitive binding assays, such as radioimmunoassays (RIA), enzyme immunoassays (EIA) and sandwich competition assays, and the different variants thereof known per se in the art; as well as the other techniques mentioned herein.

The dissociation constant may be the actual or apparent dissociation constant, as will be clear to the skilled person. Methods for determining the dissociation constant will be clear to the skilled person, and for example include the techniques mentioned herein. In this respect, it will also be clear that it may not be possible to measure dissociation constants of more than $10^{-4}$ moles/liter or $10^{-3}$ moles/liter (e.g. of $10^{-2}$ moles/liter). Optionally, as will also be clear to the skilled person, the (actual or apparent) dissociation constant may be calculated on the basis of the (actual or apparent) association constant ($K_A$), by means of the relationship [$K_D=1/K_A$].

The affinity denotes the strength or stability of a molecular interaction. The affinity is commonly given as by the $K_D$, or dissociation constant, which has units of mol/liter (or M). The affinity can also be expressed as an association constant, $K_A$, which equals $1/K_D$ and has units of (mol/liter)$^{-1}$ (or $M^{-1}$). In the present specification, the stability of the interaction between two molecules (such as an agent of the invention and its intended antigen) will mainly be expressed in terms of the $K_D$ value of their interaction; it being clear to the skilled person that in view of the relation $K_A=1/K_D$, specifying the strength of molecular interaction by its $K_D$ value can also be used to calculate the corresponding $K_A$ value. The $K_D$-value characterizes the strength of a molecular interaction also in a thermodynamic sense as it is related to the free energy (DG) of binding by the well-known relation DG=RT·ln($K_D$) (equivalently DG=−RT·ln($K_A$)), where R equals the gas constant, T equals the absolute temperature and ln denotes the natural logarithm.

The $K_D$ for biological interactions, such as the binding of the agents of the invention to the antigens as e.g. defined herein, which are considered meaningful (e.g. specific) are typically in the range of $10^{-10}$M (0.1 nM) to $10^{-5}$M (10000 nM). The stronger an interaction is, the lower is its $K_D$.

The $K_D$ can also be expressed as the ratio of the dissociation rate constant of a complex, denoted as $k_{off}$, to the rate of its association, denoted $k_{on}$ (so that $K_D=k_{off}/k_{on}$ and $K_A=k_{on}/k_{off}$). The off-rate $k_{off}$ has as unit $s^{-1}$ (where s is the SI unit notation of second). The on-rate $k_{on}$ has units $M^{-1}s^{-1}$.

As regards agents of the invention, the on-rate may vary between $10^2$ $M^{-1}s^{-1}$ to about $10^7$ $M^{-1}s^{-1}$, approaching the diffusion-limited association rate constant for bimolecular interactions. The off-rate is related to the half-life of a given molecular interaction by the relation $t_{1/2}$=ln(2)/$k_{off}$. The off-rate of immunoglobulin sequences of the invention may vary between $10^{-6}$ $s^{-1}$ (near irreversible complex with a $t_{1/2}$ of multiple days) to 1 $s^{-1}$ ($t_{1/2}$=0.69 s).

The affinity of a molecular interaction between two molecules can be measured via different techniques known per se, such as the well-known surface plasmon resonance (SPR) biosensor technique (see for example Ober et al., Intern. Immunology, 13, 1551-1559, 2001) where one molecule is immobilized on the biosensor chip and the other molecule is passed over the immobilized molecule under flow conditions yielding $k_{on}$, $k_{off}$ measurements and hence $K_D$ (or $K_A$) values. This can for example be performed using the well-known Biacore instruments.

It will also be clear to the skilled person that the measured $K_D$ may correspond to the apparent $K_D$ if the measuring process somehow influences the intrinsic binding affinity of the implied molecules for example by artefacts related to the coating on the biosensor of one molecule. Also, an apparent $K_D$ may be measured if one molecule contains more than one recognition sites for the other molecule. In such situation the measured affinity may be affected by the avidity of the interaction by the two molecules.

Another approach that may be used to assess affinity is the 2-step ELISA (Enzyme-Linked Immunosorbent Assay) procedure of Friguet et al. (J. Immunol. Methods, 77, 305-19, 1985). This method establishes a solution phase binding equilibrium measurement and avoids possible artefacts relating to adsorption of one of the molecules on a support such as plastic.

However, the accurate measurement of $K_D$ may be quite labour-intensive and as consequence, often apparent $K_D$ values are determined to assess the binding strength of two molecules. It should be noted that as long as all measurements are made in a consistent way (e.g. keeping the assay conditions unchanged) apparent $K_D$ measurements can be used as an approximation of the true $K_D$ and hence in the present document $K_D$ and apparent $K_D$ should be treated with equal importance or relevance.

Finally, it should be noted that in many situations the experienced scientist may judge it to be convenient to determine the binding affinity relative to some reference molecule. For example, to assess the binding strength between molecules A and B, one may e.g. use a reference molecule C that is known to bind to B and that is suitably labelled with a fluorophore or chromophore group or other chemical moiety, such as biotin for easy detection in an ELISA or FACS (Fluorescent activated cell sorting) or other format (the fluorophore for fluorescence detection, the chromophore for light absorption detection, the biotin for streptavidin-mediated ELISA detection). Typically, the reference molecule C is kept at a fixed concentration and the concentration of A is varied for a given concentration or amount of B. As a result an $IC_{50}$ value is obtained corresponding to the concentration of A at which the signal measured for C in absence of A is halved. Provided $K_{D\ ref}$, the $K_D$ of the reference molecule, is known, as well as the total concentration $c_{ref}$ of the reference molecule, the apparent $K_D$ for the interaction A-B can be obtained from following formula: $K_D=IC_5/(1+c_{ref}/K_{D\ ref})$. Note that if $c_{ref} \ll K_{D\ ref}$, $K_D \approx IC_{50}$. Provided the measurement of the $IC_{50}$ is performed in a consistent way (e.g. keeping $c_{ref}$ fixed) for the binders that are compared, the strength or stability of a molecular interaction can be assessed by the $IC_{50}$ and this measurement is judged as equivalent to $K_D$ or to apparent $K_D$ throughout this text.

In the context of the present invention, "systemic circulation" denotes the portion of the cardiovascular system which carries oxygenated blood away from the heart, to the body, and returns deoxygenated blood back to the heart (see e.g. Wikipedia).

In the context of the present invention, "pulmonary tissue" is for the purposes of this invention equivalent with lung tissue or lung. The lung comprises 2 distinct zones: a conducting and a respiratory zone, within which the airway and vascular compartments lie (see e.g. "Pulmonary Drug Delivery, Bechtold-Peters and Luessen, eds., supra, pages 16-28).

In the context of the present invention, "aerosol" denotes a suspension of fine solid particles or liquid droplets (or combination thereof) in a gas wherein for the purposes of this invention the particles and/or droplets comprise the agent(s) of the invention.

In the context of the present invention, "half-life" of an agent of the invention can generally be defined as described in paragraph o) on page 57 of WO 08/020079 and as mentioned therein refers to the time taken for the serum concentration of the amino acid sequence, compound or polypeptide to be reduced by 50%, in vivo, for example due to degradation of the sequence or compound and/or clearance or sequestration of the sequence or compound by natural mechanisms. The in vivo half-life of an agent of the invention can be determined in any manner known per se, such as by pharmacokinetic analysis. Suitable techniques will be clear to the person skilled in the art, and may for example generally be as described in paragraph o) on page 57 of WO 08/020079. As also mentioned in paragraph o) on page 57 of WO 08/020079, the half-life can be expressed using parameters such as the t½-alpha, t½-beta and the area under the curve (AUC). Reference is for example made to the standard handbooks, such as Kenneth, A et al: Chemical Stability of Pharmaceuticals: A Handbook for Pharmacists and Peters et al, Pharmacokinetic analysis: A Practical Approach (1996). Reference is also made to "Pharmacokinetics", M Gibaldi & D Perron, published by Marcel Dekker, 2nd Rev. edition (1982). The terms "increase in half-life" or "increased half-life" as also as defined in paragraph o) on page 57 of WO 08/020079 and in particular refer to an increase in the t½-beta, either with or without an increase in the t½-alpha and/or the AUC or both. Moreover, in the context of the present invention the term "Terminal plasma half-life" is the time required to divide the plasma concentration by two after reaching pseudo-equilibrium, and not the time required to eliminate half the administered dose. When the process of absorption is not a limiting factor, half-life is a hybrid parameter controlled by plasma clearance and extent of distribution. In contrast, when the process of absorption is a limiting factor, the terminal half-life reflects rate and extent of absorption and not the elimination process (flip-flop pharmacokinetics). The terminal half-life is especially relevant to multiple dosing regimens, because it controls the degree of drug accumulation, concentration fluctuations and the time taken to reach equilibrium.

In the context of the present invention, "bioavailability" of an inhaled aerosol comprising the agent of the invention can be determined using plasma concentration-time profiles by comparing the area under the concentration-time curve after inhalation (referred herein as "AUC-inh") with that obtained after intravenous administration (referred herein as "AUC-iv") wherein an aerosol is a suspension of fine solid particles or liquid droplets in a gas. The "absolute bioavailability" (referred herein as "F-inh") after inhalation can then be calculated by the equation F-inh=AUC-inh divided by AUC-iv (when inhaled and intravenous doses are identical).

In the context of the present invention, "tau" is a time interval and denotes the dosing interval.

In the context of the present invention, "antigen(s)" define all antigens that are druggable to the skilled person in the art and include all druggable interaction sites of an antigen. Particularly preferred antigen(s) are the antigen(s) as e.g. herein described such as human von Willebrand factor, human RANK ligand and/or viral antigen(s) such as RSV and/or avian flu virus.

As used herein, the term "antigen" is intended to include, and also refer to, any part, fragment, subunit, epitope or domain of said antigen. Any subsection of a cell wherein the antigen is associated falls within the scope of the present invention, provided it represents a druggable antigen of interest.

In particular, the present invention relates to immunoglobulin single variable domains directed to antigens in their natural conformation. In the context of the present invention, "natural conformation" means that the antigen exhibits its secondary and/or tertiary structure. In other words, the natural conformation describes the antigen in a non-denatured form, and describes a conformation wherein the conformational or linear epitopes are present. Specifically, the antigen will have the conformation that is present when the antigen is integrated into mammal, e.g. firmly attached to a cell membrane of said mammal. Antigens can be obtained in their natural conformation when present in cells comprising natural or transfected cells expressing the cell-associated antigen, cell derived membrane extracts, vesicles or any other membrane derivative harbouring antigen, liposomes, or virus particles expressing the cell associated antigen. In any of these embodiments, antigen may be enriched by suitable means. Said cell-associated antigen can be expressed on any suitable cell allowing expression of the antigen in its native or natural conformation, encompassing, but not limited to Cho, Cos7, Hek293 or cells of camelid origin.

The skilled person will appreciate that there may be different specific three dimensional conformations that are encompassed by the term "natural conformation". If, for example, a protein has two or more different conformations whilst being in a membrane environment, all these conformations will be considered "natural conformations". This is exemplified by receptors changing their conformation by activation, e.g. the different activation states of rhodopsin induced by light, or ion channels showing a "closed" or "open" conformation. The invention encompasses immunoglobulin sequences to any one of these different natural conformations, i.e. to the different kinds of conformational epitopes that may be present.

The antigen of the present invention is preferably a druggable interaction sites of an antigen that has when modulated a prophylactic and/or therapeutic effect in a mammal, e.g. a human, preferably in a mammal, e.g. human, that is at risk and/or has a disease.

In the context of the present invention, the term "interaction site" on the antigen means a site, epitope, antigenic determinant, part, domain or stretch of amino acid residues on the target or antigen that is a site for binding to a ligand, receptor or other binding partner, a catalytic site, a cleavage site, a site for allosteric interaction, a site involved in multimerisation (such as homomerization or heterodimerization) of the antigen; or any other site, epitope, antigenic determinant, part, domain or stretch of amino acid residues on the target or antigen that is involved in a biological action or mechanism of the antigen. More generally, an "interaction site" can be any site, epitope, antigenic determinant, part, domain or stretch of amino acid residues on the antigen to which an agent of the invention can bind such that the antigen (and/or any pathway, interaction, signalling, biological mechanism or biological effect in which the antigen is involved) is modulated.

In the context of the present invention, "modulating" or "to modulate" generally means either reducing or inhibiting the activity of, or alternatively increasing the activity of, a target or antigen, as measured using a suitable in vitro, cellular or in vivo assay. In particular, "modulating" or "to modulate" may mean either reducing or inhibiting the activity of, or alternatively increasing a (relevant or intended) biological activity of, a target or antigen, as measured using a suitable in vitro, cellular or in vivo assay (which will usually depend on the target or antigen involved), by at least 1%, preferably at least 5%, such as at least 10% or at least 25%, for example by at least 50%, at least 60%, at least 70%, at least 80%, or 90% or more, compared to activity of the target or antigen in the same assay under the same conditions but without the presence of the construct of the invention.

As will be clear to the skilled person. "modulating" may also involve effecting a change (which may either be an increase or a decrease) in affinity, avidity, specificity and/or selectivity of a target or antigen for one or more of its ligands, binding partners, partners for association into a homomultimeric or heteromultimeric form, or substrates; and/or effecting a change (which may either be an increase or a decrease) in the sensitivity of the target or antigen for one or more conditions in the medium or surroundings in which the target or antigen is present (such as pH, ion strength, the presence of co-factors, etc.), compared to the same conditions but without the presence of the construct of the invention. As will be clear to the skilled person, this may again be determined in any suitable manner and/or using any suitable assay known per se, depending on the target or antigen involved.

"Modulating" may also mean effecting a change (i.e. an activity as an agonist, as an antagonist or as a reverse agonist, respectively, depending on the target or antigen and the desired biological or physiological effect) with respect to one or more biological or physiological mechanisms, effects, responses, functions, pathways or activities in which the target or antigen (or in which its substrate(s), ligand(s) or pathway(s) are involved, such as its signalling pathway or metabolic pathway and their associated biological or physiological effects) is involved. Again, as will be clear to the skilled person, such an action as an agonist or an antagonist may be determined in any suitable manner and/or using any suitable (in vitro and usually cellular or in assay) assay known per se, depending on the target or antigen involved. In particular, an action as an agonist or antagonist may be such that an intended biological or physiological activity is increased or decreased, respectively, by at least 1%, preferably at least 5%, such as at least 10% or at least 25%, for example by at least 50%, at least 60%, at least 70%, at least 80%, or 90% or more, compared to the biological or physiological activity in the same assay under the same conditions but without the presence of the construct of the invention.

Modulating may for example also involve allosteric modulation of the target or antigen; and/or reducing or inhibiting the binding of the target or antigen to one of its substrates or ligands and/or competing with a natural ligand, substrate for binding to the target or antigen.

Modulating may also involve activating the target or antigen or the mechanism or pathway in which it is involved. Modulating may for example also involve effecting a change in respect of the folding or confirmation of the target or antigen, or in respect of the ability of the target or antigen to fold, to change its confirmation (for example, upon binding of a ligand), to associate with other (sub)units, or to dissociate. Modulating may for example also involve effecting a change in the ability of the target or antigen to transport other compounds or to serve as a channel for other compounds (such as ions).

Modulating may be reversible or irreversible, but for pharmaceutical and pharmacological purposes will usually be in a reversible manner.

In the context of the present invention, "non-human animal" includes, but is not limited to vertebrate, shark, mammal, lizard, camelid, llama, preferably camelids and most preferably llama or alpaca.

B) METHODS OF THE PRESENT INVENTION

The present invention relates in one aspect to a method for providing to a mammal, e.g. the systemic circulation of a mammal, but is not limited thereto, an effective amount of an immunoglobulin single variable domain and/or construct thereof that can bind to and/or have affinity for at least one antigen, as defined herein. The method comprises the following step: a) administering the immunoglobulin single variable domain and/or construct thereof to the pulmonary tissue of said mammal.

Thus, in general terms (and in a preferred way) the method of the present invention includes systemic delivery of an immunoglobulin single variable domain and/or construct thereof to a mammal mainly via pulmonary tissue absorption. In one particular embodiment, the mammal is a human. In another particular embodiment, the administration is achieved by inhaling said immunoglobulin single variable domain and/or construct thereof to the pulmonary tissue in an aerosol cloud.

One particular advantage of the present invention resides in the fact that it provides a delivery method for immunoglobulin single variable domain and/or construct thereof that is widely applicable and results in a long systemic exposure of said immunoglobulin single variable domain and/or construct thereof. The method of the invention is not limited to have e.g. serum protein binding properties, e.g. serum albumin binding, of said immunoglobulin single variable domain and/or construct thereof to achieve a long exposure but may well include such constructs. In particular, there is no requirement for extending the immunoglobulin single variable domain and/or construct thereof directed against the antigen to add an additional binding unit directed against a particular antigen, e.g. serum albumin binder, in order to extend exposure time in systemic circulation. Advantageously for some of such constructs (e.g. the Nanobody and the constructs in the experimental part of example 1), the method also implies that relatively simple dose calculation for multiple dosing based on experimentally terminal half-life, tau and bioavailability can be performed (based on the assumption that the rate limiting step of the pharmacokinetic properties of immunoglobulin single variable domain and/or construct thereof is absorption controlled). Hence, the method of the present invention is broadly applicable to any druggable antigen, in particular interaction side. In particular, e.g. in a preferred embodiment, the present method is applicable to antigens for which a potent (e.g. a sub-nanomolar IC50 in a relevant in vitro assay) immunoglobulin single variable domain and/or construct thereof, in particular Nanobody and/or construct thereof, to said antigen is available.

In a further embodiment, the method of systemic delivery via the pulmonary route may be beneficial for constructs of immunoglobulin single variable domains that bind to and/or has a specific affinity for an antigen that has a prophylactic and/or therapeutic effect when modulated and bind to and/or has a specific affinity for serum protein such as e.g. serum albumin, e.g. human serum albumin. For such a construct the lung may not be the rate limiting step anymore, and thus the half-life in this case may be driven by clearance and distribution.

Hence, the present invention is advantageous as compared to prior art methods that lack to mention properties as disclosed herein. In particular there is no teaching in the art to what extend in terms of half-life and bioavailability such a method for delivery of immunoglobulin single variable domains and/or constructs thereof to the systemic circulation of mammals such as humans is capable.

More specifically, the present invention provides a first-in-class method for delivering an effective amount of immunoglobulin single variable domains and/or constructs thereof to the systemic circulation of mammals via the pulmonary route, which, according to one specific embodiment, is provided by inhaling a pharmaceutical dosage formulation with an inhaler device.

The device should generate from the formulation an aerosol cloud of the desired particle size of the fine solid particles or liquid droplets (distribution) at the appropriate moment of the mammal's inhalation cycle, containing the right dose of the immunoglobulin single variable domains and/or constructs thereof. The following 4 requirements (formulation, particle size, time and dose) should be considered (Pulmonary Drug Delivery, Bechtold-Peters and Luessen, eds., supra, pages 125 and 126):

- The formulations that are used in the devices may vary from aqueous solutions or suspensions used in nebulizers to the propellant-based solutions or suspensions used in metered dose inhaler or even specially engineered powder mixtures for the dry powder inhalers. All these different formulations require different principles for aerosol generation, which emphasizes the mutual dependency of device and formulation (e.g. Nebulizer formulation contain water with co-solvents such as PEG, ethanol or glycine (in "Inhalation Delivery of Therapeutic Peptides and Proteins" (1997), 2 para, page 246);
- Since the site of deposition of aerosol particles depends on their (aerodynamic) size and velocity, the desired particle size of the aerosol cloud varies depending on the desired site of deposition in the lung, which is related to the therapeutic goal of the administration. Preferably the agents of the invention that are to be absorbed into the systemic circulation should be deposited in the alveoli. Hence, preferably the particle size for the agents of the invention for a human may be within the 1 to 5 micrometer range (see also e.g. in particular page 245 in "Inhalation Delivery of Therapeutic Peptides and Proteins" (1997): Mass median diameters normally range from 2 to 5 um in nebulizers);
- As the aerosol cloud can be tuned to be released at different moments during the inhalation cycle generated by the mammal, it is preferred that for the agents of the invention (to be deposited in the peripheral parts of the lung) the aerosol is released at the start of the inhalation cycle;
- The variety of the agents of the invention that is proposed to be delivered via the pulmonary route implies that doses may vary considerably and may e.g. vary e.g. for a human from a few microgram to several hundreds of microgram or even milligrams, e.g. about up to about 10 milligrams.

Various inhalation systems are e.g. described on pages 129 to 148 in the review ("Pulmonary Drug Delivery", Bechtold-Peters and Luessen, eds., supra) and include, but are not limited to, nebulizers such as e.g. vibrating mesh nebulizers, metered dose inhalers, metered dose liquid inhalers, and dry powder inhalers. Devices taking into account optimized and individualized breathing pattern for controlled inhalation manoeuvres may also be used (see e.g. AKITA® technology on page 157 of "Pulmonary Drug Delivery", Bechtold-Peters and Luessen, eds., supra). Traditionally, nebulizers have been classified into two main types: air-jet (pneumatic) and ultrasonic devices. Recently, a third type, vibrating-mesh nebulizers has been commercialized (Newman, S., Gee-Turner, A., 2005. The Omron MicroAir Vibrating mesh technology nebuliser, a 21st century approach to inhalation therapy. J. Appl. Ther. Res. 5, 29-33). Air-jet nebulizers convert liquid into aerosols by means of a high velocity gas passing through a narrow "venturi" nozzle. The fluid in the nebulizer reservoir is drawn up a feed tube and emerges as fine filaments that collapse into aerosol droplets due to surface tension. In ultrasonic nebulizers, a high frequency vibrating piezoelectric crystal is employed to generate the aerosol. A fountain of fluid is produced at the air-fluid interface. Small droplets are generated from the lower regions of the fountain whilst large droplets are generated from the apex. In both air-jet and ultrasonic nebulizers baffles in the nebulizer trap and recycle the large (primary) aerosol droplets, whilst small (secondary) droplets are released for inhalation. In air-jet nebulizers, the aerosol output comprises aerosolized droplets and solvent vapour which saturates the outgoing air. This induces cooling of the nebulizer fluid and increases solute concentration in the residual volume (Cockcroft, D. W., Hurst, T. S., Gore, B. P., 1989. Importance of evaporative water losses during standardized nebulized inhalation provocation tests. Chest 96, 505-508). Ultrasonic nebulizers are generally unsuitable for delivery of suspensions (Taylor, K. M. G., McCallion, O. N. M., 2002. Ultrasonic nebulizers. In: Swarbrick, J., Boylan, J. C. (Eds.), Encyclopedia of Pharmaceutical Technology, 2nd ed. Marcel Dekker, Inc., New York, pp. 2840-2847) and liposomes (Elhissi. A. M. A., Taylor, K. M. G., 2005. Delivery of liposomes generated from proliposomes using air-jet, ultrasonic, and vibrating-mesh nebulisers. J. Drug Deliv. Sci. Technol. 15, 261-265), and due to heat generation during atomization they may degrade labile substances such as proteins (Niven, R. W., Ip, A. Y., Mittelman, S., Prestrelski, S. J., Arakawa, T., 1995. Some factors associated with the ultrasonic nebulization of proteins. Pharm. Res. 12, 53-59).

Vibrating-mesh nebulizers may overcome the drawbacks of air-jet and ultrasonic nebulizers. Vibrating-mesh devices employ perforated plates which vibrate in order to generate the aerosol. These nebulizers do not heat the fluid during atomization and have been shown to be suitable for delivery of suspensions (Fink, J. B., Simmons, B. S., 2004. Nebulization of steroid suspension: an in vitro evaluation of the Aeroneb Go and Pari LC Plus nebulizers. Chest 126, 816S), and delicate structures such as liposomes (Wagner, A., Vorauer-Uhl, K., Katinger, H., 2006. Nebulization of liposomal rh-Cu/Zn-SOD with a novel vibrating membrane nebulizer. J. Liposome Res. 16, 113-125) and nucleic acids (Lentz, Y. K., Anchordoquy, T. J., Lengsfeld, C. S., 2006. Rationale for the selection of an aerosol delivery system for gene delivery. J. Aerosol Med. 19, 372-384). Moreover, the Aeroneb Pro vibrating-mesh nebulizer in particular is recommended for the delivery of drugs during mechanical ventilation (Pedersen, K. M., Handlos, V. N., Heslet, L., Kristensen, H. G. K., 2006. Factors influencing the in vitro deposition of tobramycin aerosol: a comparison of an ultrasonic nebulizer and a high-frequency vibrating mesh nebulizer. J. Aerosol Med. 19, 175-183). Vibrating-mesh nebulizers are divided into passively and actively vibrating-mesh devices (Newman, S., Gee-Turner, A., 2005. The Omron MicroAir Vibrating mesh technology nebuliser, a 21st century approach to inhalation therapy. J. Appl. Ther. Res. 5, 29-33). Passively vibrating-mesh devices (e.g. Omron MicroAir NE-U22 nebulizer) employ a perforated plate having up to 6000 tapered holes, approximately 3_min diameter. A vibrating Piezo-electric crystal attached to a transducer horn induces "passive" vibrations in the perforated plate positioned in front of it, resulting in extrusion of fluid through the holes and generation of the aerosol. Actively vibrating-mesh devices (e.g. Aeroneb Pro nebulizer) may employ a "micropump" system which comprises an aerosol generator consisting of a plate with up to 1000 dome-shaped apertures and a vibrating element which contracts and expands on application of an electric current. This results in upward and downward movements of the mesh by a few micrometers, extruding the fluid and generating the aerosol.

In pulmonary delivery, the generation of particles smaller than approximately 5 or 6 micrometer is considered necessary to achieve deposition as the fine particle fraction (FPF) (i.e. in the respiratory bronchioles and alveolar region) (O'Callaghan, C., Barry, P. W., 1997. The science of nebulised drug delivery.

Thorax 52, S31-S44).

However, not only the device is important to systemic delivery via the pulmonary route and/or pulmonary delivery of the agent of the invention but also the right formulation is critical to achieve an effective delivery. This can be in principle achieved by using one of the following approaches:

Administration of aqueous solutions or suspensions comprising the agent of the invention (e.g. nasal drops) into the nasal cavities;

Nebulisation of aqueous solutions or suspensions comprising the agent of the invention;

Atomization by means of liquefied propellants; and

Dispersion of dry powders.

Hence formulations of the agent of the inventions have to be adopted and adjusted to the chosen inhalation device. Appropriate formulations, i.e. the excipients in addition to the agent of the invention, are e.g. described in chapter IV of "Pulmonary Drug Delivery", Bechtold-Peters and Luessen, eds., supra.

More particularly, the present invention provides in a specific embodiment, a method for delivery an effective amount of a Nanobody and/or construct thereof that can bind to and/or have affinity for at least one antigen, as defined herein. The method comprises the following step:

a) administering the Nanobody and/or construct thereof to the pulmonary tissue of said mammal.

More particularly, the present invention provides in a specific embodiment, a method for delivery an effective amount of a Nanobody construct that can bind to and/or have affinity for at least one antigen, as defined herein. The method comprises the following step:

a) administering the Nanobody and/or construct thereof to the pulmonary tissue of said mammal; and wherein the construct comprises at least one Nanobody. The construct may also comprise more than one Nanobody, e.g. two Nanobodies or three Nanobodies.

More particularly, the present invention provides in a specific embodiment, a method for delivery an effective amount of a Nanobody construct that can bind to and/or have affinity for at least one antigen. The method comprises the following step:

a) administering the Nanobody and/or construct thereof to the pulmonary tissue of said mammal; and wherein the construct comprises at least one Nanobody. The construct may also comprise more than one Nanobody, e.g. two Nanobodies or three Nanobodies. Furthermore, the construct can bind to and/or have affinity for more than one antigen, e.g. two or three antigens wherein optionally one of the antigens is serum albumin, e.g. human serum albumin.

Furthermore, the present invention provides in a specific embodiment, a method for systemic delivery of an immunoglobulin single variable domain and/or construct thereof that can bind to and/or have affinity for at least one antigen; and wherein the immunoglobulin single variable domain and/or construct thereof has a bioavailability comparable (e.g. within 10% to 20% higher or lower) to the equivalent subcutaneous administration. In a further embodiment, the bioavailability is at least about 10%, or 20%, or 30%, or 40% or 50% of the bioavailability of the equivalent intravenous administration (absolute bioavailability).

Another aspect of the invention is the surprisingly long lasting stability of the immunoglobulin single variable domain and/or construct thereof, in particular Nanobody and/or construct thereof. E.g. it has been found that a Nanobody directed against RSV remains functional in the lung for at least 48 hours (see experimental part). Thus, methods of administration of the invention with dosage intervals of the agents of the invention such as once a day, once every $2^{nd}$, $3^{rd}$, $4^{th}$, $5^{th}$, $6^{th}$ or once every week, preferably once a day, are thought to be possible taken the estimated long lasting stability, potential bioavailability and half-life in systemic circulation.

It has also been surprisingly found, that in view of the high bioavailability of systemic delivery of the agents of the invention, e.g. as shown in the experimental part of this application, and the long lasting controlled release (e.g. the pseudo-equilibrium pharmacokinetic with relative long terminal half-life as shown in the experimental part) into systemic circulation, dosage intervals of once a day, or longer, e.g. every $2^{nd}$, $3^{rd}$, $4^{th}$, $5^{th}$, $6^{th}$, or once a week, preferably once a day may be possible. In particular, dosage intervals of the agent of the invention comprising e.g. a serum albumin binder, e.g. human serum albumin binder, as described in the previous sentence may be feasible. This underlines the particular advantage of the present invention of resulting in an easy to use, non-invasive delivery method that provides a long lasting systemic exposure of the agent of the invention allowing for once daily or longer interval dosing, e.g. up to once weekly dosing. It was unforeseeable from the prior art that such advantages can be obtained by using the pulmonary delivery route, in particular as the prior art suggests that systemic delivery via the pulmonary route is minimal (WO2007/049017).

Dose:

The appropriate dosage will of course vary depending upon, for example, the inhalation/formulation employed, the host, and the nature and severity of the condition being treated. However, in general, satisfactory results in animals are indicated to be obtained at a daily dosage of from about 0.1 to about 10 mg/kg, e.g. about 5 mg/kg animal body weight. In larger mammals, for example humans, an indicated daily dosage is in the range from about 1 to about 200 mg, preferably about 1 to about 10 mg of the compound conveniently administered as described herein.

The present invention furthermore provides a pharmaceutical composition for pulmonary administration intended for pulmonary but in particular also for systemic delivery comprising an agent of the invention in association with at least one pharmaceutically acceptable diluent or carrier. Such compositions may be formulated in conventional manner as e.g. described and/or referenced herein. Unit dosage forms contain, for example, from about 0.25 to about 10 mg, preferably about 1 mg, of an agent according to the invention.

The general principles of the present invention as set forth above will now be exemplified by reference to specific experiments. However, the invention is not to be understood as being limited thereto.

The entire contents of all of the references (including literature references, issued patents, published patent applications, and co-pending patent applications) cited throughout this application are hereby expressly incorporated by reference.

BRIEF DESCRIPTION OF A SUBSET OF THE TABLES

Table 1: Immunization scheme as described in Example 1
Table 2: Presence of insert by PCR with vector specific primers as described in Example 1
Table 3: First selection as described in Example 1
Table 4: Second selection using the rescued phages from the first selection as described in Example 1
Table 5: Second round selection using neutravidine coated tubes as described in Example 1
Table 6: Number of clones that score positive for binding to both human IgE and chimeric IgE versus the number of clones tested in ELISA as described in Example 1
Table 7: Treatment schedule
Table 8: Overview of the libraries, their diversity and % insert derived from different llama's and tissues as described in Example 7 and 8
Table 9: Immunization schedule and tissue collections
Table 10: Overview of constructed libraries
Table 11: Overview of epitope specific elution selection procedure
Table 12: Overview of 'internalization' selection procedure
Table 13: Primer sequences
Table 14: Sequence listing

EXAMPLES

Legends of a Subset of the Examples

IgE
Example 1: VHH directed against IgE
Example 2: Formulation of VHH anti-IgE
Example 3: Anti-IgE formulation
TNF-Alpha
Example 4: Selection of anti-TNF-alpha
Example 5: Stability testing of antibody fragments specific for human TNFα
Example 6: Oral administration of an anti-human TNFα specific VHH in mice
Example 7: Efficacy in an animal model for IBD
MMP12
Example 8: Immunization
Example 9: Repertoire cloning
Example 10: Rescue of the library and phage preparation Example 11: Selection of human MMP-12 specific VHH
Example 12: Specificity of selected VHH's
Example 13: Diversity of selected VHH's
Example 14: Expression and purification of VHH
Example 15: Functional characterization of selected VHH's: inhibition of MMP-12 proteolytic activity by a VHH in a colorimetric assay.
Example 16: Formulation of anti-MMP12 VHH for pulmonary delivery
Interferon Gamma
Example 17: Immunization
Example 18: Repertoire cloning
Example 19: Rescue of the library and phage preparation
Example 20: Selection of human-IFN gamma VHH
Example 21: Diversity of selected VHH's
Example 22: Expression and purification of VHH
Example 23: Topical applications of anti-IFN gamma VHH's
Therapeutic VHH-Fragments
Example 24: Expression of VHH-CDR3 of anti-TNF alpha VHH#3E
EGFR
Example 25: Immunization
Example 26: Evaluation of immune response
Example 27: Cloning of the heavy-chain antibody fragment (VHH) repertoire
Example 28: Evaluation of the cloned repertoire
Example 29: Multiple selection strategies to identify EGFR specific nanobodies
Example 30: Characterization of EGFR specific nanobodies
Example 31: EGF receptor mediated internalization of nanobodies
PDK1
Example 32: Immunisation of llamas
Example 33: Repertoire cloning
Example 34: Rescue of the library, phage preparation
Example 35: Selection
Example 36: Screening
Example 37: Screen for internalised VHH
Example 38: Screen for VHH inhibiting PDK1-Akt interaction
Example 39: Making a bispecific construct
Example 40: Endocytosis and lysis of tumor cells
Example 41: Calculation of homologies between anti-target-single domain antibodies of the invention
Example 42: Construction of a bispecific constructs containing a VHH-CDR3 fragment fused to an anti-serum albumin VHH
IgE Example 1: VHH Directed Against IgE Two llama's were immunized with human IgE, Scripps laboratories, Cat nr. I0224. The following immunization schemes were used according to Table 1.
Different sources for RNA extraction were used:
150 ml immune blood, between 4 and 10 days after the last antigen injection
lymph node biopsy 4 days after the last antigen injection
Peripheral blood lymphocytes (PBLs) were isolated by centrifugation on a density gradient (Ficoll-Paque Plus Amersham Biosciences). PBLs and lymph node were used to extract total RNA (Chomczynski and Sacchi 1987). cDNA was prepared on 200 μg total RNA with MMLV Reverse Transcriptase (Gibco BRL) using oligo d(T) oligonucleotides (de Haard et al., 1999). The cDNA was purified with a phenol/chloroform extraction, followed by an ethanol precipitation and subsequently used as template to amplify the VHH repertoire.

In a first PCR, the repertoire of both conventional (1.6 kb) and heavy-chain (1.3 kb) antibody gene segments were amplified using a leader specific primer (5'-GGCT-GAGCTCGGTGGTCCTGGCT-3'; SEQ ID NO:85) and the oligo d(T) primer (5'-AACTGGAAGAATTCGCGGC-CGCAGGAATTTTTTTTTTTTTTTTTT-3'; SEQ ID NO:86). The resulting DNA fragments were separated by agarose gel electrophoresis and the 1.3 kb fragment encoding heavy-chain antibody segments was purified from the agarose gel. A second PCR was performed using a mixture of FR1 reverse primers (WO03/054016 sequences ABL037 to ABL043) and the same oligo d(T) forward primer.

The PCR products were digested with SfiI (introduced in the FR1 primer) and BstEII (naturally occurring in framework 4). Following gel electrophoresis, the DNA fragments of approximately 400 basepairs were purified from gel and ligated into the corresponding restriction sites of phagemid pAX004 to obtain a library of cloned VHHs after electroporation of *Escherichia coli* TG1. pAX004 allows the production of phage particles, expressing the individual VHHs as a fusion protein with a c-myc tag, a hexahistidine tag and the geneIII product. The percentage insert was determined in PCR using a combination of vector based primers.

Results are summarized in Table 2.

Selections were done using chimaeric IgE instead of human IgE, used for immunization, in order to select for VHH molecules directed against the constant region of IgE. The region interacting with the Fcε-receptor is located in the constant part of IgE, more in particular in the region covered by Cε2-Cε3 as shown in FIG. 1.

A first selection was performed using the pool of PBL day4, PBL day10 and lymph node day4 libraries for each of the two llama's. Chimaeric IgE was solid phase coated at 5 μg/ml and 0.5 μg/ml and specific phages were eluted using 0.1 M glycine pH=2.5.

The results obtained are shown in Table 3.

A second selection was performed using the rescued phages from the first selection using 5 μg/ml. Chimaeric IgE was solid phase coated at 1 μg/ml and specific phages were eluted using buffy coat cells or lysozyme for 1 hr. Buffy coat cells contain cells expressing the Fcεreceptor, while lysozyme is an irrelevant protein and serves as a control. The results obtained are shown in Table 4.

Another second round selection was performed using neutravidine coated tubes and 2 nM biotinylated IgE. Specific phages were eluted using buffy coat cells or lysozyme for 1 hr. Buffy coat cells contain cells expressing the Fcεreceptor, while lysozyme is an irrelevant protein and serves as a control. The results obtained are shown in Table 5.

Individual clones obtained from the first round of selection were screened in an ELISA using solid phase coated human IgE or chimaeric IgE. The number of clones that score positive for binding to both human IgE and chimeric IgE versus the number of clones tested in ELISA are summarized in Table 6.

Clones were picked which were positive for human and chimaeric IgE binding, amplified by PCR and digested with HinfI. HinfI profiles were determined on agarose gel and representative clones for different profiles were sequenced. The sequences obtained are shown in Table 14 SEQ ID NOs: 1 to 11.

Example 2: Topical Applications of Anti-IgE VHH's

To obtain anti-allergic pharmaceutical compositions for ophthalmic topical applications, a solution of anti-IgE VHH was prepared as follows:
eye drops containing a therapeutic dose of anti-IgE VHH dissolved in 100 ml of sterilized water containing 0.9 g sodium chloride, 0.02 g sodium citrate, 0.02 g methyl parahydroxybenzoate, 0.1 g chlorobutanol and acetic acid suitable to obtain a pH of 6.5.
eye ointment containing a therapeutic dose of anti-IgE VHH was prepared according to the conventional method containing 1.0 g of liquid paraffin and a suitable amount of soft paraffin to obtain a total mixture of 100 g.

Example 3: Anti-IgE Formulation

Anti-IgE VHH's that block binding of IgE to its high-affinity receptor are of potential therapeutic value in the treatment of allergy.

Highly purified VHH#2H11 was dialysed into formulation buffer, followed by addition of lyoprotectant at an isotonic concentration. Isotonic formulation was performed as follows: VHH#2H11 at 25 mg/ml was formulated in 5 mM histidine buffer at pH 6 with 500 moles of sugar per mole antibody. This formulation is reconstituted with BWFI (0.9% benzyl alcohol) at a volume which results in a 100 mg/ml of antibody in 20 mM histidine at pH 6 with an isotonic sugar concentration of 340 nM. The binding activity of the anti-IgE VHH in the isotonic formulations was measured in an IgE receptor inhibition assay. It was found that binding activity was essentially unchanged following storage at 4° C. for up to 3 months.

TNF-Alpha

Example 4: Selection of Anti-TNF-Alpha

Two llamas were immunized with 100 μg human TNF-alpha □ per injection according to the schedule described in Example 1. The libraries (short and long immunization procedure) were constructed and selected with in vitro biotinylated TNF-alpha. The biotinylation was carried out as described by Magni et al (Anal Biochem 2001, 298, 181-188).

The incorporation of biotin in TNF was evaluated by SDS-PAGE analysis and detection with Extravidin-alkaline phosphatase conjugate (Sigma).

The functionality of the modified protein was evaluated for its ability to bind to the solid phase coated recombinant a p75 receptor. {biotinylation} In the first round of selection 400 ng and 50 ng of biotinylated TNF-alpha was captured on neutravidin (Pierce; 10 pig/ml in PBS) coated on the wells of a microtiter plate (NUNC maxisorb). Phage ($1.2 \times 10^{10}$ TU-s) were added to the wells and incubated for two hours at room temperature. After washing (20 times with PBS-tween and two times with PBS) bound phage was eluted by adding an excess of receptor (extracellular domain of CD120b or p75; 10 μM) or with cells expressing the intact TNF receptor. Between 30,000 and 100,000 phage clones were eluted with TNF from the library derived from the llama immunized using the rapid scheme, while about 10% of these numbers were obtained when eluted with BSA (3 μM; negative control).

From the other library (long immunization scheme) 10-fold high numbers were eluted with receptor and BSA, yielding the same enrichment factor (10) as observed before. New phage was prepared from the elution of 50 ng TNF (rapid immunization scheme) and 400 ng TNF (slow scheme) and used for another round of selection on 400, 50 and 10 ng of captured TNF (input: $1.2 \times 10^{10}$ phage per well). Approx. $2.5 \times 10^7$ phage were eluted with receptor (10 μM) from the well containing 400 ng and 50 ng of captured TNF and about $2 \times 10^6$ from the well with 10 ng of TNF, while the negative control (elution with 10 μM of BSA) gave only 5 to 10% of those numbers. The observed numbers of eluted phage suggest that the elution with receptor is specific and that those VHH fragments should be eluted that bind to the receptor binding site of TNF.

Individual clones were picked and grown in microtiter plate for the production of VHH in culture supernatants. ELISA screening with TNF captured on Extravidin coated plates revealed about 50% positive clones. HinFI-fingerprint analysis showed that 14 different clones were selected, which were grown and induced on 50 ml scale.

Periplasmic fractions were prepared, the VHH fragments purified with IMAC and used in an assay to analyze their antagonistic characteristics, i.e. preventing the interaction of TNF with its receptor. For this purpose the VHH (1 μM and 0.3 μM) was incubated with TNF-alpha (3 and 0.7 nM) for 1.5 hours at room temperature (in 0.2% casein/PBS). 100 μl of this mixture was transferred to a well of a microtiter plate, in which the extracellular domain of the receptor was immobilized. After an incubation of one hour the plate was washed and bound TNF was detected with alkaline phosphatase conjugated streptavidin. Two VHH fragments gave antagonistic profiles similar as obtained with 3 and 0.3 μM intact mAB Remicade (Infliximab; Centercor) in spite of the fact that the VHH is truly monomeric, whereas the dimeric appearance of the mAB probably favors the binding of the trimeric TNF-molecule. Similar experiments showing the efficacy of the VHH were performed using the murine sarcoma cell line WEHI and a human cell line expressing the TNF receptor. □ The sequences obtained are shown in Table 14 SEQ ID NOs: 12 to 13.

Example 5: Stability Testing of Antibody Fragments Specific for Human TNFα

Figure 2:
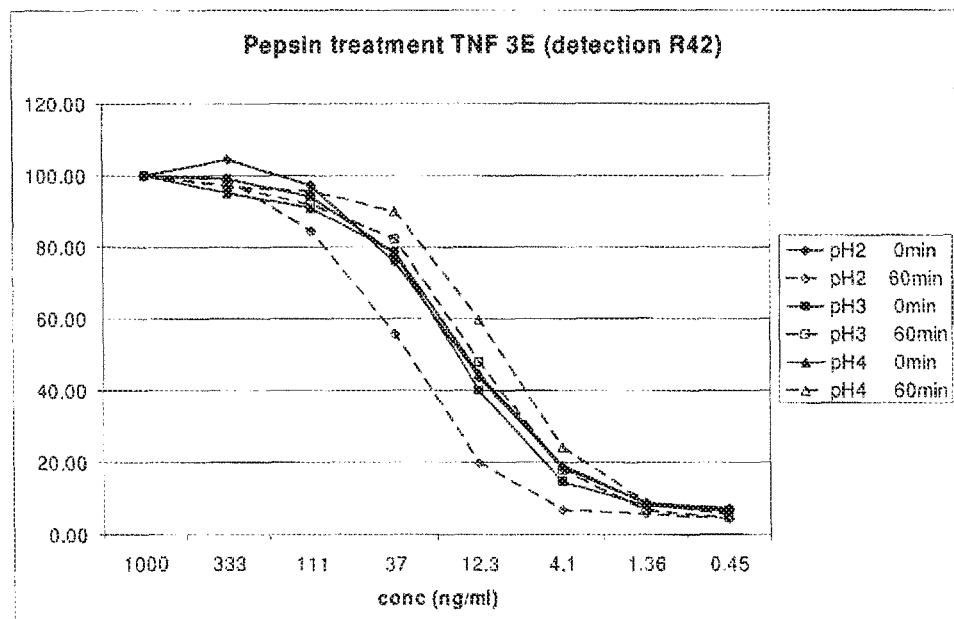
FIG. 2: ELISA of reference and pepsin-treated TNF3E at pH2.2, pH3.2 and pH4.2 (100% is the signal measured at a 1/100 dilution)

Orally administered proteins are subject to denaturation at the acidic pH of the stomach and as well to degradation by pepsin. We have selected conditions to study the resistance of the VHH TNF3E to pepsin which are supposed to mimick the gastric environment. TNF3E a VHH specific to human TNFα was produced as recombinant protein in *E. coli* and purified to homogeneity by IMAC and gelfiltration chromatography. The protein concentration after purification was determined spectrophotometrically by using the calculated molar extinction coefficient at 280 nm. Diluted solutions at 100 microgram/ml were prepared in McIlvaine buffer (J. Biol. Chem. 49, 1921, 183) at pH 2, pH3 and 4 respectively. These solutions were subsequently incubated for 15 minutes at 37° C., prior the addition of porcine gastric mucosa pepsin at a 1/30 w/w ratio. Sixty minutes after adding the protease a sample was collected and immediately diluted 100-fold in PBS pH7.4 containing 0.1% casein to inactivate the pepsin. Seven additional 3-fold dilutions were prepared from this sample for assessing the presence of functional antibody fragment by ELISA. Identical dilutions prepared from an aliquot collected prior the addition of the protease served as a reference. In the ELISA assay biotinylated TNFα was captured in wells of a microtiter plate coated with neutravidin. For both the pepsin-treated and reference samples similar serial dilutions of the samples were prepared and 100 microliter of those dilutions were added to the wells. After incubation for 1 hour the plates were washed. For the detection of VHH binding to of the captured TNFα a polyclonal rabbit anti-VHH antiserum (R42) and an anti-rabbit IgG alkaline phosphatase conjugate was used. After washing, the plates were developed with para nitrophenyl phosphate. The data plotted in FIG. 2 shows similar curves for all of the samples exposed to digestive conditions as well as for the reference samples. This indicates that the VHH 3E essentially retains its functional activity under all of the chosen conditions.

Example 6: Oral Administration of an Anti-Human TNFα Specific VHH in Mice

An antibody solution containing the anti-human TNFα specific VHH#TNF3E (100 microgram per milliliter in 100-fold diluted PBS) was prepared. Three mice which were first deprived from drinking water for 12 hours and subsequently allowed to freely access the antibody solution during the next two hours. Afterwards the mice were sacrificed and their stomachs were dissected. Immediately the content of the stomachs was collected by flushing the stomach with 500 microliter PBS containing 1% BSA. This flushed material was subsequently used to prepare serial three-fold dilutions, starting at a 1/5 dilution from the undiluted material. One hundred microliter of these samples was transferred to individual wells of a microtiter plater coated with human TNFα. After incubation for 1 hour and following extensive washing the presence of immuno-reactive material was assessed with a polyclonal rabbit anti-VHH antiserum (R42) followed by incubation with an anti-rabbit alkaline-phosphatase conjugate. The ELISA was developed with paranitrophenyl phosphate. The ELISA signals obtained after 10 minutes clearly demonstrated the presence of functional VHH TNF3E in the gastric flushings of these mice. By comparing to the standard curve we determined the concentration of the functional antibody fragment in the gastric flushing fluid to be 1.5, 12.6 and 8.6 microgram/ml for the three mice tested.

Example 7: Efficacy in an Animal Model for IBD

1) Animal Model of Chronic Colitis

Figure 3:
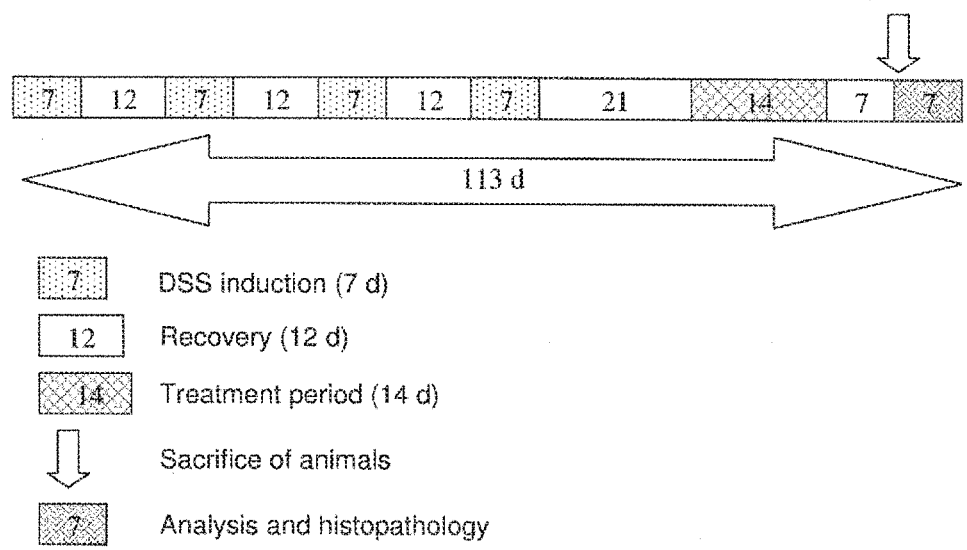
FIG. 3: Experimental setting

The efficacy of bivalent VHH constructs applied via various routes of administration was assessed in a DSS (dextran sodium sulfate) induced model of chronic colitis in BALB/c mice. This model was originally described by Okayasu et al. [Okayasu et al. Gastroenterology 1990; 98: 694-702] and modified by Kojouharoff et. al. [G. Kojouharoff et al. Clin. Exp. Immunol. 1997; 107: 353-8]. The animals were obtained from Charles River Laboratories, Germany, at an age of 11 weeks and kept in the animal facility until they reached a body weight between 21 and 22 g. Chronic colitis was induced in the animals by four DSS treatment cycles. Each cycle consisted of a DSS treatment interval (7 days) where DSS was provided with the drinking water at a concentration of 5% (w/v) and a recovery interval (12 days) with no DSS present in the drinking water. The last recovery period was prolonged from 12 to 21 days to provide for an inflammation status rather representing a chronic than an acute inflammation at the time of the treatment. Subsequent to the last recovery interval the mice were randomly assigned to groups of 8 mice and treatment with the VHH-constructs was started. The treatment interval was 2 weeks. One week after the end of the treatment interval the animals were sacrificed, the intestine was dissected and histologically examined. The experimental setting is shown schematically in FIG. 3.

2) VHH Treatment Schedule

During the VHH treatment period the mice (8 animals per group) were treated daily for 14 consecutive days with bivalent VHH#3F (VHH#3F-VHH#3F; SEQ ID No. 14) by intra-gastric or intra-venous application of 100 μg bivalent VHH 3F. An additional group of animals was treated rectally with the bivalent VHH#3F every other day for a period of 14 days. In all treatment groups a dose of 100 μg of the bivalent VHH#3F was applied at a concentration of 1 mg/ml in a buffered solution. The negative control groups received 100 μl of PBS under otherwise identical conditions. The treatment schedule is shown in Table 7.

3) Results

After the mice were sacrificed the body weight was determined and the colon was dissected. The length of the dissected colon was determined and the histology of the colon was assessed by Haematoxilin-Eosin (HE) stain (standard conditions). As compared to the negative controls (PBS treatment) the groups treated with bivalent nanobody 3F showed a prorogued colon length as well as an improved histological score [G. Kojouharoff et al. Clin. Exp. Immunol. 1997; 107: 353-8] thereby demonstrating efficacy of the treatment.

MMP12

Example 8: Immunization

One llama's (llama 5) was immunized intramuscularly with recombinant human catalytic domain of MMP12 using an appropriate animal-friendly adjuvant Stimune (Cedi Diagnostics BV, The Netherlands). The recombinant catalytic domain was acquired from Prof. H. Tschesche Universität Bielefeld and was supplied as a 56 μg/ml solution in 5 mM Tris/HCl pH=7.5, 100 mM NaCl, 5 mM CaCl$_2$ (Lang, R. et al. (2001). The llama received 6 injections at weekly intervals, the first two injections containing each 10 μg of MMP-12, the last four injections containing each 5 μg of MMP-12. Four days after the last immunization a lymph node biopsy (LN) and a blood sample (PBL1) of 150 ml was collected from the animal and serum was prepared. Ten days after the last immunization a second blood sample (PBL2) of 150 ml was taken and serum was prepared. Peripheral blood lymphocytes (PBLs), as the genetic source of the llama heavy chain immunoglobulins (HcAbs), were isolated from the blood sample using a Ficoll-Paque gradient (Amersham Biosciences) yielding 5×10$^8$ PBLs. The maximal diversity of antibodies is expected to be equal to the number of sampled B-lymphocytes, which is about 10% of the number of PBLs (5×10$^7$). The fraction of heavy-chain antibodies in llama is up to 20% of the number of B-lymphocytes. Therefore, the maximal diversity of HcAbs in the 150 ml blood sample is calculated as 10' different molecules. Total RNA was isolated from PBLs and lymph nodes according to the method of Chomczynski and Sacchi (1987).

Example 9: Repertoire Cloning cDNA was prepared on 200 μg total RNA with MMLV Reverse Transcriptase (Gibco BRL) using oligo d(T) oligonucleotides (de Haard et al., 1999). The cDNA was purified with a phenol/chloroform extraction, followed by an ethanol precipitation and subsequently used as template to amplify the VHH repertoire.

In a first PCR, the repertoire of both conventional (1.6 kb) and heavy-chain (1.3 kb) antibody gene segments were amplified using a leader specific primer (5'-GGCTGAGCTCGGTGGTCCTGGCT-3'; SEQ ID NO:87) and the oligo d(T) primer (5'-AACTGGAAGAATTCGCGGCCGCAGGAATTTTTTTTTTTTTTTTTT-3'; SEQ ID NO:88). The resulting DNA fragments were separated by agarose gel electrophoresis and the 1.3 kb fragment encoding heavy-chain antibody segments was purified from the agarose gel. A second PCR was performed using a mixture of FR1 reverse primers (WO03/054016 sequences ABL037 to ABL043) and the same oligo d(T) forward primer.

The PCR products were digested with SfiI (introduced in the FR1 primer) and BstEII (naturally occurring in framework 4). Following gel electrophoresis, the DNA fragments of approximately 400 basepairs were purified from gel and ligated into the corresponding restriction sites of phagemid pAX004 to obtain a library of cloned VHHs after electroporation of *Escherichia coli* TG1. pAX004 allows the production of phage particles, expressing the individual VHHs as a fusion protein with a c-myc tag, a hexahistidine tag and the geneIII product. The diversity obtained after electroporation of TG1 cells is presented in Table 8. The percentage insert was determined in PCR using a combination of vector based primers.

Example 10: Rescue of the Library and Phage Preparation

The library was grown at 37° C. in 10 ml 2×TY medium containing 2% glucose, and 100 µg/ml ampicillin, until the $OD_{600\ nm}$ reached 0.5. M13KO7 phages ($10^{12}$) were added and the mixture was incubated at 37° C. for 2×30 minutes, first without shaking, then with shaking at 100 rpm. Cells were centrifuged for 5 minutes at 4,500 rpm at room temperature. The bacterial pellet was resuspended in 50 ml of 2×TY medium containing 100 µg/ml ampicillin and 25 µg/ml kanamycin, and incubated overnight at 37° C. with vigorously shaking at 250 rpm. The overnight cultures were centrifuged for 15 minutes at 4,500 rpm at 40. Phages were PEG precipitated (20% poly-ethylene-glycol and 1.5 M NaCl) for 30 minutes on ice and centrifuged for 20 minutes at 4,500 rpm. The pellet was resuspended in 1 ml PBS. Phages were again PEG precipitated for 10 minutes on ice and centrifuged for 10 minutes at 14,000 rpm and 4°. The pellet was dissolved in 1 ml 0.5% skimmed milk or PBS-BSA [1 mg/ml](Sigma, Cat Nr A3059).

Example 11: Selection of Human MMP-12 Specific VHH

Phages were rescued and prepared as described above in Example 10.

Two approaches were followed to obtain MMP-12 specific binders:
a. Inactive MMP-12 Coated on PVDF Membrane
100 ng human MMP-12 catalytic domain (diluted in 33 µl PBS) was spotted on small pieces (1 cm²) of PVDF (Immobilon-P, Millipore, Cat Nr IPVH 15150) following the manufacturers guidelines, resulting in an inactive MMP due to the MeOH fixation. As controls an equal amount of lysozyme (Sigma, Cat Nr L-6876) and 33 µl PBS were also spotted and immobilized. The membrane pieces were blocked overnight in 5% skimmed milk at 4° C. and were washed 3 times with PBS before the phage preparation was applied (4×10⁹ phages in 1 ml [5% skimmed milk]). Phages and membrane pieces (in 1.5 ml tubes) were incubated for 3 hrs at room temperature with rotation. Then the membranes were transferred to 15 ml tubes and were washed 6 times with 10 ml [PBS+0.05% Tween-20]. Phages were eluted by exposing the membranes to 500 µl TEA [70 µl in 5 ml $H_2O$] for min while rotating. The solution containing the eluted phages was removed and the pH was neutralized with 1M Tris pH=7.5.

Log phase growing TG1 cells were infected with the eluted phages and serial dilutions were plated on selective medium. Enrichment was determined by the number of transfected TG1 colonies after selection obtained from the MMP-12 coated membrane as compared with the negative control where lysozyme was immobilized. Bacteria from MMP selections showing enrichment were scraped and used for a second round of selection. The bacteria were superinfected with helperphage to produce recombinant phages to do a second selection against MMP-12 (as described in Example 9). MMP-12 was immobilized as above and the membrane was blocked overnight at 4° C. in 5% skim milk. Phages ($2.5 \times 10^9$ in 1 ml) were prepared and exposed to the membranes and further selected for MMP binding as during the first round of selection. Log phase growing TG1 cells were infected with the eluted and pH neutralized phages and plated on selective medium. Enrichment was determined by the number of transfected TG1 colonies from the MMP-12 coated membrane as compared with the negative control (immobilized lysozyme).

b. Active MMP-12 Coated on Nitrocellulose Membrane
250 ng human MMP-12 catalytic domain (Biomol Research laboratories Inc, SE 138-9090) was spotted directly on a piece of Hybond-C extra (Amersham Biosciences, Cat Nr RPN 303E) following the suppliers guidelines. As control an equal volume of PBS was spotted. A 5 mm diameter disk, containing the spotted area was cut out from each membrane and was transferred to a 1.5 ml tube and blocked overnight at 4° C. in 1 ml BSA-PBS [1 mg/ml]. The disks were washed three times in 15 ml PBS and subsequently transferred and exposed to the 200 ul phage preparation in a microtiterplate well. The phages were prepared as in Example 9 but were preincubated in BSA-PBS for 15 min at room temperature. The disks were washed 5 times with PBS/0.05% Tween-20 and were blocked with PBS-BSA for 2 hrs at room temperature. Phages were eluted by exposing the membranes to 100 µl TEA [70 µl in 5 ml $H_2O$] for 10 min while rotating. The solution containing the eluted phages was removed and the pH was neutralized with 1M Tris pH=7.5.

Log phase growing TG1 cells were infected with the eluted phages and plated on selective medium. Enrichment was determined by the number of transfected TG1 colonies after selection on the MMP-12 membrane disk as compared with the negative control (PBS). Bacteria from selections with MMP-12 were scraped and used for a second round of selection.

The bacteria were superinfected with helperphage to produce recombinant phages to do a second selection against MMP-12 (as described in Example 9). MMP-12 was immobilized as above and the membrane was blocked overnight at 4° C. in PBS-BSA [1 mg/ml]. Phages ($2.5 \times 10^9$ in 1 ml) were prepared and exposed to the membranes and further selected for MMP binding as during the first round of selection. Log phase growing TG1 cells were infected with the eluted and neutralized phages and plated on selective medium. Enrichment was determined by the number of transfected TG1 colonies from the MMP-12 coated membrane as compared with the negative control.

Example 12: Specificity of Selected VHH's

Individual clones were picked, grown in 150 µl 2xTY containing 0.1% glucose and 100 µg/ml ampicillin in a microtiter plate at 37° C. until $OD_{600\ nm}$=0.6. Then 1 mM IPTG and 5 mM $MgSO_4$ was added and the culture was incubated 4 hours at 37° C. ELISA was performed on the periplasmic extracts (PE, preparation see Example 13) of the cells to examine specificity of the selected clones.

To examine the clones selected using solid phase coated human MMP-12, plates were coated with human MMP-12 catalytic domain at a concentration of 1 µg/ml overnight at 4° C. Plates were washed 5 times with PBS/0.05% Tween-20. Wells were blocked with 1% skimmed milk for 2 hrs at room temperature. Periplasmic extracts (100 µl) were applied to the wells and incubated for 1 hour at room temperature. Plates were washed 5 times with PBS/0.05% Tween-20. Detection was performed using anti-c-myc antibody, followed by anti-mouse-HRP and $ABTS/H_2O_2$ as substrate. Plates were read at 405 nm after 30 minutes incubation at room temperature.

To examine the clones selected using membrane immobilized human MMP-12, 50 ng human MMP-12 catalytic domain samples were spotted on PVDF membrane as described in the manufacturers guidelines. 50 ng lysozyme was spotted as a negative control. The membranes were blocked with skimmed milk overnight at 4° C., washed 5 times with PBS and transferred to 1.5 ml tubes. Periplasmic extracts (100 µl) were tenfold diluted in 1% skimmed milk and 1 ml was applied per membrane (2 cm²) and rotated for 1 hour at room temperature. Membranes were washed 5 times with PBS/0.05% Tween-20. Detection was performed using anti-c-myc antibody, followed by anti-mouse-HRP and DAP as substrate. Membranes were incubated with substrate at room temperature until clear spots were visible. Seven clones which were found to be MMP-12 specific binders are shown in Table 14 SEQ ID NOs 15 to 21.

In order to check for non specific binding to other MMPs a similar approach was followed in which 50 ng of active catalytic domain of MMP 1, 2, 3, 7, 9 and 13 (all from Biomol Research laboratories Inc) was immobilized on Hybond C-extra. The membranes were blocked with skimmed milk overnight at 4° C., washed 5 times with PBS and transferred to 1.5 ml tubes. Periplasmic extracts (100 µl) were tenfold diluted in 1% skimmed milk and 1 ml was applied per membrane (2 cm²) and rotated for 1 hour at room temperature. Membranes were washed 5 times with PBS/0.05% Tween-20. Detection was performed using anti-c-myc antibody, followed by anti-mouse-HRP and DAP as substrate. Membranes were incubated with substrate at room temperature until clear spots were visible. No significant detection of the seven selected VHH clones was observed on any of the MMPs other than MMP-12.

Results on binders selected against PVDF membrane immobilized human MMP-12 catalytic domain are presented in Table 14 SEQ ID NOs 15 to 21.

Results on MMP-12 inhibitors selected via Hybond membrane immobilization are presented in Table 14 SEQ ID NO 22.

Example 13: Diversity of Selected VHH's

PCR was performed using M13 reverse and genIII forward primers. The clones were analyzed using Hinf1 fingerprinting and representative clones were sequenced. Sequence analysis was performed resulting in the sequences which are presented in Table 14 SEQ ID NOs 15 to 21 for Immobilon-P selections and in Table 14 SEQ ID NO 22 for Hybond-C.

Example 14: Expression and Purification of VHH

Clones were grown in 50 ml 2xTY containing 0.1% glucose and 100 µg/ml ampicillin in a shaking flask at 37° C. until $OD_{600\ nm}$=2. 1 mM IPTG and 5 mM $MgSO_4$ was added and the culture was incubated for 3 more hours at 37° C. Cultures were centrifuged for 10 minutes at 4,500 rpm at 4° C. The pellet was frozen overnight at −20° C. Next, the pellet was thawed at room temperature for 40 minutes, re-suspended in 1 ml PBS/1 mM EDTA/1M NaCl and shaken on ice for 1 hour. Periplasmic fraction was isolated by centrifugation for 10 minutes at 4° C. at 4,500 rpm. The supernatant containing the VHH was loaded on Ni-NTA (Qiagen) and purified to homogeneity on an Äkta FPLC chromatography system (Amersham Biosciences). The VHH were eluted from the Ni-NTA using 25 mM citric acid pH=4.0 and directly applied on a cation exchange column equilibrated in 25 mM citric acid pH=4.0 (Source 30S in a HR5/5 column. Amersham Biosciences). The VHH were eluted with 1M NaCl in PBS and further purified on a size exclusion column (Superdex 75 HR10/30, Amersham Biosciences) equilibrated in MMP-12 assay buffer [50 mM HEPES, 100 mM NaCl, 0.05% Brij-35]. The yield of VHH was calculated according to the extinction coefficient and peak surface area.

Example 15: Functional Characterization of Selected VHH's: Inhibition of MMP-12 Proteolytic Activity by a VHH in a Colorimetric Assay VHHs were expressed and purified as described in Example 13. Purified VHH was analyzed for the ability to inhibit human MMP-12 catalytic domain using the MMP-12 Colorimetric Assay Kit for Drug Discovery (AK-402) from BIOMOL Research Laboratories. The experimental method conditions described in the Kit were followed.

The inhibitor supplied with the Kit (P1115-9090) was used as positive control at the recommended concentration. VHH were applied at a concentration of 7 µM. The assay was performed in the microtiterplate supplied with the BIOMOL Kit and MMP-12 proteolytic activity was followed in a plate reader (405 nm) at 37° C.

Figure 4:
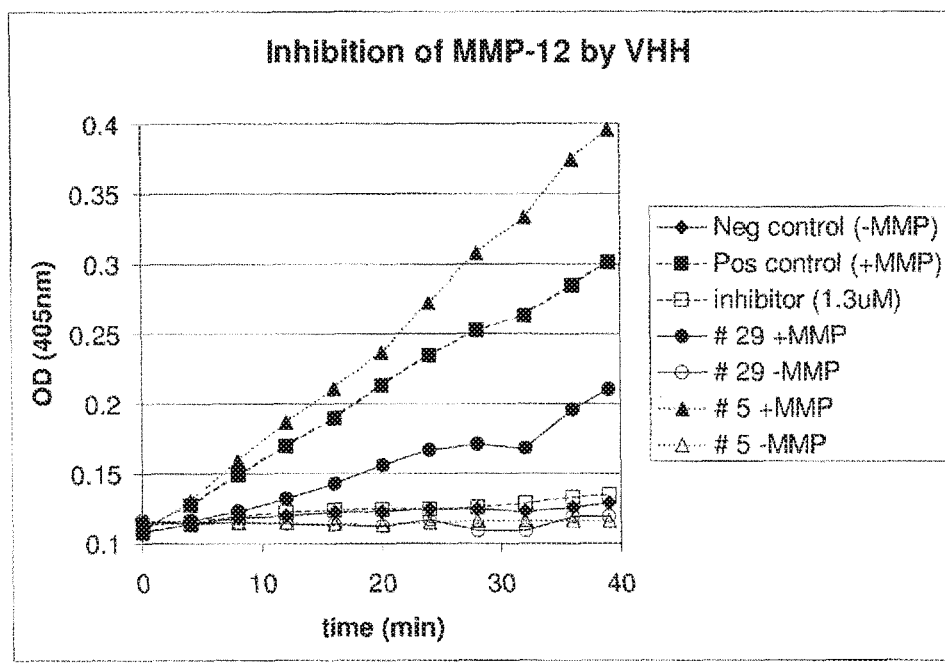
FIG. 4: Capacity of VHH clones to inhibit the proteolytic activity of human catalytic domain of MMP12

The results of one inhibitory VHH and an inactive VHH are presented in FIG. 4 together with a positive control.

Only one VHH molecule (clone P5-29) from selections using active MMP-12 coated on nitrocellulose (Example 12) showed inhibition of human MMP-12 catalytic domain. All other MMP-12 binders (only clone P5-5 is shown), although they bind MMP-12, did not inhibit MMP-12.

Example 16: Formulation of Anti-MMP12 VHH for Pulmonary Delivery

A 100% formulation of antibody was prepared by dissolving 5 mg of VHH in 1.0 ml of deionized water. The pH of the solution was 6.5. A 90% formulation of antibody was prepared by dissolving 4.5 mg of VHH in 1.0 ml of 2 mM citrate buffer. A 70% formulation of antibody was prepared by dissolving 3.5 mg of VHH in 1 mg/ml of excipient in 1 ml of citrate buffer at pH 6.5. The various classes of excipients used were as follows: Sugar excipients: sucrose, lactose, mannitol, raffinose and trehalose. Polymeric excipients: ficoll and PVP. Protein excipients: HSA.

Dry powders of the above formulations were produced by spray drying using a Buchi Spray Dryer.

The particle size distribution was measure by centrifugal sedimentation.

Interferon-Gamma

Example 17: Immunization

Four llama's (llama 5, 6, 22 and 23) were immunized intramuscularly with human IFN-γ (PeproTech Inc, USA, Cat Nr: 300-02) using an appropriate animal-friendly adjuvant Stimune (Cedi Diagnostics BV, The Netherlands). Two llama's (llama 29 and 31) were immunized intramuscularly with mouse IFN-γ (Protein Expression & Purification core facility, VIB-RUG, Belgium) using an appropriate animal-friendly adjuvant Stimune (Cedi Diagnostics BV, The Netherlands). The llama's received 6 injections at weekly intervals, the first two injections containing each 100 μg of IFN-γ, the last four injections containing each 50 μg of IFN-γ. Four days after the last immunization a blood sample (PBL1) of 150 ml and a lymph node biopsy (LN) was collected from each animal and sera were prepared. Ten days after the last immunization a second blood sample (PBL2) of 150 ml was taken from each animal and sera were prepared. Peripheral blood lymphocytes (PBLs), as the genetic source of the llama heavy chain immunoglobulins (HcAbs), were isolated from the blood sample using a Ficoll-Paque gradient (Amersham Biosciences) yielding $5 \times 10^8$ PBLs. The maximal diversity of antibodies is expected to be equal to the number of sampled B-lymphocytes, which is about 10% of the number of PBLs ($5 \times 10^7$). The fraction of heavy-chain antibodies in llama is up to 20% of the number of B-lymphocytes. Therefore, the maximal diversity of HcAbs in the 150 ml blood sample is calculated as $10^7$ different molecules. Total RNA was isolated from PBLs and lymph nodes according to the method of Chomczynski and Sacchi (1987).

Example 18: Repertoire Cloning cDNA was prepared on 200 μg total RNA with MMLV Reverse Transcriptase (Gibco BRL) using oligo d(T) oligonucleotides (de Haard et al., 1999). The cDNA was purified with a phenol/chloroform extraction, followed by an ethanol precipitation and subsequently used as template to amplify the VHH repertoire.

In a first PCR, the repertoire of both conventional (1.6 kb) and heavy-chain (1.3 kb) antibody gene segments were amplified using a leader specific primer (5'-GGCTGAGCTCGGTGGTCCTGGCT-3'; SEQ ID NO:89) and the oligo d(T) primer (5'-AACTGGAAGAATTCGCGGCCGCAGGAATTTTTTTTTTTTTTTTTT-3'; SEQ ID NO:90). The resulting DNA fragments were separated by agarose gel electrophoresis and the 1.3 kb fragment encoding heavy-chain antibody segments was purified from the agarose gel. A second PCR was performed using a mixture of FR1 reverse primers (WO03/054016 sequences ABL037 to ABL043) and the same oligo d(T) forward primer.

The PCR products were digested with SfiI (introduced in the FR1 primer) and BstEII (naturally occurring in framework 4). Following gel electrophoresis, the DNA fragments of approximately 400 basepairs were purified from gel and ligated into the corresponding restriction sites of phagemid pAX004 to obtain a library of cloned VHHs after electroporation of *Escherichia coli* TG1, pAX004 allows the production of phage particles, expressing the individual VHHs as a fusion protein with a c-myc tag, a hexahistidine tag and the geneIII product. The diversity obtained after electroporation of TG1 cells is presented in Table 1. The percentage insert was determined in PCR using a combination of vector based primers.

Example 19: Rescue of the Library and Phage Preparation

The library was grown at 37° C. in 10 ml 2×TY medium containing 2% glucose, and 100 μg/ml ampicillin, until the OD$_{600\ nm}$ reached 0.5. M13KO7 phages ($10^{12}$) were added and the mixture was incubated at 37° C. for 2×30 minutes, first without shaking, then with shaking at 100 rpm. Cells were centrifuged for 5 minutes at 4,500 rpm at room temperature. The bacterial pellet was resuspended in 50 ml of 2×TY medium containing 100 μg/ml ampicillin and 25 μg/ml kanamycin, and incubated overnight at 37° C. with vigorously shaking at 250 rpm. The overnight cultures were centrifuged for 15 minutes at 4,500 rpm at 4° C. Phages were PEG precipitated (20% poly-ethylene-glycol and 1.5 M NaCl) for 30 minutes on ice and centrifuged for 20 minutes at 4,500 rpm. The pellet was resuspended in 1 ml PBS. Phages were again PEG precipitated for 10 minutes on ice and centrifuged for 10 minutes at 14,000 rpm and 4° C. The pellet was dissolved in 1 ml PBS-0.1% casein.

Example 20: Selection of Human IFN-γ Specific VHH

Phages were rescued and prepared as described above in example 17

Two approaches were followed to obtain IFN-γ specific binders:

a. Solid Phase Coated IFN-γ

Microtiter wells were coated with human IFN-γ at different concentrations of 10-0.4 μg/well overnight at 4° C. Plates were washed 5 times with PBS/0.05% Tween-20. Wells were blocked with PBS+1% caseine for 2 hrs at room temperature. Phages were incubated for 2 hrs at room temperature. Wells were washed 20 times with PBS+0.05% Tween-20. The two final washes were performed using PBS. Specific phages were eluted using 1 to 2 μg of IFN-γ R1 (R&D Systems, Cat Nr: 673-IR/CF) for 1 hr. As negative control elutions were performed using 10 μg Ovalbumine (Sigma, A2512) as irrelevant protein. Log phase growing TG1 cells were infected with the eluted phages and plated on selective medium. Enrichment was determined by the number of transfected TG1 colonies after selection using the receptor for elution as compared with negative control using ovalbumine for elution. Bacteria from selections showing enrichment were scraped and used for a second round of selection.

The bacteria were superinfected with helperphage to produce recombinant phages as described in example 3. Microtiter wells were coated with IFN-γ at different concentrations of 2-0.1 μg/well overnight at 4° C. Plates were washed 5 times with PBS/0.05% Tween-20. Wells were blocked with PBS+1% caseine for 2 hrs at room temperature. Phages were incubated for 2 hrs at room temperature. Wells were washed 20 times with PBS+0.05% Tween-20. The two final washes were performed using PBS. Specific phages were eluted using 1 to 2 μg of IFN-γ R1 or 10 μg Ovalbumine as irrelevant protein for 1 hr, subsequently overnight at 4° C. and subsequently, phages were eluted using 0.1 M glycine pH 2.5 for 15 minutes at room temperature and neutralized with 1M Tris-HCl pH=7.5. Log phase growing TG1 cells were infected with the eluted and neutralized phages and plated on selective medium. Enrichment was determined by the number of transfected TG1 colonies after selection using the receptor for elution as compared with negative control using ovalbumine for elution.

b. Biotinylated IFN-γ

Microtiter wells were coated with neutravidine at a concentration of 2 μg/ml overnight at 4° C. Plates were washed 5 times with PBS/0.05% Tween-20. Wells were blocked with PBS+1% caseine for 2 hrs at room temperature. Biotinylated human IFN-γ at a concentration of 100-10 ng/well was captured overnight at 4° C. Plates were washed 5 times with PBS/0.05% Tween-20. Phages were incubated for 2 hrs at room temperature. Wells were washed with PBS+0.05% Tween-20. The two final washes were performed using PBS. Specific phages were eluted using 1 to 2 μg of IFN-γ R1 (R&D Systems, Cat Nr: 673-IR/CF) for 1 hr. As negative control elutions were performed using 10 μg Ovalbumine (Sigma, A2512) as irrelevant protein. Log phase growing TG1 cells were infected with the eluted phages and plated on selective medium. Enrichment was determined by the number of transfected TG1 colonies after selection using the receptor for elution as compared with negative control using ovalbumine for elution. Bacteria from selections showing enrichment were scraped and used for a second round of selection. Bacteria were superinfected with helperphage to produce recombinant phages. Microtiter wells were coated with neutravidine at a concentration of 2 μg/ml overnight at 4° C. Plates were washed 5 times with PBS/0.05% Tween-20. Wells were blocked with PBS+1% caseine for 2 hrs at room temperature. Biotinylated human IFN-γ at a concentration of 20-2.5 ng/100 μl was captured overnight at 4° C. Plates were washed 5 times with PBS/0.05% Tween-20. Phages were incubated for 2 hrs at room temperature. Wells were washed 20 times with PBS+0.05% Tween-20. The two final washes were performed using PBS. Specific phages were eluted using 1 to 2 μg of IFN-γ R1 or 10 μg Ovalbumine as irrelevant protein for 1 hr, subsequently overnight at 4° C. and subsequently, phages were eluted using 0.1 M glycine pH 2.5 for 15 minutes at room temperature and neutralized with 1M Tris-HCl pH=7.5. Log phase growing TG1 cells were infected with the eluted and neutralized phages and plated on selective medium. Enrichment was determined by the number of transfected TG1 colonies after selection using the receptor for elution as compared with negative control using ovalbumine for elution.

Example 21: Diversity of Selected VHH's

PCR was performed using M13 reverse and genIII forward primers. The clones were analyzed using Hinf1 fingerprinting and representative clones were sequenced. Sequence analysis was performed resulting in the sequences presented in Table 4 for human IFN-γ (SEQ ID No. 45-70).

Example 22: Expression and Purification of VHH

Small scale expressions were started after transformation of DNA into WK6 *Escherichia coli* cells.

Clones were grown in 50 ml 2×TY containing 0.1% glucose and 100 μg/ml ampicillin in a shaking flask at 37° C. until $OD_{600\ nm}$=2. 1 mM IPTG and 5 mM $MgSO_4$ was added and the culture was incubated for 3 more hours at 37° C. Cultures were centrifuged for 10 minutes at 4,500 rpm at 4° C. The pellet was frozen overnight at −20° C. Next, the pellet was thawed at room temperature for 40 minutes, re-suspended in 1 ml PBS/1 mM EDTA/1M NaCl and shaken on ice for 1 hour. Periplasmic fraction was isolated by centrifugation for 10 minutes at 4° C. at 4,500 rpm. The supernatant containing the VHH was loaded on TALON (Clontech) and purified to homogeneity. The yield of VHH was calculated according to the extinction coefficient.

Example 23: Topical Applications of Anti-IFN Gamma VHH's

1: To obtain anti-allergic pharmaceutical compositions for ophthalmic topical applications, a solution of at least one anti-IFN gamma VHH was prepared as follows:
  eye drops containing a therapeutic dose of anti-IFN gamma VHH dissolved in 100 ml of sterilized water containing 0.9 g sodium chloride, 0.02 g sodium citrate, 0.02 g methyl parahydroxybenzoate, 0.1 g chlorobutanol and acetic acid suitable to obtain a pH of 6.5.
- eye ointment containing a therapeutic dose of anti-IFN gamma VHH was prepared according to the conventional method containing 1.0 g of liquid paraffin and a suitable amount of soft paraffin to obtain a total mixture of 100 g.

2: To obtain anti-inflammatory pharmaceutical applications, topical preparations of the present invention contained at least one anti-IFN gamma VHH and a pharmaceutically acceptable carrier. They were prepared as follows:

Preparation of Base Cream

The reagents for preparing the base cream are as follows (contents for 100 kg base cream): Dimethyl silicon oil (17 kg), Liquid paraffin (9 kg), Stearic acid (7.5 kg), Cetyl alcohol (1 kg), Stearyl alcohol (3 kg), Glycerol (20 kg), Ethylparaben (0.1 kg), Peregal A-20 (0.45 kg), Softener SG (0.85 kg), 0.01 M Phosphate Buffer (pH 7.2)(41.1 kg)

The stainless steel tank was placed into a thermostat water bath and heated to 80° C., which took approximately 10 minutes. The liquid was thoroughly mixed. Then, emulsifying and homogenizing equipment was placed into the open stainless steel tank, the mixture was stirred for 20 minutes at 3500 rpm until fully emulsified. The temperature of the thermostat water bath was cooled naturally to room temperature, until the mixture became a semi-solid cream. The mixture was being continually stirred.

Preparation of Liquid Antibody Mixture

VHH#MP3B1SRA was prepared in accordance with Example 22. The lyophilized antibodies were reconstituted with 0.01 M phosphate buffer (pH 7.2) to a concentration of 2 mg/ml. For 1000 gm of base cream, 45 mg of VHH#MP3B1SRA antibody was added.

Therapeutic VHH-Fragments

Example 24: Expression of a VHH-CDR3 Fragment of Anti-TNFα VHH#3E

The CDR3 region of VHH#3E was amplified by using a sense primer located in the framework 4 region (Forward: CCCCTGGCCCCAGTAGTTATACG; SEQ ID NO:91) and an anti-sense primer located in the framework 3 region (Reverse: TGTGCAGCAAGAGACGG; SEQ ID NO:92).

In order to clone the CDR-3 fragment in pAX10, a second round PCR amplification was performed with following primers introducing the required restriction sites:

```
Reverse primer Sfi1:
                                        SEQ ID NO: 93
GTCCTCGCAACTGCGGCCCAGCCGGCCTGTGCAGCAAGAGACGG Forward primer Not1:
                                        SEQ ID NO: 94
GTCCTCGCAACTGCGCGGCCGCCCCCTGGCCCCAGTAGTTATACG
```

The PCR reactions were performed in 50 µl reaction volume using 50 pmol of each primer. The reaction conditions for the primary PCR were 11 min at 94° C., followed by 30/60/120 sec at 94/55/72° C. for 30 cycles, and 5 min at 72° C. All reaction were performed with 2.5 mM MgCl2, 200 mM dNTP and 1.25 U AmpliTaq God DNA Polymerase (Roche Diagnostics, Brussels, Belgium).

After cleavage with SfiI and NotI the PCR product was cloned in pAX10.
EGFR

Example 25: Immunization

After approval of the Ethical Committee of the Faculty of Veterinary Medicine (University Ghent, Belgium), 4 llamas (024, 025, 026 and 027) were immunized with the tumor antigen epidermal growth factor receptor (EGFR) according to all current animal welfare regulations. To generate an antibody dependent immune response (Table 9), two animals were injected with intact human vulvar squamous carcinoma cells (A431, ATCC CRL 1555), expressing EGFR on its cell surface, while A431 derived membrane extracts were administered to two other llamas (026 and 027). Each animal received seven doses of subcutaneously administered antigens at weekly intervals (Table 9). When immunizing with intact cells, each dose consisted of $10^8$ freshly harvested A431 cells. The dose for immunization with membrane extracts consisted of vesicles prepared from $10^8$ A431 cells. Vesicles were prepared according to Cohen and colleagues (Cohen S, Ushiro H, Stoscheck C, Chinkers M, 1982. A native 170,000 epidermal growth factor receptor-kinase complex from shed plasma membrane vesicles. J. Biol. Chem. 257:1523-31). Vesicles were stored at −80° C. before administration. Two extra injections of eight microgram purified EGFR (Sigma) in an emulsion with the adjuvant Stimune (CEDI Diagnostics B.V., Lelystad, The Netherlands) were administered intramuscularly to llama 025 (Table 9).

Example 26: Evaluation of Immune Response

Figure 5:
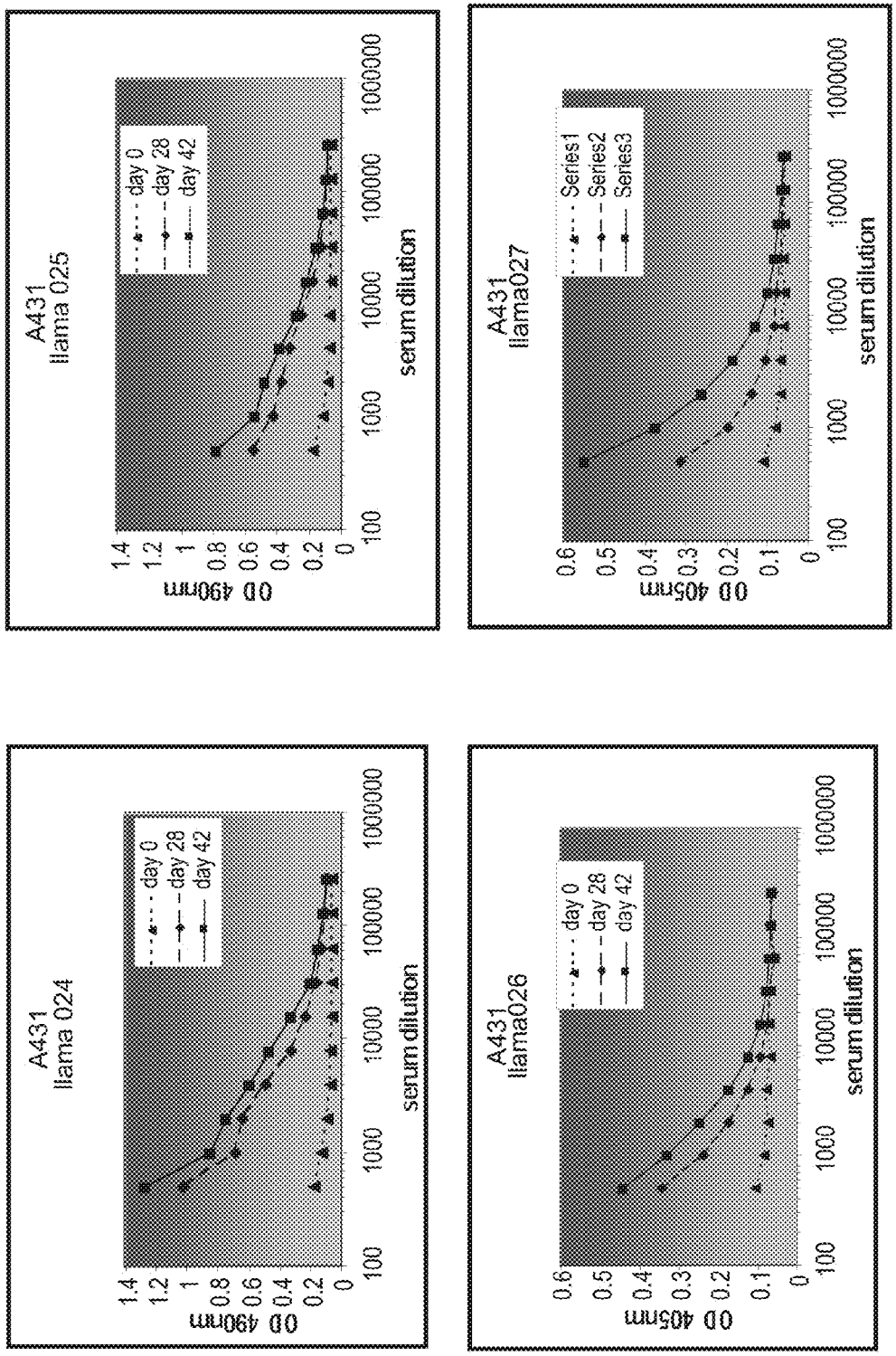
FIG. 5: ELISA to detect A431 specific antibody titers in llama serum.

At day 0, 28 and 42, 10 ml of (pre-)immune blood was collected and serum was used to evaluate the induction of the immune responses in the 4 animals. A first ELISA was performed to verify whether the animals generated antibodies that recognized A431 epitopes. After coating a tissue-culture treated 96-well plate with gelatin (0.5% in PBS for 10 minutes), the excess of gelatin was removed and A431 cells were grown overnight in the microwells to confluency. Cells were fixed with 4% paraformaldehyde in PBS for 30 minutes at room temperature. Subsequently, the fixative was blocked with 100 mM glycine in PBS for 10 minutes, followed by blocking of the wells with a 4% skim milk-PBS solution, again for 10 minutes. Serum dilutions of immunized animals were applied and A431 specific antibodies were detected with a polyclonal anti-llama antiserum developed in rabbit, followed by a secondary goat anti-rabbit horse radish peroxidase (HRP) conjugate (Dako, Denmark). For all four animals, immunization with intact cells or membrane vesicles resulted in the induction of a significant A431-specific antibody titer (FIG. 5).

Figures 1, 6:
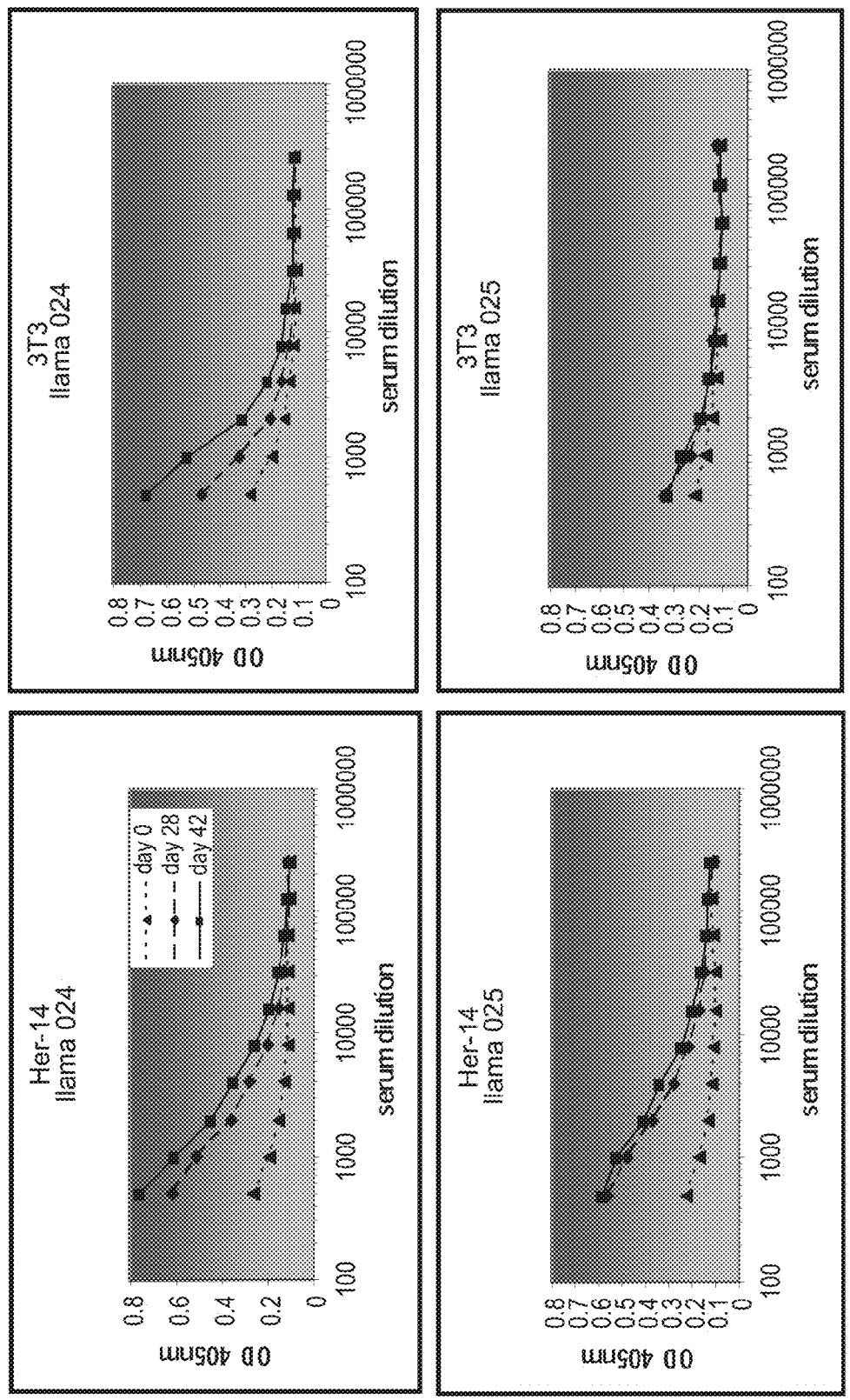
FIG. 6: Detection of EGFR specific antibody titers in llama serum.
Figures 2, 6:
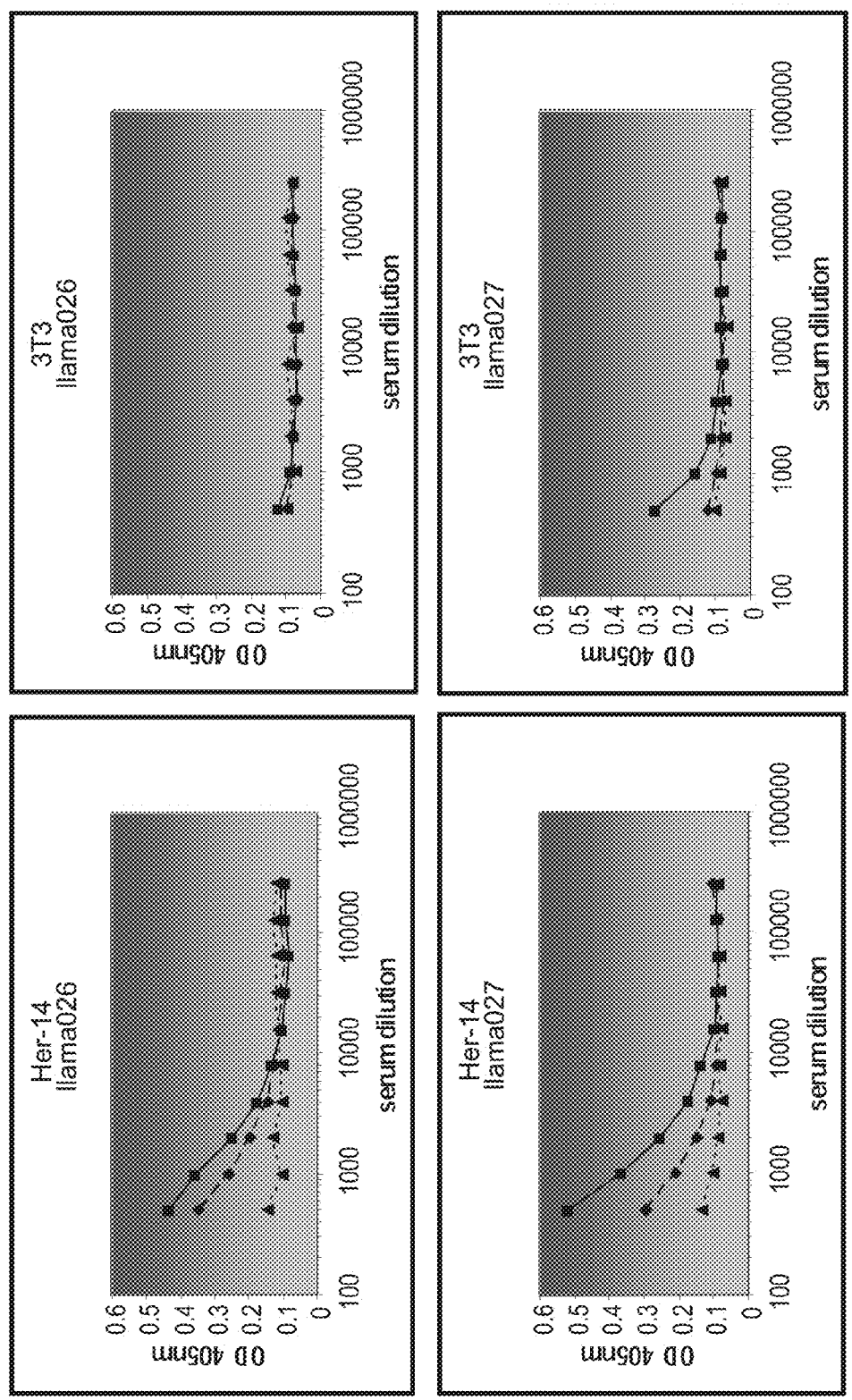

To verify whether the induced llama antibodies were EGFR specific, antibody titers in serum was evaluated on mouse fibroblasts expressing human EGFR (Her-14) and compared to the parental mouse fibroblasts cell line NIH3T3 clone 2.2 (3T3), similarly performed as described above (FIG. 6). Again, the serum titer of antibodies binding to Her-14 was higher compared to the titer for the parental 3T3 cells, indicating that circulating serum antibodies were EGFR specific.

Figure 7:
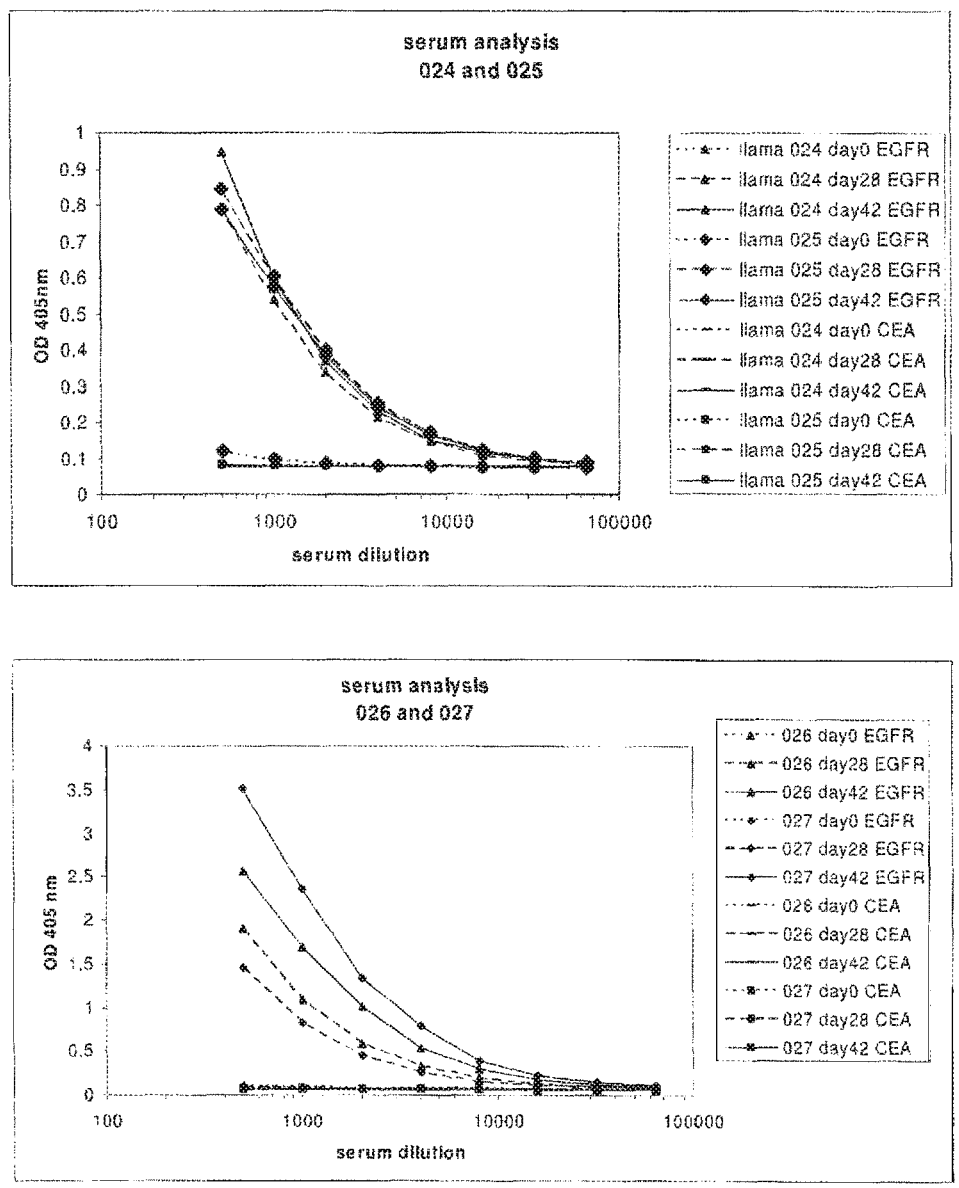
FIG. 7: Detection of EGFR specific antibody titers in serum of llama 024 and 025 and of llama 026 and 027.

Finally, the serum response in immunized animals was verified on solid-phase coated purified EGFR. Purified EGFR (Sigma) and the irrelevant carcino embryonic antigen (CEA, Scripps), both at 1 µg/ml, were immobilized overnight at 4° C. in a 96 well Maxisorp plate (Nunc). Wells were blocked with a casein solution (1% in PBS). After addition of serum dilutions, specifically bound immunoglobulins were detected using a rabbit anti-llama antiserum followed by a goat anti-rabbit alkaline phosphatase conjugate (Sigma), showing that for all animals a significant antibody dependent immune response against EGFR was induced (FIG. 7).

Example 27: Cloning of the Heavy-Chain Antibody Fragment (VHH) Repertoire

Since little is known on the immunoglobulin ontogeny of camelids, B-cell containing tissues of distinct origin and of different time points were collected for each animal (Table 9). After tissue collection, total RNA was isolated according to the procedure described by Chomczynski and Sacchi. (Chomczynski P and Sacchi N. 1987. Single-step method of RNA isolation by acid guanidinium thiocyanate-phenol-chloroform extraction. Anal Biochem 162:156-159). The procedure to clone the VHH repertoire is based on a method described in patent application WO 03/054016. cDNA was prepared on total RNA with MMLV Reverse Transcriptase (Invitrogen) using oligo d(T) oligonucleotides (de Haard H J, van Neer N, Reurs A, Hufton S E, Roovers R C, Henderikx P, de Bruine A P, Arends J W, Hoogenboom H R. 1999. A large non-immunized human Fab fragment phage library that permits rapid isolation and kinetic analysis of high affinity antibodies. J. Biol. Chem. 274:18218-30). The amounts of RNA of the distinct tissues used for cDNA synthesis is listed in Table 10. The cDNA was purified with a phenol/chloroform extraction, followed by an ethanol precipitation and subsequently used as template to amplify the VHH repertoire.

In a first PCR, the repertoire of both conventional (1.6 kb) and heavy chain (1.3 kb) antibody gene segments were amplified using a leader specific primer (ABL002) and ABL010, an oligo d(T) primer (for a list of primers see Table 13). The resulting DNA fragments were separated by agarose gel electrophoresis. The amplified 1.3 kb fragment, encoding heavy chain antibody segments was purified from the agarose gel and used as template in a nested PCR using a mixture of FR1 primers (ABL037-ABL043) and ABL010. The PCR products were digested with SfiI (introduced in the FR1 primer) and BstEII (naturally occurring in FR4). Following gel electrophoresis, the DNA fragment of approximately 400 basepairs was purified from gel and 330 ng of amplified VHH repertoire was ligated into the corresponding restriction sites of one microgram of phagemid pAX004 to obtain a library after electroporation of *Escherichia coli* TG1. pAX004 allows the production of phage particles, expressing the individual VHHs as a fusion protein with the geneIII product. The size of the libraries obtained from the distinct tissues collected from the immunized llamas is described in Table 10. As a quality control, a colony PCR using the M13 reverse and a geneIII primer was performed on 24 randomly picked colonies of each library and the percentage of clones containing an insert of the correct size was calculated (Table 10).

Example 28: Evaluation of the Cloned Repertoire

Figure 8:
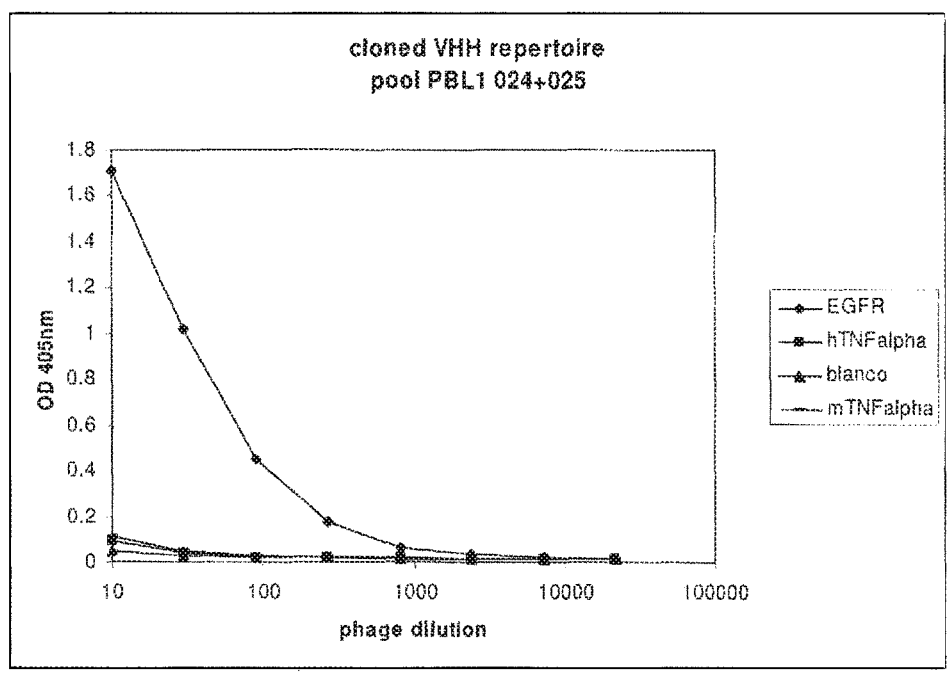
FIG. 8: Phage response to EGFR

In a polyclonal phage ELISA, the specificity of the cloned phage repertoire was evaluated on EGFR and on an irrelevant antigen (TNFα). To generate recombinant virions expressing the VHH repertoire as fusion proteins with the geneIII product, the library was grown at 37° C. in ml 2×TY medium containing 2% glucose, and 100 µg/ml ampicillin, until the $OD_{600\ nm}$ reached 0.5. M13KO7 phages ($10^{12}$) were added and the mixture was incubated at 37° C. for 2×30 minutes, first without shaking, then with shaking at 100 rpm. Cells were centrifuged for 5 minutes at 4,500 rpm at room temperature. The bacterial pellet was resuspended in 50 ml of 2×TY medium containing 100 µg/ml ampicillin and 25 µg/ml kanamycin, and incubated overnight at 37° C. with vigorously shaking at 250 rpm. The overnight cultures were centrifuged for 15 minutes at 4,500 rpm at 4° C. and supernatant was used to concentrate the phages. Phages were PEG precipitated (20% poly-ethylene-glycol and 1.5 M NaCl) for 30 minutes on ice and centrifuged for 20 minutes at 4,500 rpm. The pellet was resuspended in 1 ml PBS. Phages were again PEG precipitated for 10 minutes on ice and centrifuged for 10 minutes at 14,000 rpm and 4° C. The pellet was dissolved in 1 ml PBS. One µg/ml of EGFR or TNFα was immobilized in a 96 well Maxisorp plate (Nunc) and incubated overnight at 4° C. Plates were washed 5 times with PBS/0.05% Tween-20 and wells were blocked with a casein solution (1% in PBS) and phage dilutions were added for 2 hrs at room temperature. Bound phages were detected using the anti-M13 gpVIII-HRP conjugated monoclonal antibody (Amersham Biosciences) and $ABTS/H_2O_2$ as substrate. Plates were read at 405 nm after 15 minutes incubation at room temperature. An example of a phage response from a pool of phages rescued from PBL1 libraries of animals 024 and 025 is depicted in FIG. 8.

Example 29: Multiple Selection Strategies to Identify EGFR Specific Nanobodies

Libraries were rescued by growing the bacteria to logarithmic phase ($OD_{600}$=0.5), followed by infection with helper phage to obtain recombinant phages expressing the repertoire of cloned VHHs on tip of the phage as gpIII fusion protein (as described in Example 18). When selecting for EGFR specific antibodies, two distinct selection strategies have been followed.
Selection by Epitope Specific Elution
A first selection strategy was based on the fact that EGFR can be purified by affinity chromatography through ligand elution. Four different elution conditions, applying an excess of molecules that compete for the ligand binding site or overlapping epitope(s) were carried out (Table 11). When selection was performed on A431 or Her-14 cells, unselected recombinant phages were mixed for 20 minutes at 4° C. with $6×10^6$ blood cells (mainly monocytes, T- and B-cells) or $2×10^7$ 3T3s, respectively, to deplete for recombinant phages that recognize common, non EGFR-specific epitopes. Unbound phages were then incubated with EGFR+ selection cells for 2 hours followed by 6 washes with ice-cold PBS. Phages were subsequently eluted with an excess of EGF ligand, mouse monoclonal 2e9 (Defize L H, Moolenaar W H, van der Saag P T, de Laat S W 1986. Dissociation of cellular responses to epidermal growth factor using anti-receptor monoclonal antibodies. EMBO J. 5:1187-92) or EGFR antagonistic antibodies 225 and 528 (Sato J D, Kawamoto T, Le A D, Mendelsohn J, Polikoff J, Sato G H 1983. Biological effects in vitro of monoclonal antibodies to human epidermal growth factor receptors. Mol. Biol. Med. 1:511-529). All selection steps were performed at 4° C. to avoid receptor mediated phage internalization. Logarithmically grown E. coli TG1 was infected with the eluted phages and grown overnight at 37° C. on selective medium 2×TY Ap100 and 2% glucose. Cells were scraped and used in a next round of panning whenever required. Two or three rounds of panning were performed to enrich for EGFR specific recombinant phages (Table 11). Whenever purified antigen was used for selection (Table 11), EGFR was immobilized at 1 µg/ml on Maxisorp microtiter plates.
Selection for Internalizing VHH Fragments
A second selection strategy was based on the observation that after binding of the ligand to the receptor, EGFR mediated cell signaling can be downregulated by the mechanism of receptor internalization. To identify recombinant phages that are able to internalize through cell surface molecules, the protocol described by Poul and colleagues (Poul M A, Becerril B, Nielsen U B, Morisson P, Marks J D. 2000. Selection of tumor-specific internalizing human antibodies from phage libraries. J. Mol. Biol. 301:1149-61.) was followed. Unselected recombinant phages were added to approximately $2×10^7$ mouse fibroblast 3T3s for 30 minutes at 4° C. in ice cold binding medium (bicarbonate buffered DMEM; 10% FCS (fetal calf serum); 25 mM Hepes), supplemented with 2% skim milk to deplete for non-specific VHHs. Unbound phages were subsequently incubated with pre-cooled EGFR+ selection cells (Her-14 or A431) in binding medium for 1.5 hours at 4° C., followed by six washes with ice-cold PBS to remove non-bound phages. Cells were covered with pre-warmed binding medium and immediately transferred to 37° C. for 20 minutes, to allow internalization. Subsequently, cells were cooled down to 4° C. and were stripped with mild acid (500 mM NaCl; 100 mM glycine pH2.5) incubations during 10 minutes to remove surface bound recombinant phages. Cells were released from extracellular matrix by trypsinization. Resuspended cells were then lyzed during 4 minutes with 100 mM TEA at 4° C. to release internalized phages. Logarithmically grown E. coli TG1 was infected with the eluted phages and grown overnight at 37° C. on selective medium (2×TY Ap100 with 2% glucose). The libraries used for a single round of selection on A431 and in parallel on Her-14 are summarized in Table 12.

Example 30: Characterization of EGFR Specific Nanobodies

Figure 10:
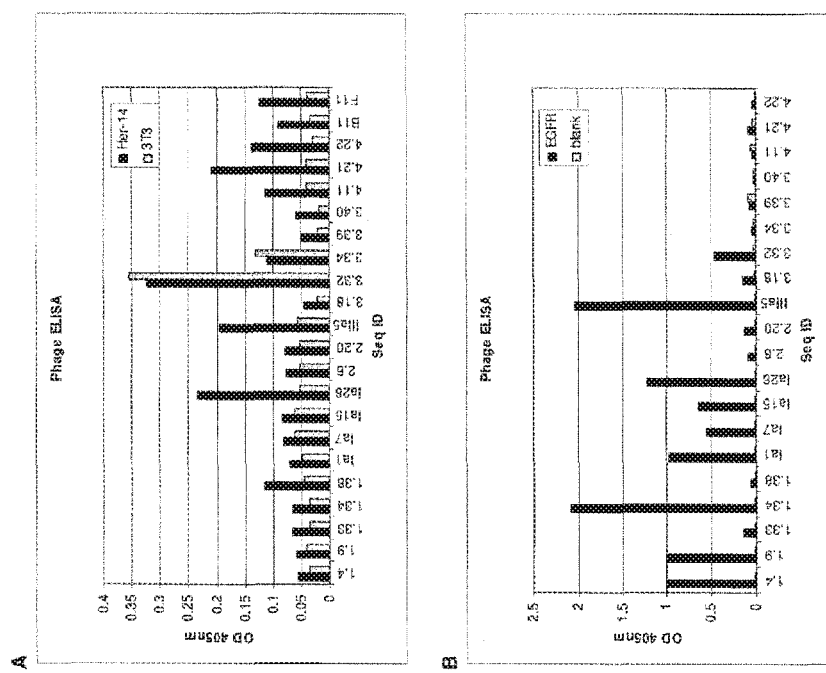
FIGS. 10A and 10B: Phage ELISA on cells (FIG. 10A) or on solid-phase immobilized EGFR (FIG. 10B) of the 20 unique EGFR specific clones identified via the epitope specific elution selection procedure

To verify EGFR specificity of individual clones after the epitope specific elution procedure of panning, a phage ELISA was performed on individual clones. 47 randomly picked clones for each selection procedure (1, 2, 3, 4, Ia and IIIa; Table 11) were grown to logarithmic phase ($OD_{600}$=0.5), followed by infection with helper phage to obtain recombinant phages as described in Example 18. A phage ELISA was performed both on solid-phase coated EGFR (comparing to non-coated well) as on gelatin coated Her-14 cells (comparing to 3T3). The presence of EGFR specific VHH was verified by using approximately $10^9$ recombinant phage particles of each clone before detection with an anti-M13 gpVIII-HRP conjugated monoclonal antibody. With clones that scored positive in phage ELISA on cells and/or on solid-phase immobilized EGFR (Table 11), a HinfI fingerprint analysis was performed (data not shown). The nucleotide sequence was determined for a representative clone of each distinct fingerprint, resulting in 5, 8, 3, 4, 7, and 4 different sequences for conditions, 1, Ia, 2, IIIa, 3 and 4, respectively. Amino acid sequence alignment of these 31 binders (FIG. 9) indicated that 20 of them were unique (listed in Table 14 SEQ ID Nos 23 to 42). The EGFR specificity of the 20 unique clones in phage ELISA (both on cells and on solid-phase coated EGFR) is shown in FIG. 10.

For the selection according to the internalization protocol, a phage ELISA on cells with a total of 84 individual clones was performed, similarly as for the clones identified by the epitope specific elution selection procedure. After HinfI fingerprint analysis, nucleotide sequence determination and amino acid sequence alignment to the above described panel of 20 unique binders (data not shown), 2 new anti-EGFR clones, EGFR-B11 and clone EGFR-F11, were identified (Table 14 SEQ ID NOs: 43 to 44). The EGFR specificity of both clones in phage ELISA on cells is shown in FIG. 10, panel A.

Example 31: EGF Receptor Mediated Internalization of Nanobodies

Figure 11A:
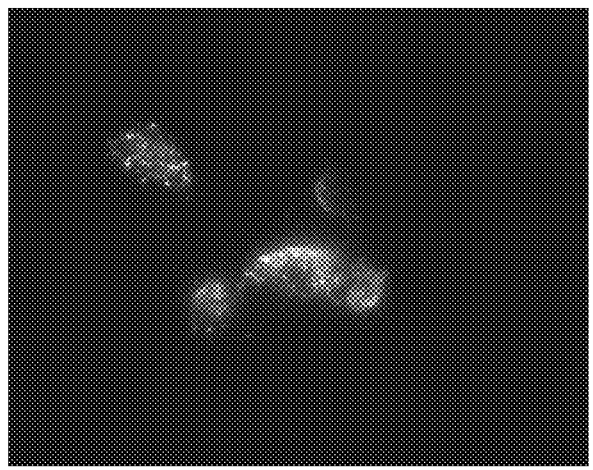
FIGS. 11A-11C: Effect of nanobody EGFR-IIIa42 on receptor internalization and signalling. Fluorescence microscopy visualization of EGFR-IIIa42 under conditions that allow internalization, with Her-14 (FIG. 11A) or 3T3 (FIG. 11B). A Western blot that shows the effect of EGFR-IIIa42 on receptor tyrosin kinase activity is represented in FIG. 11C.
Figure 11B:
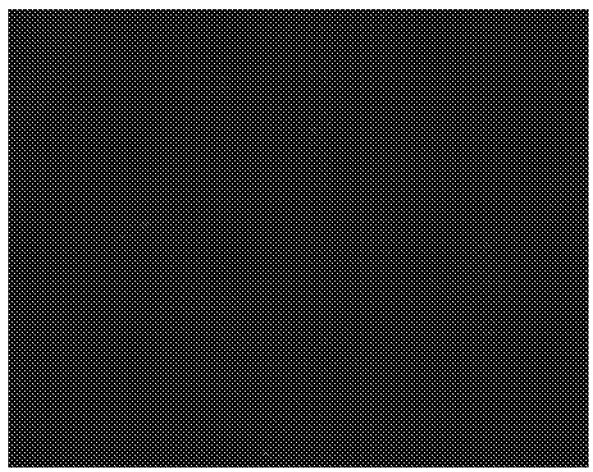
Figure 11C:
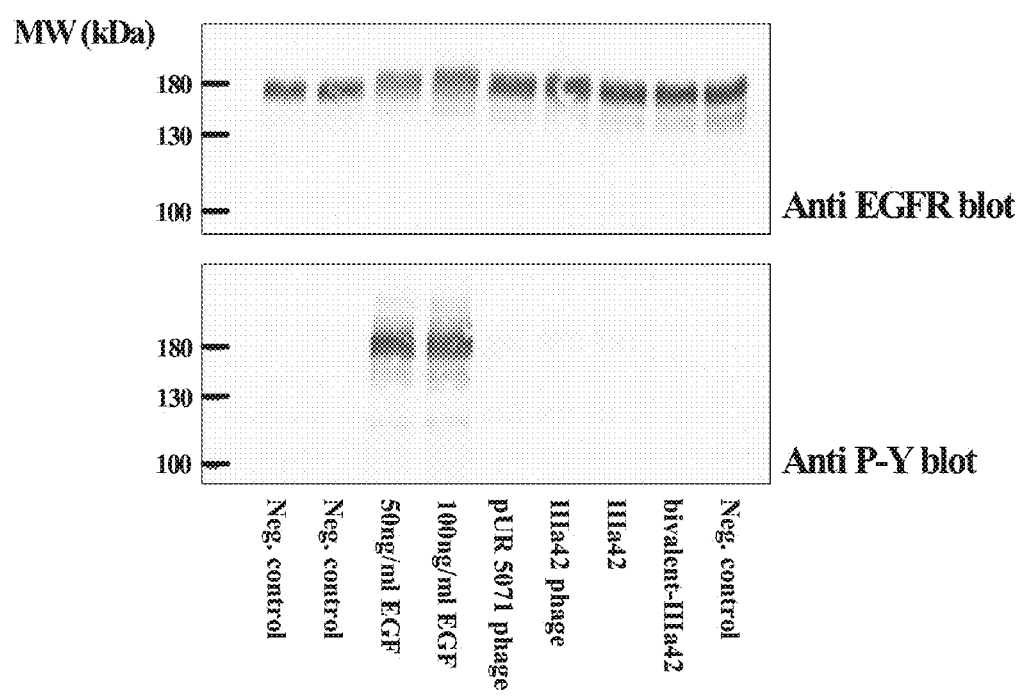

Her-14 and 3T3 cells were grown overnight on glass cover slips, washed with binding medium (see Example 19) and cooled down to 4° C. for 20 minutes. Phages were prepared of nanobody EGFR-IIIa42 as described in Example 18 and approximately $10^{12}$ recombinant virions, diluted in binding medium supplemented with 2% skim milk, were added to the ice cold cells for 1 hour at 4° C. Cells were washed once with ice cold PBS to remove non bound phages. Subsequently, the cells were shifted to 37° C. for 20 minutes to allow phage internalization and again cooled down to 4° C. Cells were washed twice with PBS. Following, cell surface bound phages were removed by two acid washes with stripping buffer (150 mM NaCl, 125 mM HAc) for seven minutes at room temperature. After two washes with PBS, cells were fixed with 4% paraformaldehyde in PBS for 30 minutes at room temperature, and again washed twice with PBS. Fixed cells were then permeabilized in 0.2% Triton X-100 in PBS for 5 minutes at room temperature, followed by two washes with PBS and remaining fixative was blocked with 100 mM glycin in PBS for 10 minutes at room temperature. Cells were washed with PBS-0.5% (w/v) gelatin and internalized phage was visualized by staining with anti-M13 gpVIII-FITC (Amersham Biosciences) followed by an anti-mouse FITC labeled monoclonal antibody and subsequent visualization by fluorescence microscopy. FIG. 11 shows that EGFRIIIa42 is able to internalize Her-14 (panel A) but not 3T3 cells (panel B). Subsequently, FACS analysis demonstrated that nanobody EGFR-IIIa42 is able to bind both A431 and Her-14, but not 3T3 (data not shown).

To demonstrate the effect of EGF receptor specific nanobodies on receptor signalling, cells were seeded at 100,000 cells per well in 12-well tissue culture plates in medium (DMEM) containing 10% (v/v) serum. After 8 hours, cells were washed once with medium (DMEM) containing low (0.5% v/v) serum and serum-starved overnight in the same medium. The day of the assay, medium was refreshed with binding medium (DMEM/0.5% FCS/25 mM Hepes and 2% skim milk) and when appropriate, ligand or nanobody (mono- or bivalent) was added at 37° C. After 15 minutes, cells were quickly cooled down on ice and washed twice with ice-cold PBS (10 mM Na-phosphate; 150 mM NaCl, pH 7.4). Total cell lysates were prepared by scraping the cells off the plate in 50 µl protein sample buffer. Proteins were size-separated on 6% (w/v) poly-acrylamide gels (20 µl loaded per gel on two parallel gels) and blotted to PVDF membrane (Roche). Blots were stained for total amount of EGFR with a rabbit polyclonal antiserum to the receptor (Santa Cruz) and for phosphorylated receptor using a monoclonal anti phospho-tyrosine antibody (PY-20; Transduction Labs), followed by an appropriate in donkey developed and peroxidase conjugated secondary antibody (anti-rabbit or anti-mouse). The detection was performed by enhanced chemoluminescence using Western Lightning™ substrate (Perkin Elmer Life Sciences). Surprisingly, anti-EGFR-IIIa42 nanobody did not activate EGFR+ cells deprived from EGF, indicated by the lack of receptor Tyr kinase phosphorylation (FIG. 11, panel C). The positive control, in which EGF was added in two concentrations to the cells, clearly induced phosphorylation of the receptor and thus induces activation of the cells.

PDK1

Example 32 (1): Immunisation of Llamas 2 llamas are immunised with a cocktail of recombinant EGF receptor and with PDK1. The lamas are boosted with a cell line overexpressing the EGF receptor. The immunization schemes are summarised in Table 15.

Example 33: Repertoire Cloning

Different sources for RNA extraction are used:
150 ml immune blood, between 4 and 10 days after the last antigen injection
lymph node biopsy 4 days after the last antigen injection Peripheral blood lymphocytes (PBLs) are isolated by centrifugation on a density gradient (Ficoll-Paque Plus Amersham Biosciences). PBLs and lymph node are used to extract total RNA (Chomczynski and Sacchi 1987) followed by synthesis of cDNA using a hexanucleotide random primer. The repertoire is amplified using two hinge-specific primers: AACAGTTAAGCTTCCGCTTGCGGCCGCG-GAGCTGGGGTCTTCGCTGTGGTGCG (SEQ ID NO:95) and AACAGTTAAGCTTCCGCTTGCGGCCGCTGGTT-GTGGTTTTGGTGTCTTGGGTT (SEQ ID NO:125) and a framework 1 specific primer: GAGGTBCARCTGCAG-GASTCYGG (SEQ ID NO:96). Fragments are digested with PstI and NotI and cloned into a phagemid vector. The repertoire is transformed in TG1 electrocompetent cells and plated on LB agar plates containing 100 µg/ml ampicillin and 2% glucose. Colonies are screened for the presence of insert by PCR with vector specific primers.

Example 34: Rescue of the Library, Phage Preparation

Libraries are grown at 37° C. in 60 ml 2×TY medium containing 2% glucose, and 100 µg/ml ampicillin, until the OD600 nm reached 0.5. M13KO7 phages (1012) are added and the mixture is incubated at 37° C. for 2×30 minutes, first without shaking, then with shaking at 100 rpm. Cells are centrifuged for 10 minutes at 4500 rpm at room temperature. The bacterial pellet is resuspended in 300 ml of 2×TY medium containing 100 µg/ml ampicillin and 25 µg/ml kanamycin, and incubated overnight at 30° C. with vigorously shaking at 250 rpm. The overnight cultures are centrifuged for 15 minutes at 10.000 rpm at 4° C. Phages are PEG precipitated (20% poly-ethylene-glycol and 1.5 M NaCl) and centrifuged for 30 minutes at 10.000 rpm. The pellet is resuspended in 20 ml PBS. Phages are again PEG precipitated and centrifuged for 30 minutes at 20,000 rpm and 4° C. The pellet is dissolved in 5 ml PBS. Phages are titrated by infection of TG1 cells at OD600 nm=0.5 and plating on LB agar plates containing 100 µg/ml ampicillin and 2% glucose. The number of transformants indicates the number of phages (pfu). The phages are stored at −80° C. with 15% glycerol.

Example 35: Selection

Immunotubes are coated with 2 µg/ml EGFR, 2 g/ml PDK1 or with PBS containing 1% casein. After overnight incubation at 4° C., the tubes are blocked with PBS containing 1% casein, for 3 hours at RT. 200 µl phages of the three libraries of llama 005 and of the three libraries of llama006 are pooled and added to the immunotubes with a final volume of 2 ml in PBS for EGFR and in 50 mM Tris HCl (pH 7.4), 150 mM KCl, 1.0 mM DTT, 1 mM MgCl2 and 0.3 mg/ml BSA for PDK1.

After 2 hours incubation at RT, the immunotubes are washed 10× with PBS-Tween and 10× with PBS. Bound phages are eluted with 2 ml 0.2 M glycin buffer pH=2.4. Eluted phages are allowed to infect exponentially growing TG1 cells, and are then plated on LB agar plates containing 100 µg/ml ampicillin and 2% glucose. Examples of results which might be obtained from the panning are presented in Tables 16 and 17.

Example 36: Screening

A microtiter plate is coated with 2 µg/ml EGFR or 2 µg/ml PDK1, overnight at 4° C. Plates are blocked for two hours at room temperature with 300 µl 1% casein in PBS. The plates are washed three times with PBS-Tween. Periplasmic extracts are prepared from single colonies and applied to the wells of the microtiter plate. Plates are washed six times with PBS-Tween, after which binding of VHH is detected by incubation with mouse anti-Histidine mAB 1/1000 in PBS for 1 hour at RT followed by anti-mouse-alkaline phosphatase conjugate 1/2000 in PBS, also for 1 hour at RT. Staining is performed with the substrate PNPP (p-nitrophenyl-phosphate, 2 mg/ml in 1M diethanolamine, 1 mM Mg$_2$SO$_4$, pH9.8) and the signals are measured after 30 minutes at 405 nm. An example of the expected number of positive clones versus the number of clones tested in ELISA for each selection is presented in Table 18.

Example 37: Screen for Internalised VHH

Individual clones specific for the EGFR are amplified by PCR and cloned in a phage engineered to package the green fluorescent protein reporter gene driven by the CMV promoter (Poul M A et al, J Mol Biol, 1999, 288: 203-211). Phages are prepared and incubated with tumor cells (A431) overexpressing EGFR. Phages that endergo EGFR mediated endocytosis are be measured by GFP expression. 1 VHH (EGFR-21) would be expected to show a very high expression of GFP and would be used for further analysis. In another approach internalised phage is stained with anti-phage antibodies (poly- or monoclonal) after permeabilization of cells by treatment with cold methanol as described by Larocca and colleagues (Larocco et al, Molecular Therapy, 2001, 3: 476-484) and by Poul and colleagues (Poul M A et al, J Mol Biol, 1999, 288: 203-211).

Example 38: Screen for VHH Inhibiting PDK1-Akt Interaction

PDK1 is coated in a microtiter plate as described above and after blocking the plates, the wells are incubated with 100 µg/ml Akt for one hour at RT. Then (without washing) 100 µl periplasmic extract is added to those wells and VHH binding is measured as described above. VHH that are not able to bind to PDK1 would be scored as inhibitors for the interaction between PDK1 and Akt. The expected number of inhibiting VHH versus the number of VHH tested in inhibition ELISA is summarized in Table 19.

Example 39: Making a Bispecific Construct

A bispecific construct is prepared (Conrath et al, J Biol Chem, 2001, 276: 7346-7350) of EGFR-21 and 5 different strong inhibiting VHHs (PD-1, PD-7, PD-32, PD-33 and PD-72) for PDK1. Protein is prepared and purified to homogeneity for the 5 bispecific constructs and shown to be stable by western blot analysis.

Example 40: Endocytosis and Lysis of Tumor Cells

Bispecific constructs are incubated with tumor cells (A431) overexpressing EGFR. All constructs that successfully endocytosed would be shown by confocal microscopy. One of the constructs, EGFR-21-PD-32, would be expected to able to inhibit cell growth and finally lead to cell death.

Example 41: Calculation of Homologies Between Anti-Target-Single Domain Antibodies of the Invention The degree of amino acid sequence homology between anti-target single domain antibodies of the invention was calculated using the Bioedit Sequence Alignment Editor. The calculations indicate the proportion of identical residues between all of the sequences as they are aligned by ClustalW. (Thompson, J. D., Higgins, D. G. and Gibson, T. J. (1994) CLUSTAL W: improving the sensitivity of progressive multiple sequence alignment through sequence weighting, position specific gap penalties and weight matrix choice. Nucleic Acids Research, submitted, June 1994). Table 20 indicates the fraction homology between anti-TNF-alpha VHHs of the invention. Table 21 indicates the percentage homology between anti-IFN-gamma VHHs of the invention.

Example 42: Construction of a Bispecific Constructs Containing a VHH-CDR3 Fragment Fused to an Anti-Serum Albumin VHH A functional portion, the CDR3 region of MP2F6SR, was amplified by using a sense primer located in the framework 4 region (F6 CRD3 Forward:CTGGCCCCAGAAGTCAT-ACC; SEQ ID NO:97) and an anti-sense primer located in the framework 3 region (F6 CDR3 Reverse primer:TGTG-CATGTGCAGCAAACC; SEQ ID NO:98).

In order to fuse the CDR-3 fragment with the anti-serum albumin VHH MSA-21, a second round PCR amplification was performed with following primers:

```
F6 CDR3 Reverse primer Sfil:
                                    (SEQ ID NO: 99)
GTCCTCGCAACTGCGGCCCAGCCGGCCTGTGCATGTGCAGCAAACC F6 CDR3 Forward primer Not1:
                                    (SEQ ID NO: 100)
GTCCTCGCAACTGCGCGGCCGCCTGGCCCCAGAAGTCATACC
```

The PCR reactions were performed in 50 ml reaction volume using 50 pmol of each primer. The reaction conditions for the primary PCR were 11 min at 94° C., followed by 30/60/120 sec at 94/55/72° C. for 30 cycles, and 5 min at 72° C. All reaction were performed with 2.5 mM MgCl2, 200 mM dNTP and 1.25 U AmpliTaq God DNA Polymerase (Roche Diagnostics, Brussels, Belgium).

After cleavage of the VHH gene of MSA clones with restriction enzymes Pst1/BstEII the digested products were cloned in pAX11 to obtain clones with a VHH at the C-terminus of the multicloning site. The clones were examined by PCR using vector based primers. From clones yielding a 650 bp product, DNA was prepared and used as acceptor vector to clone the CDR3 of MP2F6SR, after cleavage of the PCR product with restriction enzymes SfiI/NotI to allow N-terminal expression of CDR3 in fusion with a MSA VHH.

Tables

TABLE 1

Immunization scheme as described in Example 1

| Day | Llama 2 | Llama 4 |
|---|---|---|
| 0 | 100 µg | 100 µg |
| 7 | 100 µg | |
| 14 | 50 µg | |
| 21 | 50 µg | 100 µg |
| 28 | 50 µg | |
| 35 | 50 µg | |
| 42 | | 50 µg |
| 70 | | 50 µg |

TABLE 2

Presence of insert by PCR with vector specific primers as described in Example 1

| | #days after last injection | Source RNA | Size of the library | % insert |
|---|---|---|---|---|
| Llama002 | 4 | Lymph | $1.3 \times 10^7$ | 89 |
| | 4 | PBL | $1.9 \times 10^7$ | 95 |
| | 10 | PBL | $1.1 \times 10^8$ | 70 |
| Llama004 | 4 | PBL | $1.7 \times 10^8$ | 96 |
| | 4 | Lymph | $4.9 \times 10^7$ | >95 |
| | 10 | PBL | $2.2 \times 10^6$ | >95 |

TABLE 3

First selection as described in Example 1

| | 5 µg/ml | 0.5 µg/ml | 0 µg/ml (blanco) |
|---|---|---|---|
| Llama 2 (pool PBL day 4, PBLday 10, lymph node day 4) | $1.4\ 10^6$ | $2.7\ 10^5$ | $1.5\ 10^4$ |
| Enrichment compared to blanco | 400 x | 18 x | |
| Llama 4 (pool PBL day 4, PBLday 10, lymph node day 4) | $3.3\ 10^6$ | $4.5\ 10^5$ | $7.2\ 10^4$ |
| Enrichment compared to blanco | 140 x | 6.25 x | |

TABLE 4

Second selection using the rescued phages from the first selection as described in Example 1

| | 1 µg/ml Elution buffy coat cells | 1 µg/ml Elution Lysozyme | 0 µg/ml Elution buffy coat cells | 0 µg/ml Elution Lysozyme |
|---|---|---|---|---|
| Llama 2 (selection 5 µg/ml IgE: 400 x enrichment) | $1.2\ 10^8$ | $1.2\ 10^8$ | $6\ 10^3$ | $3\ 10^3$ |
| Enrichment compared to lysozyme elution | No enrichment | | | 2x |
| Llama 4 (selection 5 µg/ml IgE: 140 x enrichment) | $1.3\ 10^8$ | $2\ 10^7$ | $3\ 10^3$ | $3\ 10^3$ |
| Enrichment compared to lysozyme elution | 6.5 x | | No enrichment | |

TABLE 5

Second round selection using neutravidine coated tubes as described in Example 1

| | 2 nM IgE Elution buffy coat cells | 2 nM IgE Elution Lysozyme | 0 nM IgE Elution buffy coat cells | 0 nM IgE Elution Lysozyme |
|---|---|---|---|---|
| Llama 2 (selection 5 µg/ml IgE: 400 x enrichment) | $1.5\ 10^8$ | $1.5\ 10^7$ | $3\ 10^5$ | $3\ 10^3$ |
| Enrichment compared to lysozyme elution | 10 x | | | |
| Llama 4 (selection 5 µg/ml IgE: 140 x enrichment) | $3.3\ 10^7$ | $2.2\ 10^7$ | $3\ 10^3$ | $6\ 10^3$ |
| Enrichment compared to lysozyme elution | 1.5 x | | | |

TABLE 6

Number of clones that score positive for binding to both human IgE and chimeric IgE versus the number of clones tested in ELISA as described in Example 1

| | Selection with 5 µg/ml | Selection with 0.5 µg/ml |
|---|---|---|
| Llama 002 | 39/47 | 21/47 |
| Llama 004 | 45/47 | 46/47 |

TABLE 7

Treatment schedule

| Group | Animals | Description | Schedule |
|---|---|---|---|
| 1 | 8 | negative control 1 | daily 100 µl PBS i.p.+ ip |
| 2 | 8 | negative control 2 rectal | every other day 100 µl PBS rectal for 2 weeks |
| 3 | 8 | negative control 3 intragastric | daily 100 µl PBS intragastric for 14 consecutive days |
| 4 | 8 | positive control 1 dexamethasone | 5 µg i.p. for 7 consecutive days |
| 5 | 8 | positive control 2 IL10 expressing *l. lactis* | applied orally once per day for 14 consecutive days |
| 6 | 8 | bivalent VHH 3F intra-gastric | daily 100 µg bivalent VHH $3F_2$ intragastric on 14 consecutive days |
| 7 | 8 | bivalent VHH 3F i.p. | daily 100 µg bivalent VHH 3F i.p. for 14 consecutive days |

TABLE 7-continued

Treatment schedule

| Group | Animals | Description | Schedule |
|---|---|---|---|
| 8 | 8 | bivalent VHH 3F rectally | 100 µg bivalent VHH 3F rectally in 100 µl PBS every other day for two weeks |

TABLE 8

Overview of the libraries, their diversity and % insert derived from different llama's and tissues as described in Example 7 and 8

| Animal | Antigen | Source | Titer | % Insert |
|---|---|---|---|---|
| Llama 5 | Human MMP-12 | PBL time 1 | $2.1 \cdot 10^8$ | 94% |
| Llama 5 | Human MMP-12 | PBL time 2 | $7.5 \cdot 10^6$ | 92% |
| Llama 5 | Human MMP-12 | Lymph node | $7.8 \cdot 10^8$ | 100% |

TABLE 9

Immunization schedule and tissue collections

| Day | Llama 024 | Llama 025 | Llama 026 | Llama 027 |
|---|---|---|---|---|
| 0 | intact cells | intact cells | vesicles | vesicles |
| 7 | intact cells | intact cells | vesicles | vesicles |
| 14 | intact cells | intact cells | vesicles | vesicles |
| 21 | intact cells | intact cells | vesicles | vesicles |
| 28 | intact cells | intact cells | vesicles | vesicles |
| 35 | intact cells | intact cells | vesicles | vesicles |
| 42 | intact cells | intact cells | vesicles | vesicles |
| 46 | 150 ml blood sample (PBL1) | 150 ml blood sample (PBL1) | 150 ml blood sample (PBL1) lymph node | 150 ml blood sample (PBL1) lymph node |
| 47 | lymph node spleen bone marrow | | | |
| 49 | | purified EGFR | 150 ml blood sample (PBL2) | 150 ml blood sample (PBL2) |
| 55 | | purified EGFR | | |
| 59 | | 150 ml blood sample (PBL2) | | |
| 60 | | lymph node spleen bone marrow | | |

TABLE 10

Overview of constructed libraries

| Animal | Tissue | RNA (µg) | Size ($\times 10^8$) | % Insert |
|---|---|---|---|---|
| Llama 024 | PBL1 | 200 | 0.25 | 83 |
| Llama 024 | Lymph node ileum | 40 | 2.3 | 78 |
| Llama 024 | Lymph node bow | 150 | 0.17 | 100 |
| Llama 024 | Bone marrow | 97 | 1.5 | 83 |
| Llama 024 | Spleen | 160 | 0.16 | 95 |
| Llama 025 | PBL1 | 200 | 0.06 | 95 |
| Llama 025 | Lymph node (ileum + bow) | 200 | 0.8 | 96 |
| Llama 025 | Bone marrow | 200 | 0.045 | 88 |
| Llama 025 | Spleen | 200 | 2 | 86 |
| Llama 025 | PBL2 | 200 | 0.13 | 83 |
| Llama 026 | PBL1 + lymph node | 100 + 200 | 2.46 | 85 |
| Llama 027 | PBL1 + lymph node | 100 + 200 | 1.08 | 92 |

TABLE 11

Overview of epitope specific elution selection procedure

| Elution condition | Elution molecule | Selection: antigen format Round I | Round II | Round III | ΦELISA Her-14 | ΦELISA EGFR | Binder families |
|---|---|---|---|---|---|---|---|
| 1 Ia | EGF | A431 | Her-14 EGFR | — | 1/47 5/47 | 24/47 23/47 | 6 8 |
| 2 IIIa | 2e9 | A431 | Her-14 EGFR | — | 2/47 11/47 | 32/47 32/47 | 5 4 |
| 3 | 225 | A431 | A431 | Her-14 EGFR | 8/47 20/47 | 28/47 31/47 | 5 |
| 4 | 528 | A431 | A431 | Her-14 EGFR | 16/47 22/47 | 10/47 29/47 | 5 |

TABLE 12

Overview of 'internalization' selection procedure

| Library | Selection cells | Selected antibody fragment |
|---|---|---|
| Pool lymph node, bone marrow, spleen and PBL1 (024 + 025) | Her-14 | A2 |
| Pool bone marrow (024 + 025) | A431 | A4, A9, B11 |
| Pool PBL1 (024 + 025) | A431 | F11 |

TABLE 13

Primer sequences

| Name | SEQ ID NO | Sequence 5' |
|---|---|---|
| ABL002 | 101 | GGCTGAGCTCGGTGGTCCTGGCT |
| ABL010 | 102 | AACTGGAAGAATTCGCGGCCGCA GGAATTTTTTTTTTTTTTTTTT |
| ABL037 | 103 | CATGCCATGACTCGCGGCCCAGC CGGCCATGGCCGAGGTGCAGCTG GTGGAGTCTGG |

TABLE 13-continued

Primer sequences

| Name | SEQ ID NO | Sequence 5' |
|---|---|---|
| ABL038 | 104 | CATGCCATGACTCGCGGCCCAGC CGGCCATGGCCGATGTGCAGCTG GTGGAGTCTGG |
| ABL039 | 105 | CATGCCATGACTCGCGGCCCAGC CGGCCATGGCCGCGGTGCAGCTG GTGGAGTCTGG |
| ABL040 | 106 | CATGCCATGACTCGCGGCCCAGC CGGCCATGGCCGCCGTGCAGCTG GTGGATTCTGG |
| ABL041 | 107 | CATGCCATGACTCGCGGCCCAGC CGGCCATGGCCCAGGTGCAGCTG GTGGAGTCTGG |
| ABL042 | 108 | CATGCCATGACTCGCGGCCCAGC CGGCCATGGCCCAGGTACAGCTG GTGGAGTCTGG |
| ABL043 | 109 | CATGCCATGACTCGCGGCCCAGC CGGCCATGGCCCAGGTAAAGCTG GAGGAGTCTGG |
| geneIII | 110 | CCACAGACAGCCCTCATAG |
| M13 rev | 111 | GGATAACAATTTCACACAGG |

TABLE 14

Sequence listing

| SEQ ID NO | NAME | SEQUENCE |
|---|---|---|
| | Anti-IgE VHH | |
| 1 | VHH#2C3 | QVQLQDSGGGLVQPGGSLRLSCRASGRIFRINAM GWYRQAPGKQRELVATITSTGSTNFADSVRGRFT IYRDGAKRTVDLRLNSLKPEDTAVYFCNADVREY DLGPWRQYWGQGTQVTVSS |
| 2 | VHH#4G12 | QVQLQESGGGVVQPGGSLRLSCSVSGTSISNRVM AWFRQAPGKQRDFVAYITSAVNTDYADFVKGRFT ISRDNAQNMVHLQKNSLKPEDTAVYYCNVLKDTW FRTPYDYYWGQGTQVTVSS |
| 3 | VHH#2C1 | QVQLQESGGGLVQPGDSLRLSCVVSGRTLSYSSL AWFRQAPGKERDFVAALSLTTYYADSVKGRFTIS RDNAKNTVYLQMNSLKPDDTADYFCATARTRTDY APLLSAASTYDAWGQGTQVTVSL |
| 4 | VHH#2H3 | QVQLQESGGGLVQAGGSLRLSCAASGRSSRYYAM GWFRQGPGKEREFVAAVNWNGDSTYYADSVKGRF TISRGNAENTAYLQMNSLVPEDTAVYYCAKRMNA GLGYSAASYQYWGQGTQVTVSL |
| 5 | VHH#2D12 | QVQLQESGGGLVQAGDSLRLSCAASGLTFLEHVM AWFRQTPGKEREFVGAIDWSGRRITYTDSVKGRF TISRDNAKNTVYLQMNTLKPEDTAVYYCAADRTY SYSSTGYYWGQGTQVTVSS |
| 6 | VHH#2G4 | QVQLQDSGGGLVQADSLRLSCAASGLTFLEHVM AWFRQTPGKEREFVGAIDWSGRRITYTDSVKGRF TISRDNAKNTVYLQKNTLKPEDTAVYYCAADRTY SYSSTCYYWCQTQVTVSS |
| 7 | VHK#4C5 | QVQLQESGGGLVQAGGSLRLSCAASGRTLSSYTM AWFRQAPGKEREFVASISSSGISTYYADSVKGRF TISRDIAKNTVYLQMNSLKPEDTAVYYCAAKYRY YSTLYTKSGEYDYWGQGTQVTVSS |
| 8 | VHH#4A2 | QVQLQDSGGGLVQAGGSLRLSCEASGRTISSYAM AWFRQAPGKEREFVASISSSGVSKHYADSVKGRF TISNDKVKNTVYLQMNSLKPEDTAVYFCAAKYRY YSSYYTKSGDYDYWGQGTQVTVSS |
| 9 | VHH#2D4 | QVQLQESGGGLVQAGGSLRLSCAASGLTFSTYAM GWFRQAPGKEREFVAAVSYSGSYYADSVKGRFTI SRDNAKNTVYLQMASLKPEDTAVYYCAARNRGYS TYAGVYDYWGQGTQVTVSS |
| 10 | VHH#2B6 | QVQLQDSGGGLVQAGGSLRLSCAASGVTFSSYAM GWFRQAPGKEREFVASITWIGGGTYYADSVKGRF TISRDHAGNTVYLQMNTLKPDDTAVYYCALDRRS STYYLMKGEYDYRGRGTQVTVSS |
| 11 | VHH#2H11 | QVQLQESGGGLVQAGGSLRLSCAASGVTFSSYAM GWFRQAPGKEREFVASITWTGTGTYYADSVKGRF TISRDHAGTTVYLQMNSLKPEDTAVYYCAVDRRS STYYLMKGEYDYRGRGTQVTVSS |
| | Anti-TNF alpha VHH | |
| 12 | VHH#3E-His tag | QVQLQESGGGLVQPGGSLRLSCAASGRTFSDHSG YTYTIGWFRQAPKEREFVARIYWSSGNTYYADSV KGRFAISRDIAKNTVDLTMNNLEPEDTAVYYCAA RDGIPTSRSVESYNYWGQGTQVTVSSAAAEQKLI SEEDLNGAAHHHHHH |
| 13 | VHH#3F | QVQLQDSGGGLVQAGGSLRLSCAASGGTFSSIIM AWFRQAPGKEREFVGAVSWSGGTTVYADSVLGRF EISRDSARKSVYLQKNSLKPEDTAVYYCAARPYQ KYNWASASYNVWGQGTQVTVSS |
| 14 | VHH#3F/VHH#3F | QVQLQDSGGGLVQAGGSLRLSCAASGGTFSSIIM AWFRQAPGKEREFVGAVSWSGGTTVYADSVLGRF EISRDSARKSVYLQKNSLKPEDTAVYYCAARPYQ KYNWASASYNVWGQGTQVTVSSEPKTPKPQPAAA QVQLQDSGGGLVQAGGSLRLSCAASGGTFSSIIM AWFRQAPGKEREFVGAVSWSGGTTVYADSVLGRF EISRDSARKSVYLQKNSLKPEDTAVYYCAARPYQ KYNWASASYNVWGQGTQVTVSS |
| | Human MMP-12 specific VHH | |
| 15 | MMP-12 P1-1 | QVQLQESGGGLVQPGCSLRLSCVASGFTFSDYPM AWVRQAPGKCLEWISVINSGGVNTSYAASVKGRF TISRDNAKNTLFLQMNSLKPEDTAVYYCAKYSLK NEQYWRGQGTQVTVSS |
| 16 | MMP-12 P1-3 | QVQLQESGGGLVQPGGSLRLSCAASGSIFSIDGM GWYRQAPGKQRERKQRELVAAITSGGSTKYADSV KGRFTISRDNANDTVYLQMNTLKPEDTAVYYCNA VLLRRGIVYDYWGQGKQVTVSS |
| 17 | MMP-12 P1-7 | QVQLQESGGGSVKAGGSLRLSCAASGSIFSIDGM GWYRQAPGKQRERKQRELVAAITSGGSTKYADSV KGRFTISRDNANDTVYLQMNTLKPEDTAVYYCNA VLLRRGIVYDYWGQGKQVTVSS |
| 18 | MMP-12 P1-26 | QVQLQESGGGLVRAGGSLRLSCVASGRTLSKYRM GWFRQFPGKERELVAEIEWKSSSTWYRDSVKGRF TISRDNAKNTVYLRMNSLKPEDTAVYYCAAATLG EPLVKYTYWGQGTQVTVSS |
| 19 | MMP-12 P1-33 | QVQLQESGGGLVQPGGSLRLSCAASGSIFSIDGK GWYRQAPGKQRERKQRELVAAITSGGSTKYADSV KGRFTISRDNANDTVYLQMNTLKPEDTAVYYCNA VLLRRGIVYDYWGQGKQVTVSS |
| 20 | MMP-12 F1-41 | QVQLQDSGGGLVRTGDSLRLSCVVFGGTISTYAM GWFRRAPGKEREFVAAIDASGGFTEYADSVRGRF RIARDNPLSAVYLQMNSLKPEDTAFYYCAADKDR DTVVRFTTTPNEYDYWGQGTQVTVSS |

TABLE 14-continued

Sequence listing

| SEQ ID NO | NAME | SEQUENCE |
|---|---|---|
| 21 | MMP-12 P1-44 | QVQLQESGGGLVQPGGSLRLSCAASGFTFNNHWL YWVRQAQGKGLEWVSAINPGGSTVYLDSVKGRFT ISRGNTKNTLYLQMNSLKSEDTAVYYCTKAMAWA TDWDEYDLWGQGTQVTSS |
| 22 | MMP-12 P5-29 | QVQLQESGGGLVQAGGSLRLSCAASGRTFTVYTT GWFRQAPGKEREFVAAIDWSGSSTYYTDSVKGRF TISRDNTKNTVYLQMNSLKPEDTAVYYCAARDAI VGVTDTSGYRYWGQGTQVTVSS |

Anti-EGFR VHH

| SEQ ID NO | NAME | SEQUENCE |
|---|---|---|
| 23 | EGFR-1.4 | EVQLVESGGGLVQAGGSLRLSCAASGRTFSNYVM GWFRQAPGKERDFWGIIGRSGGDNTYYADSVKGR FTISWDNAKNTMYLQMNSLKPEDTAVYYCAASTY SRDTIFTKWANYNYWGQGTQVTVSS |
| 24 | EGFR-1.9 | QVQLQESGGGLVKAGGSLRLSCAASGRTFSSYVM GWFRQAPGKEREFVGAIHWSGGRTYYADSVKGRF TISSDNAKNTLYLQMNSLKPEDTAVYYCAASRII YSYVNYVNPGEYDYWGQGTQVTVSS |
| 25 | EGFR-1.33 | EVQLVESGGGLVQPGGSLRLSCAASGFTFSSHYM SWFRQAPGKEREFVAAITSSSRTYYTESVKGRFT ISRDNAKNTVYLQMNSLKSEDTAVYYCAADRTFY GSTWSKYDYRGQGTQVTVSS |
| 26 | EGFR-1.34 | QVQLQESGGCLVQAGGSLRLSCAASCRTFSKYAM CWFRQAPGKEREFVSAISWSDGSTYYADSVKGRF TISRDNAKNTVYLQVNSLKPEDTAVYYCAATYLV DVWAVHVPIRPYEYDYWGQGTQVTVSS |
| 27 | EGFR-1.38 | QVQLQDSGGGLVQAGDSLRLSCAASGRSFGGYAM GWFRQAPGKEREFVAAISWSGGSTYYADSLKGRF TISRDNAKNTVYLQMNSLKPEDTALYYCAAGLRP SPNYNHERSYDYWGQGTQVTVSS |
| 28 | EGFR-Ia1 | QVQLQESGCGLVQAGGSLLLSCAASGRTFSSYAM GWFRQAPGKEREFVAAINWSGSTSYADSVKGRF TISRDNTKNTVYLQMNSLKPEDTAAFYCAATYNP YSRDHYFPRMTTEYDYWGQGTQVTVSS |
| 29 | EGFR-Ia7 | QVQLQESGGRLVQTGGSLRLSCAASGGTFGTYAL GWFRQAPGKEREFVAAISRFGSTYYADSVKGRFT ISRDNANNTVYLEMNSLKPEDTAVYYCAAREGVA LGLRNDANYWCQCTQVTVSS |
| 30 | EGFR-Ia15 | QVQLQDSGGGLVQAGGSLRLSCAASGGTFSSYAM GWFRQAPGKEREFVAAIGLNTYYADSVKGRFTIS RDWAKNTVYLQMNSLKPEDTAVYYCAARTSGVVG GTPKRYDYWGQGTQVTVSS |
| 31 | EGFR IIIa42 | EVQLVESGGGSVQAGGSLKLSCAASGRSFSTYAM GWFRQAPGQDREFVATISWTDSTDYADSVKGRFT ISRDNAKNTGYLQMNSLKPEDTAVYYCAADRWAS SRRNVDYDYWGQGTQVTVSS |
| 32 | EGFR-2.6 | QVQLQESGGGLVQAGGSLRLSCAASGRTFSNYAM GWFRQAPGKEREFVAAINWGGGNTYADSVKGRF TISRDNAKNTVYLQMNSLKPEDTAVYYCAASEWG GSDYDHDYDYWGQGTQVTVSS |
| 33 | EGFR-2.20 | EVQLVESGGGLVQAGGSLRLSCAASGRSFSSYAM AWFRQAPGKEREFVAAISWGGGSTYYAVSVKGRF TISRDNAKNTVYLQHNSLKPEDTARYYCAADETF HSSAYGEYEYWGQGTQVTVSS |
| 34 | EGFR-IIIa5 | EVQLVESGGGLVQAGGSLRLSCTASGRTFSSYAM GWFRQTPGKEREFVAAITSSGGSTYYADSVKGRF TISRDNAKSTMYLQMDSLMLDDTSVYYCAADSSR PQYSDSALRRILSLSNSYPYWGQGTQVTVSS |
| 35 | EGFR-3.18 | EVQLVESGGGLVQPGGSLRLSCVASGFTFADYAM SWVRQAPGKGLQWVSSISYNGDTTYYAESMKDRF TISRDNAKNTLYLQMNSLKSEDTAVYYCASSGSY YPGHFESWGQGTQVTVSS |
| 36 | EGFR-3.32 | QVQLQESGGGLVQAGGSLRLSCAASGRTFSGYAM GWFRQAPGEEREFVAAISWRGTSTYYGDSAKGRF TISRDNAKNTVYLQMNSLKPEDTAVYYCAAGSHS DYAPDYDYWGQGTQVTVSS |
| 37 | EGFR-3.34 | QVQLQESGGGLVQAGGSLRLSCAASGRTFSSYAI GWFRQAPGKEREFVAAISWGGSNTYYADSVKGRF TISRDNAKNTVYLQMNSLKPEDTAVYYCAAGEVS NSDYAYEYDYWGQGTQVTVSS |
| 38 | EGFR-3.39 | QVQLQESGGGLVQTGGSLRLSCAASGRYIMGWFR QAPGKEREFVAGISRSGASTAYADSVKDRFTISR DSALNTVYLQMNSLKAEDTAVYFCAAALAIRLGI PRGETEYEYWGQGTQVTVSS |
| 39 | EGFR-3.40 | QVKLEESGGGLVQAGGSLRLSCSASGLTFSNYAM AWFRQAPGKEREFVATISQRGGMRHYLDSVKDRF TISRDNAKNTVYLQMNSLKPDDTAVYYCAADLMY GVDRRYDYWGRGTQVTVSS |
| 40 | EGFR-4.11 | QVKLEESGGGLVQAGDSLRLSCAASGRSFSSITM GWFRQAPGKERQFVSAINSNGNRYYADSVKGRFT ISRDNAKNTVYLQKNSLKPEDTAVYYCAAVQAYS SSSDYYSQEGAYDYWGQGTQVTVSS |
| 41 | EGFR-4.21 | EVQLVESGGGLVQAGGSLRLSCAVSGRTFSSMGW FRQAPGKEREFVATINLSGDRTDYADSVKGRFTI SRDNPKMTVYLQMDSLEPEDSAVYYCAGTSLYPS NLRYYTLPGTYADWGQGTQVTVSS |
| 42 | EGFR-4.22 | QVKLEESGGGLVQAGGSLRLSCAASGSIFSINAM GWYRQAPGKQRELVARITGTGTGITGAVSTNYAD SVKGRFTISRDNARNTVYLQMNSLKPEDTAVYYC AADRSRTIWPDYWGQGTQVTVSS |
| 43 | EGFR-B11 | QVQLQDSGGGLVQAGGSLRLSCAASRFSSAQYAI GWFRQAPGKEREGVSYITFSGGPTGYADSVKGRF TVSRDNAKNTVYLQMNSLKPEDTAVYYCAARPYT RPGSMWVSSLYDNWGQGTQVTVSS |
| 44 | EGFR-F11 | QVQLQESGGRLVQAGGSLRLSCAASEHTFRGYAI GWFRQAPGKEREFVSSITYDGTLTNYADSVTGRF TISRDNAKNTVYLQMNSLKPEDTAVYYCAAGYSY RYTTLNQYDSWGQGTQVTVSS |

Anti-human IFN gamma VHH

| SEQ ID NO | NAME | SEQUENCE |
|---|---|---|
| 45 | MP3D2SRA | QVQLQDSGGGTVQAGGSLRLSCAASGRTFSDYAV GWFRQAPGKEREFVARILWTGASRSYANSVDGRF TVSTDNAKNTVYLQKNSLKPEDTAIYYCAALPSN IITTDYLRVYYWGQGTQVTVSS |
| 46 | MP3A3SR | QVQLQDSGGGTVQAGGSLRLSCAASGRTFSNYAV GWFRQAPGKEREFVARIKWSGCSRSYANSVDGRF TVSTDNAKNTVYLQKNSLKPEDTAIYYCA?LPSN IITTDYLRVYYWGQGTQVTVSS |
| 47 | MP3C5SR | QVQLQESGGGLVQAGGSLRLSCAAAGISGSVFSR TPMGWYRQAPGKQRELVAGILTSGATSYAESVKG RFTISRDNAKNTVYLQMNSLSPEDTAEYYCNTYP TWVLSWGQGTQVTVSS |
| 48 | MP3C1SR | QVQLQDSGGGLVQAGGSLRLSCAAAGISGSVFSR TPMGWYRQAPGKQRELVAGILSSGATVYAESVKG RFTISRDNAKNTVYLQMNSLSPEDTAEYYCNTYP TWVLSWGQGTQVTVSS |

TABLE 14-continued

Sequence listing

| SEQ ID NO | NAME | SEQUENCE |
|---|---|---|
| 49 | MP3G8SR | QVQLQESGGGLVQAGGSLRLSCAAAGISGSVFSRTPMGWYRQAPGKQRELVAGILSSGATAYAESVKGRFTISRDNAKNTVYLQMNSLSPEDTAEYYCNTYPTWVLSWGQGTQVTVSS |
| 50 | MP3D2BR | QVQLQESGGGLVQPGESLRLSCAASRGIFRFNAGGWYRQAPGKQRELVAFIGVDNTTRYIDSVKGRFTISRDNAKTTVYLQMNSLQPEDTAVYYCNKVPYIDWGQGTQVTVSS |
| 51 | MP3H6SRA | QVQLQESGGGLVQAGGSLRLSCAASGRTFSTYNMGWFRQAPGKEREFVAGISWNGGSIYYTSSVEGRFTISRDNAENTVYLQMNSLKPEDTGVYYCASKGRPYGVPSPRQGDYDYWGQGTQVTVSS |
| 52 | MP3B4SRA | QVQLQESGGGLVQAGGSLRLSCAASGRTFSTYNMGWFRQAPGKEREFVAGISWNGGSIYYTSSVEGRFTISRDNAENTVYLQMNSLKPEDTGVYYCASKGRPYGVPSPRQGDYDYWGQGTQVTVSS |
| 53 | MP4E4BR | QVQLQESGGGLVQAGGSLRLSCAASGRTFSIYNMGWFRQAPGKEREFVAAISWNGGSIYYTSSVEGRFTISRDNAINTVYLQMNSLKPEDTGVYYCASKGRPYGVPSPRQGEYDYWGQGTQVTVSS |
| 54 | MP4H8SR | QVQLQESGGGLVQAGGSLRLSCAASGRTFNIYNMGWFRQAPGKERDFVAAISWNGGSIYYTSSVEGRFTISRDNAENTVYLQMNSLKPEDTGVYYCASKGRPYGVPSPRQGDYDYWGQGTQVTVSS |
| 55 | MP2F6SR | QVKLEESGGGLVQAGGSLRLSCAASGRTFNNYNMGWFRQAPGKEREFVAAISWNGGSTYYDDSVKGRFTISRDNANNLVYLQMNSLNFEDTAVYYCACAANPYGIPQYRENRYDFWGQGTQVTVSS |
| 56 | MP3D1BR | QVQLQESGGGLVQAGGSLRLSCAASGRTFDNYNMGWFRQAPGKEREFVAAISWNGGSTYYDDSVKGRFTISRDNFQKLVYLQMNSLKLEDTAVYYCACAANPYGIPQYREWRYDFWGQGTQVTVSS |
| 57 | MP2B5BR | QVQLVESGGRLVQAGGSLRLSCIASGRTISDYAAGWFRQAPGKEREFLASVTWGFGSTSYADSVKGRFTISRDKAKDTVYLQMNTLEPDDTSVYYCASSPRYCAGYRCYVTASEFDSWGQGTQVTVSS |
| 58 | MP2C1BR | QVKLEESGGRLVQAGGSLRLSCIASGRTISDYAAGWFRQAPGKEREFLASVSWGFGSTYYADSVKGRFTISRDTAKDTVYLQMNTLEPDDTSVYYCASSPRYCAGYRCYATASEFDSWGQGTQVTVSS |
| 59 | MP4A12SR | QVQLQESGGRLVQAGGSLRLSCIASGRTISDYAACWFRQAPGKEREFLASVTWGFGSTYYADSVKGRFTISRDKAKDTVYLQMNTLEPDDTSAYYCASSPRYCAGYRCYVTASEFDSWGPGTQVTVSS |
| 60 | MP3F4SRA | QVQLQDSGGGLVQAGDSLRLSCAASGRSFSSYGMGWFRQAPGKEHEFVAGIWRSGVSLYYTDSVKGRFTISRDDAKMTVSLQMNSLKPEDTAVYYCAAEATFPTWSRGRFADYDYRGQGTQVTVSS |
| 61 | MP3D3BR | QVQLQESGGGLVQAGDSLRLSCTASGRSFSSVGMGWFRQAPGKDHEFVAGIWRSGVSLYYADSVKGRFTISRDDAKMTVSLQMNGLKPEDTAVYYCAAEATFPTWNRGTFADYDYRGQGTQVTVSS |
| 62 | MP3E5BR | QVQLQESGGGLVQAGDSLRLSCAASGRSFSSYGMGWFRQAPGKEHEFVACIWRSGVSLYYADSVKGRFTISRDDAKMTVSLQMNGLKPEDTAVYYCAAEATFPTWNRGSFADYDYRGQGTQVTVSS |
| 63 | MP3C7SRA | QVQLQESGGGLVQAGDSLRLSCAASGRSFSSYGMGWFRQAPGKEHEFVAGIWRSGVSLYYADSVKGRFTISRDDAKMTVSLQMNSLKPEDTAVYYCAAEATFPTWNRGRFADYDYSGQGTQVTVSS |
| 64 | MP2F1BR | AVQLVESGGGLVQTGDSLRLSCVASGGTFSRYAMGWFRQAPGKEREFVARIGYSGRSISYATSVEGRFAISRDNAKNTVYLQMSLKPEDTAVYYCASLVSGTLYQADYWGQGTQVTVSS |
| 65 | MP2C5BR | QVQLVESGGGLVQTGDSLRLSCVASGGTFSRYAMGWFRQPPGKERDFVARIGYSGQSISYATSVEGKFAISRDNAKNTVYLQMSLKPEDTAVYYCASLVSGTLYKPNYWGQGTQVTVSS |
| 66 | MP2C10BR | QVKLEESGGGLVQAGGSLRLSCAASGLTYTVGWFRQAPGKEREFVAAISWSGGSALYADSVKGRFTISRDNAKNTVYLQMGSLEPEDTAYYSCAAPGTRYYGSNQVNYNYWGQGTQVTVSS |
| 67 | MP2G5SR | QVKLEESGGGLVQAGDSLRLSCAASGLTYTVGWFRQAPGKEREFVAAIDWSGGSALYADSVKGRFTISRDNTKNTVYLQMGSLEPEDTAVYWCAAPGTRYHGRNQVNYNYWGQGTQVTVSS |
| 68 | MP3B1SRA | QVQLQESGGGLVQPGGSLRLSCAASGFTSSNYAMSWVRQAPGKGLEWVSSINSRTGSITYADSVKGRFTITLDNAKNTLYLQMNSLKPEDTAVYYCASRVDDRVSRGQGTQVTVSS |
| 69 | MP2F10SR | QVQLVESGGGLVQAGGSLRLSCAASGRTISSFRMGWFRRAPGEEREFVAFVRSNGTSYYADSVEGRFTITRDNAKNTVYLRMDSLKPEDTAVYYCAAATRDYGGSFDYWGQGTQVTVSS |
| 70 | MP3A7SRA | QVQLQDSGGGLVQAGGSLRLSCAASGRTFSSFRMGWFRRAPGEEREFVAFVRSNGTSYYADSVEGRFTITRDNAKNTVYLRMDSLKPEDTAVYYCAAATRDYGGSFDYWGQGTQVTVSS |

Anti mouse serum albumin VHH

| SEQ ID NO | NAME | SEQUENCE |
|---|---|---|
| 71 | MSA21 | QVQLQESGGGLVQPGGSLRLSCEASGFTFSRFGMTWVRQAPGKGVEWVSGISSLGDSTLYADSVKGRFTISRDNAKNTLYLQMNSLKPEDTAVYYCTIGGSLNPGGQGTQVTVSS |
| 72 | MSAc16 | AVQLVESGGGLVQAGDSLRLSCVVSGTTFSSAAMGWFRQAPGKEREFVGAIKWSGTSTYYTDSVKGRFTISRDNVKNTVYLQKNNLKPEDTGVYTCAADRDRYRDRMGPMTTTDFRFWGQGTQVTVSS |
| 73 | MSAc112 | QVKLEESGGGLVQTGGSLRLSCAASGRTFSSFAMGWFRQAPGREREFVASIGSSGITTNYADSVKGRFTISRDNAKNTVYLQMNSLKPEDTGLCYCAVNRYGIPYRSGTQYQNWGQGTQVTVSS |
| 74 | MSAc110 | EVQLEESGGGLVQPGGSLRLSCAASGLTFNDYAMGWYRQAPGKERDKVATISIGGRTYYADSVKGRFTISRDNAKNTVYLQMNSLKPEDTAIYYCVAHRQTVVRGPYLLWGQGTQVTVSS |
| 75 | MSAc114 | QVQLVESGGKLVQAGGSLRLSCAASGRTFSNYAMGWFRQAPGKEREFVAGSGRSNSYNYYSDSVKGRFTISRDNAKNTVYLQMNSLKPEDTAVYYCAASTNLWPRDRNLYAYWGQGTQVTVSS |
| 76 | MSAc116 | EVQLVESGGGLVQAGDSLRLSCAASGRSLGIYRKGWFRQVPGKEREFVAAISWSGGTTRYLDSVKGRFTISRDSTKNAVYLQMNSLKPEDTAVYYCAVDSSGRLYWTLSTSYDYWGQGTQVTVSS |
| 77 | MSAc119 | QVQLVEFGGGLVQAGDSLRLSCAASGRSLGIYKMAWFRQVPGKEREFVAAISWGGTTRYIDSVKGRFTLSRDNTKNMVYLQMNSLKPDDTAVYYCAVDSSGRLYWTLSTSYDYWGQGTQVTVSS |

TABLE 14-continued

Sequence listing

| SEQ ID NO | NAME | SEQUENCE |
|---|---|---|
| 78 | MSAc15 | EVQLVESGGGLVQAGGSLSLSCAASGRTFSPYTM GWFRQAPGKEREFLAGVTWSGSSTFYGDSVKGRF TASRDSAKNTVTLEMNSLNPEDTAVYYCAAAYGG GLYRDPRSYDYWGRGTQVTVSS |
| 79 | MSc11 | AVQLVESGGGLVQAGGSLRLSCAASGFTLDAWPI AWFRQAPGKEREGVSCIRDGTTYYADSVKGRFTI SSDNANNTVYLQTNSLKPEDTAVYYCAAPSGPAT GSSHTFGIYWNLRDDYDNWGQGTQVTVSS |
| 80 | MSAc115 | EVQLVESGGGLVQAGGSLRLSCAASGFTFDHYTI GWFRQVPGKEREGVSCISSSDGSTYYADSVKGRF TISSDNAKNTVYLQMNTLEPDDTAVYYCAAGGLL LRVEELQASDYDYWGQGIQVTVSS |
| 81 | MSAc18 | AVQLVDSGGGLVQPGGSLRLSCTASGFTLDYYAI GWFRQAPGKEREGVACISNSDGSTYYGDSVKGRF TISRDNAKTTVYLQMNSLKPEDTAVYYCATADRH YSASHHPFADFAFNSWGQGTQVTVSS |
| 82 | MSAc17 | EVQLVESGGGLVQAGGSLRLSCAAYGLTFWRAAM AWFRRAPGKERELVVARNWDGSTRYADSVKGRF TISRDNAKNTVYLQMNSLKPEDTAVYYCAAVRTY GSATYDIWGQGTQVTVSS |
| 83 | MSAc120 | EVQLVESGGGLVQDGGSLRLSCIFSGRTFANYAM GWFRQAPGKEREFVAAINRNGGTTNYADALKGRF TISRDNTKNTAFLQMNSLKPDDTAVYYCAAREWP FSTIFSGWRYWGQGTQVTVSS |
| 84 | MSAc14 | DVQLVESGGGWVQPGGSLRLSCAASGPTASSHAI GWFRQAPGKEREFVVGINRGGVTRDYADSVKGRF AVSRDNVKNTVYLQMNRLKPEDSAIYICAAKPEY SFTAMSKGDMDYWGKGTLVTVSS |

TABLE 15

Immunisation scheme according to Example 32

| Day of immunization | Llama 005 EGFr | Llama006 EGFr | Llama005 PDK1 | Llama006 PDK1 |
|---|---|---|---|---|
| 0 | 100 µg | | 40 µg | 40 µg |
| 7 | 100 µg | | 40 µg | |
| 14 | 50 µg | | 20 µg | |
| 21 | 50 µg | 40 µg | 20 µg | 40 µg |
| 28 | 50 µg | | 20 µg | |
| 35 | 50 µg | | 20 µg | |
| 42 | | 20 µg | | 20 µg |
| 70 | | 20 µg | | 20 µg |

TABLE 16

Results of panning according to Example 35

| llama | Source RNA | Elution conditions | Pfu EGFr | Pfu casein | Enrichment |
|---|---|---|---|---|---|
| 005 | Pool of the 3 libraries | 0.2M glycin, pH 2.4 | $1 \times 10^7$ | $1 \times 10^4$ | 1000 |
| 006 | Pool of the 3 libraries | 0.2M glycin, pH 2.4 | $5 \times 10^6$ | $1 \times 10^4$ | 500 |

TABLE 17

Results of panning according to Example 35

| llama | Source RNA | Elution conditions | Pfu PDK1 | Pfu casein | Enrichment |
|---|---|---|---|---|---|
| 005 | Pool of the 3 libraries | 0.2M glycin, pH 2.4 | $1 \times 10^8$ | $1 \times 10^4$ | 10000 |
| 006 | Pool of the 3 libraries | 0.2M glycin, pH 2.4 | $9 \times 10^7$ | $1 \times 10^4$ | 9000 |

TABLE 18

Number of positive clones after screening according to Example 36

| target | Llama005 | Llama006 |
|---|---|---|
| EGFr | 26/95 | 38/95 |
| PDK1 | 93/95 | 87/95 |

TABLE 19

Number of inhibiting VHH vs number of VHH tested in inhibition ELISA according to Example 38

| target | Llama005 | Llama006 |
|---|---|---|
| PDK1 | 56/93 | 63/87 |

TABLE 20

Fractional homologies between anti-TNF-alpha VHHs of the invention.

| SEQ | VHH#1A | VHH#7B | VHH#2B | VHH#3E | VHH#3G | VHH#10A | VHH#2G | VHH#1F | VHH#9C |
|---|---|---|---|---|---|---|---|---|---|
| VHH#1A | 1.000 | 0.601 | 0.764 | 0.596 | 0.622 | 0.600 | 0.682 | 0.629 | 0.609 |
| VHH#7B | — | 1.000 | 0.604 | 0.635 | 0.645 | 0.943 | 0.653 | 0.616 | 0.933 |
| VHH#2B | — | — | 1.000 | 0.620 | 0.645 | 0.611 | 0.682 | 0.661 | 0.629 |
| VHH#3E | — | — | — | 1.000 | 0.875 | 0.641 | 0.713 | 0.689 | 0.620 |
| VHH#3G | — | — | — | — | 1.000 | 0.651 | 0.779 | 0.740 | 0.637 |
| VHH#10A | — | — | — | — | — | 1.000 | 0.658 | 0.614 | 0.935 |
| VHH#2G | — | — | — | — | — | — | 1.000 | 0.741 | 0.653 |
| VHH#1F | — | — | — | — | — | — | — | 1.000 | 0.616 |
| VHH#9C | — | — | — | — | — | — | — | — | 1.000 |
| VHH#11E | — | — | — | — | — | — | — | — | — |
| VHH#10C | — | — | — | — | — | — | — | — | — |
| VHH#4B | — | — | — | — | — | — | — | — | — |

TABLE 20-continued

Fractional homologies between anti-TNF-alpha VHHs of the invention.

| | | | | | | | | |
|---|---|---|---|---|---|---|---|---|
| VHH#10D | — | — | — | — | — | — | — | — | — |
| VHH#12B | — | — | — | — | — | — | — | — | — |
| VHH#9E | — | — | — | — | — | — | — | — | — |
| VHH#3F | | | | | | | | | |

| | SEQ | VHH#11E | VHH#10C | VHH#4B | VHH#10D | VHH#12B | VHH#9E | VHH#3F |
|---|---|---|---|---|---|---|---|---|
| | VHH#1A | 0.601 | 0.614 | 0.818 | 0.642 | 0.747 | 0.596 | 0.604 |
| | VHH#7B | 0.933 | 0.719 | 0.593 | 0.614 | 0.620 | 0.616 | 0.624 |
| | VHH#2B | 0.620 | 0.637 | 0.796 | 0.634 | 0.951 | 0.620 | 0.645 |
| | VHH#3E | 0.643 | 0.612 | 0.604 | 0.648 | 0.596 | 0.674 | 0.682 |
| | VHH#3G | 0.637 | 0.653 | 0.645 | 0.689 | 0.622 | 0.708 | 0.716 |
| | VHH#10A | 0.935 | 0.725 | 0.592 | 0.612 | 0.626 | 0.622 | 0.637 |
| | VHH#2G | 0.669 | 0.685 | 0.666 | 0.746 | 0.650 | 0.701 | 0.717 |
| | VHH#1F | 0.616 | 0.664 | 0.661 | 0.714 | 0.645 | 0.709 | 0.717 |
| | VHH#9C | 0.941 | 0.743 | 0.601 | 0.622 | 0.645 | 0.600 | 0.616 |
| | VHH#11E | 1.000 | 0.719 | 0.601 | 0.622 | 0.637 | 0.608 | 0.624 |
| | VHH#10C | — | 1.000 | 0.650 | 0.606 | 0.637 | 0.600 | 0.632 |
| | VHH#4B | — | — | 1.000 | 0.611 | 0.796 | 0.588 | 0.629 |
| | VHH#10D | — | — | — | 1.000 | 0.619 | 0.674 | 0.674 |
| | VHH#12B | — | — | — | — | 1.000 | 0.604 | 0.637 |
| | VHH#9E | — | — | — | — | — | 1.000 | 0.854 |
| | VHH#3F | | | | | | | 1.000 |

TABLE 21

Percentage homologies between anti-IFN-gamma VHHs of the invention

| | % Homology | | | | | | | | | | | |
|---|---|---|---|---|---|---|---|---|---|---|---|---|
| | MP3D2SRA | MP3A3SR | MP3C5SR | MP3C1SR | MP3G8SR | P3D2BR | MP3H6SRA | MP3B4SRA | MP4E4BR | MP4H8SR | MP2F6SR | MP3D1BR |
| MP3D2SRA | X | 96 | 66 | 66 | 66 | 62 | 71 | 71 | 71 | 70 | 68 | 69 |
| MP3A3SR | — | X | 66 | 66 | 66 | 62 | 72 | 72 | 72 | 71 | 70 | 71 |
| MP3C5SR | — | — | X | 97 | 98 | 73 | 65 | 65 | 64 | 63 | 63 | 63 |
| MP3C1SR | — | — | — | X | 98 | 72 | 64 | 64 | 64 | 62 | 62 | 62 |
| MP3G8SR | — | — | — | — | X | 73 | 65 | 65 | 64 | 63 | 63 | 63 |
| MP3D2BR | — | — | — | — | — | X | 63 | 63 | 63 | 62 | 63 | 64 |
| MP3H6SRA | — | — | — | — | — | — | X | 100 | 97 | 97 | 80 | 81 |
| MP3B4SRA | — | — | — | — | — | — | — | X | 97 | 97 | 80 | 81 |
| MP4E4BR | — | — | — | — | — | — | — | — | X | 97 | 81 | 82 |
| MP4H8SR | — | — | — | — | — | — | — | — | — | X | 81 | 81 |
| MP2F6SR | — | — | — | — | — | — | — | — | — | — | X | 94 |
| MP3D1BR | — | — | — | — | — | — | — | — | — | — | — | X |
| MP2B5BR | — | — | — | — | — | — | — | — | — | — | — | — |
| MP2C1BR | — | — | — | — | — | — | — | — | — | — | — | — |
| MP4A12SR | — | — | — | — | — | — | — | — | — | — | — | — |
| MP3F4SRA | — | — | — | — | — | — | — | — | — | — | — | — |
| MP3D3BR | — | — | — | — | — | — | — | — | — | — | — | — |
| MP3E5BR | — | — | — | — | — | — | — | — | — | — | — | — |
| MP3C7SRA | — | — | — | — | — | — | — | — | — | — | — | — |
| MP2F1BR | — | — | — | — | — | — | — | — | — | — | — | — |
| MP2C5BR | — | — | — | — | — | — | — | — | — | — | — | — |
| MP2C10BR | — | — | — | — | — | — | — | — | — | — | — | — |
| MP2G5SR | — | — | — | — | — | — | — | — | — | — | — | — |
| MP3B1SRA | — | — | — | — | — | — | — | — | — | — | — | — |
| MP2F10SR | — | — | — | — | — | — | — | — | — | — | — | — |
| MP3A7SRA | — | — | — | — | — | — | — | — | — | — | — | — |
| MP4C10SR | — | — | — | — | — | — | — | — | — | — | — | — |
| MP4D5BR | — | — | — | — | — | — | — | — | — | — | — | — |
| MP3F1SRA | — | — | — | — | — | — | — | — | — | — | — | — |
| MP6D6BR | — | — | — | — | — | — | — | — | — | — | — | — |
| MP6B1BR | — | — | — | — | — | — | — | — | — | — | — | — |
| MP6A8BR | — | — | — | — | — | — | — | — | — | — | — | — |
| MP6B12BR | — | — | — | — | — | — | — | — | — | — | — | — |
| MP6C11BR | | | | | | | | | | | | |
| MP6B10BR | | | | | | | | | | | | |

TABLE 21-continued

Percentage homologies between anti-IFN-gamma VHHs of the invention

% Homology

| | MP2B5BR | MP2C1BR | MP4A12SR | MP3F4SRA | MP3D3BR | MP3E5BR | MP3C7SRA | MP2F1BR | MP2C5BR | MP2C10BR | MP2G5SR | MP3B1SRA |
|---|---|---|---|---|---|---|---|---|---|---|---|---|
| MP3D2SRA | 65 | 63 | 64 | 68 | 66 | 67 | 68 | 71 | 70 | 68 | 67 | 63 |
| MP3A3SR | 65 | 63 | 64 | 68 | 66 | 67 | 68 | 72 | 72 | 69 | 67 | 64 |
| MP3C5SR | 60 | 58 | 59 | 64 | 64 | 65 | 66 | 65 | 65 | 65 | 63 | 63 |
| MP3C1SR | 58 | 57 | 58 | 65 | 64 | 64 | 65 | 64 | 63 | 64 | 62 | 63 |
| MP3G8SR | 59 | 58 | 59 | 64 | 64 | 65 | 66 | 65 | 64 | 65 | 63 | 63 |
| MP3D2BR | 59 | 58 | 58 | 62 | 61 | 62 | 63 | 64 | 63 | 63 | 63 | 63 |
| MP3H6SRA | 67 | 68 | 67 | 75 | 71 | 73 | 75 | 73 | 71 | 73 | 71 | 64 |
| MP3B4SRA | 67 | 68 | 67 | 75 | 71 | 73 | 75 | 73 | 71 | 73 | 71 | 66 |
| MP4E4BR | 68 | 69 | 68 | 73 | 70 | 71 | 73 | 73 | 71 | 73 | 71 | 66 |
| MP4H8SR | 66 | 66 | 66 | 72 | 69 | 71 | 72 | 71 | 71 | 72 | 71 | 64 |
| MP2F6SR | 65 | 68 | 64 | 70 | 67 | 69 | 71 | 67 | 65 | 73 | 69 | 63 |
| MP3D1BR | 65 | 66 | 65 | 71 | 69 | 71 | 72 | 67 | 65 | 70 | 63 | 63 |
| MP2B5BR | X | 66 | 63 | 63 | 64 | 64 | 64 | 65 | 63 | 64 | 65 | 60 |
| MP2C1BR | | X | 95 | 63 | 64 | 64 | 64 | 62 | 61 | 66 | 62 | 59 |
| MP4A12SR | | | X | 63 | 64 | 64 | 64 | 62 | 60 | 63 | 62 | 59 |
| MP3F4SRA | | | | X | 94 | 96 | 97 | 69 | 67 | 68 | 68 | 62 |
| MP3D3BR | | | | | X | 98 | 96 | 70 | 68 | 67 | 67 | 62 |
| MP3E5BR | | | | | | X | 98 | 70 | 68 | 68 | 69 | 63 |
| MP3C7SRA | | | | | | | X | 71 | 69 | 69 | 70 | 63 |
| MP2F1BR | | | | | | | | X | 94 | 66 | 67 | 63 |
| MP2C5BR | | | | | | | | | X | 66 | 67 | 63 |
| MP2C10BR | | | | | | | | | | X | 94 | 62 |
| MP2G5SR | | | | | | | | | | | X | 62 |
| MP3B1SRA | | | | | | | | | | | | X |
| MP3A7SRA | | | | | | | | | | | | |
| MP4C10SR | | | | | | | | | | | | |
| MP4D5BR | | | | | | | | | | | | |
| MP3F1SRA | | | | | | | | | | | | |
| MP6D6BR | | | | | | | | | | | | |
| MP6B1BR | | | | | | | | | | | | |
| MP6A8BR | | | | | | | | | | | | |
| MP6B12BR | | | | | | | | | | | | |
| MP6C11BR | | | | | | | | | | | | |
| MP6B10BR | | | | | | | | | | | | |

% Homology

| | MP2F10SR | MP3A7SRA | MP4C10SR | MP4D5BR | MP3F1SRA | MP6D6BR | MP6B1BR | MP6A8BR | MP6B12BR | MP6C11BR | MP6B10BR |
|---|---|---|---|---|---|---|---|---|---|---|---|
| MP3D2SRA | 67 | 68 | 60 | 72 | 65 | 68 | 67 | 66 | 67 | 76 | 70 |
| MP3A3SR | 66 | 67 | 60 | 73 | 65 | 67 | 67 | 65 | 66 | 77 | 71 |
| MP3C5SR | 64 | 64 | 61 | 67 | 60 | 74 | 63 | 60 | 63 | 70 | 64 |
| MP3C1SR | 64 | 65 | 60 | 67 | 59 | 73 | 63 | 60 | 62 | 70 | 65 |
| MP3G8SR | 65 | 65 | 61 | 66 | 60 | 73 | 63 | 61 | 63 | 71 | 64 |
| MP3D2BR | 63 | 63 | 63 | 65 | 58 | 73 | 64 | 60 | 63 | 68 | 67 |
| MP3H6SRA | 75 | 75 | 63 | 71 | 69 | 71 | 71 | 68 | 70 | 82 | 70 |

TABLE 21-continued

Percentage homologies between anti-IFN-gamma VHHs of the invention

| | | | | | | | | | | | |
|---|---|---|---|---|---|---|---|---|---|---|---|
| MP3B4SRA | 75 | 75 | 63 | 71 | 69 | 71 | 71 | 68 | 70 | 82 | 70 |
| MP4E4BR | 75 | 75 | 63 | 72 | 70 | 71 | 71 | 68 | 70 | 80 | 71 |
| MP4H8SR | 73 | 73 | 62 | 70 | 67 | 69 | 69 | 67 | 67 | 79 | 71 |
| MP2F6SR | 71 | 70 | 62 | 69 | 66 | 67 | 67 | 68 | 69 | 78 | 69 |
| MP3D1BR | 71 | 71 | 62 | 68 | 66 | 67 | 67 | 69 | 67 | 79 | 70 |
| MP2B5BR | 66 | 63 | 57 | 63 | 84 | 65 | 65 | 63 | 62 | 70 | 65 |
| MP2C1BR | 66 | 63 | 56 | 61 | 85 | 65 | 65 | 63 | 62 | 70 | 65 |
| MP4A12SR | 65 | 65 | 56 | 61 | 84 | 64 | 64 | 65 | 62 | 70 | 71 |
| MP3F4SRA | 67 | 67 | 60 | 72 | 63 | 63 | 63 | 64 | 65 | 76 | 69 |
| MP3D3BR | 67 | 67 | 60 | 70 | 64 | 68 | 68 | 66 | 64 | 75 | 71 |
| MP3E5BR | 68 | 68 | 61 | 72 | 64 | 66 | 66 | 65 | 66 | 77 | 71 |
| MP3C7SRA | 69 | 69 | 61 | 72 | 64 | 68 | 68 | 66 | 64 | 78 | 67 |
| MP2F1BR | 68 | 67 | 62 | 70 | 63 | 67 | 67 | 62 | 63 | 74 | 67 |
| MP2C5BR | 67 | 66 | 59 | 69 | 66 | 69 | 69 | 64 | 68 | 73 | 73 |
| MP2C10BR | 68 | 66 | 59 | 67 | 65 | 67 | 67 | 64 | 66 | 74 | 73 |
| MP2G5SR | 67 | 65 | 91 | 67 | 60 | 67 | 67 | 68 | 69 | 73 | 65 |
| MP3B1SRA | 66 | 65 | 61 | 67 | 65 | 67 | 67 | 65 | 67 | 69 | 68 |
| MP2F10SR | X | 97 | 61 | 68 | 63 | 71 | 71 | 65 | 67 | 77 | 69 |
| MP3A7SRA | — | X | 61 | 64 | 58 | 65 | 65 | 63 | 66 | 77 | 63 |
| MP4C10SR | — | — | X | 64 | 64 | 64 | 64 | 65 | 66 | 66 | 73 |
| MP4D5BR | — | — | — | X | 68 | 69 | 68 | 63 | 65 | 71 | 68 |
| MP3F1SRA | — | — | — | — | X | 65 | 65 | 64 | 63 | 77 | 73 |
| MP6D6BR | — | — | — | — | — | X | 70 | 65 | 70 | 76 | 71 |
| MP6B1BR | — | — | — | — | — | — | X | 78 | 81 | 75 | 66 |
| MP6A8BR | — | — | — | — | — | — | — | X | 75 | 74 | 68 |
| MP6B12BR | — | — | — | — | — | — | — | — | X | 73 | 77 |
| MP6C11BR | — | — | — | — | — | — | — | — | — | X | 68 |
| MP6B10BR | — | — | — | — | — | — | — | — | — | — | X |

References

Okayasu I, Hatakeyama S, Yamada M, Ohkusa T, Inagaki Y, Nakaya R. A novel method in the induction of reliable experimental acute and chronic ulcerative colitis in mice. Gastroenterology 1990; 98:694-702.

Kojouharoff G, Hans W, Obermeier F, Mannel D N, Andus T, Scholmerich J, Gross V, Falk W. Neutralization of tumour necrosis factor (TNF) but not of IL-1 reduces inflammation in chronic dextran sulphate sodium-induced colitis in mice. Clin Exp Immunol 1997; 107:353-8.

MMP12

Salmela M T, Pender S L, Reunala T, MacDonald T. Saarialho-Kere U.

Gut, 2001; 48(4):496-502

Parallel expression of macrophage metalloelastase (MMP-12) in duodenal and skin lesions of patients with dermatitis herpetiformis.

Chavey C, Mari B, Monthouel M N, Bonnafous S, Anglard P, Van Obberghen E, Tartare-Deckert S.

J. Biol. Chem., 2003; 278: 11888-11896.

Matrix metalloproteinases are differentially expressed in adipose tissue during obesity and modulate adipocyte differentiation.

Churg A, Wang R D, Tai H, Wang X, Xie C, Dai J, Shapiro S D, Wright J L.

Am. J. Respir. Crit. Care Med., 2003; 167: 1083-1089.

Macrophage Metalloelastase Mediates Acute Cigarette Smoke-Induced Inflammation Via TNF-alpha Release.

R Lang, A Kocourek, M Braun, H Tschesche, R Huber, W Bode, K Maskos

J Mol Biol. September 2001; 312(4): 731-42.

Substrate specificity determinants of human macrophage elastase (MMP-12) based on the 1.1 A crystal structure.

Yoshikatsu Kaneko, Minoru Sakatsume, Yuansheng Xie, Takeshi Kuroda, Michiko Igashima, Ichiei Narita and Fumitake Gejyo The Journal of Immunology, 2003, 170: 3377-3385.

Macrophage Metalloelastase as a Major Factor for Glomerular Injury in Anti-Glomerular Basement Membrane Nephritis Ding Y. Shimada Y, Gorrin-Rivas M J, Itami A, Li Z, Hong T, Maeda M, Komoto I, Kawabe A, Kaganoi J, Imamura M.

Oncology 2002; 63(4):378-84.

Clinicopathological significance of human macrophage metalloelastase expression in esophageal squamous cell carcinoma.

Kerkela E, Ala-Aho R, Jeskanen L, Rechardt O, Grenman R, Shapiro S D, Kahari V M, Saarialho-Kere U.

J Invest Dermatol 2000 June; 114(6):1113-9

Expression of human macrophage metalloelastase (MMP-12) by tumor cells in skin cancer.

Example 43: Pharmacokinetics of RSV NB2, ALX-0081 & RANKL008A in the Male Wistar Rat after Single Intratracheal or Intravenous Administration

TABLE B-1

43.1 test items:

| Name | Alternative names | SEQ ID NO: | Reference | Amino acid sequence |
|---|---|---|---|---|
| RSV NB2 | 191D3 | 144 | SEQ ID NO: 159 in U.S. provisional 61/139,130 | EVQLVESGGGLVQAGG SLRLSCEASGRTYSRY GMGWFRQAPGKEREFV AAVSRLSGPRTVYADS VKGRFTISRDNAENTV YLQMNSLKPEDTAVYT CAAELTNRNSGAYYYA WAYDYWGQGTQVTVSS |
| ALX-0081 | 12A2H1-3a-12A2H1 | 145 | SEQ ID NO: 98 in WO2006122825 | EVQLVESGGGLVQPGG SLRLSCAASGRTFSYN PMGWFRQAPGKGRELV AAISRTGGSTYYPDSV EGRFTISRDNAKRMVY LQMNSLRAEDTAVYYC AAAGVRAEDGRVRTLP SEYTFWGQGTQVTVSS AAAEVQLVESGGGLVQ PGGSLRLSCAASGRTF SYNPMGWFRQAPGKGR ELVAAISRTGGSTYYP DSVEGRFTISRDNAKR MVYLQMNSLRAEDTAV YYCAAAGVRAEDGRVR TLPSEYTFWGQGTQVI VSS |
| RANK L008a | | 146 | SEQ ID NO: 759 WO2008142164 | EVQLVESGGGLVQPGG SLRLSCAASGFIFSSY PMGWFRQAPGKGREFV SSITGSGGSTYYADSV KGRFTISRDNAKNTLY LQMNSLRPEDTAVYYC AAYIRPDTYLSRDYRK YDYWGQGTLVTVSSGG GGSGGGSEVQLVESGG GLVQPGNSLRLSCAAS GFTFSSFGMSWVRQAP GKGLEWVSSISGSGSD ILYADSVKGRFTISRD NAKTILYLQMNSLRPE DTAVYYCTIGGSLSRS SQGTLVTVSSGGGGSG GGSEVQLVESGGGLVQ PGGSLRLSCAASGFTF SSYPMGWFRQAPGKGR EFVSSITGSGGSTYYA DSVKGRFTISRDNAKN TLYLQMNSLRPEDTAV YYCAAYIRPDTYLSRD YRKYDYWGQGILVTVS S |

Animal Model 101 male Wistar rats (approximately 300 gram and 11 weeks old) were used for this study, a strain bred by Charles River Laboratories, Germany. The animals were held for at least 6 days for adaptation. Following the initial health check, the animals were weighed and allocated by means of a computerized randomization program to the test groups; only healthy animals were used.

The sterile test substances were thawed in a water bath at 25° C. while swirling gently for 10 minutes. For intratracheal dosing, no further dilutions were required. For intravenous administration, the required amount of test substance was diluted aseptically in sterile DPBS ((Dulbecco's modified) Phosphate Buffered Saline) down to the desired concentrations. The test item formulations were freshly prepared within 4 hours prior to dosing.

Dose and Route of Administration

The different test groups and the dose levels are given in Table B-2. The i.v. bolus dose was given into a tail vein. The amount of test item for i.v. administration was adjusted to each animal's current body weight. The i.t. dose was administered intratracheally with a syringe with a blunt stainless steel dosing needle, after deep anesthetization with isoflurane. The amount of test item for i.t. administration was set to 100 µL/animal, irrespective of body weight. The average body weight of intratracheally dosed animals was on average 0.315 kg (RSV NB2 group), 0.317 kg (ALX-0081 group), 0.323 kg (RANKL008A group), corresponding to a mean dose per b.w. were calculated at 3.6 mg/kg (RSV NB2 group), 3.1 mg/kg (ALX-0081 group), 3.2 mg/kg (RANKL008A group),

TABLE B-2

Study design

| Group | Substance | Route | Single Dose (mg/kg) | Number of animals |
|---|---|---|---|---|
| 1 | RSV NB2 | i.v. | 4 | 3 |
| 2 | ALX-0081 | i.v. | 5 | 3 |
| 3 | RANKL008A | i.v. | 5 | 3 |
| 4 | RSV NB2 | i.t. | 3.6 | 28 |
| 5 | ALX-0081 | i.t. | 3.1 | 28 |
| 6 | RANKL008A | i.t. | 3.2 | 28 |
| 7 | — | — | — | 8 |

Blood and BALF Sampling and Processing.

After i.v. dosing, blood was sampled (approximately 300 µL) at 0.05, 0.25, 0.5, 1, 2, 4, 6, and 24 hours from the tail vein of RSV NB2- and ALX-0081-dosed animals and at 0.05, 0.25, 0.5, 1, 2, 4, 8, 24, and 48 hours from RANKL008A-dosed animals. All blood samples were placed on melting ice. Within approximately 30 minutes after sampling, the blood samples were centrifuged at 5° C. for 10 minutes (1500 g). Citrated plasma was stored in polypropylene tubes at approximately ≤−75° C. until dispatch on dry ice to the Sponsor.

After intratracheal dosing, blood, lungs, and BALF were collected (at necropsy following deep anaesthesia with isoflurane) at 0.05, 0.333, 1, 2, 4, 6, and 24 hours from RSV NB2-dosed rats and ALX-0081-dosed rats and at 0.05, 0.333, 1, 2, 4, 8 and 24 hours from animals dosed with RANKL008A. By means of an aorta punction 4 mL of blood was withdrawn. Within 42 minutes after sampling, the blood samples were centrifuged at 5° C. for 10 minutes (1500 g). Citrated plasma was stored in polypropylene tubes at approximately ≤−75° C. until dispatch on dry ice to the Sponsor. Following the removal of blood, lungs were harvested. First, the lungs including trachea were rinsed with iced DPBS and weighed. Then, BALF was collected. Five mL lavage fluid (DPBS) was carefully put into the lungs. After approximately 10 seconds, as much fluid as possible was returned to the syringe. BALF was transferred to an empty tube and directly stored on melting ice. This procedure was repeated. The second collection of BALF was added to the first collection. The volume of BALF that was collected was documented and reported. Subsequently, BALF was stored at approximately ≤−75° C. until dispatch on dry ice to the Sponsor.

Determination of RSV NB2 in Rat Plasma or BALF 96-well microtiter plates (Maxisorp, Nunc-) were coated overnight at 4° C. with 100 µL hRSV (12.5 µg/mL, Hytest). Thereafter wells were aspirated, blocked (RT, 1 h, PBS-0.1% casein) and washed. The standards, QC, and predilutions of the test samples were prepared in a non-coated (polypropylene) plate in 100% rat plasma or BALF and incubated for 30 min at RT while shaking at 600 rpm. A 1/10 dilution of the samples in PBS-0.1% casein (final concentration of rat plasma or BALF is 10%) was transferred to the coated plate and incubated for 1 hr at RT while shaking at 600 rpm. After three washing steps with PBS-0.05% Tween20, the plates were incubated with polyclonal rabbit anti-Nanobody monoclonal K1 (1/2000 in PBS-0.1% casein, in-house) for 1 hr at RT while shaking at 600 rpm. After 3 washing steps with PBS-0.05% Tween20, 100 µl horseradish peroxidase (HRP) labeled polyclonal goat anti-rabbit (1/2000 in PBS-0.1% casein, DakoCytomation) was incubated for 1 hr at RT while shaking at 600 rpm. Visualization was performed covered from light for 20 min with 100 µL 3,3′,5,5′-tetramethylbenzidine (esTMB, SDT, diluted 1/3). After 20 min, the colouring reaction was stopped with 100 µL 1N HCl. The absorbance was determined at 450 nm and corrected for background absorbance at 620 nm. Concentration in each sample was determined based on a sigmoidal standard curve. The lower limit of quantification (LLOQ) and upper limit of quantification (ULOQ) of the different assays are listed in Table B-3.

TABLE B-3

LLOQ and ULOQ for determination of RSV NB2 in rat plasma and BALF samples

| PK ELISA | LLOQ (ng/ml) | | ULOQ (ng/ml) | |
|---|---|---|---|---|
| | Plate level | Plasma/BALF level | Plate level | Plasma/BALF level |
| RSV NB2 | 0.4 | 4.0 | 20.0 | 200.0 |

Determination of ALX-0081 in Rat Plasma or BALF 96-well microtiter plates (Maxisorp, Nunc) were coated overnight at 4° C. with 100 µL vWF in PBS (2.5 µg/mL, Haemate P1200/500-ZLB Behring). Thereafter wells were aspirated, blocked (RT, 1 h, PBS-0.1% casein) and washed. The standards, QC, and predilutions of the test samples were prepared in a non-coated (polypropylene) plate in 100% rat plasma or BALF and incubated for 30 min at RT while shaking at 600 rpm. A 1/5 dilution of the samples in PBS-0.1% casein (final concentration of rat plasma or BALF is 20%) was transferred to the coated plate and incubated for 1 hr at RT while shaking at 600 rpm. After three washing steps with PBS-0.05% Tween20, the plates were incubated with the anti-ALX0081 NB vWF12B2-GS9-12B2-BIO (1 µg/ml in PBS-0.1% casein, in-house) for 30 min at RT while shaking at 600 rpm. After 3 washing steps with PBS-0.05% Tween20, 100 µl streptavidin-HRP (1/2000 in PBS-0.1% casein, DakoCytomation) was incubated for 30 min at RT while shaking at 600 rpm. Visualization was performed covered from light for 15 min with 100 µL 3,3′,5,5′-tetramethylbenzidine (esTMB, SDT, diluted 1/3). After 15 min, the coloring reaction was stopped with 100 µL 1N HCl. The absorbance was determined at 450 nm and corrected for background absorbance at 620 nm. Concentration in each sample was determined based on a sigmoidal standard curve. The LLOQ and ULOQ of the different assays are listed in Table B-4.

TABLE B-4

LLOQ and ULOQ for determination of ALX-
0081 in rat plasma and BALF samples

| | LLOQ (ng/ml) | | ULOQ (ng/ml) | |
|---|---|---|---|---|
| PK ELISA | Plate level | Plasma/BALF | Plate level | Plasma/BALF |
| ALX-0081 | 0.75 | 3.75 | 40.0 | 200.0 |

TABLE B-5

LLOQ and ULOQ for determination of RANKL008A
in rat plasma and BALF samples

| | LLOQ (ng/ml) | | ULOQ (ng/ml) | |
|---|---|---|---|---|
| PK ELISA | Plate level | Plasma/BALF level | Plate level | Plasma/BALF level |
| RANKL008A | 0.1 | 1.0 | 7.5 | 75.0 |

Determination of RANKL008A in Rat Plasma or BALF 96-well microtiter plates (Maxisorp, Nunc) were coated overnight at 4° C. with 100 µL neutravidin in PBS (2 µg/mL, Pierce,). Wells were aspirated and blocked. After 3 washing steps with PBS-0.05% Tween20, biotinylated RANKL (0.5 µg/mL in PBS-0.1% casein, in-house,) was captured by incubating 100 µL for 1 hr at RT while shaking at 600 rpm. After this incubation step, wells were washed. The standards, QC, and predilutions of the test samples were prepared in a non-coated (polypropylene) plate in 100% rat plasma or BALF and incubated for 30 min at RT while shaking at 600 rpm. A 1/10 dilution of the samples in PBS-0.1% casein (final concentration of rat plasma or BALF is 10%) was transferred to the coated plate and incubated for 1 hr at RT while shaking at 600 rpm. After three washing steps with PBS-0.05% Tween20, the plates were incubated with polyclonal rabbit anti-Nanobody® monoclonal R23 (1/2000 in PBS-0.1% casein, in-house) for 1 hr at RT while shaking at 600 rpm. After 3 washing steps with PBS-0.05% Tween20, 100 µl horseradish peroxidase (HRP) labelled polyclonal goat anti-rabbit (1/5000 in PBS-0.1% casein, DakoCytomation) was incubated for 1 hr at RT while shaking at 600 rpm. Visualization was performed covered from light for 10 min with 100 µL 3,3',5,5'-tetramethylbenzidine (esTMB, SDT, diluted 1/3). After 10 min, the coloring reaction was stopped with 100 µL 1N HCl. The absorbance was determined at 450 nm and corrected for background absorbance at 620 nm. Concentration in each sample was determined based on a sigmoidal standard curve. The LLOQ and ULOQ of the different assays are listed in Table B-5.

Non-Compartmental Pharmacokinetic Data Analysis

Individual plasma and mean BALF concentration-time profiles of all rats were subjected to a non-compartmental pharmacokinetic analysis (NCA) using WinNonlin Professional Software Version 5.1 (Pharsight Corporation, Mountain View Calif., USA). The pre-programmed Models 200 and 201 were used to analyse the intratracheal and intravenous data, respectively. The linear-up/log down trapezoidal rule was used to calculate the area under the concentration-time data. Nominal times were considered except when the actual time deviated more than 5% of the nominal, the actual time was used. In the calculation of the t½, at least 3 data points were considered except where indicated. When at least three individual values were available, mean and SD was calculated.

43.2 Results

Plasma Concentrations of RSV NB2, ALX-0081 and RANKL008A

Figure 13:
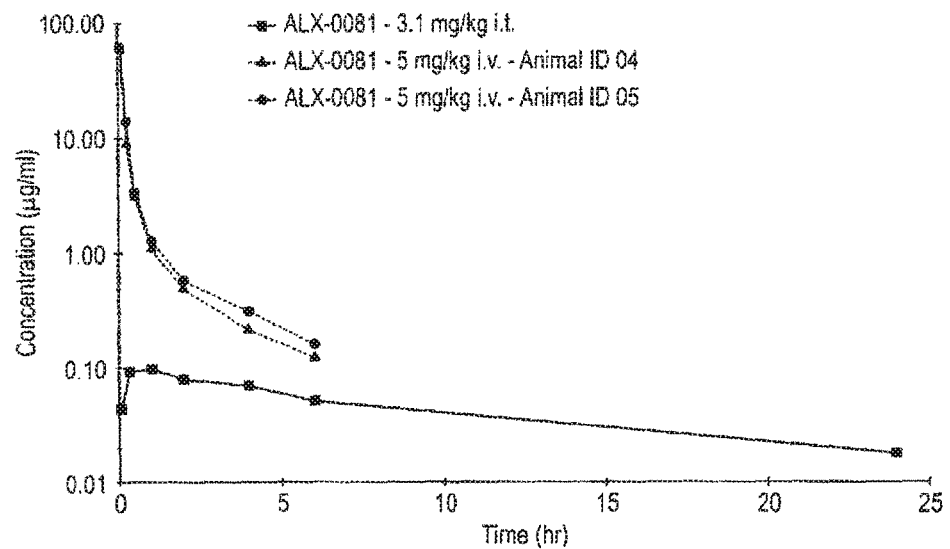
FIG. 13: Individual (i.v.) and mean (i.t.) observed plasma concentration-time plot of ALX-0081 (i.v. 5 mg/kg; i.t. 3.1 mg/kg).
Figure 14:
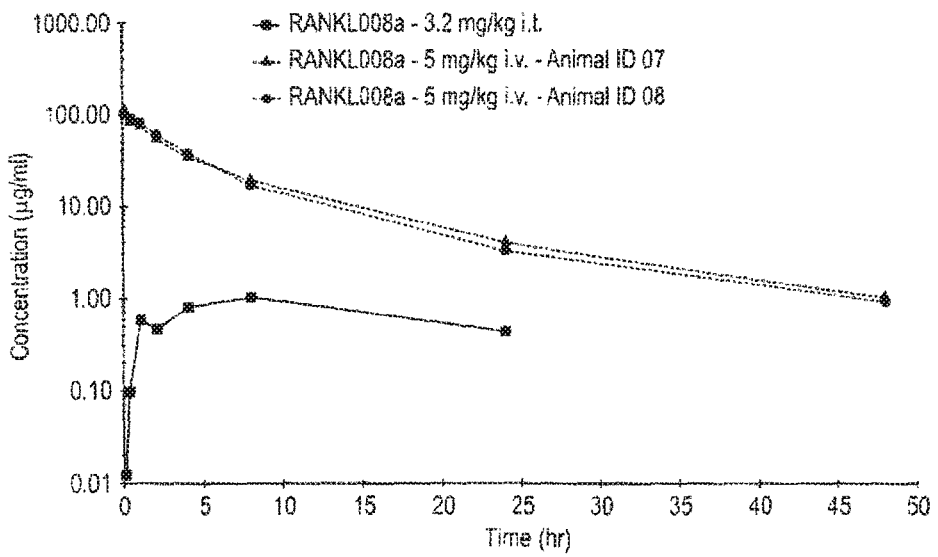
FIG. 14: Individual (i.v.) and mean (i.t.) observed plasma concentration-time plot of RANKL008A (i.v. 5 mg/kg; i.t. 3.2 mg/kg).
Figure 15:
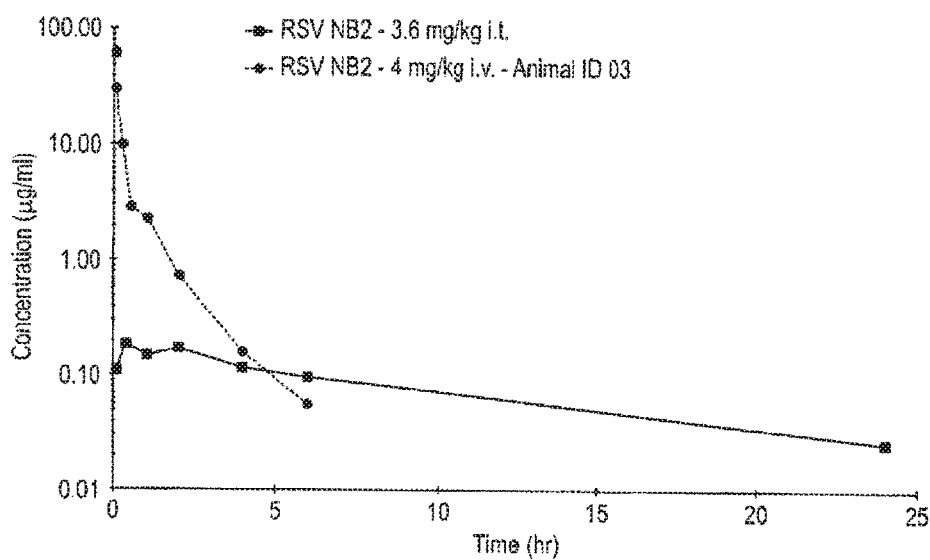
FIG. 15: Individual (i.v.) and mean (i.t.) observed plasma concentration-time plot of RSV NB2 (i.v. 4 mg/kg; i.t. 3.6 mg/kg).
Figure 16:
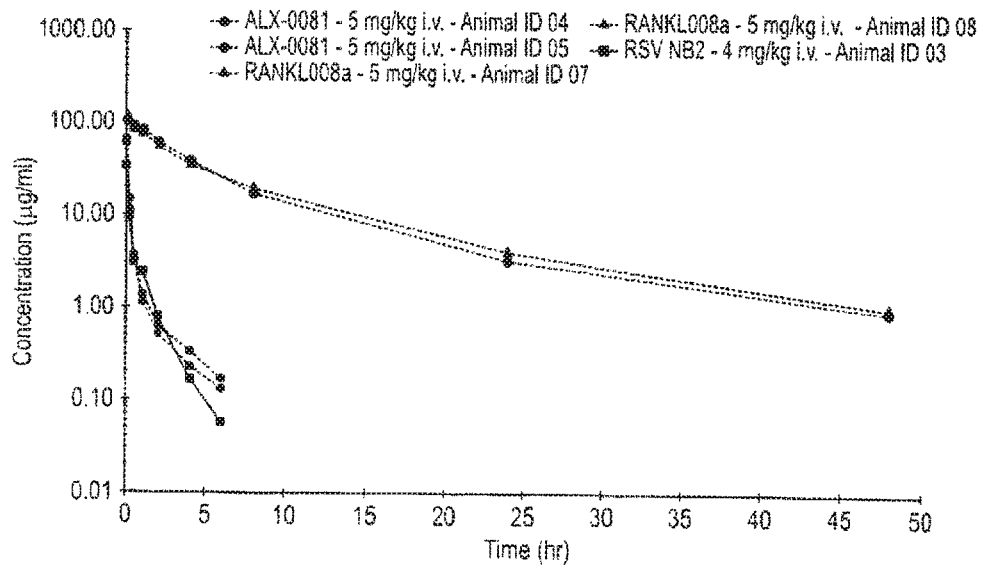
FIG. 16: Individual observed plasma concentration-time plot of RSV NB2, ALX-0081, and RANKL008A after a single i.v. bolus dose of RSV NB2 (4 mg/kg), ALX-0081 (5 mg/kg) and RANKL008A (5 mg/kg), respectively to male Wistar rats.

The observed plasma concentration-time data of the individual animals after a single i.v. administration and of the mean (n=4 animals/time-point; destructive sampling) plasma concentration-time data after a single i.t. administration of RSV NB2, ALX-0081, and RANKL008A are shown in FIG. 16 (i.v. data for all compounds), FIG. 15 (RSV NB2 i.v. and i.t. data), FIG. 13 (ALX-0081 i.v. and i.t. data), and FIG. 13 (RANKL008A i.v. and i.t. data). The individual (i.v.) and both individual and mean plasma concentrations (i.t.) are listed in Tables B-6, B-7 and B-8, respectively.

TABLE B-6

Individual plasma concentration-time data of RSV NB2, ALX-0081, and RANKL008A after a single i.v. bolus dose of RSV NB2 (4 mg/kg), ALX-0081 (5 mg/kg), and RANKL008A (5 mg/kg), respectively, to male Wistar rats.

| | Plasma concentration after i.v. Administration (µg/mL) | | | | | | | | |
|---|---|---|---|---|---|---|---|---|---|
| Nominal | RSV NB2 | | | ALX-0081 | | | RANKL008A | | |
| Time | ID 1 | ID 2 | ID 3 | ID 4 | ID 5 | ID 6 | ID 7 | ID 8 | ID 9 |
| 3 min | 23.6 | 34.5 | 32.1 | 60.4 | 63.2 | NS | 94.3(1) | 107 | 100 |
| 15 min | 5.16 | 10.7 | 10.6 | 9.18 | 14.1 | NS | 95.7 | 94.8 | 92.8 |
| 30 min | 3.61 | 5.91 | 3 | 3.15 | 3.37 | 4.55 | 88.4 | 85.9 | 74.1 |
| 1 hr | NS(2) | 5.12 | 2.36 | 1.09 | 1.31 | 1.84 | 81.5 | 73.8 | NS |
| 2 hr | NS | NS | 0.763 | 0.498 | 0.594 | NS | 58.7 | 55.9 | NS |
| 4 hr | NS | NS | 0.161 | 0.219 | 0.315 | 0.328 | 35.8 | 35.1 | NS |
| 6 hr | NS | NS | 0.056 | 0.125 | 0.161 | 0.116 | / | / | / |
| 8 hr | /(3) | / | / | / | / | / | 17.1 | 18.8 | NS |
| 24 hr | BQL(4) | NS | BQL | BQL | BQL | BQL | 3.17 | 3.94 | NS |
| 48 hr | / | / | / | / | / | / | 0.902 | 0.988 | NS |

(1)5 min instead of 3 min
(2)NS: No sample could be obtained due to technical difficulties)
(3)No sampling per protocol
(4)BQL: Below Quantification Limit

TABLE B-7

Individual plasma concentration-time data of RSV NB2, ALX-0081, and RANKL008A after a single i.t. dose of RSV NB2 (3.6 mg/kg), ALX-0081 (3.1 mg/kg) and RANKL008A (3.2 mg/kg), respectively, to male Wistar rats.

Plasma concentration after i.t. Administration (µg/mL)

| Nominal Time | RSV NB2 ID | Concentration | ALX-0081 ID | Concentration | RANKL008A ID | Concentration |
|---|---|---|---|---|---|---|
| 3 min(1) | 10 | 0.158 | 38 | 0.056 | 66 | 0.004 |
|  | 11 | 0.085 | 39 | 0.013 | 67 | 0.030 |
|  | 12 | 0.081 | 40 | 0.029 | 68 | 0.006 |
|  | 13 | 0.127 | 41 | 0.077 | 69 | 0.005 |
| 20 min | 14 | 0.204 | 42 | 0.102 | 70 | 0.072 |
|  | 15 | 0.167 | 43 | 0.102 | 71 | 0.081 |
|  | 16 | 0.131 | 44 | 0.097 | 72 | 0.151 |
|  | 17 | 0.267 | 45 | 0.070 | 73 | 0.083 |
| 1 hr | 18 | 0.202 | 46 | 0.122 | 74 | 0.401 |
|  | 19 | 0.167 | 47 | 0.112 | 75 | 0.541 |
|  | 20 | 0.120 | 48 | 0.049 | 76 | 0.305 |
|  | 21 | 0.120 | 49 | 0.109 | 77 | 1.077 |
| 2 hr | 22 | BQL | 50 | 0.041 | 78 | 0.279 |
|  | 23 | 0.230 | 51 | 0.100 | 79 | 0.389 |
|  | 24 | 0.091 | 52 | 0.084 | 80 | 0.705 |
|  | 25 | 0.202 | 53 | 0.091 | 81 | 0.489 |
| 4 hr | 26 | 0.113 | 54 | 0.069 | 82 | 0.965 |
|  | 27 | 0.150 | 55 | 0.077 | 83 | 0.601 |
|  | 28 | 0.080 | 56 | 0.053 | 84 | 0.934 |
|  | 29 | 0.129 | 57 | 0.085 | 85 | 0.672 |
| 6/8 hr(3) | 30 | 0.125 | 58 | 0.034 | 86 | 0.869 |
|  | 31 | 0.071 | 59 | 0.048 | 87 | 1.42 |
|  | 32 | 0.108 | 60 | 0.070 | 88 | 1.16 |
|  | 33 | 0.091 | 61 | 0.059 | 89 | 0.606 |
| 24 hr | 34 | 0.024 | 62 | 0.014 | 90 | 0.493 |
|  | 35 | 0.024 | 63 | 0.022 | 91 | 0.450 |
|  | 36 | 0.025 | 64 | 0.014 | 92 | 0.434 |
|  | 37 | 0.036 | 65 | 0.020 | 93 | 0.342 |

(1) 4 min instead of 3 min
(2) BQL: below the limit of quantification
(3) 6 hr for RSV NB2 and ALX-0081, 8 hr for RANKL008A.

TABLE B-8

Mean (n = 4) plasma concentration-time data of RSV NB2, ALX-0081, and RANKL008A after a single i.t. dose of RSV NB2 (3.6 mg/kg), ALX-0081 (3.1 mg/kg) and RANKL008A (3.2 mg/kg), respectively, to male Wistar rats.

Plasma concentration after i.t. Administration (µg/mL)

| Nominal Time | RSV NB2 (ID 10-37) Average | SD | ALX-0081 (ID 38-65) Average | SD | RANKL008A (ID 66-93) Average | SD |
|---|---|---|---|---|---|---|
| 3 min | 0.113 | 0.037 | 0.044 | 0.028 | 0.012 | 0.013 |
| 20 min | 0.192 | 0.058 | 0.093 | 0.015 | 0.097 | 0.037 |
| 1 hr | 0.152 | 0.040 | 0.098 | 0.033 | 0.581 | 0.345 |
| 2 hr | 0.175(1) | 0.074 | 0.079 | 0.026 | 0.465 | 0.181 |
| 4 hr | 0.118 | 0.030 | 0.071 | 0.014 | 0.793 | 0.184 |
| 6 hr | 0.099 | 0.023 | 0.052 | 0.015 | /(1) | / |
| 8 hr | / | / | / | / | 1.01 | 0.35 |
| 24 hr | 0.027 | 0.006 | 0.018 | 0.004 | 0.430 | 0.063 |

(1) N = 3
(2) No sampling planned per protocol

Plasma Pharmacokinetic Analysis of RSV NB2, ALX-0081, and RANKL008A

An overview of the basic pharmacokinetic parameters obtained by non-compartmental PK analysis of RSV NB2 (4 mg/kg i.v. & 3.6 mg/kg i.t.), ALX-0081 (5 mg/kg i.v. & 3.1 mg/kg i.t.) and RANKL008A (5 mg/kg i.v. & 3.2 mg/kg i.t.) is given in Tables B9-B11.

TABLE B-9

Individual Basic Pharmacokinetic parameters of RSV NB2, ALX-0081, and RANKL008A after a single i.v. dose of RSV NB2 (4 mg/kg), ALX-0081 (5 mg/kg) and RANKL008A (5 mg/kg) to male Wistar Rats.

i.v.: RSV NB2 4 mg/kg; ALX-0081/RANKL008A 5 mg/kg

| Parameter | Unit | ALX-0081 ID 4 | ALX-0081 ID 5 | RANKL008A ID 7 | RANKL008A ID 8 | RSV NB2 ID 3 |
|---|---|---|---|---|---|---|
| C(0) | ug/mL | 96.7 | 92.0 | 94.3 | 110 | 42.3 |
| Vss | mL/kg | 255 | 250 | 91.5 | 92.8 | 250 |
| CL | mL/hr/kg | 363 | 311 | 9.17 | 8.82 | 363 |
| MRT | hr | 0.702 | 0.804 | 9.98 | 10.5 | 0.690 |
| t½ λz | hr | 2.01 | 2.12 | 13.2(1) | 12.0(1) | 0.926 |
| λz Lower | hr | 2 | 2 | 24 | 24 | 0.5 |
| λz Upper | hr | 6 | 6 | 48 | 48 | 6 |
| AUClast | hr*ug/mL | 13.4 | 15.6 | 528 | 550 | 11.0 |
| AUCextrap | % | 2.51 | 3.09 | 3.16 | 3.03 | 0.560 |
| AUCinf | hr*ug/mL | 13.8 | 16.1 | 545 | 567 | 11.0 |
| AUCinf/D | hr*kg/mL | 0.0028 | 0.0032 | 0.1091 | 0.1134 | 0.0028 |

(1) Only 2 data points were considered

TABLE B-10

Mean Basic Pharmacokinetic parameters of RSV NB2, ALX-0081, and RANKL008A after a single i.v. dose of RSV NB2 (4 mg/kg), ALX-0081 (5 mg/kg) and RANKL008A (5 mg/kg) to Wistar Rats.

i.v.: RSV NB2 4 mg/kg; ALX-0081/RANKL008A 5 mg/kg

| | | ALX-0081 | | RANKL008A | | |
|---|---|---|---|---|---|---|
| Parameter | Unit | Average | CV % | Average | CV % | RSV NB2 |
| C(0) | ug/mL | 94.3 | 4 | 102 | 11 | 42.3 |
| Vss | mL/kg | 252 | 1 | 92.1 | 1 | 250 |
| CL | mL/hr/kg | 337 | 11 | 9.00 | 3 | 363 |
| MRT | hr | 0.753 | 10 | 10.2 | 4 | 0.690 |
| t½ λz | hr | 2.06 | 4 | 12.6(1) | 7 | 0.926 |
| λz Lower | hr | 2 | 0 | 24 | 0 | 0.5 |
| λz Upper | hr | 6 | 0 | 48 | 0 | 6 |
| AUClast | hr*ug/mL | 14.5 | 10 | 539 | 3 | 11.0 |
| AUCextrap | % | 2.80 | 15 | 3.09 | 3 | 0.560 |
| AUCinf | hr*ug/mL | 14.9 | 11 | 556 | 3 | 11.0 |
| AUCinf/D | hr*kg/mL | 0.003 | 9 | 0.111 | 3 | 0.003 |

(1)Only 2 data points were considered

TABLE B-11

Basic Pharmacokinetic parameters of RSV NB2, ALX-0081, and RANKL008A after a single i.v. dose of RSV NB2 (3.6 mg/kg), ALX-0081 (3.1 mg/kg) and RANKL008A (3.2 mg/kg) to Wistar Rats.

| i.t. administration | | ALX-0081 | RANKL008A | RSV NB2 |
|---|---|---|---|---|
| Parameter | Unit | 3.1 mg/kg | 3.2 mg/kg | 3.6 mg/kg |
| Vss/F | mL/kg | 36339 | 2833 | 21853 |
| CL/F | mL/hr/kg | 2407 | 130 | 1641 |
| MRT | hr | 15.1 | 21.7 | 13.3 |
| t½ λz | hr | 10.5 | 13.0(1) | 9.48 |
| λz Lower | hr | 2 | 8 | 4 |
| λz Upper | hr | 24 | 24 | 24 |
| AUClast | hr*ug/mL | 1.02 | 16.5 | 1.83 |
| AUCextrap | % | 20.8 | 32.8 | 16.8 |
| AUCinf | hr*ug/mL | 1.29 | 24.6(2) | 2.19 |
| tmax | hr | 1 | 8 | 0.330 |
| Cmax | ug/ml | 0.098 | 1.01 | 0.192 |
| AUCinf/D | hr*kg/mL | 0.0004 | 0.0077 | 0.0006 |
| F | % | 13.9 | 6.90 | 22.1 |

(1)Only 2 data points were considered
(2)Interpret with caution due to high % extrapolated AUC
Vss/F = MRT*CL (MRT not corrected for MAT)
Estimation F incorrect if CL i.v. and CL i.t. are different;
Note
dose i.v. ≠ i.t.

The PK parameters discussed herein were obtained using non-compartmental analysis (NCA). For rat 1 and 2 (RSV NB2 i.v.), rat 6 (ALX-0081 i.v.) and rat 9 (RANKL008A i.v.) difficulties in blood sampling occurred, and due to the limited data, these animals were excluded from subsequent pharmacokinetic calculations. The terminal parameters for some of the animals were calculated based on only two data-points ($R^2$ indicated in red in the tables) in the terminal phase, and should thus be interpreted with caution.

Figure 19:
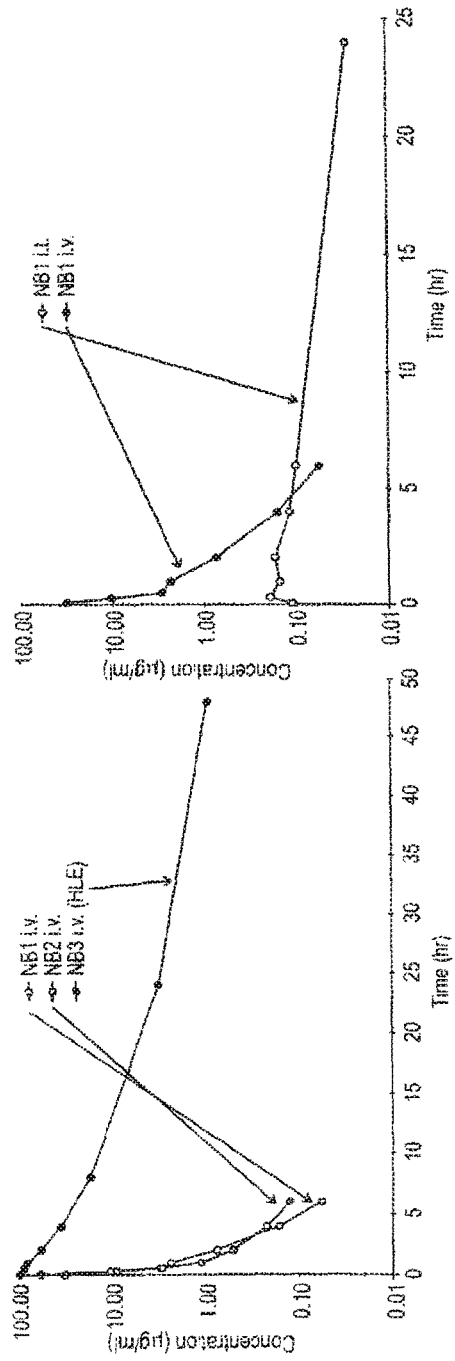
FIG. 19: Bioavailability in plasma of pulmonary administered vs i.v. administered Nanobodies.

After i.v. administration of RSV NB2 (4 mg/kg) and ALX-0081 (5 mg/kg) comparable plasma PK profiles were observed (FIG. 19). This was also reflected in similar pharmacokinetic parameters for the monovalent RSV NB2 and bivalent ALX-0081. The mean clearance was estimated at 363 mL/hr/kg and 337 mL/hr/kg for RSV NB2- and ALX-0081-dosed rats. The corresponding mean Vss values were 250 mL/kg (RSV NB2) and 252 mL/kg (ALX-0081). The plasma concentrations of these Nanobodies® were only detectable up to six hours (detection limits of ca 4 ng/mL) and the terminal half-lives were calculated at 0.926 hours for RSV NB2 and 2.06 hours for ALX-0081. For the trivalent RANKL008A administered intravenously (5 mg/kg), substantially lower mean clearance (9.00 mL/hr/kg) and Vdss values (92.1 mL/kg) were calculated. The terminal half-lives was appreciably longer (12.6 hours). This is explained by the fact that RANKL008A is a half-life extended Nanobody (through binding of the ALB8 component) which is cross reactive with rat albumin, albeit with lower affinity relative to human serum albumin.

After i.t. administration of RSV NB2 (3.6 mg/kg), ALX-0081 (3.1 mg/kg) and RANKL008A (3.2 mg/kg), comparable terminal half-lives in the plasma were observed for the three Nanobodies® (RSV NB2: 9.48 hr, ALX-0081: 10.5 hr and RANKL008A: 13.0 hr). For RSV NB2 and ALX-0081 the half-lives were longer after i.t. administration than after i.v. administration. It is conceivable that for these rapidly cleared compounds, the absorption is the rate limiting step resulting in flip-flop kinetics (i.e. kinetics are absorption rate controlled and the terminal phase is driven by the slow absorption from the site of administration (the lung) to the systemic circulation).

The exposure after i.t. administration was lower for all Nanobodies as compared to that after i.v. administration. This resulting bioavailabilies were 22.1%, 13.9%, and 6.9% for RSV NB2 (16.6 kD), ALX-0081 (27.9 kD), and RANKL008A (40.9 kD), respectively. The bioavailability seems to decrease with increasing molecular weight, but this trend needs to be confirmed when more data become available.

For lung topical applications (RSV NB2), a high pulmonary exposure is desired. It could be expected that a faster and more complete absorption (resulting in a higher bioavailability) would not benefit pulmonary exposure. Therefore, RSV Nanobodies with a higher molecular weight (e.g. a trivalent RSV Nanobody) could possibly lead to enhanced local (pulmonary) exposures and reduced systemic exposures.

The current data indicate that systemic exposure to Nanobodies can be achieved after intratracheal administration, suggesting that the pulmonary route may be viable as non-invasive method of delivery of Nanobodies. In addition, the use of specific delivery formulations and/or devices could significantly improve bioavailability after pulmonary application. It is suggested that the bioavailability may be improved around 5 times in animals (i.t. vs. aerosol—see e.g. table 2 in Patton J., Fishburn S., Weers J. The Lung as a Portal of Entry for Systemic Drug Delivery. 2004. Proc Am Thorac Soc Vol 1. pp 338-344).

BALF Concentrations of RSV NB2, ALX-0081 and RANKL008A

Figure 17:
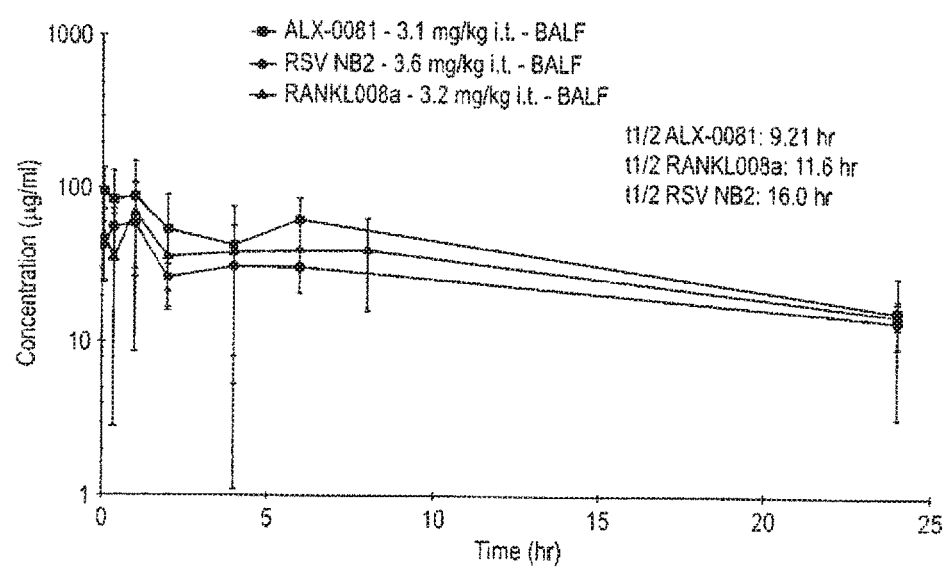
FIG. 17: Mean (+SD) observed BALF concentration-time profiles of RSV NB2, ALX-0081, and RANKL008A after a single intratracheal administration of RSV NB2 (3.6 mg/kg), ALX-0081 (3.1 mg/kg) and RANKL008A (3.2 mg/kg) to male rats.

The mean observed BALF concentration-time profiles after a single intratracheal administration of RSV NB2, ALX-0081 and RANKL008A to male rats is shown in FIG. 17. Individual and mean BALF concentrations are listed in Tables B-12 and B-13, respectively.

TABLE B-12

Individual observed BALF concentrations of RSV NB2, ALX-0081, and RANKL008A after a single i.t. administration of RSV NB2 (3.6 mg/kg), ALX-0081 (3.1 mg/kg) and RANKL008A (3.2 mg/kg) to male rats.

| | BALF concentrations after i.t. Administration (µg/mL) | | | | | |
|---|---|---|---|---|---|---|
| | RSV NB2 | | ALX-0081 | | RANKL008A | |
| Nominal Time | ID | Concentration | ID | Concentration | ID | Concentration |
| 3 min(1) | 10 | 46.2 | 38 | 145 | 66 | 32.3 |
| | 11 | 65.0 | 39 | 57.9 | 67 | 56.1 |
| | 12 | 23.0 | 40 | 69.2 | 68 | 27.0 |
| | 13 | 36.7 | 41 | 115 | 69 | 80.2 |
| 20 min | 14 | 32.8 | 42 | 40.4 | 70 | 14.4 |
| | 15 | 54.8 | 43 | 148 | 71 | 87.9 |
| | 16 | 70.2 | 44 | 93.4 | 72 | 43.3 |
| | 17 | 68.1 | 45 | 55.7 | 73 | 22.4 |
| 1 hr | 18 | 134 | 46 | 179 | 74 | 124 |
| | 19 | 50.7 | 47 | 80.6 | 75 | 70.3 |
| | 20 | 35.8 | 48 | 62.4 | 76 | 33.8 |
| | 21 | 18.4 | 49 | 35.8 | 77 | 49.8 |
| 2 hr | 22 | BQL(2) | 50 | 33.7 | 78 | 16.1 |
| | 23 | 22.1 | 51 | 36.9 | 79 | 58.3 |
| | 24 | 26.1 | 52 | 111 | 80 | 49.0 |
| | 25 | 32.6 | 53 | 37.1 | 81 | 22.3 |
| 4 hr | 26 | 14.9 | 54 | 32.7 | 82 | 24.8 |
| | 27 | 60.9 | 55 | 2.44 | 83 | 11.4 |
| | 28 | 45.0 | 56 | 85.1 | 84 | 95.0 |
| | 29 | 4.81 | 57 | 50.5 | 85 | 24.9 |
| 6/8 hr(3) | 30 | 24.4 | 58 | 36.2 | 86 | 15.6 |
| | 31 | 43.6 | 59 | 90.1 | 87 | 42.1 |
| | 32 | 21.6 | 60 | 51.9 | 88 | 72.4 |
| | 33 | 33.1 | 61 | 74.6 | 89 | 30.2 |
| 24 hr | 34 | 9.53 | 62 | 20.9 | 90 | 32.7 |
| | 35 | 19.1 | 63 | 13.2 | 91 | 14.6 |
| | 36 | 10.7 | 64 | 16.5 | 92 | 7.48 |
| | 37 | 17.0 | 65 | 14.6 | 93 | 6.91 |

(1)4 min instead of 3 min
(2)Below the quantification limit
(3)6 h for RSV NB2 and ALX-0081; 8 h for RANKL008A

TABLE B-13

Mean observed BALF concentrations of RSV NB2, ALX-0081, and RANKL008A after a single i.t. administration of RSV NB2 (3.6 mg/kg), ALX-0081 (3.1 mg/kg) and RANKL008A (3.2 mg/kg) to male rats.

| | BALF concentration after i.t. Administration (µg/mL) | | | | | |
|---|---|---|---|---|---|---|
| | ALX-0081 (ID 38-65) | | RANKL008A (ID 66-93) | | RSV NB2 (ID 10-37) | |
| Nominal Time | Average | SD | Average | SD | Average | SD |
| 3 min | 96.8 | 40.4 | 48.9 | 24.4 | 42.7 | 17.6 |
| 20 min | 84.3 | 47.9 | 35.7 | 32.9 | 56.5 | 17.2 |
| 1 hr | 89.4 | 62.4 | 69.4 | 39.2 | 59.7 | 51.1 |
| 2 hr | 54.6 | 37.5 | 36.4 | 20.4 | 26.9 | 5.3 |
| 4 hr | 42.7 | 34.6 | 39 | 37.9 | 31.4 | 26.1 |
| 6 hr | 63.2 | 23.9 | 40.1 | 24.1 | /(2) | / |
| 8 hr | / | / | / | / | 30.7 | 9.9 |
| 24 hr | 16.3 | 3.4 | 15.4 | 12.1 | 14.1 | 4.7 |

(1) 4 min instead of 3 min
(2)No sampling scheduled

The terminal half-lives of the three Nanobodies in BALF were based on the two last data-points only, and should therefore be interpreted with caution. Of note is also that there was quite some inter-individual variability as indicated by the large standard deviations (see Table B-13). After i.t. administration, comparable terminal half-lives were observed in plasma (RSV NB2 9.48 hr, ALX-0081 10.5 hr and RANKL008A 13.0 hr) and in BALF (RSV NB2 16.0 hr, ALX-0081 9.21 hr and RANKL008A 11.6 hr), supporting the notion that the plasma kinetics are likely absorption rate controlled.

Following intratracheal administration, exposure to the RSV NB2, ALX-0081, RANKL008A Nanobodies exposure was observed for at least 24 hours in BALF (i.e. the last sampling time for BALF).

Amounts of RSV NB2, ALX-0081 and RANKL008A in BALF

After intratracheal dosing broncho-alveolar lavage fluid (BALF) was collected at necropsy as described above.

Theoretically, the amount of Nanobody in the lung at a given time-point can be obtained by multiplying the measured concentration of each BALF sample by the volume of DPBS added (10 mL), provided that the Nanobody® is efficiently washed out. These individual calculated amounts and their corresponding mean (+SD) values are listed in Table B-14 and B-15, respectively.

TABLE B-14

Individual theoretical amount (BALF Concentration × 10 mL) of RSV NB2, ALX-0081, and RANKL008A in BALF after single i.t. administration of RSV NB2 (3.6 mg/kg), ALX-0081 (3.1 mg/kg) and RANKL008A (3.2 mg/kg) to male Wistar rats.

| | BALF Theoretical Amount after i.t. Administration (µg) | | | | | |
|---|---|---|---|---|---|---|
| | RSV NB2 | | ALX-0081 | | RANKL008A | |
| Nominal Time | ID | Amount | ID | Amount | ID | Amount |
| 3 min(1) | 10 | 462 | 38 | 1446 | 66 | 323 |
| | 11 | 650 | 39 | 579 | 67 | 561 |
| | 12 | 230 | 40 | 692 | 68 | 270 |
| | 13 | 367 | 41 | 1155 | 69 | 802 |
| 20 min | 14 | 328 | 42 | 404 | 70 | 144 |
| | 15 | 548 | 43 | 1479 | 71 | 879 |
| | 16 | 702 | 44 | 934 | 72 | 433 |
| | 17 | 681 | 45 | 557 | 73 | 224 |
| 1 hr | 18 | 1338 | 46 | 1788 | 74 | 1238 |
| | 19 | 507 | 47 | 806 | 75 | 703 |
| | 20 | 358 | 48 | 624 | 76 | 338 |
| | 21 | 184 | 49 | 358 | 77 | 498 |

TABLE B-14-continued

Individual theoretical amount (BALF Concentration × 10 mL) of RSV NB2, ALX-0081, and RANKL008A in BALF after single i.t. administration of RSV NB2 (3.6 mg/kg), ALX-0081 (3.1 mg/kg) and RANKL008A (3.2 mg/kg) to male Wistar rats.

| Nominal Time | RSV NB2 ID | Amount | ALX-0081 ID | Amount | RANKL008A ID | Amount |
|---|---|---|---|---|---|---|
| 2 hr | 22 | BQL(2) | 50 | 337 | 78 | 161 |
|  | 23 | 221 | 51 | 369 | 79 | 583 |
|  | 24 | 261 | 52 | 1109 | 80 | 490 |
|  | 25 | 326 | 53 | 371 | 81 | 223 |
| 4 hr | 26 | 149 | 54 | 327 | 82 | 248 |
|  | 27 | 609 | 55 | 24.4 | 83 | 114 |
|  | 28 | 450 | 56 | 851 | 84 | 950 |
|  | 29 | 48.1 | 57 | 505 | 85 | 249 |
| 6/8 hr(3) | 30 | 244 | 58 | 362 | 86 | 156 |
|  | 31 | 436 | 59 | 901 | 87 | 421 |
|  | 32 | 216 | 60 | 519 | 88 | 724 |
|  | 33 | 331 | 61 | 746 | 89 | 302 |
| 24 hr | 34 | 95.3 | 62 | 209 | 90 | 327 |
|  | 35 | 191 | 63 | 132 | 91 | 146 |
|  | 36 | 107 | 64 | 165 | 92 | 74.8 |
|  | 37 | 170 | 65 | 146 | 93 | 69.1 |

(1)4 min instead of 3 min
(2)Below the quantification limit
(3)6 h for RSV NB2 and ALX-0081; 8 h for RANKL008A

TABLE B-15

Mean (+/−SD; n = 4) theoretical amount (BALF Concentration × 10 mL) of RSV NB2, ALX-0081, and RANKL008A in BALF after single i.t. administration of RSV NB2 (3.6 mg/kg), ALX-0081 (3.1 mg/kg) and RANKL008A (3.2 mg/kg) to male Wistar rats.

| Nominal Time | RSV NB2 (ID 10-37) Average | SD | ALX-0081 (ID 38-65) Average | SD | RANKL008A (ID 66-93) Average | SD |
|---|---|---|---|---|---|---|
| 3 min(1) | 427 | 176 | 968 | 404 | 489 | 244 |
| 20 min | 565 | 172 | 843 | 479 | 420 | 329 |
| 1 hr | 597 | 511 | 894 | 624 | 694 | 392 |
| 2 hr | 269 | 53 | 546 | 375 | 364 | 204 |
| 4 hr | 314 | 261 | 427 | 346 | 390 | 379 |
| 6 hr | 307 | 99 | 632 | 239 | /(2) | / |
| 8 hr | / | / | / | / | 401 | 241 |
| 24 hr | 141.0 | 47.2 | 163 | 34 | 154 | 121 |

(1)4 min instead of 3 min
(2)No sampling scheduled

Note however that large variations occurred in the recovery of the BALF. For some animals it was possible to recover 9.5 mL fluid after injecting 10 mL DPBS, while for other animals only 3 mL was recovered. Furthermore, since the lavage is performed twice and combined in a single vial, it is impossible to determine how much volume was recovered from the first or second lavage separately. In addition, it is also unknown whether there are differences in the concentration of the first and second lavage.

The result is that overestimations of the true amount of Nanobody may occur when the measured BALF concentrations are simply multiplied with the theoretical volume of 10 mL DPBS.

Alternatively, if the amount of Nanobody is estimated by multiplying the measured concentration of each BALF sample by the actual recovered volume of BALF, this may result in underestimations of the actual amount of Nanobody in case significant amounts of Nanobody are present in unrecovered BALF.

Therefore, the true amount of Nanobody in BALF should theoretically be comprised between the amount calculated via the theoretical BALF volume and the actual BALF volume. It is important to note that the larger the recovered volume, the more accurate the calculations are expected to be. Since the average recovered volume is on average ca. 7 mL (Table B-16), both calculation methods should not provide very different results. The individual calculated amounts and mean (+SD) values based on actual recovered volumes are listed in Table B-17 and B-18, respectively.

TABLE B-16

Individual recovered volume of BALF after two lavages with DPBS (2 × 5 mL) after a single i.t. administration of RSV NB2 (3.6 mg/kg), ALX-0081 (3.1 mg/kg) and RANKL008A (3.2 mg/kg) to male Wistar rats.

| Nominal Time | RSV NB2 ID | BALF (mL) | ALX-0081 ID | BALF (mL) | RANKL008A ID | BALF (mL) |
|---|---|---|---|---|---|---|
| 3 min(1) | 10 | 5.5 | 38 | 7.5 | 66 | 8.0 |
|  | 11 | 6.5 | 39 | 6.5 | 67 | 8.0 |
|  | 12 | 8.5 | 40 | 8.5 | 68 | 4.0 |
|  | 13 | 7.5 | 41 | 7.5 | 69 | 8.5 |
| 20 min | 14 | 8.0 | 42 | 7.0 | 70 | 7.5 |
|  | 15 | 6.0 | 43 | 8.0 | 71 | 3.0 |
|  | 16 | 6.5 | 44 | 8.0 | 72 | 6.0 |
|  | 17 | 8.5 | 45 | 7.5 | 73 | 8.0 |
| 1 hr | 18 | 6.5 | 46 | 8.0 | 74 | 7.0 |
|  | 19 | 6.5 | 47 | 7.5 | 75 | 6.0 |
|  | 20 | 7.5 | 48 | 8.0 | 76 | 7.5 |
|  | 21 | 7.5 | 49 | 7.0 | 77 | 8.0 |
| 2 hr | 22 | 5.5 | 50 | 8.0 | 78 | 6.0 |
|  | 23 | 6.0 | 51 | 8.0 | 79 | 7.5 |
|  | 24 | 6.5 | 52 | 6.5 | 80 | 8.0 |
|  | 25 | 7.0 | 53 | 7.5 | 81 | 8.0 |
| 4 hr | 26 | 5.5 | 54 | 8.0 | 82 | 7.0 |
|  | 27 | 5.0 | 55 | 8.0 | 83 | 6.5 |
|  | 28 | 9.5 | 56 | 9.0 | 84 | 7.0 |
|  | 29 | 8.0 | 57 | 7.5 | 85 | 7.5 |
| 6/8 hr(2) | 30 | 7.0 | 58 | 8.0 | 86 | 7.0 |
|  | 31 | 7.0 | 59 | 9.0 | 87 | 6.5 |
|  | 32 | 7.0 | 60 | 6.0 | 88 | 7.5 |
|  | 33 | 8.5 | 61 | 8.5 | 89 | 9.0 |
| 24 hr | 34 | 6.5 | 62 | 7.5 | 90 | 8.0 |
|  | 35 | 6.5 | 63 | 7.5 | 91 | 7.5 |
|  | 36 | 7.5 | 64 | 8.5 | 92 | 8.0 |
|  | 37 | 7.0 | 65 | 6.5 | 93 | 5.5 |

(1)4 min instead of 3 min
(2)6 h for RSV NB2 and ALX-0081; 8 h for RANKL008A

TABLE B-17

Individual actual amount (BALF Concentration × recovered volume) of RSV NB2, ALX-0081, and RANKL008A in BALF after a single intratracheal administration of RSV NB2 (3.6 mg/kg), ALX-0081 (3.1 mg/kg) and RANKL008A (3.2 mg/kg) to male rats.

| Nominal Time | RSV NB2 ID | Amount | ALX-0081 ID | Amount | RANKL008A ID | Amount |
|---|---|---|---|---|---|---|
| 3 min(1) | 10 | 254 | 38 | 1084 | 66 | 258 |
|  | 11 | 422 | 39 | 377 | 67 | 449 |
|  | 12 | 195 | 40 | 588 | 68 | 108 |
|  | 13 | 275 | 41 | 866 | 69 | 682 |

TABLE B-17-continued

Individual actual amount (BALF Concentration × recovered volume) of RSV NB2, ALX-0081, and RANKL008A in BALF after a single intratracheal administration of RSV NB2 (3.6 mg/kg), ALX-0081 (3.1 mg/kg) and RANKL008A (3.2 mg/kg) to male rats.

| Nominal Time | BALF Actual Amount after i.t. Administration (μg) | | | | | |
|---|---|---|---|---|---|---|
| | RSV NB2 | | ALX-0081 | | RANKL008A | |
| | ID | Amount | ID | Amount | ID | Amount |
| 20 min | 14 | 262 | 42 | 283 | 70 | 108 |
| | 15 | 329 | 43 | 1183 | 71 | 264 |
| | 16 | 456 | 44 | 747 | 72 | 260 |
| | 17 | 579 | 45 | 418 | 73 | 179 |
| 1 hr | 18 | 869 | 46 | 1430 | 74 | 867 |
| | 19 | 330 | 47 | 605 | 75 | 422 |
| | 20 | 269 | 48 | 499 | 76 | 254 |
| | 21 | 138 | 49 | 250 | 77 | 399 |
| 2 hr | 22 | BDL | 50 | 270 | 78 | 96.4 |
| | 23 | 132 | 51 | 295 | 79 | 438 |
| | 24 | 170 | 52 | 721 | 80 | 392 |
| | 25 | 228 | 53 | 278 | 81 | 179 |
| 4 hr | 26 | 81.9 | 54 | 262 | 82 | 174 |
| | 27 | 305 | 55 | 19.5 | 83 | 74.3 |
| | 28 | 428 | 56 | 766 | 84 | 665 |
| | 29 | 38.5 | 57 | 379 | 85 | 187 |
| 6/8 hr(2) | 30 | 171 | 58 | 289 | 86 | 109 |
| | 31 | 305 | 59 | 811 | 87 | 274 |
| | 32 | 151 | 60 | 311 | 88 | 543 |
| | 33 | 281 | 61 | 634 | 89 | 272 |
| 24 hr | 34 | 62.0 | 62 | 157 | 90 | 262 |
| | 35 | 124 | 63 | 98.7 | 91 | 110 |
| | 36 | 80.0 | 64 | 140 | 92 | 59.9 |
| | 37 | 119 | 65 | 95.2 | 93 | 38.0 |

(1)4 min instead of 3 min
(2)6 h for RSV NB2 and ALX-0081; 8 h for RANKL008A

TABLE B-18

Mean actual amount (BALF Concentration × recovered volume) of RSV NB2, ALX-0081, and RANKL008A in BALF after a single intratracheal administration RSV NB2 (3.6 mg/kg), ALX-0081 (3.1 mg/kg) and RANKL008A (3.2 mg/kg) to male rats.

| Nominal Time | BALF actual amount after i.t. Administration (μg) | | | | | |
|---|---|---|---|---|---|---|
| | RSV NB2 (ID 10-37) | | ALX-0081 (ID 38-65) | | RANKL008A (ID 66-93) | |
| | Average | SD | Average | SD | Average | SD |
| 3 min(1) | 287 | 97 | 729 | 310 | 374 | 248 |
| 20 min | 406 | 140 | 658 | 401 | 203 | 74 |
| 1 hr | 401 | 322 | 696 | 512 | 485 | 265 |
| 2 hr | 177 | 48 | 391 | 220 | 276 | 165 |
| 4 hr | 213 | 185 | 357 | 311 | 275 | 265 |
| 6 hr | 227 | 77 | 512 | 254 | /(2) | / |
| 8 hr | / | / | / | / | 299 | 180 |
| 24 hr | 96.5 | 30.4 | 123 | 30 | 117 | 101 |

(1)4 min instead of 3 min
(2)No sampling scheduled per protocol

By dividing the calculated amount of Nanobody® by the actual amount dosed (RSV NB2: 1.14 mg, ALX-0081: 0.985 mg, RANKL008A: 1.03 mg), the recovered fraction of the dose (expressed as %) was calculated. Individual amounts and their corresponding mean (+SD) values, expressed as % of the administered dose, and based on the theoretical BALF volume (10 mL) and actual recovered volumes are listed in Tables B-19 to B-22.

TABLE B-19

Individual theoretical amount (BALF Concentration × 10 mL) expressed as % of the dose of RSV NB2, ALX-0081, and RANKL008A in BALF after a single i.t. administration of RSV NB2 (3.6 mg/kg), ALX-0081 (3.1 mg/kg) and RANKL008A (3.2 mg/kg) to male Wistar rats.

| Nominal Time | BALF Theoretical Amount expressed as % of the dose | | | | | |
|---|---|---|---|---|---|---|
| | RSV NB2 | | ALX-0081 | | RANKL008A | |
| | ID | Amount/D (%) | ID | Amount/D (%) | ID | Amount/D (%) |
| 3 min(1) | 10 | 40.5 | 38 | 147 | 66 | 31.3 |
| | 11 | 57.0 | 39 | 58.8 | 67 | 54.4 |
| | 12 | 20.2 | 40 | 70.2 | 68 | 26.2 |
| | 13 | 32.2 | 41 | 117 | 69 | 77.8 |
| 20 min | 14 | 28.7 | 42 | 41.0 | 70 | 14.0 |
| | 15 | 48.1 | 43 | 150 | 71 | 85.4 |
| | 16 | 61.6 | 44 | 94.8 | 72 | 42.0 |
| | 17 | 59.7 | 45 | 56.5 | 73 | 21.8 |
| 1 hr | 18 | 117.3 | 46 | 182 | 74 | 120 |
| | 19 | 44.5 | 47 | 81.8 | 75 | 68.3 |
| | 20 | 31.4 | 48 | 63.3 | 76 | 32.8 |
| | 21 | 16.2 | 49 | 36.3 | 77 | 48.4 |
| 2 hr | 22 | BQL(2) | 50 | 34.3 | 78 | 15.6 |
| | 23 | 19.3 | 51 | 37.5 | 79 | 56.6 |
| | 24 | 22.9 | 52 | 113 | 80 | 47.6 |
| | 25 | 28.6 | 53 | 37.6 | 81 | 21.7 |
| 4 hr | 26 | 13.1 | 54 | 33.2 | 82 | 24.1 |
| | 27 | 53.4 | 55 | 2.48 | 83 | 11.1 |
| | 28 | 39.5 | 56 | 86.4 | 84 | 92.3 |
| | 29 | 4.22 | 57 | 51.3 | 85 | 24.2 |
| 6/8 hr(3) | 30 | 21.4 | 58 | 36.7 | 86 | 15.1 |
| | 31 | 38.3 | 59 | 91.5 | 87 | 40.9 |
| | 32 | 18.9 | 60 | 52.7 | 88 | 70.3 |
| | 33 | 29.0 | 61 | 75.8 | 89 | 29.3 |
| 24 hr | 34 | 8.36 | 62 | 21.2 | 90 | 31.8 |
| | 35 | 16.8 | 63 | 13.4 | 91 | 14.2 |
| | 36 | 9.36 | 64 | 16.7 | 92 | 7.26 |
| | 37 | 15.0 | 65 | 14.9 | 93 | 6.71 |

(1)4 min instead of 3 min
(2)Below the quantification limit
(3)6 h for RSV NB2 and ALX-0081; 8 h for RANKL008A

TABLE B-20

Individual actual amount (BALF Concentration × recovered volume) normalized by dose (%) of RSV NB2, ALX-0081, and RANKL008A in BALF after i.t. administration of RSV NB2 (3.6 mg/kg), ALX-0081 (3.1 mg/kg) and RANKL008A (3.2 mg/kg) to male Wistar rats.

| Time | BALF Actual Amount expressed as % of the dose | | | | | |
|---|---|---|---|---|---|---|
| | RSV NB2 | | ALX-0081 | | RANKL008A | |
| | ID | Amount/D (%) | ID | Amount/D (%) | ID | Amount/D (%) |
| 3 min(1) | 10 | 22.3 | 38 | 110 | 66 | 25.1 |
| | 11 | 37.0 | 39 | 38.2 | 67 | 43.6 |
| | 12 | 17.1 | 40 | 59.7 | 68 | 10.5 |
| | 13 | 24.1 | 41 | 87.9 | 69 | 66.2 |
| 20 min | 14 | 23.0 | 42 | 28.7 | 70 | 10.5 |
| | 15 | 28.8 | 43 | 120 | 71 | 25.6 |
| | 16 | 40.0 | 44 | 75.8 | 72 | 25.2 |
| | 17 | 50.8 | 45 | 42.4 | 73 | 17.4 |
| 1 hr | 18 | 76.3 | 46 | 145 | 74 | 84.1 |
| | 19 | 28.9 | 47 | 61.4 | 75 | 41.0 |
| | 20 | 23.6 | 48 | 50.6 | 76 | 24.6 |
| | 21 | 12.1 | 49 | 25.4 | 77 | 38.7 |
| 2 hr | 22 | BQL(2) | 50 | 27.4 | 78 | 9.4 |
| | 23 | 11.6 | 51 | 30.0 | 79 | 42.5 |
| | 24 | 14.9 | 52 | 73.2 | 80 | 38.1 |
| | 25 | 20.0 | 53 | 28.2 | 81 | 17.3 |

TABLE B-20-continued

Individual actual amount (BALF Concentration × recovered volume) normalized by dose (%) of RSV NB2, ALX-0081, and RANKL008A in BALF after i.t. administration of RSV NB2 (3.6 mg/kg), ALX-0081 (3.1 mg/kg) and RANKL008A (3.2 mg/kg) to male Wistar rats.

| | BALF Actual Amount expressed as % of the dose | | | | | |
|---|---|---|---|---|---|---|
| | RSV NB2 | | ALX-0081 | | RANKL008A | |
| Time | ID | Amount/D (%) | ID | Amount/D (%) | ID | Amount/D (%) |
| 4 hr | 26 | 7.19 | 54 | 26.6 | 82 | 16.9 |
| | 27 | 26.7 | 55 | 1.98 | 83 | 7.21 |
| | 28 | 37.5 | 56 | 77.8 | 84 | 64.6 |
| | 29 | 3.37 | 57 | 38.5 | 85 | 18.1 |
| 6/8 hr(3) | 30 | 15.0 | 58 | 29.4 | 86 | 10.6 |
| | 31 | 26.8 | 59 | 82.3 | 87 | 26.6 |
| | 32 | 13.2 | 60 | 31.6 | 88 | 52.7 |
| | 33 | 24.6 | 61 | 64.4 | 89 | 26.4 |
| 24 hr | 34 | 5.44 | 62 | 15.9 | 90 | 25.4 |
| | 35 | 10.9 | 63 | 10.0 | 91 | 10.6 |
| | 36 | 7.02 | 64 | 14.2 | 92 | 5.81 |
| | 37 | 10.5 | 65 | 9.66 | 93 | 3.69 |

(1) 4 min instead of 3 min
(2) Below the quantification limit
(3) 6 h for RSV NB2 and ALX-0081; 8 h for RANKL008A

TABLE B-21

Mean (+SD: n = 4) theoretical amount (BALF Concentration × 10 mL) normalized y dose (%) of RSV NB2, ALX-0081, and RANKL008A in BALF after i.t. administration of SV NB2 (3.6 mg/kg), ALX-0081 (3.1 mg/kg) and RANKL008A (3.2 mg/kg) to male Wistar rats.

| | BALF theoretical amount expressed as % of the dose | | | | | |
|---|---|---|---|---|---|---|
| | RSV NB2 (ID 10-37) | | ALX-0081 (ID 38-65) | | RANKL008A (ID 66-93) | |
| Time | Average | SD | Average | SD | Average | SD |
| 4 min | 37.5 | 15.5 | 98.3 | 41.0 | 47.5 | 23.7 |
| 20 min | 49.5 | 15.1 | 85.6 | 48.6 | 40.8 | 32.0 |
| 1 hr | 52.3 | 44.8 | 90.7 | 63.3 | 67.4 | 38.0 |
| 2 hr | 23.6 | 4.7 | 55.5 | 38.1 | 35.4 | 19.8 |
| 4 hr | 27.6 | 22.9 | 43.4 | 35.1 | 37.9 | 36.8 |
| 6 hr | 26.9 | 8.7 | 64.2 | 24.3 | /(2) | / |
| 8 hr | / | / | / | / | 38.9 | 23.4 |
| 24 hr | 12.4 | 4.1 | 16.5 | 3.4 | 15.0 | 11.7 |

(1) 4 min instead of 3 min
(2) No sampling scheduled per protocol

TABLE B-22

Mean actual amount (BALF Concentration × recovered volume) normalized by dose (%) of RSV NB2, ALX-0081, and RANKL008A in BALF after i.t. administration of RSV NB2 (3.6 mg/kg), ALX-0081 (3.1 mg/kg) and RANKL008A (3.2 mg/kg) to male Wistar rats.

| | BALF actual amount expressed as % of the dose | | | | | |
|---|---|---|---|---|---|---|
| | RSV NB2 (ID 10-37) | | ALX-0081 (ID 38-65) | | RANKL008A (ID 66-93) | |
| Time | Average | SD | Average | SD | Average | SD |
| 3 min(1) | 25.1 | 8.5 | 74.0 | 31.5 | 36.3 | 24.1 |
| 20 min | 35.7 | 12.3 | 66.8 | 40.7 | 19.7 | 7.2 |
| 1 hr | 35.2 | 28.2 | 70.7 | 51.9 | 47.1 | 25.7 |
| 2 hr | 15.5 | 4.2 | 39.7 | 22.3 | 26.8 | 16.0 |
| 4 hr | 18.7 | 16.2 | 36.2 | 31.6 | 26.7 | 25.7 |
| 6 hr | 19.9 | 6.8 | 51.9 | 25.8 | /(2) | / |
| 8 hr | / | / | / | / | 29.1 | 17.5 |
| 24 hr | 8.46 | 2.66 | 12.5 | 3.1 | 11.4 | 9.8 |

(1) 4 min instead of 3 min
(2) No sampling scheduled per protocol

By dividing the calculated amount of Nanobody by the actual amount dosed, the recovered fraction of the dose could be compared across time: The highest mean amount to dose percentages via actual and theoretical volume are 35.7% and 49.5% for RSV NB2 (After 20 minutes), 74.0% and 98.3% for ALX-0081 (After 4 minutes) and 47.1% and 67.4% for RANKL008A (After 1 hour), respectively. Thus for ALX-0081 almost the total fraction of the dose could be recovered in the BALF, while for RSV NB2 and RANKL008A, the fraction was lower: approximately 50% of the. The highest individual amount to dose percentages via actual and theoretical volume are 76.6% and 117.3% for RSV NB2, 145% and 182% for ALX-0081 and 84.1% and 120% for RANKL008A at time-point 1 hour post-dose. As expected, the variability was appreciable.

After 24 hours, the fraction of the dose recovered in BALF was lower for all Nanobodies than at earlier time-points. The mean fraction recovered ranged from 12.4% to 16.5% via the theoretical volume and ranged from 8.46% to 12.5% via the actual volumes for the three tested Nanobodies.

43.3 Conclusions

After i.v. administration to rats, similar PK characteristics were observed for RSV NB2 and ALX-0081. For RANKL008A, substantially lower clearance values and longer terminal half-lives were observed. This may be explained by binding of the anti-HSA Nanobody of RANKL008A to rat albumin.

The current data show that systemic exposure to Nanobodies can be achieved after intra-tracheal administration, indicating that the pulmonary route may be viable as non-invasive method for the delivery of Nanobodies. The data also indicate that the systemic bioavailability seems to decrease with increasing molecular weight.

After i.t. administration comparable terminal plasma half-lives were observed for the three Nanobodies. For RSV NB2 and ALX-0081 the plasma half-lives are longer after i.t. administration than after i.v. administration, indicating that that absorption is the rate limiting (the drug is slowly absorbed from its site of dosing (i.e. the lung) to the systemic circulation). Comparable terminal half-lives were observed both in plasma and in BALF, supporting the notion that the kinetics may be absorption rate controlled.

Following intra-tracheal administration, the RSV NB2, ALX-0081, RANKL008A Nanobody exposure in BALF was observed for at least 24 hours (i.e. the last sampling time for BALF).

Following intra-tracheal administration, systemic exposure to the RSV NB2, ALX-0081 Nanobody in plasma was observed for at least 24 hours (i.e. the last sampling time of plasma after intra-tracheal administration. Following i.v. administration both of these Nanobodies without anti-HSA were no longer detectable at 24 hours in plasma.

Figure 18:
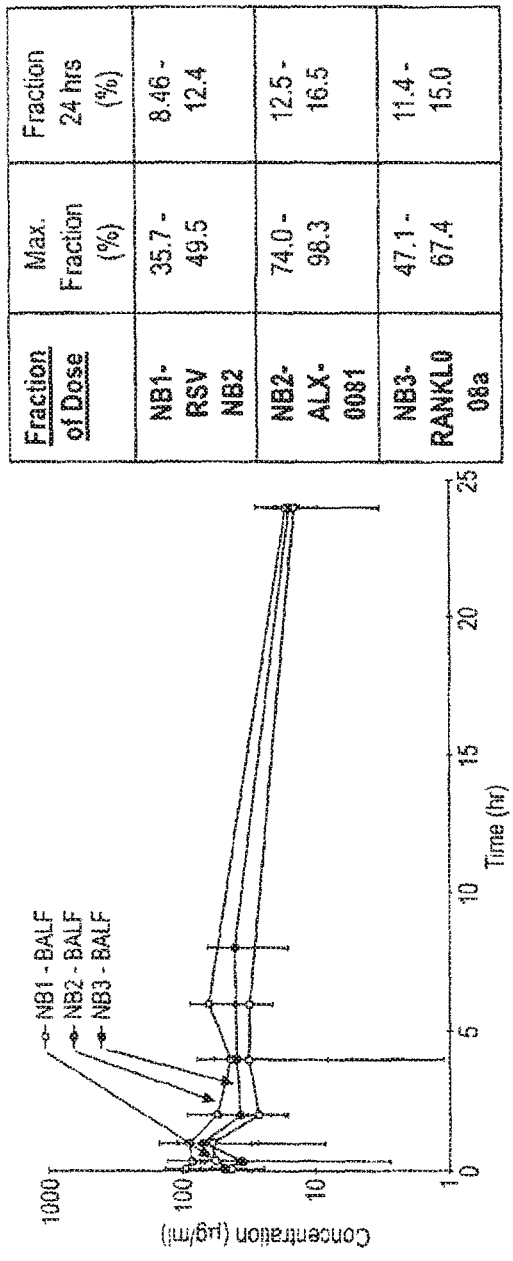
FIG. 18: Pulmonary delivered Nanobodies are stable in the lung for at least 24 hrs post-administration.

FIG. 18 and FIG. 19 further illustrate these experimental results.

Example 44.1: Intranasal Delivery of Bivalent Nanobody RSV101 Protects Against Infection and Replication of Respiratory Syncytial Virus (RSV) Strain A2 in Mice Compounds:

serum-free medium, were infected with serial dilutions of cleared lung homogenates. Four hours after infection the medium was removed and replaced by fresh medium containing 1% FCS and 0.5% agarose. Two to three days after infection the agarose overlay was removed to allow staining of RSV-plaques by an anti-RSV antibody.

Figure 20:
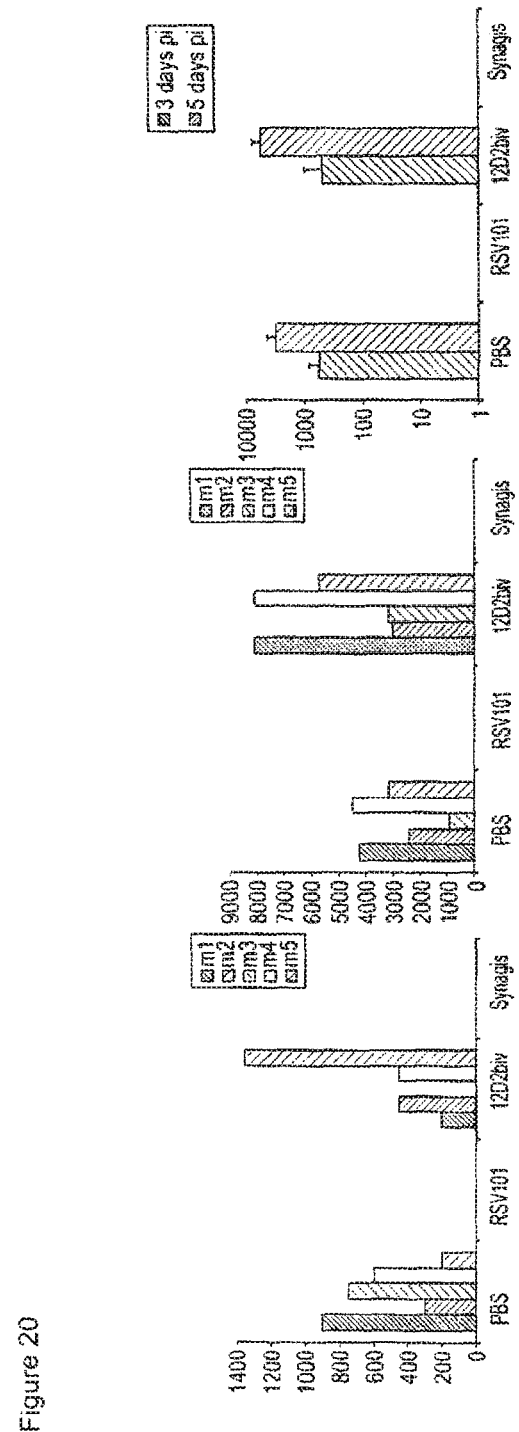
FIG. 20: Intranasal inoculation of bivalent Nanobody 191-D3 (RSV101) prevents in vivo infection and replication of RSV A2 strain. Titers of infectious RSV in the lung homogenates (pfu/lung) prepared three and five days post infection (detection limit below 100 pFU).

Infectious virus (pfu/lung) was recovered from all animals in the negative control groups (PBS and 12D2biv) in lung homogenates on day 3 (FIG. 20, left panel) and 5 after challenge (FIG. 20, middle panel). In FIG. 20, the right panel the mean of infectious virus titers (pfu/lung) is represented. None of the animals in the RSV101 and Synagis-treated group had detectable infectious virus on day 3 and 5 post challenge.

| Name | Alternative names | SEQ ID NO: | Reference | Amino acid sequence |
|---|---|---|---|---|
| RSV101 | NB2-15GS-NB2 | 147 | a bivalent construct in which two units of NB2 (191D3) are linked by a 15GS linker. This Nanobody is binding to the F-protein of RSV and potently neutralizes RSV in vitro as assessed by the microneutralization assay- see example 4.3 (IC50 of 191D3 for the RSV Long strain is about 250 nM; IC50 of RSV101 for the RSV Long strain is about 0.1 nM). | EVQLVESGGGLVQAGGSLR LSCEASGRTYSRYGMGWFR QAPGKEREFVAAVSRLSGP RTVYADSVKGRFTISRDNA ENTVYLQMNSLKPEDTAVY TCAAELTNRNSGAYYYAWA YDYWGQGTQVTVSSGGGGS GGGGSGGGGSEVQLVESGG GLVQAGGSLRLSCEASGRT YSRYGMGWFRQAPGKEREF VAAVSRLSGPRTVYADSVK GRFTISRDNAENTVYLQMN SLKPEDTAVYTCAAELTNR NSGAYYYAWAYDYWGQGTQ VTVSSAAAEQKLISEEDLN GAAHHHHHH |
| 12D2biv | | | Bivalent control nanobody construct | Not available |
| Palivizumab | Synagis | | MedImmune product; Synagis is indicated for the prevention of serious lower respiratory tract disease caused by RSV in children at high risk of RSV disease (US FDA approved). e.g. American Academy of Pediatrics. "Red Book: 2006 Report of the Committee on Infectious Diseases, 27$^{th}$ ed." Pp562-565 | |

To test the capacity of Nanobody RSV101 to neutralize virus in vivo, a mouse model was used. In this model, female Balb/c mice (9-10 weeks old) were inoculated intranasally with 100 ug of purified RSV101 dissolved in 50 ul PBS. As an irrelevant Nanobody control the bivalent Nanobody 12D2biv was used. In addition, one group of mice received 100 ug Palivizumab (Synagis) and a fourth group received PBS only. Five hours later, $10^6$ infectious units of the RSV A2 strain were administered intra-nasally. Four days and 1 day before virus infection and 1 and 4 days after infection mice were treated with cyclophosphamide (first dosing at 3 mg/kg; subsequent dosing at 2 mg/kg all administered s.c.) to suppress the immune system and as such to increase virus replication.

Three and 5 days after viral challenge, mice were killed; lungs were removed, homogenized and cleared from tissue by centrifugation. Sub-confluent Hep-2 cells, incubated in Example 44.2: After Intranasal Administration Nanobody RSV101 Remains Functionally Active in the Lungs for at Least 72 Hours In order to test whether nanobodies or palivizumab antibodies might still be present in lungs 3 and 5 days after inoculation, lung homogenates of PBS treated mice were pre-incubated for 1 h with the same volume of lung homogenates from the different experimental groups, prepared either three of five days post-infection.

Figure 21:
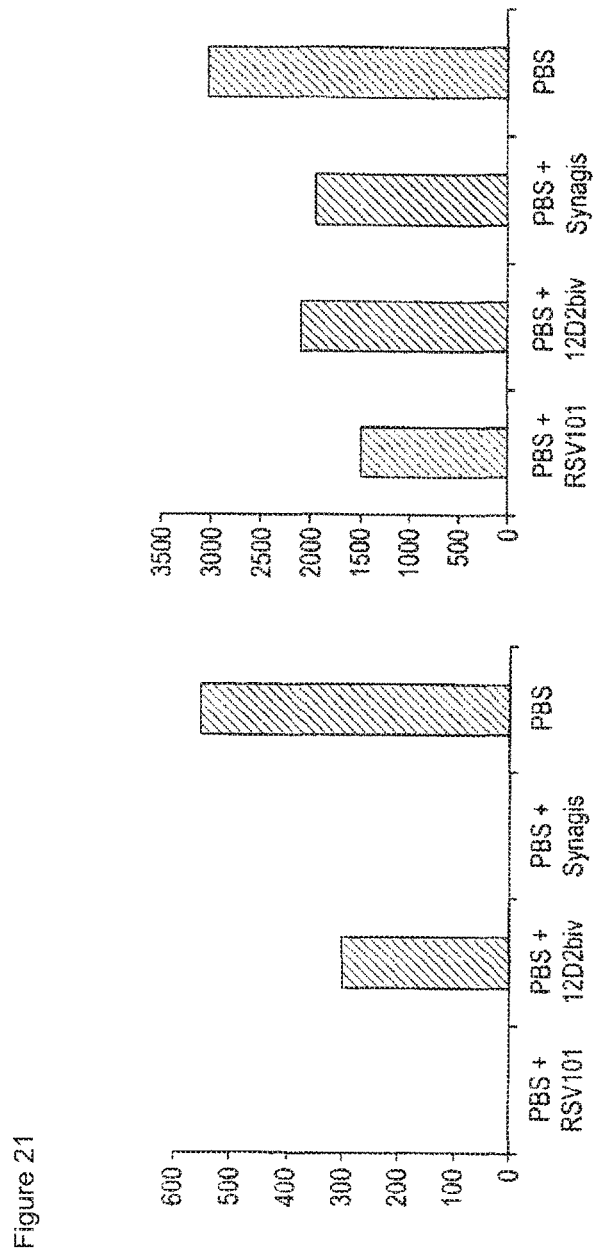
FIG. 21: Functional Nanobody RSV101 remains detectable for at least 3 days following intranasal inoculation in mice.

As shown in FIG. 21 (left panel), incubation of lung homogenates from PBS treated mice with lung homogenates prepared three days after infection from either RSV101 or palivizumab but not 12D2biv treated mice neutralized the virus present in the lung homogenates from PBS treated mice. In contrast, none of the lung homogenates of mice treated with RSV101 or Synagis prepared five days after infection could severely neutralize the virus present in the lung homogenates of PBS treated mice (FIG. 21 right panel).

Taken together, these data show that the functional bivalent Nanobody RSV101 remains present in the lungs for at least 72 hours after administration.

Example 44.3: Viral RNA is not Detected in the Lungs of Mice Ore-Treated Intranasally with RSV101

The results described in example 44.1 demonstrated that no infectious virus was present in the lungs of mice treated with RSV101. However, there was still the possibility that virus had infected cells and that viral genomic RNA was replicated with release of non-infectious viral particles or without release of viral particles. To investigate this possibility, the presence of viral RNA was determined by qPCR. RNA was isolated from 100 ul of each long homogenate (1000 ul prepared 5 days post-infection. By the use of an M-gene specific primer RSV genomic RNA specific cDNA was synthesized and quantified by qPCR (in duplicate). The level of viral genomic RNA in each lung homogenate was calculated relative to a lung sample which showed the lowest qRT-PCR signal (normalized to value of 1). As shown in Table B-23, the presence of relative viral genomic RNA in lungs of mice treated with RSV101 and Synagis® was reduced strongly compared to PBS or 12D2biv treated mice.

TABLE B-23

Relative viral genomic RNA in lungs of treated mice 5 days post viral inoculation

| Mouse | PBS | RSV101 | 12D2biv | Synagis |
|---|---|---|---|---|
| 1 | 170.69 | 16.96 | 214.74 | 4.82 |
| 2 | 53.45 | 10.96 | 466.40 | 4.81 |
| 3 | 471.42 | 3.84 | 350.39 | 7.20 |
| 4 | 404.66 | 5.60 | 418.76 | 6.32 |
| 5 | 342.39 | 2.19 | 193.26 | 4.15 |
| Mean | 288.52 | 7.91 | 328.71 | 5.46 |
| SD | 172.47 | 6.04 | 121.32 | 1.25 |

Example 45: Pulmonary Delivery Studies with Nanobodies Against HA Pseudotyped Viruses The following description of the construction of HA pseudotyped viruses and assays performed taken from (1). A sensitive retroviral pseudotype assay for influenza H5N1-neutralizing antibodies. Influenza and Other Respiratory Viruses 1(3), 105-112)

References (1). Temperton N J, Hoschler K, Major D et. al. A sensitive retroviral pseudotype assay for influenza H5N1-neutralizing antibodies. Influenza and Other Respiratory Viruses 2007 1(3), 105-112

(17) Besnier C, Takeuchi Y, Towers G. Restriction of lentivirus in monkeys. Proc Natl Acad Sci USA 2002; 9:11920-11925.

(19) Op De Beeck A, Voisset C, Bartosch B et al. Characterization of functional hepatitis C virus envelope glycoproteins. J Virol 2004; 78:2994-3002.

(20) Naldini L, Blomer U, Gallay P et al. In vivo gene delivery and stable transduction of nondividing cells by a lentiviral vector. Science 1996; 272:263-267.

Example 45.1: The HA-Pseudotyped Neutralization Assay

| Name | Alternative names | SEQ ID NO: | Reference | Amino acid sequence |
|---|---|---|---|---|
| 202-A5 | | 149 | U.S. provisional 61/139,130 | EVQLVESGGDLVQPGGSLR LSCAASGFIFRGYWMTWVR QAPGKGLEWVSSINNIGEE AYYVDSVKGRFTISRDNAK NTLYLQMNSLKSEDTAVYY CVKDWASDYAGYSPNSQGT QVTVSS |
| 202-A10 | | 150 | U.S. provisional 61/139,130 | EVQLVESGGGLVQAGDSLR LSCIDSGRTFSDYPIGWFR QAPGKEREFVAAIYAIGGD VYYADSVKGRFTISRDNAK NTVYLQMSSLKPEDTAIYS CAVASGGGSIRSARRYDYW GRGTQVTVSS |
| 202-A12 | | 151 | U.S. provisional 61/139,130 | EVQLVESGGGLVQAGGSLR LSCAASGGIFSSYAMGWFR QAPGKERDFVSAITWSGGS TYYADSVKGRFTISRDNAK NTVYLQMNSLKPEDTAVYY CAADDQKYDYIAYAEYEYD YWGQGTQVTVSS |
| 202-B7 | | 152 | U.S. provisional 61/139,130 | EVQLVESGGGLVQPGGSLR LSCAASGFTFRGYWMSWVR QAPGKGLEWVSAINNVGDE VYYADSVKGRFTISRDNAK NTLYLQMNSLKSEDTAVYY CTRDWFDDPNKNEYKGQGT QVTVSS |
| 202-B10 | | 153 | U.S. provisional 61/139,130 | EVQLVESGGGLVQPGGSLR LSCAASGFTFRGYWMSWVR QAPGKGLEWVSAINNVGDE VYYADSVKGRFTISRDNAK NTLYLQMNSLKSEDTAVYY CTRDWYNDPNKNEYKGQGT QVTVSS |
| 202-C1 | | 154 | U.S. provisional 61/139,130 | KVQLVESGGDLVQPGGSLR LSCAASGFTFRGYWMTWVR QAPGKGLEWVSSINNIGEE AYYVDSVKGRFTISRDNAK NTLYLQMNSLKSEDTAVYY CVKDWASDYAGYSPNSQGT QVTVSS |
| 202-C2 | | 155 | U.S. provisional 61/139,130 | EVQLVESGGDLVQPGGSLR LSCAASGFTFRGYWMTWVR QAPGKGLEWVSSINNIGEE AYYVDSVKGRFTISRDNAK NTLYLQMNSLKSEDTAVYY CVKDWASDYAGYSPNSQGT QVTVSS |
| 202-C8 | | 156 | U.S. provisional 61/139,130 | EVQLVESGGGLVQPGGSLR LSCIGSGFTFSSYWMDWVR QTPGKDLEYVSGISPSGSN TDYADSVKGRFTISRDNAK NTLYLQMNSLKPEDTALYY CRRSLILTDSPDLRSQGIQ VTVSS |
| 202-C9 | | 157 | U.S. provisional 61/139,130 | EVQLVESGGGLVQPGGSLR LSCAASGFTFRGYWMSWVR QAPGKGLEWVSAINNVGGE TYYADSVKGRFTISRDNAK NALYLQMNSLKSEDTAVYY CARDWYNDPNKNEYKGQGT QVTVSS |

-continued

| Name | Alternative names | SEQ ID NO: Reference | Amino acid sequence |
|---|---|---|---|
| 202-D5 | | 158 U.S. provisional 61/139,130 | EVQLVESGGGLVQAGGSLR LSCAASGSTGSSTAMGWSR QAPGKQREWVASISSAGTI RYVDSVKGRFTISRDNAKN TGYLQMNSLKPEDTAVYYC YVVGNFITYWGRGTQVTVS S |
| 202-D8 | | 159 U.S. provisional 61/139,130 | EVQLVESGGGLVQPGGSLR LSCAASGFTFRGYWMSWVR QAPGKGLEWVSAINNVGDE VYYADSVKGRFTISRDNAK NTLYLQMNSLKSEDTAVYY CTRDWYNDPNKNEYKGQGT QVTVSS |
| 202-E4 | | 160 U.S. provisional 61/139,130 | EVQLVESGGGLVQAGGSLR LSCAASVSAFSEYAMGWYR QAPGKQREFVATINSLGGT SYADSVKGRFTISRDNAKN IVYLQMNSLKPEDTAVYYC TLYRANLWGQGTQVTVSS |
| 202-E5 | | 161 U.S. provisional 61/139,130 | EVQLVESGGGLVQPGGSLR LSCAASGFTFRGYWMTWVR QAPGKGLEWVSSINNIGEE TYYVDSVKGRFTISRDNAK NTLYLQMNSLKSEDTAVYY CVKDWASDYAGYSPNSQGT QVTVSS |
| 202-E6 | | 162 U.S. provisional 61/139,130 | EVQLVESGGGLVQAGGSLR LSCAASGRIFSSYAMGWFR QAPGKEREFVAAISWSGRI TYYADFVKGRFTISRDNAK NIVYLQMNSLKPEDTAVYY CAADLSPGNEYGEMMEYEY DYWGEGTQVTVSS |
| 202-E7 | | 163 U.S. provisional 61/139,130 | EVQLVESGGGLVQPGGSLR LSCAASGFTFRGYWMSWVR QAPGKGLEWVSAINNVGEE TYYADSVKGRFTISRDNAK NTLYLQMNSLKSEDTAAYY CARDWYNDPNKNEYKGQGT QVTVSS |
| 202-E11 | | 164 U.S. provisional 61/139,130 | EVQLVESGGGLVQPGGSLR LSCAASGFTFRGYWMSWVR QAPGKGLEWVSAINNVGDE VYYADSVKGRFTISRDNAK NTLYLQMNSLKSEDTAVYY CTRDWYNDPNKNEYKGQGT QVTVSS |
| 202-F3 | | 165 U.S. provisional 61/139,130 | EVQLVESGGDLVQPGGSLR LSCAASGFTFRGYWMTWVR QAPGKGLEWVSSINNIGEE AYYVDSVKGRFTISRDNAK NTLYLQMNSLKSEDTAVYY CVKDWASDYAGYSPNSQGT QVTVSS |
| 202-F4 | | 166 U.S. provisional 61/139,130 | EVQLVESGGDLVQPGGSLR LSCAASGFTFRGYWMTWVR QAPGKGLEWVSSINNIGEE AYYVDSVKGRFTISRDNAK NTLYLQMNSLKSEDTAVYY CVKDWASDYAGYSPNSQGT QVTVSS |
| 202-F8 | | 167 U.S. provisional 61/139,130 | EVQLVESGGGLVQPGGSLR LSCAASGLIFSSYDMGWFR QAPGEERAFVGAISRSGDV RYVDPVKGRFTITRDNAKN TVYLQMNSLKPEDTAVYYC AADADGWWHRGQAYHWWGQ GTQVTVSS |
| 202-G3 | | 168 U.S. provisional 61/139,130 | EVQLMESGGGLVQAGGSLR LSCAASGRTFSGYTMGWFR QAPGKGREWVAGISWSGDS TYYADSVKGRFTISREDAK NTVYLQMNSLKPGDTADYY CAAECAMYGSSWPPPCMDW GQGTQVTVSS |
| 202-G8 | | 169 U.S. provisional 61/139,130 | EVQLVESGGGSVQPGGSLR LSCAASGFIFRGYWMSWVR QAPGKGLEWVSAINNLGGD TYYADSVKGRFTISRDNAK NMLYLQMNSLKAEDTAVYY CARDWYDDPNKNEYKGQGT QVTVSS |
| 202-G11 | | 170 U.S. provisional 61/139,130 | EVQLVESGGGLVQPGGSLR LSCAASGFTFRGYWMSWVR QAPGKGLEWVSAINNVGGE TYYADSVKGRFTISRDNAK NTLYLQMNSLKSEDTAAYY CARDWYNDPNKNEYKGQGT QVTVSS |
| 203-B1 | | 171 | EVQLVESGGDLVQPGGSLR LSCAASGFTFRGYWMTWVR QAPGKGLEWVSSINNVGEE TYYADSVKGRFTISRDNAK NTLYLQMNSLKSEDTAVYY CVKDWESSYAGYSPNSQGT QVTVSS |
| 203-H1 | | 172 | EVQLVESGGGVVQAGGSLR LSCAASGLTFDIYSMGWFR QQPGKEREFVASIGRSGNS TNYASSVKDRFTISRDNAK KLVYLEMNSLTVEDAAVYV CAAKDGPLITHYSTTSMYW GQGTQVTVSS |
| 203-E12 | | 173 | EVQLVESGGGLVQPGGSLR LSCAASGFTFRGYWMSWVR QAPGKGLEWVSAINNVGDE VYYADSVKGRFIISRDNAK NTLYLQMNSLKSEDTAVYY CTRDWYNDPNKNEYKGQGT QVTVSS |
| 203-H9 | | 174 | EVQLVESGGGLVQPGGSLR LSCTGSGFTFSSYWMDWVR QTPGKDLEYVSGISPSGGN TDYADSVKGRFTISRDNAK NTLYLQMNSLQPEDTALYY CRRSLILTDSPDLRSQGTQ VTVSS |
| 203-B12 | | 175 | EVQLVESGGGLVQPGGSLR LSCAASGFTFSSYAMGWVR RAPGEGLEWVSSISSGGAL PTYADSVKGRFTISRDNVK NTLYLQMNSLKPEDTAVYS CEKYAGSMWTSERDAWGQG TQVTVSS |

-continued

| Name | Alternative names | SEQ ID NO: Reference | Amino acid sequence |
|---|---|---|---|
| 203-A9 | | 176 | EVQLVESGGGLVQAGDSLR LSCIDSGRIFSDYPIGWFR QAPGKEREFVAAIYPTDDN PTGPNAYYADSVKGRFTIS RDNAKKITVYLQMSSLKPE DTAIYSCAVASGGGSIISA RRYDYWGQGTQVTVSS |
| 203-D9 | | 177 | EVQLVESGGGWVQAGDSLR LSCAASGRTLSSYAMAWFR QAPGKERDFVTGITWNGGS TYYADSVKGRFTISRDNAK NIVYLQMNSLKPEDTAVYY CAABQNTYGYMDRSDYEYD YWGQGTQVTVSS |
| 189-E2 | | 178 | KVQLVESGGGLVQPGGSLR LSCAASGSIFSINAMGWYR QAPGKQRELVAHIASSGST IYADSVKGRFTISRDNAKN TVYLQMNSLKPEDTAVYYC NTRGPAAHEVRDYWGQGTQ VTVSS |
| 191-D3 | | 184 | EVQLVESGGGLVQAGGSLR LSCEASGRTYSRYGMGWFR QAPGKEREFVAAVSRLSGP RTVYADSVKGRFTISRDNA ENTVYLQMNSLKPEDTAVY TCAAELTNRNSGAYYYAWA YDYWGQGTOVINSS |

Plasmids and Cell Lines.

Plasmid pl.18/VN1194 HA was constructed at NIBSC (UK). The full-length HA ORF from A/Vietnam/1194/04 was amplified by PCR and cloned into the expression vector pl.18. This backbone plasmid is a pUC-based plasmid incorporating promoter and Intron A elements from human cytomegalovirus. The MLV and HIV gag/pol constructs has been described previously. The luciferase (Luc) reporter construct MLV-Luc has been described (19). Vesicular stomatitis virus envelope protein (VSV-G) expression vector pMDG has been described previously (20). All cell lines were cultured in Dulbecco's modified eagle medium (DMEM) with Glutamax and high glucose (Gibco, Paisley, Scotland, UK), supplemented with 10% fetal calf serum and penicillin/streptomycin, except for 293T cells (15% fetal calf serum).

Viral Vector Production and Infection of Target Cells

Confluent plates of 293T cells were split 1:4 the day before transfection. Each plate of 293T cells was transfected with 1 g gag/pol construct, 1.5 ug Luc reporter construct, and 1.5 ug HA- or VSV-G-expressing construct by using the Fugene-6 transfection reagent. At 24 h post-transfection, 1 U of exogenous neuraminidase (Sigma, St. Louis, Mo., USA) was added to induce the release of HA-pseudotyped particles from the surface of the producer cells. Supernatant was harvested 48 and 72 h post-transfection, filtered through 0.45-lm filters, and stored at −80° C. MLV vector titers were measured on human 293T, quail QT6, canine MDCK, porcine PK15 and ST-IOWA cells and are presented as infectious units (IU) per milliliter. Briefly, cells were infected with vector, and Luc titers were determined 72 h later by Luc assay. Titers were expressed as RLU for Luc.

MLV(HA) Pseudotype Neutralization Assay

Serum samples (5 ul) were heat inactivated at 56° C. for 30 min, twofold serially diluted in culture medium, and mixed with MLV(HA) virions (10.000 RLU for Luc) at a 1:1 v/v ratio. Purified Nanobodies (10 or 20 ul) were diluted to 100 ul and twofold serially diluted in culture medium, and mixed with MLV(HA) virions (10.000 RLU for Luc) at a 1:1 v/v ratio. After incubation at 37° C. for 1 h, 1×10$^4$ 293T cells were added to each well of a 96-well flat-bottomed plate. Relative light units (RLU) for Luc were evaluated 48 h later by luminometry using the Promega Bright-Glo system (Promega, Madison, Wis., USA) according to the manufacturer's instructions. IC90/IC50-neutralizing antibody titers were determined as the highest serum dilution resulting in a 90/50% reduction of infection (as measured by marker gene transfer) compared with a pseudotype virus only control. For Luc, titers <100 are designated negative.

Figure 22:
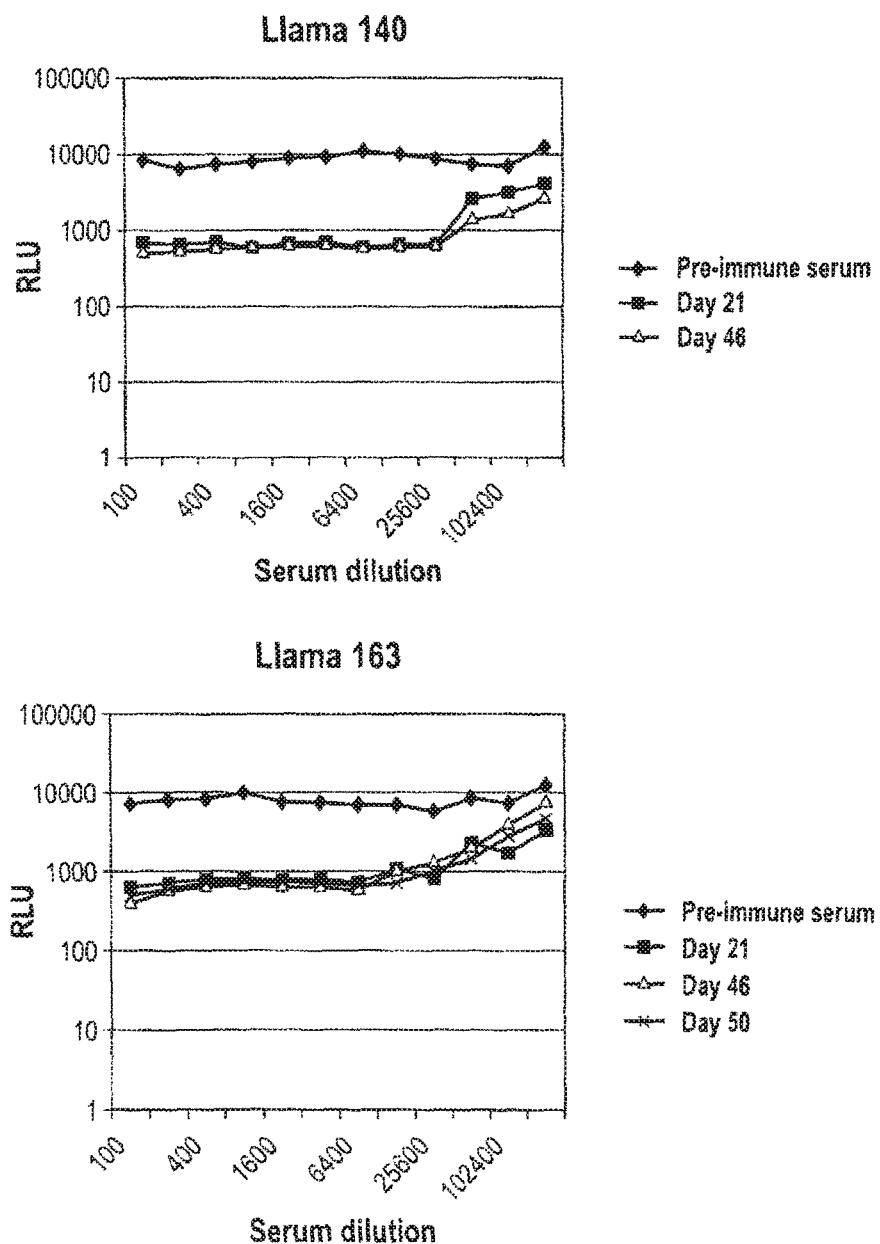
FIG. 22: Virus neutralizing titers of llama serum after immunization with hemagglutinin.

Example 45.2: Llamas Develop High Virus-Neutralizing Antibody Titers after Immunizations with Purified H5 HA Sera taken from immunized llamas before (pre-immune) and 21 and 48 days after the first immunization was tested in the pseudotyped neutralization assay as described in example 45.1. (FIG. 22). Pre-immune serum showed no neutralizing activity, while IC90s of 25600 to 51200 were present in llama 140 and 163, respectively.

Figure 23:
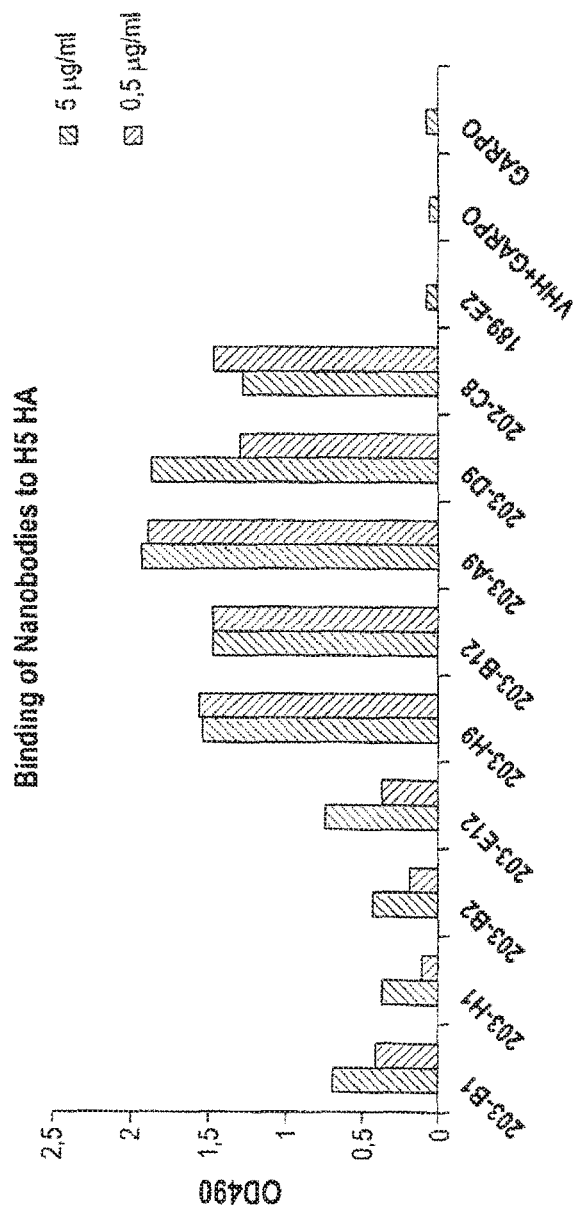
FIG. 23: Binding assay with a dilution series of purified anti-H5 HA Nanobodies.

Example 45.3: Identification of Nanobodies that Block the Interaction of HA with Sialic Acid on Fetuin (FIGS. 23 and 24)

Hemagglutinin (HA) on Influenza viruses binds sialic acid on cells during infection. The sialic acid binding site the HA forms a pocket which is conserved between Influenza strains. Most HAs of avian influenza viruses preferentially recognize sialic acid receptors containing the α(2,3) linkage to galactose on carbohydrate side chains (human viruses, the α(2,6) linkage). To increase the chance of isolating neutralizing Nanobodies, a functional selection approach can be used—identify Nanobodies that compete with soluble 2,3 sialic acid (or 2,6 sialic acid for some mutational drift variants). This would select for Nanobodies targeting the sialic acid binding site of HA. These Nanobodies are likely to be the most potent at neutralizing H5N1.

We have selected Nanobodies binding to H5N1 HA and to identify the Nanobodies binding to the sialic acid binding site the following experiments were performed. Fetuin (from fetal calf serum, F2379, Sigma-Aldrich) was coated (10 μg/ml) in a 96 well plate and incubated over night at 4° C. The plate was blocked in 2% BSA and then 0.7 μg/ml biotinylated HA (HA-bio) and 10 μl of periplasmic fractions or purified Nanobodies were added for competition. After incubation for 1 hour, HRP conjugated streptavidin was added and incubated for 1 hour. Binding specificity of HA-bio not recognized by periplasmic fractions or purified nanobodies was determined based on OD values compared to controls having received no Nanobody. Results of competition between periplasmic fractions or purified Nanobodies and fetuin for binding to HA-bio is shown in FIGS. 23, 24 and 25. Several Nanobody clones showed competition which may indicate that the competing Nanobodies recognize the sialic acid binding site on the HA.

Example 45.4: Identification of Nanobodies 202-C8, 203-B12 and 203-H9 that Neutralize HA Pseudotyped Virus (FIGS. 25 and 26)

Several purified Nanobodies were tested in the pseudo typed virus neutralization assay described in Example 45.1.

Figure 26:
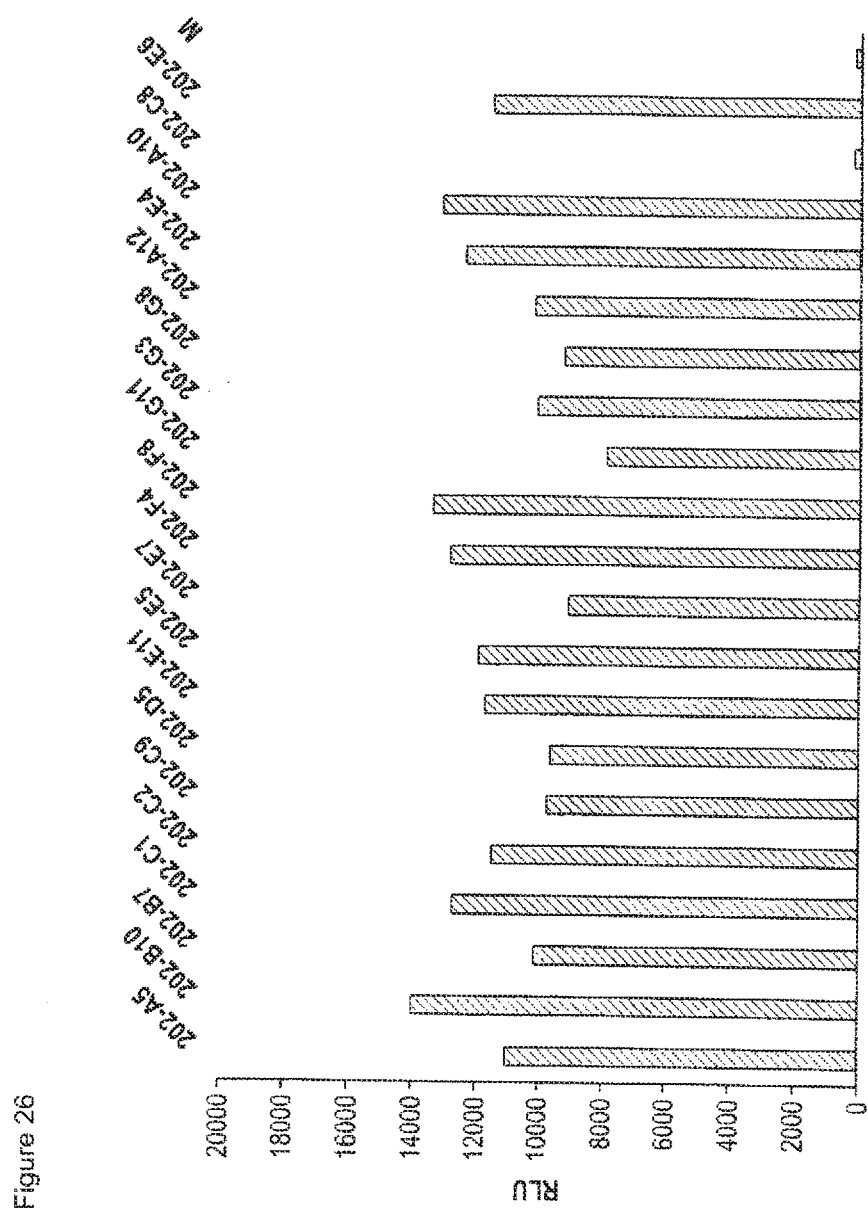
FIG. 26: Identification of the neutralizing Nanobody 202-C8.
Figure 27:
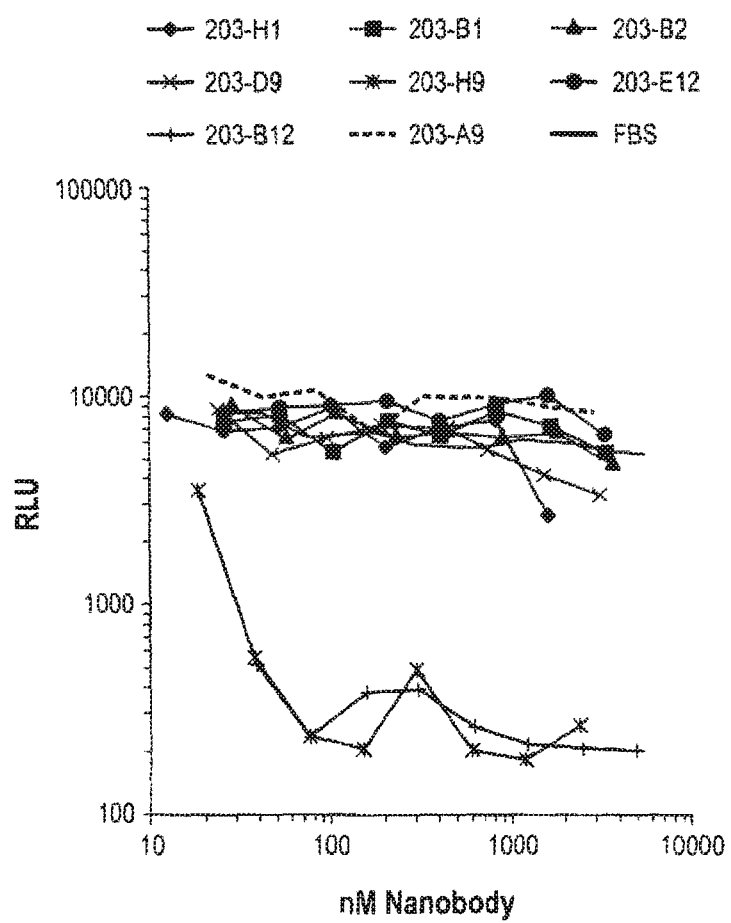
FIG. 27: Identification of the neutralizing Nanobodies 203-B12 and 203-H9.

In FIG. 26, the neutralization of a single 10 fold dilution of different Nanobodies is shown and only Nanobody 202-C8 strongly reduced luciferase activity, indicative for a virus neutralizing activity of this Nanobody. The identification of two more virus-neutralizing Nanobodies 203-B12 and 203-H9 is depicted in FIG. 27.

Figure 28:
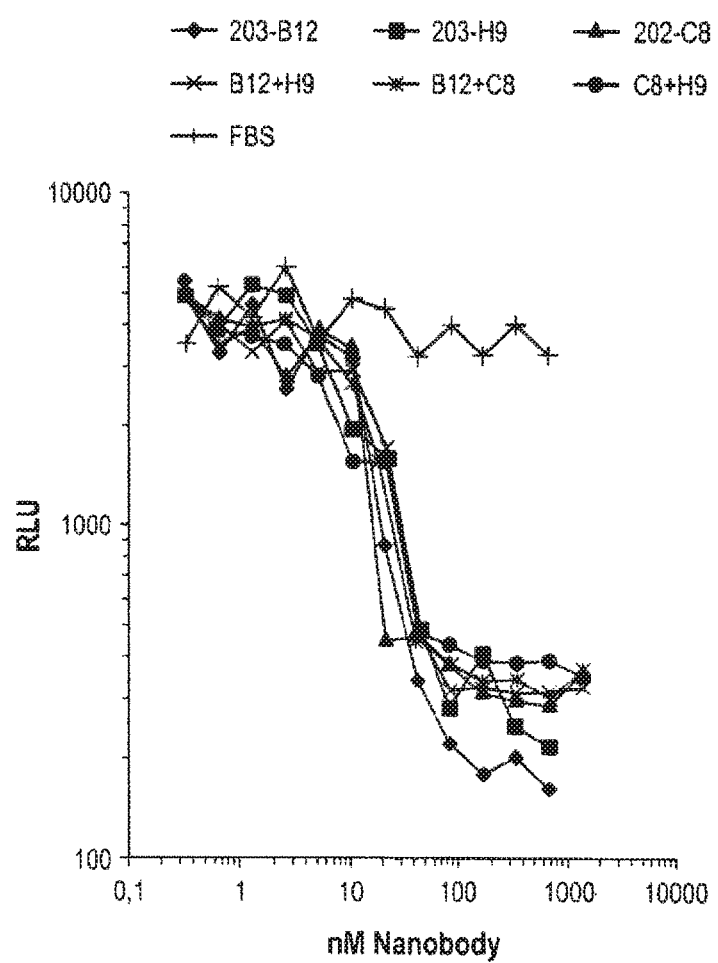
FIG. 28: Combinations of Nanobodies 202-C8, 203-H9 and 203-B12 do not result in increased neutralization.
Figure 29:
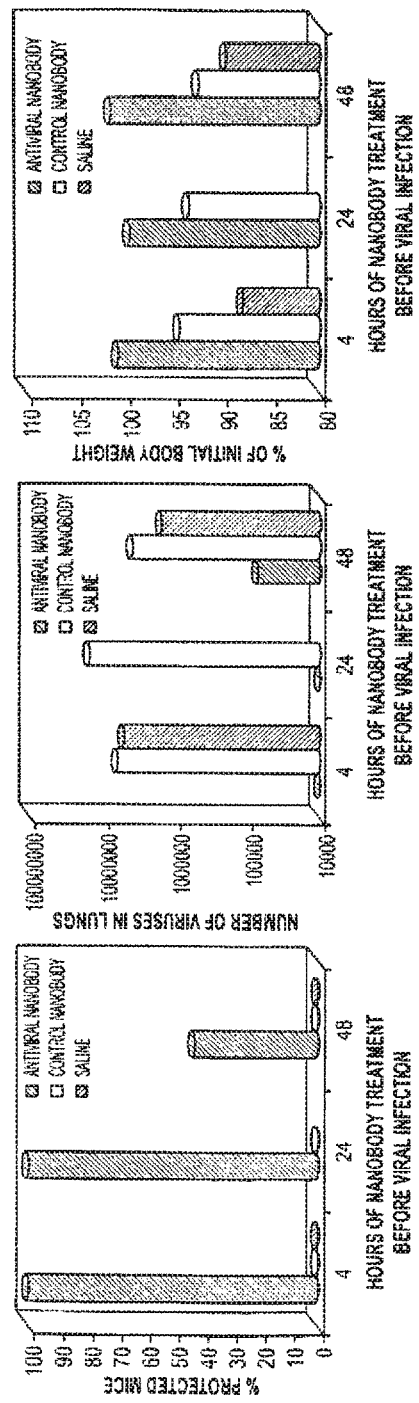
FIG. 29: Intranasal delivery of Nanobody 202-C8 protects against infection and replication of mouse-adapted NIBRG-14 virus.
Figure 30:
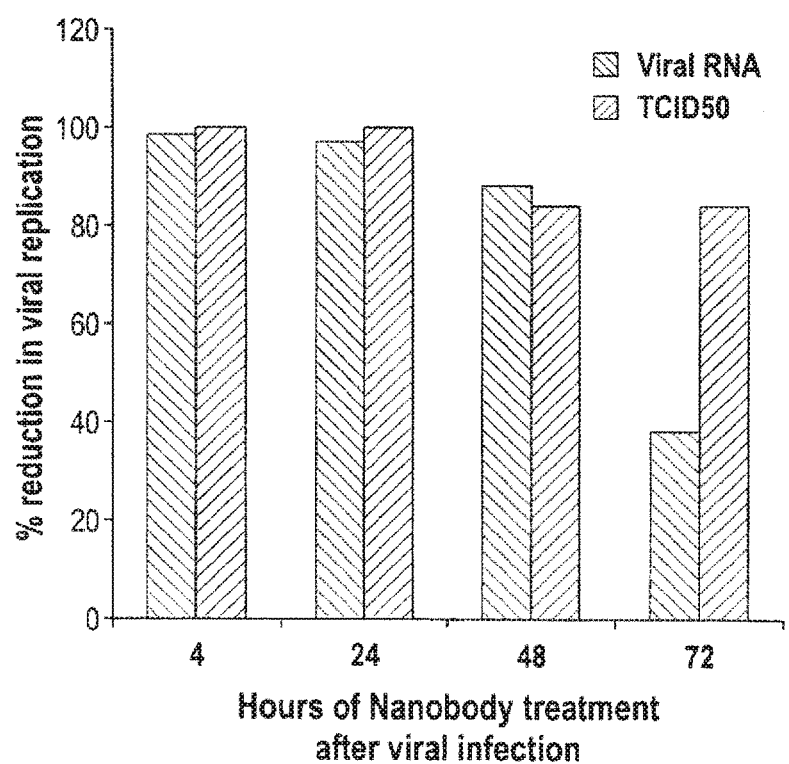
FIG. 30: Nanobody (202-c8)2 reduces viral replication when administered up to 72 hours after viral infection. Infectious titers (TCID50/ml) and viral RNA in the lungs were determined 96 hours after viral infection. % reduction was calculated by comparing with infectious titers and RNA levels from mice treated with the control Nanobody (191 D3)2.

Example 45.5: Combinations of Nanobodies 202-C8. 203-B12 and 203-H9 do not Result in Increased Neutralization Combined treatment with different virus neutralizing antibodies might results in additive or even synergistic neutralizing effect. However, this was not observed when combinations of 202-C8 with 203-B12 or 202-C8 with 203-H9 or 203-812 with 203-H9 were tested in the pseudotyped neutralization assay (FIG. 28).

Example 45.6: In Vivo Neutralization of Influenza Virus by Nanobody 202-C8

To test the capacity of Nanobody 202-C8 to neutralize virus in vivo, a mouse model was used. In this model, female Balb/c mice (6-7 weeks old) were inoculated intranasally with 100 ug of purified 202-C8 dissolved in 50 ul PBS. As an irrelevant Nanobody control the RSV Nanobody 191-D3 was used. In addition, one group of mice received PBS only. Four hours later, 1 LD50 of the mouse adapted NIBRG-14 was administered intranasally. The NIBRG-14 virus contains the HA (with the polybasic cleavage site removed) and the NA of the A/Vietnam/1194/2004 (H5N1) virus. The internal viral genes are of the A/Puerto Rico/8/1934(H1N1).

Four and six days after viral challenge, mice were killed, lungs were removed and homogenized. Viral titers (TCID50) were determined by infection of MDCK cells with serial dilutions of lung homogenates. The presence of virus in cell supernatant was determined by hemagglutination assays. Titers were calculated according the method of Muench and Reed. A value of "0" was entered if no virus was detected. The geometric mean and standard deviation are reported for each group at each time point.

Mice treated with 202-C8 never showed any sign of disease during the whole experiment. The PBS and 191D3-treated mice showed clinical signs, including ruffled fur, inactivity, hunched posture, and depression.

Virus was recovered from all animals in the negative control groups (PBS and 191-D3) in lung homogenates on day 4 and 6 after challenge. None of the animals in the 202-C8-treated group had virus detectable virus titers on day 4 and 6 post challenge (Table B-24).

TABLE B-24

| Viral titers in mouse 4 and 6 days post inoculation | | | | | |
|---|---|---|---|---|---|
| Group | Mouse 1 | Mouse 2 | Mouse 3 | Geo. Mean | StDev |
| Day 4 lung titers (TCID50/ml lung homogenate) | | | | | |
| PBS (n = 3) | 355656 | 63246 | 63246 | 160716 | 137843 |
| 191D3 (n = 3) | 112468 | 112468 | 632456 | 285797 | 245124 |
| 202-C8 (n = 3) | 0 | 0 | 0 | 0 | 0 |
| Day 6 lung titers (TCID50/ml lung homogenate) | | | | | |
| PBS (n = 3) | 63426 | 112468 | 112468 | 96121 | 23119 |
| 191-D3 (n = 3) | 63246 | 112468 | 112468 | 96061 | 23203 |
| 202-C8 (n = 3) | 0 | 0 | 0 | 0 | 0 |

Example 45.7: After Intranasal Administration Nanobody 202-C8 Remains Functionally Active in the Lungs for at Least 48 Hours To test how long Nanobody 202-C8 remains active in the lungs after intranasal inoculation, female Balb/c mice (6-7 weeks old) were inoculated intranasally with 100 ug of purified 202-C8 dissolved in 50 ul PBS. As an irrelevant Nanobody control the RSV Nanobody 191-D3 was used. In addition, one group of mice received PBS only. All mice received 1 LD50 of the mouse adapted NIBRG-14 intranasally, but virus was given 4, 24 or 48 hours after inoculation of the Nanobodies. Four days after viral challenge, mice were killed, lungs were removed and homogenized. Viral titers (TCID50) were determined by infection of MDCK cells with serial dilutions of lung homogenates. The presence of virus in cell supernatant was determined by hemagglutination assays. Titers were calculated according the method of Muench and Reed. A value of "0" was entered if no virus was detected. The geometric mean and standard deviation are reported for each group at each time point (Table B-25).

Mice pretreated with 202-C8 never showed any signs of disease during the whole experiment. The PBS and 191D3-treated mice showed clinical signs, including ruffled fur, inactivity, hunched posture, and depression and a reduction in body weight (FIG. 29, right panel).

Virus was recovered from all animals pretreated with the control Nanobody 191-D3 or PBS. Virus could not be detected in the lungs of mice that were treated with 202-C8, 4 and 24 hours before virus inoculation. No virus could be detected in lungs of three mice of seven treated with 202-C8 48 hours before virus inoculation (FIG. 29, left panel and Table B-25). Viral titers in the remaining 4 mice were on average reduced 50 fold compared to the viral titers found in the lungs of mice treated with 191-D3 48 hours before vial inoculation.

Taken together, these data show that the monovalent Nanobody 202-C8 remains actively present in the lungs for at least 48 hours after administration.

TABLE B-25

| | Weight Day 0 | Weight Day 1 | Weight Day 2 | Weight Day 3 | Weight Day 4 | Lung titer Day 4 |
|---|---|---|---|---|---|---|
| LBG4 4 h mouse 1 | 18.15 | 18.32 | 17.67 | 18.5 | 18.23 | 0 |
| LBG4 4 h mouse 2 | 20.67 | 20.42 | 20.43 | 20.94 | 20.93 | 0 |
| LBG4 4 h mouse 3 | 19.72 | 19.67 | 18.97 | 19.68 | 19.77 | 0 |
| average | 19.51 | 19.47 | 19.02 | 19.71 | 19.64 | 0 |
| St. Dev. | 1.27 | 1.06 | 1.38 | 1.22 | 1.35 | 0 |
| LBG4 24 h mouse 1 | 18.76 | 18.81 | 18.52 | 18.83 | 18.85 | 0 |
| LBG4 24 h mouse 2 | 19.48 | 19.62 | 18.99 | 18.96 | 19.13 | 0 |

TABLE B-25-continued

| | Weight Day 0 | Weight Day 1 | Weight Day 2 | Weight Day 3 | Weight Day 4 | Lung titer Day 4 |
|---|---|---|---|---|---|---|
| LBG4 24 h mouse 3 | 18.73 | 18.55 | 18.18 | 18.34 | 18.32 | 0 |
| LBG4 24 h mouse 4 | 19.19 | 19.27 | 18.9 | 19.48 | 19.32 | 0 |
| LBG4 24 h mouse 5 | 18.95 | 19.24 | 18.36 | 18.96 | 19.06 | 0 |
| LBG4 24 h mouse 6 | 18.99 | 18.81 | 18.21 | 18.66 | 18.91 | 0 |
| average | 19.02 | 19.05 | 18.53 | 18.87 | 18.93 | 0 |
| St. Dev. | 0.28 | 0.39 | 0.35 | 0.38 | 0.34 | 0 |
| LBG4 48 h mouse 1 | 17.88 | 17.5 | 17.44 | 17.43 | 17.81 | 9355 |
| LBG4 48 h mouse 2 | 17.29 | 17.01 | 16.94 | 17.11 | 17.37 | 355656 |
| LBG4 48 h mouse 3 | 19.42 | 19.08 | 19.2 | 19.33 | 19.44 | 93550 |
| LBG4 48 h mouse 4 | 19.47 | 19.53 | 18.89 | 19.31 | 19.51 | 0 |
| LBG4 48 h mouse 5 | 19.73 | 19.55 | 19.34 | 19.54 | 20.02 | 0 |
| LBG4 48 h mouse 6 | 18.92 | 18.84 | 18.72 | 18.47 | 18.91 | 63250 |
| LBG4 48 h mouse 7 | 17.94 | 17.65 | 17.82 | 17.74 | 19.49 | 0 |
| average | 18.66 | 18.45 | 18.34 | 18.42 | 18.94 | 74544 |
| St. Dev. | 0.95 | 1.04 | 0.93 | 1.00 | 0.98 | 129378 |
| PBS 4 h mouse 1 | 18.97 | 18.89 | 18.69 | 18.05 | 16.95 | 3556500 |
| PBS 4 h mouse 2 | 18.15 | 18.36 | 18.13 | 17.32 | 15.95 | 6325000 |
| PBS 4 h mouse 3 | 19.54 | 19.9 | 19.68 | 18.11 | 16.87 | 6325000 |
| average | 18.89 | 19.05 | 18.83 | 17.83 | 16.59 | 5402167 |
| St. Dev. | 0.70 | 0.78 | 0.78 | 0.44 | 0.56 | 1598394 |
| PBS 48 h mouse 1 | 20.01 | 19.73 | 19.59 | 18.76 | 17.66 | 3556500 |
| PBS 48 h mouse 2 | 21.43 | 21.68 | 20.9 | 20.06 | 19.39 | 632500 |
| PBS 48 h mouse 3 | 18.78 | 19.02 | 18.74 | 17.67 | 16.8 | 632500 |
| average | 20.07 | 20.14 | 19.74 | 18.83 | 17.95 | 1607167 |
| St. Dev. | 1.33 | 1.38 | 1.09 | 1.20 | 1.32 | 1688172 |
| LBG3 4 h mouse 1 | 20.3 | 20.42 | 20.11 | 19.72 | 19.28 | 6324600 |
| LBG3 4 h mouse 2 | 18.39 | 18.54 | 18.66 | 18.38 | 18.33 | 9355000 |
| LBG3 4 h mouse 3 | 18.39 | 18.82 | 18.44 | 17.77 | 16.3 | 3556500 |
| average | 19.03 | 19.26 | 19.07 | 18.62 | 17.97 | 6412033 |
| St. Dev. | 1.10 | 1.01 | 0.91 | 1.00 | 1.52 | 2900239 |
| LBG3 24 h mouse 1 | 18.94 | 18.63 | 18.62 | 18.21 | 18.29 | 6324600 |
| LBG3 24 h mouse 2 | 19.46 | 19.62 | 19.4 | 18.48 | 18.09 | 63250000 |
| LBG3 24 h mouse 3 | 19.63 | 19.58 | 19.83 | 19.18 | 18.51 | 2000000 |
| LBG3 24 h mouse 4 | 19.03 | 18.94 | 19.07 | 18.45 | 17.49 | 6325000 |
| LBG3 24 h mouse 5 | 18.91 | 18.72 | 19 | 17.84 | 17.32 | 935500 |
| average | 19.19 | 19.10 | 19.18 | 18.43 | 17.94 | 15767020 |
| St. Dev. | 0.33 | 0.47 | 0.46 | 0.49 | 0.51 | 26657313 |
| LBG3 48 h mouse 1 | 19.5 | 19.39 | 18.93 | 19.04 | 18 | 3556500 |
| LBG3 48 h mouse 2 | 19.53 | 19.3 | 19.2 | 18.76 | 17.94 | 3556500 |
| LBG3 48 h mouse 3 | 20.02 | 20.23 | 20.46 | 19.81 | 19.26 | 9355000 |
| LBG3 48 h mouse 4 | 18.21 | 18.09 | 18.12 | 17.75 | 17.29 | 935500 |
| LBG3 48 h mouse 5 | 18.38 | 18.17 | 18.32 | 17.92 | 16.53 | 6325000 |
| LBG3 48 h mouse 6 | 21.19 | 20.83 | 20.55 | 20.34 | 18.98 | 632460 |
| average | 19.47 | 19.34 | 19.26 | 18.94 | 18.00 | 4060160 |
| St. Dev. | 1.10 | 1.09 | 1.04 | 1.02 | 1.02 | 3322192 |

Note
LBG4 = 202-C8;
LBG3 = 191-D3

Example 46: Further Studies with an Anti-RSV Nanobody Construct

Example 46.1: Prophylactic Study with RSV407 in Cotton Rat

| SEQ ID NO: | Reference | Name | Amino Acid Sequence |
|---|---|---|---|
| 179 | SEQ ID NO: 2415 in PCT/EP2009/056975 | RSV407 | EVQLVESGGGLVQAGGSLS ISCAASGGSLSNYVLGWFR QAPGKEREFVAAINWRGDI TIGPPNVEGRFTISRDNAK NTGYLQMNSLAPDDTAVYY CGAGTPLNPGAYIYDWSYD YWGRGTQVTVSSGGGGSGG GGSGGGGSEVQLVESGGGL VQAGGSLSISCAASGGSLS NYVLGWFRQAPGKEREFVA AINWRGDITIGPPNVEGRF TISRDNAKNTGYLQMNSLA PDDTAVYYCGAGTPLNPGA YIYDWSYDYWGRGTQVTVS SGGGGSGGGGSGGGGSEVQ LVESGGGLVQAGGSLSISC AASGGSLSNYVLGWFRQAP GKEREFVAAINWRGDITIG PPNVEGRFTISRDNAKNTG YLQMNSLAPDDTAVYYCGA GTPLNPGAYIYDWSYDYWG RGTQVTVSSAAAEQKLISE DLNGAAHHHHHH |

In this study cotton rats are treated either i.m. or intra-nasally with RSV neutralizing Nanobody constructs (RSV 407) or control (PBS). Viral RSV challenge is administered intranasally 1 hour later. At day 4, animals are sacrificed and RSV titers determined by Q-PCR in nasal and lung washes as well as in nasal and lung tissue.

RSV407 is a trivalent Nanobody construct consisting of 3 identical building blocks linked by 15GS spacers. The building block is binding the F protein of RSV and can neutralize RSV infection of the Long strain with an IC50 of about 50-100 nM. By formatting into a trivalent construct neutralization potency increased to an IC50 of about 100 pM on the RSV Long strain.

Example 46.2: Therapeutic Study with RSV407 in Cotton Rat

RSV therapeutic studies have been described in the past; e.g. by Crowe and colleagues (PNAS 1994; 91:1386-1390) and Prince and colleagues (Journal of Virology 1987; 61:1851-1854).

In this study cotton rats are intra-nasally infected with RSV. Twenty-four hours after infection a first group of animals are treated with RSV neutralizing Nanobody constructs (RSV 407) or control (PBS). Treatment is administered to pulmonary tissue by intranasal or aerosol administration. Treatment is repeated at 48 and 72 hours. At day 4 animals are sacrificed and RSV titers determined by Q-PCR in nasal and lung washed as well as in nasal and lung tissue.

In the second group treatment is only initiated 3 days after infection and repeated at day 4 and 5. Finally at day 6 animals are sacrificed and RSV titers determined by Q-PCR in nasal and lung washed as well as in nasal and lung tissue.

Example 46.3: Luna to Systemic with Nanobody Construct Against RSV

In this study the lung tissue of rats is exposed to an RSV neutralizing Nanobody (RSV407) by intratracheal or aerosol administration. Serum and BAL samples are taken at regular time points up to 3 days after administration. The Nanobody concentration is measured by means of ELISA and samples are subjected to RSV microneutralization (see below). By combining the information from the ELISA and the neutralization assay the RSV IC50 of each sample can be determined to assess systemic bioavailability of functional RSV Nanobody.

Microneutralization: The hRSV micro neutralization assay is used to investigate in vitro neutralization capacity of selected purified hRSV Nanobodies. In here, Hep2 cells are seeded at a concentration of $1.5 \times 10^4$ cells/well into 96-well plates in DMEM medium containing 10% fetal calf serum (FCS) supplemented with Penicillin and Streptomycin (100 U/ml and 100 µg/ml, respectively) and incubated for 24 hours at 370 in a 5% $CO_2$ atmosphere. A standard quantity of hRSV strain Long LM-2 (Accession No. P12568; ATCC VR-26) is pre-incubated with serial dilutions of samples in a total volume of 50 µl for 30 minutes at 37° C. The medium of the Hep2 cells is replaced with the premix to allow infection for 2 hours, after which 0.1 ml of assay medium is added. The assay is performed in DMEM medium supplemented with 2.5% fetal calf serum and Penicillin and Streptomycin (100 U/ml and 100 µg/ml, respectively). Cells are incubated for an additional 72 hours at 37° C. in a 5% CO2 atmosphere, after which cells are fixed with 80% cold acetone (Sigma-Aldrich, St. Louis, Mo.) in PBS (100 µl/well) for minutes at 4° C. and left to dry completely. Next the presence of the F-protein on the cell surface is detected in an ELISA type assay. Thereto, fixed Hep2 cells are blocked with 2% Bovine Serum Albumin (BSA) solution in PBS for 1 hour at room temperature, than incubated for 1 hour with anti-F-protein polyclonal rabbit serum (Corral et al. 2007, BMC Biotech 7: 17) or Synagis® (2 µg/ml). For detection goat Anti-rabbit-HRP conjugated antibodies or goat Anti-Human IgG, Fcγ fragment specific-HRP (Jackson ImmunoResearch, West Grove, Pa.) is used, after which the ELISA is developed according to standard procedures.

Example 47: Luna to Systemic with Nanobody Against RANKL (See WO 2008/142164 for RANKL Nanobodies and Constructs Thereof)

In this study the lung tissue of first group of cynomolgus monkey is exposed to a half-life extended Nanobody construct against RANKL (RANKL 008a or RANKL180 or RANKL010a) by intratracheal or aerosol administration. Urine, serum and BAL samples are taken at regular time points up to 3 month after administration. The Nanobody concentration is measured by means of ELISA to determine the systemic pharmacokinetics of this half-life extended Nanobody. The pharmacodynamic effect of the RANKL Nanobody is assessed by measuring the decline of N-telopeptide (NTx), a biomarker for bone turnover, in serum and urine.

A second group of animals is treated and analyzed in exactly the same way, however in this case the HSA binding Nanobody building block is omitted (RANKL13hum5-9GS-RANKL13hum5 or RANKL18-30GS-RANKL18 or RANKL18hum6-30GS-RANKL18hum6) and thus the Nanobody is half-life extended.

Example 48: Therapeutic Efficacy of Intranasal-Delivered Nanobody

| Construct name | SEQ ID NO | Ref. SEQ ID NO | Amino Acid Sequence |
|---|---|---|---|
| 202-C8-9GS-202-C8 or (202-c8)2 | 180 | 2423 in PCT/EP2009/056975 | EVQLVESGGGLVQPGGSLR LSCTGSGFTFSSYWMDWVR QTPGKDLEYVSGISPSGSN TDYADSVKGRFTISRDNAK NTLYLQMNSLKPEDTALYY CRRSLTLTDSPDLRSQGTQ VTVSSGGGSGGGGSEVQLV ESGGGLVQPGGSLRLSCIG SGFTESSYWMDWVRQTPGK DLEYVSGISPSGSNTDYAD SVKGRFTISRDNAKNTLYL QMNSLKPEDTALYYCRRSL TLTDSPDLRSQGTQVTVSS |
| 191 D3-15GS-191 D3 or (191-d3)2 | 181 | 2382 in PCT/EP2009/056975 | EVQLVESGGGLVQAGGSLR LSCEASGRTYSRYGMGWFR QAPGKEREFVAAVSRLSGP RTVYADSVKGRFTISRDNA ENTVYLQMNSLKPEDTAVY TCAAELTNRNSGAYYYAWA YDYWGQGTQVIVSSGGGGS GGGGSGGGGSEVQLVESGG GLVQAGGSLRLSCEASGRT YSRYGMGWFRQAPGKEREE VAAVSRLSGPRIVYADSVK GRFTISRDNAENTVYLQMN SLKPEDTAVYTCAAELTNR NSGAYYYAWAYDYWGQGTQ VIVSSAAAEQKLISEEDLN GAAHHHHHH |

Twelve groups of mice ranging in size from 4 to 6 animals were challenged with 1 LD50 of the NIBRG-14 virus (see Table B-26). The NIBRG-14 virus (Temperton N J, Hoschler K, Major D et al. A sensitive retroviral pseudotype assay for influenza H5N1-neutralizing antibodies. Influenza and Other Respiratory Viruses 2007 1: 105-112) contains the HA (with the polybasic cleavage site removed) and the NA of the A/Vietnam/1194/2004 (H5N1) virus. The internal viral genes are of the A/Puerto Rico/8/1934(H1N1). 4, 24, 48 and 72 after the viral inoculation, mice were inoculated intranasally with 60 µg (202-c8)2 or 60 µg of the irrelevant control Nanobody (191-D3)2. Mice were monitored daily for weight loss (Table B-29) and at day 4 (96 hours) post viral infection, mice were scarified to prepare lung homogenates. Infectious viral titers (Table B-27) and viral RNA (Table B-28) in lung homogenates were determined.

In lungs of 4 mice that received Nanobody (202-c8)2, 4 hours after viral inoculation, no infectious virus could be detected in lung homogenates obtained at 96 hours post infection. A comparison of viral RNA in these lungs with those in the lungs of mice that were treated with (191-d3)2 demonstrated a 98.58% reduction in viral RNA.

In 3 out of 5 mice that received Nanobody (202-c8)2 24 hours after infection, no infectious virus could be detected while titers were very low in the two remaining animals. A comparison of viral RNA in these lungs with those in the lungs of mice that were treated with (191-d3)2 demonstrated a 97.22% reduction in viral RNA.

In lungs of mice that received Nanobody (202-c8)2, 48 hours after viral infection, a 84.26% reduction in viral titers was observed when compared to infectious viral titers in mice treated with (191-D3)2 at 48 hours post infections. A comparison of viral RNA in these lungs with those in the lungs of mice that were treated with (191-d3)2 demonstrated a 88.08% reduction in viral RNA.

Even when the Nanobody (202-c8)2 was administered 72 hours after viral challenge, very little infectious virus was detected in lung homogenates (i.e. a 84% reduction compared to (191-d3)2 treated mice). A comparison of viral RNA in these lungs with those in the lungs of mice that were treated with (191-d3)2 demonstrated a 38.21% reduction in viral RNA.

Figure 31:
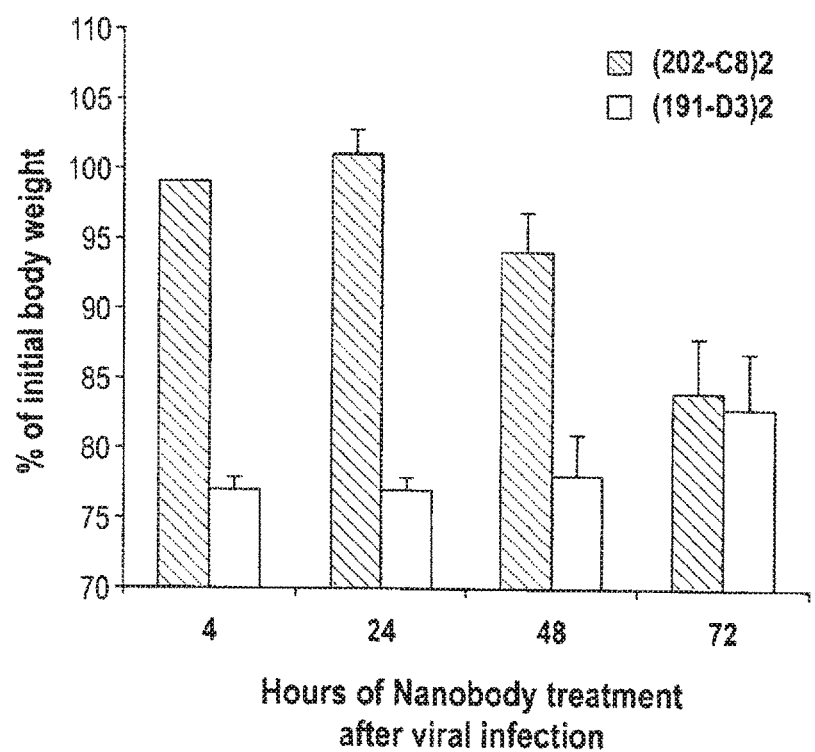
FIG. 31: Nanobody (202-C8)2 prevents viral-induced reduction in body weight when administered up to 48 hours after viral challenge. A comparison of body weights at 96 hours p.i. is shown as % of initial body weight
Figure 32:
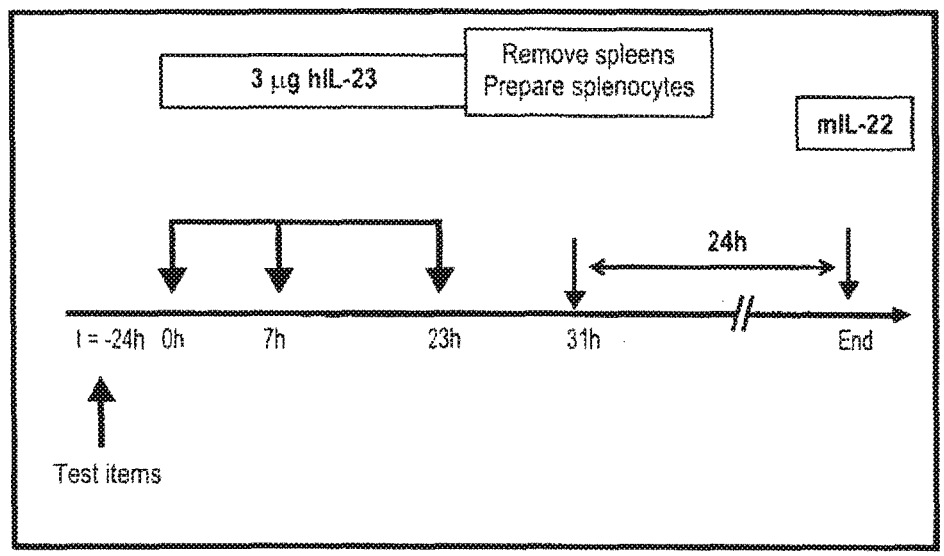
FIG. 32: Setup of the acute in vivo mouse splenocyte model.
Figure 33:
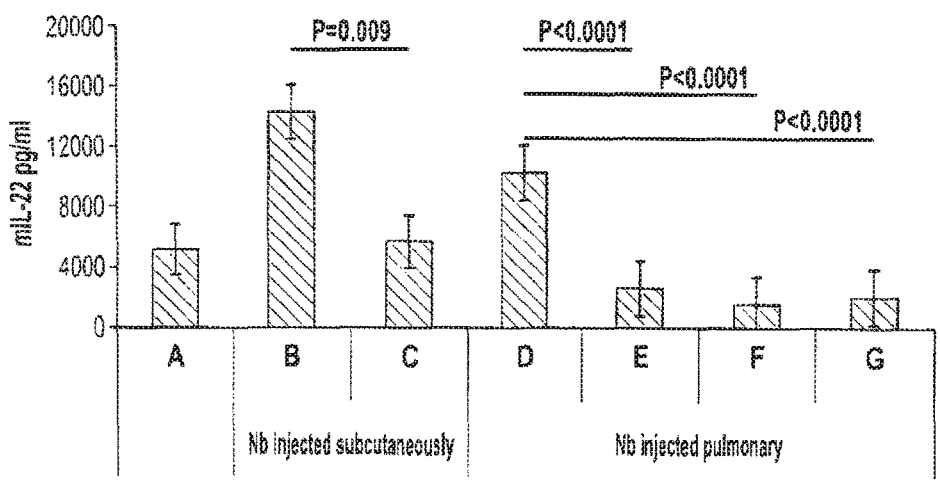
FIG. 33: Graph showing the results obtained in Example 7 for the inhibition of the mIL-22 synthesis in a mouse splenocyte assay upon administration of P23IL0075 via different routes of administration, i.e. i.t. and s.c., (A) basal level, i.e. no induction mIL-22; (B) S.c. administration of PBT; (C) S.c. administration of P23IL0075; (D) I.t. administration of PBT; (E) I.t. administration of P23IL0075 (low dose); (F) I.t. administration of P23IL0075 (high dose); (G) I.t. administration of P23IL0075 (high dose, other buffer)

Administration of (202-c8)2 not only inhibited viral replication, it also prevented virus-induced morbidity. As shown in Table B-29 and FIG. 31, administration of (202-c8)2 at 4, 24 and 48 hours after the viral challenge protected against viral-induced weight loss. When the Nanobody was administered 72 after infection, this viral-induced reduction in body weight was no longer prevented.

Overall these data demonstrated that a single therapeutic administration of a virus neutralizing Nanobody even up to 72 hours after viral infection inhibited substantially viral replication. In addition, prevention of virus-induced morbidity was prevented by administration of the Nanobody up to 48 hours after viral infection. This demonstrates that pulmonary delivery of Nanobodies is a powerful method to treat viral pulmonary infections.

TABLE B-26

Groups and number of mice in each group

| | h after viral inoculation | | | |
|---|---|---|---|---|
| | 4 | 24 | 48 | 72 |
| (202-C8)2 | 4 | 5 | 6 | 6 |
| (191-D3)2 | 4 | 5 | 6 | 6 |

TABLE B-27

Infectious viral titers (TCID50/ml) in lung homogenates of mice challenged on day 0 and inoculated with Nanobodies at 4, 24, 48 or 96 hours after infection

| Cage (number) | Nanobody | Nanbody administration (h p.i.) | TCID50/ml at 96 h p.i. |
|---|---|---|---|
| 1 (1) | (202-c8)2 | 4 | 0 |
| 1 (2) | (202-c8)2 | 4 | 0 |
| 1 (3) | (202-c8)2 | 4 | 0 |
| 1 (4) | (202-c8)2 | 4 | 0 |
| 2 (1) | (191-D3)2 | 4 | 79432826 |
| 2 (2) | (191-D3)2 | 4 | 25118864 |
| 2 (3) | (191-D3)2 | 4 | 158489319 |
| 2 (4) | (191-D3)2 | 4 | >1000000000 |
| 3 (1) | (202-c8)2 | 24 | 0 |
| 3 (2) | (202-c8)2 | 24 | 0 |
| 3 (3) | (202-c8)2 | 24 | 0 |
| 3 (4) | (202-c8)2 | 24 | 2511886 |
| 3 (5) | (202-c8)2 | 24 | 125893 |
| 4 (1) | (191-D3)2 | 24 | 100000000 |
| 4 (2) | (191-D3)2 | 24 | 158489319 |
| 4 (3) | (191-D3)2 | 24 | 79432823 |
| 4 (4) | (191-D3)2 | 24 | 158489319 |
| 4 (5) | (191-D3)2 | 24 | >1000000000 |
| 6 (1) | (202-c8)2 | 48 | 501187 |
| 6 (2) | (202-c8)2 | 48 | 158489319 |
| 6 (3) | (202-c8)2 | 48 | 12589254 |
| 6 (4) | (202-c8)2 | 48 | 158489319 |
| 6 (5) | (202-c8)2 | 48 | 158489319 |
| 6 (6) | (202-c8)2 | 48 | 158489319 |
| 7 (1) | (191-D3)2 | 48 | 79432823 |
| 7 (2) | (191-D3)2 | 48 | 501187233 |
| 7 (3) | (191-D3)2 | 48 | >1000000000 |
| 7 (4) | (191-D3)2 | 48 | >1000000000 |
| 7 (5) | (191-D3)2 | 48 | 501187233 |
| 7 (6) | (191-D3)2 | 48 | >1000000000 |
| 9 (1) | (202-c8)2 | 72 | 158489319 |
| 9 (2) | (202-c8)2 | 72 | 158489319 |
| 9 (3) | (202-c8)2 | 72 | 158489319 |
| 9 (4) | (202-c8)2 | 72 | nd |
| 9 (5) | (202-c8)2 | 72 | nd |
| 9 (6) | (202-c8)2 | 72 | nd |
| 10 (1) | (191-D3)2 | 72 | >1000000000 |
| 10 (2) | (191-D3)2 | 72 | >1000000000 |
| 10 (3) | (191-D3)2 | 72 | >1000000000 |
| 10 (4) | (191-D3)2 | 72 | nd |
| 10 (5) | (191-D3)2 | 72 | nd |
| 10 (6) | (191-D3)2 | 72 | nd |

TABLE B-28

Viral titers (RT-PCR) in lung homogenates of mice challenged on day 0 and inoculated with Nanobodies at 4, 24, 48 or 72 hours after infection.

| Cage (number) | Nanobody | Nanbody administration (h p.i.) | Average Cp | SD | $\frac{1}{2}^{Cp}$ | Average | % reduction compared to (191-D3)2 |
|---|---|---|---|---|---|---|---|
| 1 (1) | (202-c8)2 | 4 | 33.23 | 0.19 | 9.90E−11 | 5.96E−08 | 98.58 |
| 1 (2) | (202-c8)2 | 4 | 34.21 | 0.45 | 5.05E−11 | | |
| 1 (3) | (202-c8)2 | 4 | 30.05 | 0.40 | 8.98E−10 | | |
| 1 (4) | (202-c8)2 | 4 | 22.01 | 0.06 | 2.37E−07 | | |
| 2 (1) | (191-D3)2 | 4 | 18.78 | 0.36 | 2.23E−06 | 4.19E−06 | 0.00 |
| 2 (2) | (191-D3)2 | 4 | 18.53 | 0.44 | 2.65E−06 | | |
| 2 (3) | (191-D3)2 | 4 | 18.36 | 0.42 | 2.97E−06 | | |
| 2 (4) | (191-D3)2 | 4 | 16.78 | 0.18 | 8.92E−06 | | |

TABLE B-28-continued

Viral titers (RT-PCR) in lung homogenates of mice challenged on day 0 and inoculated with Nanobodies at 4, 24, 48 or 72 hours after infection.

| Cage (number) | Nanobody | Nanbody administration (h p.i.) | Average Cp | SD | $\frac{1}{2}^{Cp}$ | Average | % reduction compared to (191-D3)2 |
|---|---|---|---|---|---|---|---|
| 3 (1) | (202-c8)2 | 24 | 24.64 | 0.25 | 3.82E−08 | 2.64E−07 | 97.22 |
| 3 (2) | (202-c8)2 | 24 | 22.91 | 0.27 | 1.27E−07 | | |
| 3 (3) | (202-c8)2 | 24 | 24.53 | 0.39 | 4.13E−08 | | |
| 3 (4) | (202-c8)2 | 24 | 19.99 | 0.22 | 9.58E−07 | | |
| 3 (5) | (202-c8)2 | 24 | 22.62 | 0.27 | 1.55E−07 | | |
| 4 (1) | (191-D3)2 | 24 | 17.58 | 2.70 | 5.10E−06 | 9.49E−06 | 0.00 |
| 4 (2) | (191-D3)2 | 24 | 17.03 | 1.40 | 7.49E−06 | | |
| 4 (3) | (191-D3)2 | 24 | 16.27 | 0.30 | 1.27E−05 | | |
| 4 (4) | (191-D3)2 | 24 | 16.06 | 0.07 | 1.46E−05 | | |
| 4 (5) | (191-D3)2 | 24 | 17.01 | 0.02 | 7.58E−06 | | |
| 6 (1) | (202-c8)2 | 48 | 24.24 | 0.31 | 5.04E−08 | 7.52E−07 | 88.08 |
| 6 (2) | (202-c8)2 | 48 | 19.26 | 0.31 | 1.60E−06 | | |
| 6 (3) | (202-c8)2 | 48 | 21.15 | 0.27 | 4.30E−07 | | |
| 6 (4) | (202-c8)2 | 48 | 19.87 | 0.23 | 1.04E−06 | | |
| 6 (5) | (202-c8)2 | 48 | 19.81 | 0.07 | 1.09E−06 | | |
| 6 (6) | (202-c8)2 | 48 | 21.66 | 0.02 | 3.01E−07 | | |
| 7 (1) | (191-D3)2 | 48 | 17.15 | 0.23 | 6.86E−06 | 6.31E−06 | 0.00 |
| 7 (2) | (191-D3)2 | 48 | 17.69 | 0.06 | 4.73E−06 | | |
| 7 (3) | (191-D3)2 | 48 | 18.17 | 0.41 | 3.39E−06 | | |
| 7 (4) | (191-D3)2 | 48 | 16.95 | 0.05 | 7.88E−06 | | |
| 7 (5) | (191-D3)2 | 48 | 16.82 | 0.49 | 8.62E−06 | | |
| 7 (6) | (191-D3)2 | 48 | 17.26 | 0.11 | 6.36E−06 | | |
| 9 (1) | (202-c8)2 | 72 | 21.66 | 0.41 | 3.02E−07 | 2.35E−06 | 38.21 |
| 9 (2) | (202-c8)2 | 72 | 18.30 | 0.12 | 3.10E−06 | | |
| 9 (3) | (202-c8)2 | 72 | 18.09 | 0.23 | 3.58E−06 | | |
| 9 (4) | (202-c8)2 | 72 | 18.93 | 0.06 | 2.00E−06 | | |
| 9 (5) | (202-c8)2 | 72 | 18.26 | 0.18 | 3.19E−06 | | |
| 9 (6) | (202-c8)2 | 72 | 18.97 | 0.16 | 1.94E−06 | | |
| 10 (1) | (191-D3)2 | 72 | 17.74 | 0.33 | 4.56E−06 | 3.81E−06 | 0.00 |
| 10 (2) | (191-D3)2 | 72 | 18.15 | 0.27 | 3.45E−06 | | |
| 10 (3) | (191-D3)2 | 72 | 18.38 | 0.03 | 2.94E−06 | | |
| 10 (4) | (191-D3)2 | 72 | 18.11 | 0.05 | 3.94E−06 | | |
| 10 (5) | (191-D3)2 | 72 | 17.75 | 0.07 | 4.53E−06 | | |
| 10 (6) | (191-D3)2 | 72 | 18.00 | 0.06 | 3.82E−06 | | |

TABLE B-29

Body weights of mice challenged on day 0 and inoculated with Nanobodies at 4, 24, 48 or 96 hours after infection

| Cage (number) | Nanobody | Nanbody administration (h p.i.) | Weight 4 h p.i. | Weight 24 h p.i. | Weight 48 h p.i. | Weight 72 h p.i. |
|---|---|---|---|---|---|---|
| 1 (1) | (202-c8)2 | 4 | 18.06 | 17.22 | 17.06 | 17.32 |
| 1 (2) | (202-c8)2 | 4 | 18.94 | 18.77 | 18.65 | 18.54 |
| 1 (3) | (202-c8)2 | 4 | 18.61 | 18.02 | 17.86 | 17.97 |
| 1 (4) | (202-c8)2 | 4 | 18.18 | 17.92 | 17.67 | 17.38 |
| 2 (1) | (191-D3)2 | 4 | 18.16 | 17.84 | 17.54 | 15.11 |
| 2 (2) | (191-D3)2 | 4 | 18.14 | 17.40 | 17.28 | 15.35 |
| 2 (3) | (191-D3)2 | 4 | 18.63 | 18.15 | 17.69 | 15.78 |
| 2 (4) | (191-D3)2 | 4 | 18.83 | 18.29 | 17.98 | 15.37 |
| 3 (1) | (202-c8)2 | 24 | 18.05 | 17.41 | 17.55 | 18.15 |
| 3 (2) | (202-c8)2 | 24 | 18.11 | 17.41 | 17.42 | 16.97 |
| 3 (3) | (202-c8)2 | 24 | 18.34 | 17.93 | 18.41 | 18.49 |
| 3 (4) | (202-c8)2 | 24 | 18.18 | 18.07 | 18.19 | 18.35 |
| 3 (5) | (202-c8)2 | 24 | 16.62 | 16.29 | 15.81 | 16.24 |
| 4 (1) | (191-D3)2 | 24 | 18.56 | 18.05 | 17.42 | 15.33 |
| 4 (2) | (191-D3)2 | 24 | 18.06 | 17.27 | 17.48 | 15.46 |
| 4 (3) | (191-D3)2 | 24 | 19.34 | 18.82 | 18.69 | 16.47 |
| 4 (4) | (191-D3)2 | 24 | 19.23 | 18.82 | 18.61 | 16.48 |
| 4 (5) | (191-D3)2 | 24 | 18.03 | 17.62 | 17.07 | 15.09 |
| 6 (1) | (202-c8)2 | 48 | 19.14 | 18.38 | 18.67 | 17.22 |
| 6 (2) | (202-c8)2 | 48 | 17.67 | 17.84 | 17.95 | 16.91 |
| 6 (3) | (202-c8)2 | 48 | 18.19 | 17.57 | 17.75 | 16.92 |
| 6 (4) | (202-c8)2 | 48 | 18.04 | 17.89 | 18.00 | 16.49 |
| 6 (5) | (202-c8)2 | 48 | 17.91 | 17.56 | 18.08 | 16.71 |
| 6 (6) | (202-c8)2 | 48 | 18.22 | 17.81 | 18.24 | 15.91 |
| 7 (1) | (191-D3)2 | 48 | 18.70 | 17.70 | 18.18 | 15.59 |
| 7 (2) | (191-D3)2 | 48 | 18.89 | 18.97 | 19.02 | 16.65 |
| 7 (3) | (191-D3)2 | 48 | 18.03 | 17.19 | 17.59 | 15.76 |
| 7 (4) | (191-D3)2 | 48 | 17.44 | 16.78 | 17.12 | 14.87 |
| 7 (5) | (191-D3)2 | 48 | 19.08 | 19.00 | 19.32 | 16.98 |
| 7 (6) | (191-D3)2 | 48 | 18.18 | 17.84 | 18.38 | 16.47 |
| 9 (1) | (202-c8)2 | 72 | 18.86 | 17.86 | 18.08 | 17.23 |
| 9 (2) | (202-c8)2 | 72 | 17.36 | 18.12 | 17.98 | 16.81 |
| 9 (3) | (202-c8)2 | 72 | 18.21 | 17.40 | 17.80 | 15.97 |
| 9 (4) | (202-c8)2 | 72 | 17.77 | 16.33 | 16.64 | 15.42 |
| 9 (5) | (202-c8)2 | 72 | 17.91 | 18.24 | 18.33 | 16.69 |
| 9 (6) | (202-c8)2 | 72 | 17.65 | 17.84 | 17.91 | 17.69 |
| 10 (1) | (191-D3)2 | 72 | 17.93 | 18.03 | 18.36 | 16.57 |
| 10 (2) | (191-D3)2 | 72 | 18.30 | 16.86 | 17.18 | 15.40 |
| 10 (3) | (191-D3)2 | 72 | 17.60 | 18.02 | 17.94 | 16.80 |
| 10 (4) | (191-D3)2 | 72 | 16.40 | 17.06 | 17.24 | 15.91 |
| 10 (5) | (191-D3)2 | 72 | 18.19 | 17.43 | 17.60 | 16.55 |
| 10 (6) | (191-D3)2 | 72 | 18.05 | 17.48 | 17.65 | 16.09 |

Example 49: Use of Nebulizer Device for Pulmonary Delivery of P23IL0075 for Systemic Delivery During Pre-Clinical Efficacy Study

| Construct names | SEQ ID NO | Ref. SEQ ID NO | Amino Acid Sequence |
|---|---|---|---|
| P23IL0075 or 119A3v16-9GS-ALB8-9GS-81A12v5 (81A12v5 is equal 81Al2v4 with a (S49A) replacement) | 148 | For 119A3v16 and 81a12v4 compare SEQ ID NO: 2578 and SEQ ID NO: 2584 in WO 2009/068627 | EVQLLESGGGLVQPGGSLRLSCAASGRIFSLPASGNIFNLLTIAWYRQAPGKGRELVATINSGSRTYYADSVKGRFTISRDNSKKILYLQMNSLRPEDTAVYYCQTSGSGSPNFWGQGTLVTVSSGGGGSGGGSEVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSSGGGGSGGGSEVQLLESGGGLVQPGGSLRLSCAASGRILSSYAMGWFRQAPGKGREFVARISQGGTAIYYADSVKGRFTISRDNSKNTLYLQMNSLRPEDTAVYYCAKDPSPYYRGSAYLLSGSYDSWGQGTLVTVSS |

This study was designed to evaluate the ability of a Nanobody to reach the systemic circulation in therapeutic amounts when delivered via the lung using a nebulizer device and to provide protection against a systemic inflammatory disease. The Nanobody tested was P23IL0075, which consists of 2 anti-IL23 Nanobody building blocks and 1 anti-serum albumin Nanobody building block (SEQ ID 148). The in vivo efficacy of P23IL0075 in acute in vivo mouse splenocyte model following pulmonary delivery was compared to the efficacy following subcutaneous delivery.

In short, C57BL/6J female mice (purchased from Charles River), 10-12 weeks old and weighing about 25 g, were used. An acclimatization period of at least one week was incorporated before the start of the experiment. Test items were administrated 24 hours before the first of three hIL-23 injections on t=0 h, 7 h and 23 h. Spleens were removed on t=31 h. Splenocytes were prepared and ex vivo stimulated for 24 h after which mIL-22 levels were measured in the supernatant. The outline of the study is summarized below in FIG. 32.

Drug was delivered to the animals at a 0.3 mg/kg dose subcutaneously, or at a 3 mg/kg or 7.8 mg/kg dose via the pulmonary route using the PennCentury MicroSprayer® device (PennCentury MicroSprayer—Model IA-1C; 1.25" tip after the bend; FMJ-250 high pressure syringe). The subcutaneous 3 mg/kg dose was delivered as a 100 µL sample, whilst the pulmonary delivered 3 mg/kg and 7.8 mg/kg doses were delivered intratracheally in a total volume of 50 µL using the Microsprayer device. All P23IL0075 Nanobody samples were formulated in D-PBS+0.01% Tween20. In addition, the 7.8 mg/kg P23IL0017 Nanobody sample was formulated in 10 mM Histidine pH 6, 10% sucrose and administered intratracheally using the Microsprayer device.

24 hours after administration of the drug, the animals received an intraperitoneal injection of 3 µg human IL-23 (hIL23, full human IL23, i.e. composed of alpha subunit p19 (GenBank locus: NM_016584) and the p40 subunit of interleukin 12 (GenBank Locus: NM_002187) in a volume of 100 µL (t=0). 7 hours and 23 hours after this first injection, the animals received an additional intraperitoneal injection of 3 µg hIL-23.

The mice from group A received PBS instead of hIL-23 at the same time points.

The test groups are shown in Table B-30.

TABLE B-30

| Overview of the test groups. | | |
|---|---|---|
| Group | Test Article + route | Induction |
| A | — | 3 × PBS intraperitoneally 100 µl |
| B | PBT administered subcutaneously (s.c.) 100 µl | 3 × 3 µg H IL-23 intraperitoneally 100 µl |
| C | 0.30 mg/kg P23IL0075 administered subcutaneously (s.c.) 100 µl | 3 × 3 µg H IL-23 intraperitoneally 100 µl |
| D | PBT administered intratracheally (i.t.) 50 µl | 3 × 3 µg H IL-23 intraperitoneally 100 µl |
| E | 3.0 mg/kg P23IL0075 administered intratracheally (i.t.) 50 µl | 3 × 3 µg H IL-23 intraperitoneally 100 µl |
| F | 7.8 mg/kg P23IL0075 administered intratracheally (i.t.) 50 µl | 3 × 3 µg H IL-23 intraperitoneally 100 µl |
| G | 7.8 mg/kg P23IL0075 administered intratracheally (i.t.) 50 µl | 3 × 3 µg H IL-23 intraperitoneally 100 µl |

Exactly 31 h after the first hIL-23 injection, mice were bled for serum preparation and subsequently sacrificed. Spleens were removed and further processed for the ex vivo experiments. Briefly, splenocytes were isolated by homogenizing the spleens between frosted glass slides. Subsequently, splenocytes were washed and resuspended at a concentration of $10^6$ cells/ml in RPMI1640 supplemented with 10% FCS, 10 U/ml penicillin, 100 µg/ml streptomycin, 1% non-essential amino acids, 1% sodium pyruvate, 2.5 mM HEPES and 0.00035% 2-mercapto ethanol. The cells were seeded at 200,000 cells/200 µl/well in a 96-well culture plate pre-coated with hamster anti-mouse CD3e antibody (5 µg/mL in PBS, overnight at 4° C.). For each spleen, 6 wells were seeded. The 96-well plates were incubated for 24 hours in a humidified $CO_2$ incubator. A commercial sandwich ELISA kit for mouse IL-22 (Antigenix) was used to measure the amount of mIL-22 in each of the 6 splenocyte supernatants. For each mouse, the mean mIL-22 concentration was calculated from the 6 replicate measurements.

The results are shown in FIG. 33, which is a graph showing the results obtained in this Example 49 for the inhibition of the mIL-22 synthesis in a mouse splenocyte assay upon pulmonary administration of P23IL0075 using the PennCentury Microsprayer device and compared with the inhibition of the mIL-22 synthesis upon subcutaneous administration. The results from group C were normalized to the mean mIL-22 concentration of group B, which was injected with hIL-23 only. The results from groups E, F and G were normalized to the mean mIL-22 concentration of group D, which was injected with hIL-23 only.

Subcutaneous delivery of 0.3 mg/kg P23IL0075 Nanobody significantly blocked synthesis of mIL-22 to basal levels (P=0.009). Surprisingly, pulmonary delivery of 7.8 mg/mL P23IL0075 Nanobody was also shown to significantly inhibit synthesis of mIL-22 to basal levels (P<0.0001), demonstrating that P23IL0075 Nanobody is systemically released after pulmonary delivery. There was also no difference in the therapeutic efficacy of P23IL0075 Nanobody formulated in D-PBS+0.01% Tween20

(P<0.0001) as compared with P23IL0075 Nanobody formulated in 10 mM Histidine pH 6, 10% sucrose (P<0.0001). Interestingly, pulmonary delivery of a 3 mg/kg dose of P23IL0075 also significantly inhibited mIL-22 synthesis (P<0.0001). There was no clear difference in the inhibition of mIL-22 synthesis provided by the 3 mg/kg (P<0.0001) and 7.8 mg/kg pulmonary delivered doses.

Example 50: Systemic Circulation and Functionality of Pulmonary Administered and Systemically Delivered Nanobodies/Nanobody Construct Sequences Used:

| Construct name | SEQ ID NO | Ref. SEQ ID NO | Amino Acid Sequence |
|---|---|---|---|
| 4.10-Alb11 | 182 | SEQ ID NO: 113 in WO2009080714 | MAQVQLQESGGGLVQAGGS LRLSCAASGFTLGYYAIGW FRQAPGNEREGLSVITSGG GAIYYADSVKGRFTISRDN VKNIVSLQMNSLKPEDTAV YYCARVRAAFTSTTWTSPK WYDYWGQGTQVTVSSGGGG SGGGSEVQLVESGGGLVQP GNSLRLSCAASGFTFRSFG MSWVRQAPGKEPEWVSSIS GSGSDTLYADSVKGRFTIS RDNAKTTLYLQMNSLKPED TAVYYCTIGGSLSRSSQGI QVTVSSAAAEQKLISEEDL NGAAHHHHHH |
| IL6R202 | 183 | SEQ ID NO: 568 in WO2008020079 | EVQLVESGGGLVQPGGSLR LSCAASGFTFSDYDIGWFR QAPGKGREGVSGISSSDGN TYYADSVKGRFTISRDNAK NTLYLQMNSLRPEDTAVYY CAAEPPDSSWYLDGSPEFF KYWGQGTLVTVSSGGGGSG GGSEVQLVESGGGLVQPGN SLRLSCAASGFTFSSFGMS WVRQAPGKGLEWVSSISGS GSDTLYADSVKGRFTISRD NAKTTLYLQMNSLRPEDTA VYYCTIGGSLSRSSQGTLV TVSS |

Example 50.1: Intratracheal Administration of 2 Doses of 250 µg 4.10 Nanobodies Increases Circulating Levels of Leptin in Mice A first group of 10 mice received two doses of 250 µg 4.10-Alb11 Nanobody construct through intra-tracheal inoculation. A second group of 10 mice received two doses of 250 µg IL6R202 Nanobody construct through intra-tracheal inoculation (i.t.). A third group of 7 mice received two doses of 250 µg 4.10-Alb11 Nanobody construct through intra-peritoneal injection (i.p.). A fourth group of 7 mice received two doses of 250 µg IL6R202 Nanobody construct through intra-peritoneal injection. The first dose was given on day 0, the second dose on day 2. Blood was taken one day before the first dose was given and one day after the second dose was given. Levels of leptin and Nanobody were determined. Data is represented as average±SD.

Figure 34A:
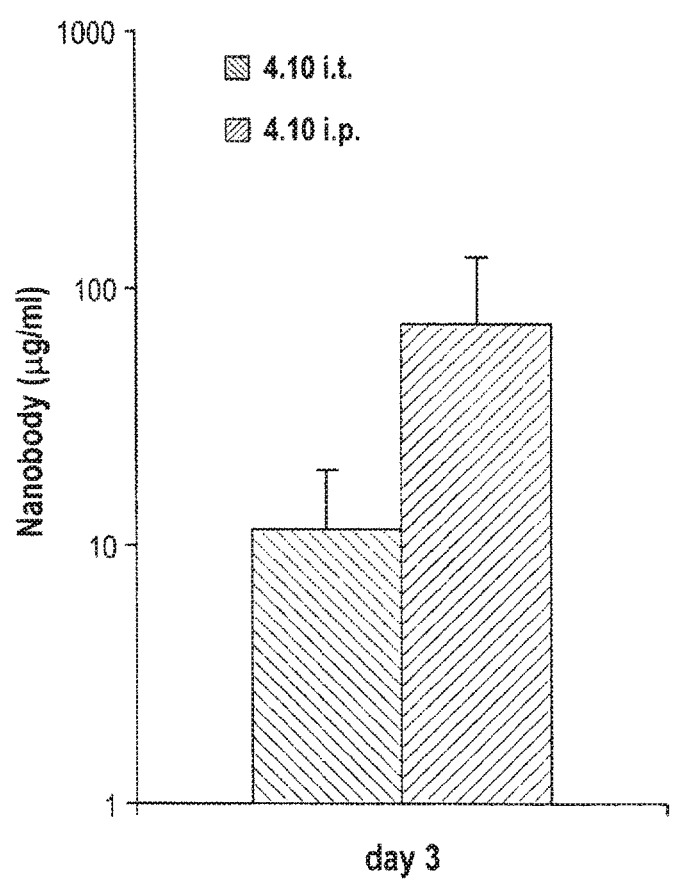
FIGS. 34A-34C: I.t. and i.p. administration of nanobody construct 4.10-Alb1 in mice.
Figure 34B:
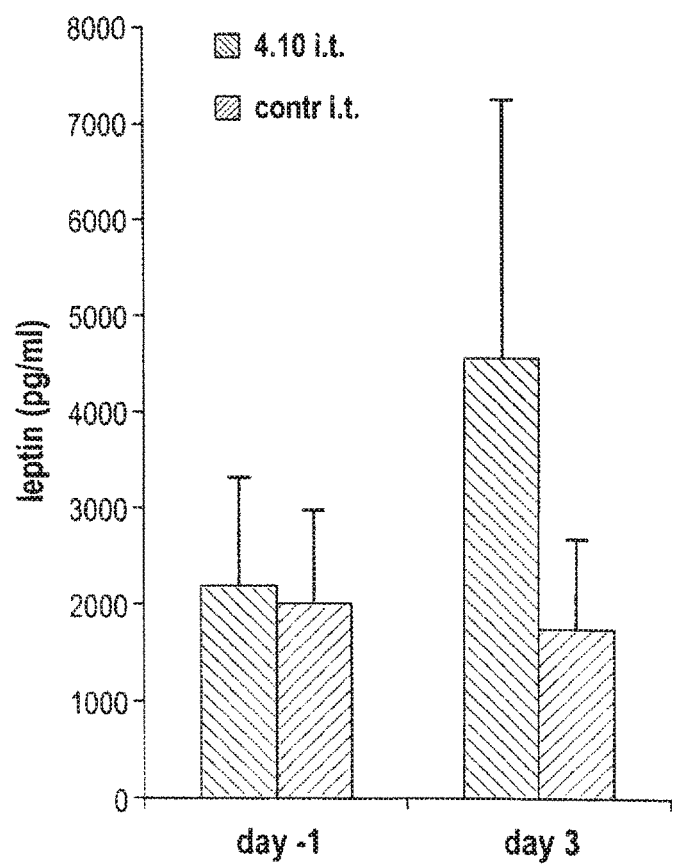
Figure 34C:
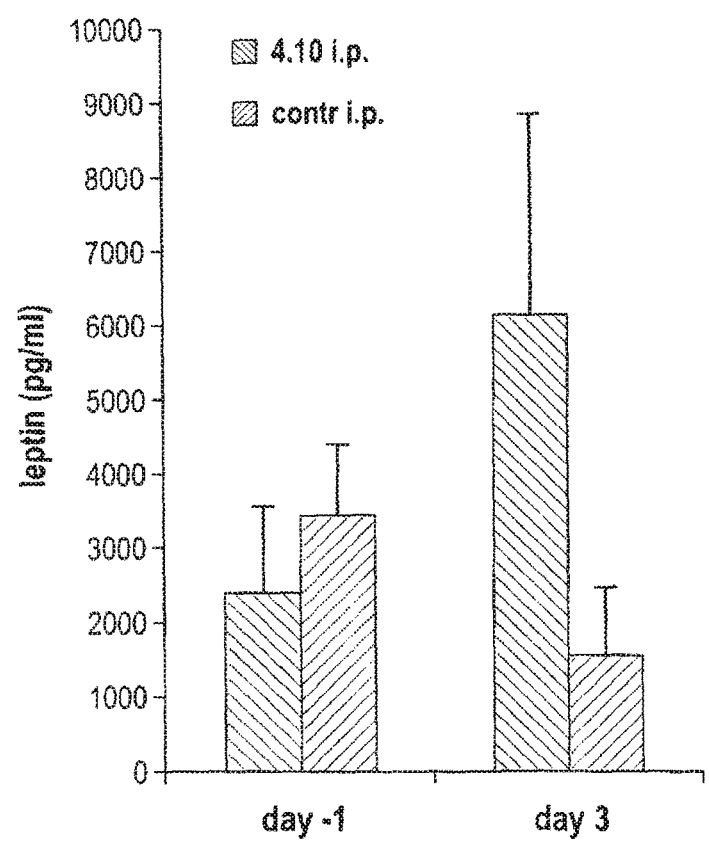

As shown in FIG. 34, following i.t. injection of two doses of 4.10-Alb1, this Nanobody construct 4.10-Alb1 was clearly detected in blood (11.7±8.08 µg/ml). This is ~16% of what was detected following the i.p. injections (73.8±61.5 µg/ml). Because the Elisa assay used to quantify this Nanobody depends on the interaction with a leptin receptor fragment, this data indicates that the Nanobodies present in circulation after i.t. and i.p. administration were intact, functional Nanobodies. This was further supported as also increased concentrations of leptin were detected in blood of mice treated with this Nanobody irrespective of the route of inoculation (FIG. 34b (i.t.) and FIG. 34c (i.p.)).

Example 50.2: Dose Dependent Increase of Circulating Leptin Levels Following i.t Administration of 4 Increasing Amounts of 4.10-Alb1 Nanobody Constructs Mice were given increasing amounts of 4.10-Alb-1 nanobody construct at day 0, 3, 6 and 9. On day 0, mice received 25 µg, on day 3 mice received 50 µg, on day 6 mice received 125 µg and on day 9 mice received 250 µg of 4.10-Alb-1 nanobody construct. Nanobodies were given i.p. or i.t. The i.t. groups consisted of 10 mice, the i.p. treated groups consisted of 7 mice. One day after each 4.10-Alb-1 nanobody construct administration blood was collected.

Figure 35A:
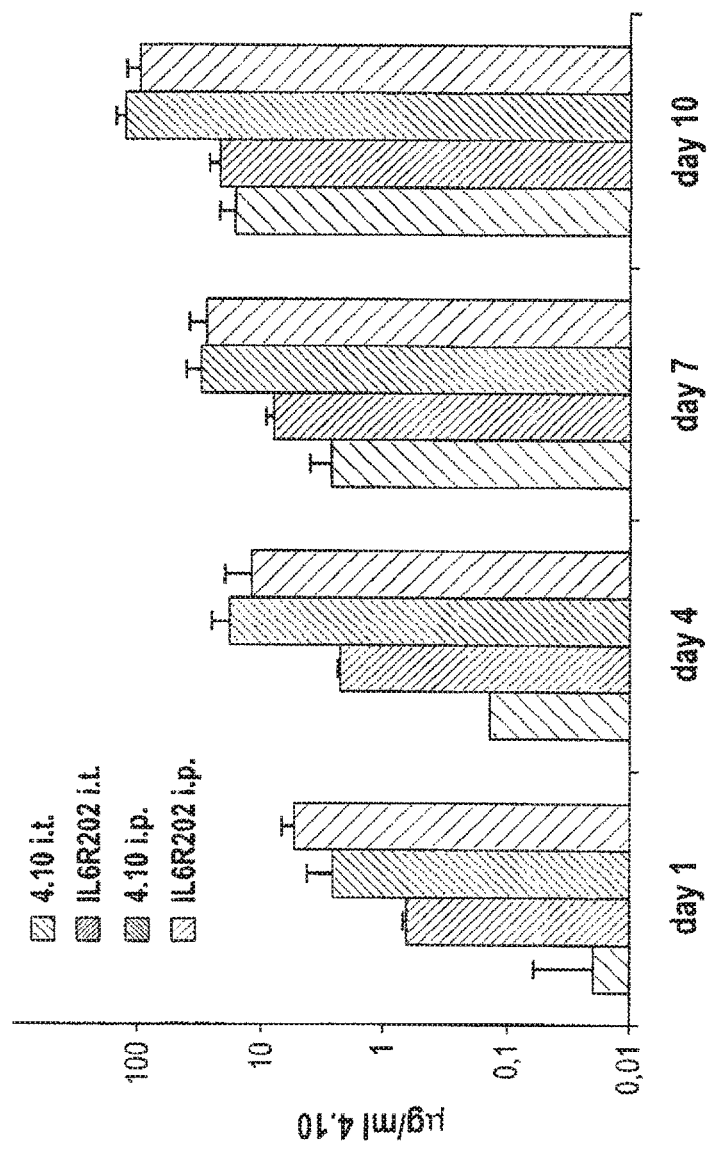
FIGS. 35A-35C: Dose dependent increase of circulating leptin levels following i.t. administration of 4 increasing amounts of 4.10-Alb1 Nanobody constructs.

As shown in FIG. 35a. Nanobody constructs 4.10-Alb1 and IL6R202 were detected in blood following each i.t. inoculation. Inoculation of a higher amount resulted in higher concentrations present in blood. As expected, concentrations of Nanobody constructs in blood were higher following i.p. injections. Because the Elisa assays used to quantify these Nanobody constructs depend on the interaction with a leptin receptor fragment or IL6 receptor fragment, this data indicates that the Nanobody constructs present in circulation after i.t. and i.p. administration were intact, i.e. functional Nanobody constructs.

Figure 35B:
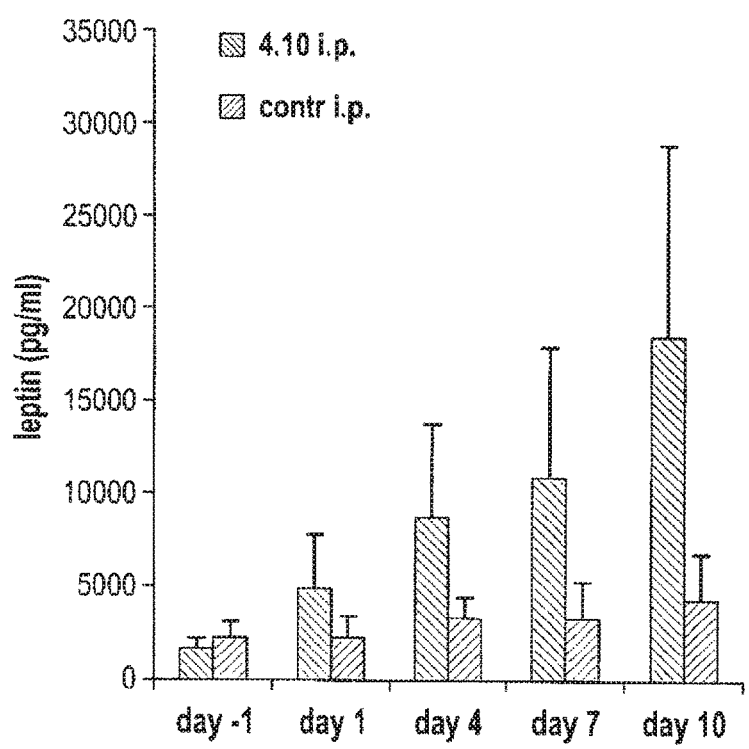
Figure 35C:
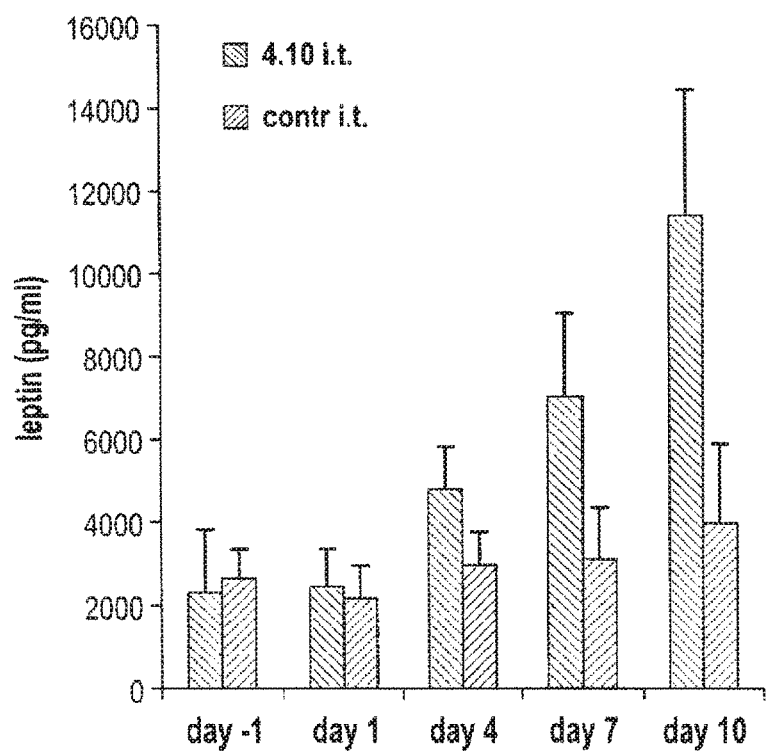

One day after the i.p injection of 25 µg leptin levels were already increased when compared to IL6R202 injected animals (FIG. 35b). Leptin levels increased further after each additional injection with the 4.10-Alb-1 nanobody construct. After intratracheal inoculation increased leptin levels were detected for the first time after the inoculation of the second dose of 50 µg (FIG. 35c). Levels further increased after inoculation of the 125 and 250 µg doses.

Figure 36A:
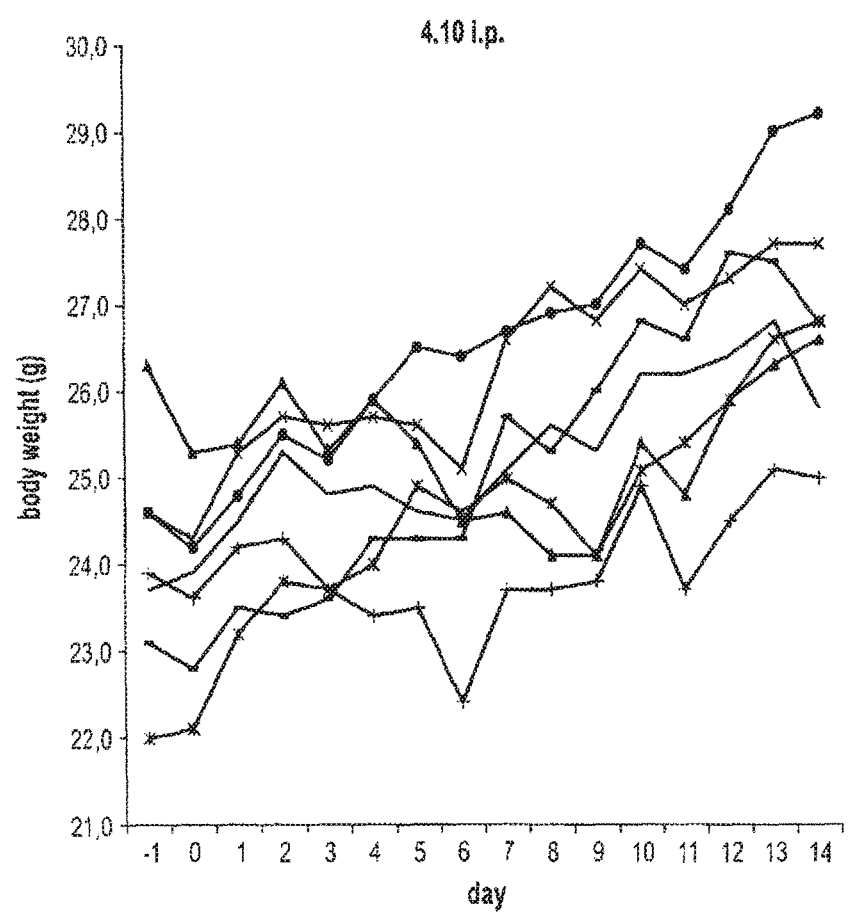
Figure 36B:
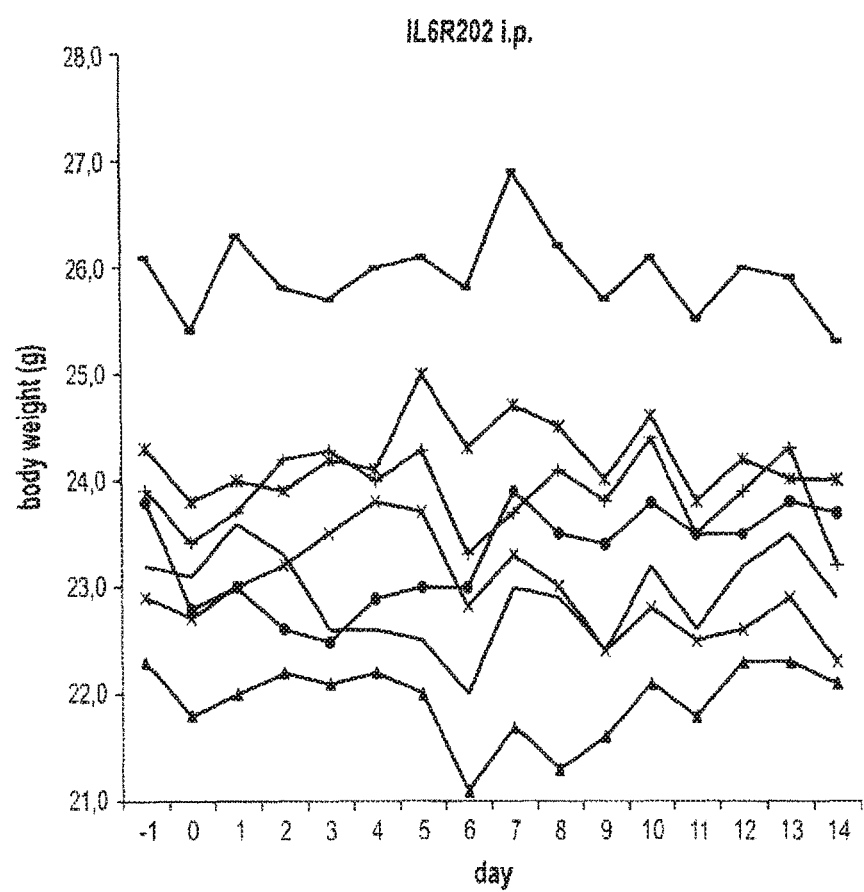
Figure 36C:
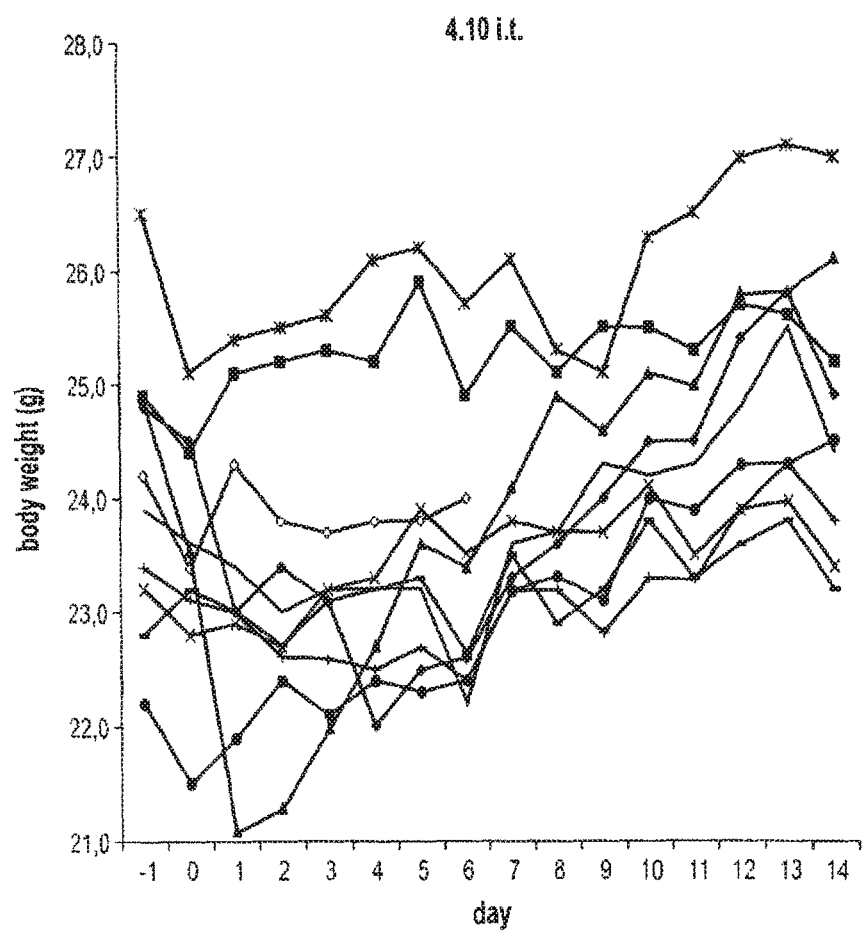
Figure 36D:
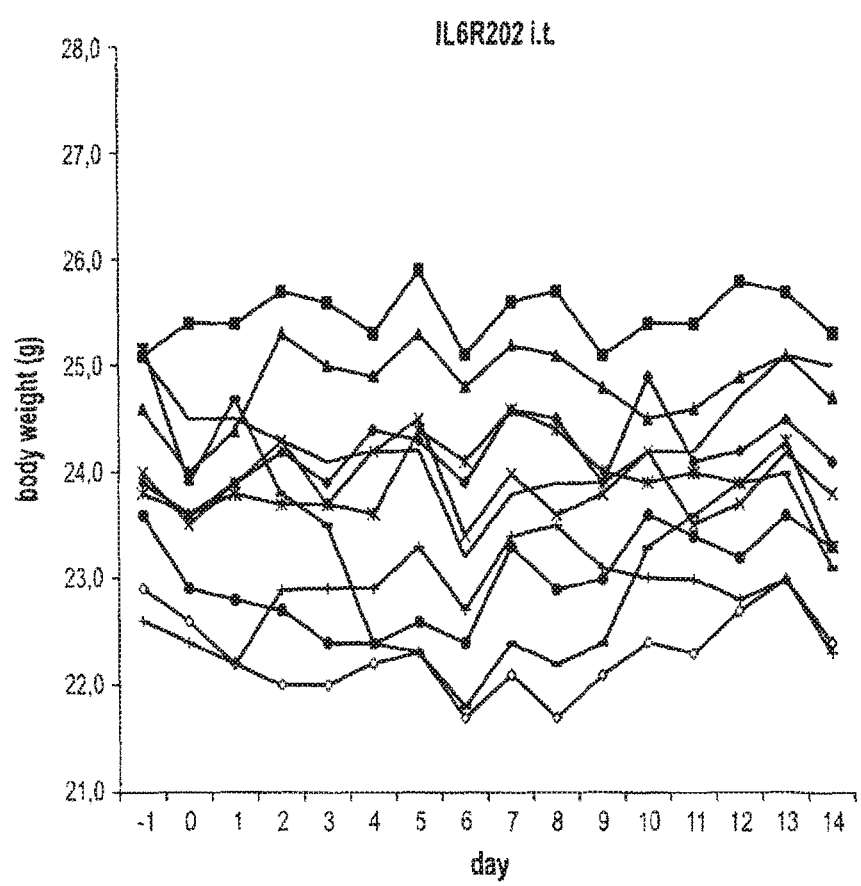
Figure 36F:
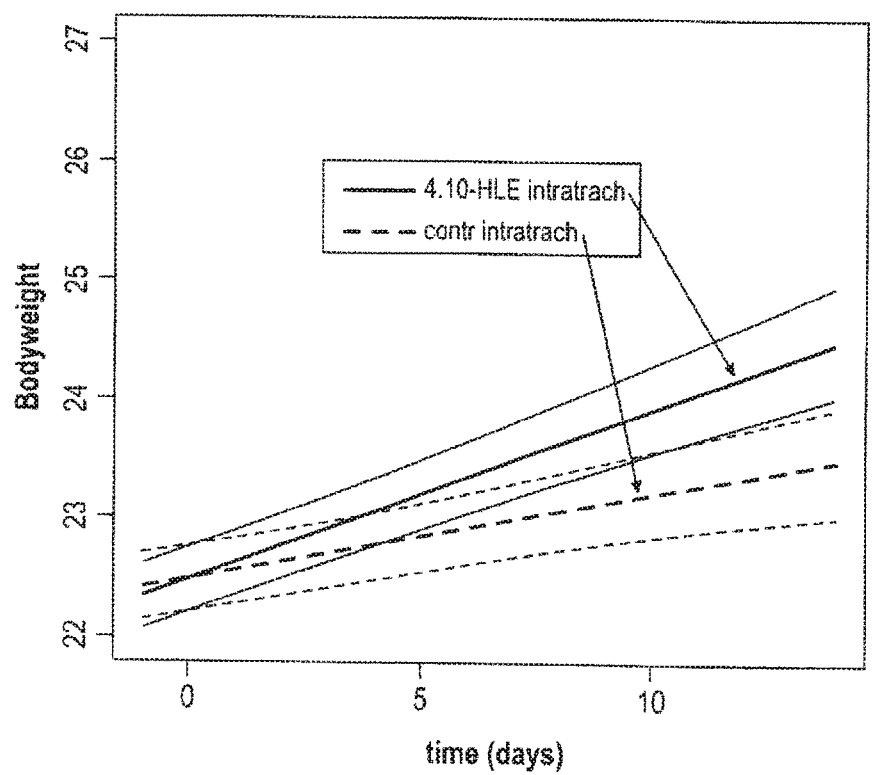

Example 50.3: Increase in Body Weight Following i.t. Administration of 4 Increasing Amounts of 4.10 Nanobodies During the Nanobody treatment as described in example 8.2, body weight of all animals was determined daily. As expected, the body weight of mice that received 4.10-Alb1 via i.p. injections clearly gained weight (FIG. 36a) while control mice did not (FIG. 36b). Also for the mice that were treated i.t. with the 4.10-Alb1 Nanobody construct body weight showed a tendency to increase more than the body weight of control treated animals (FIG. 36c and FIG. 36d).

To model bodyweight as a function of time, while incorporating the different treatment groups as well as the intra mouse variation we fit a mixed model in SAS using the following code:

```
proc mixed data=Bodyweight;
class mouse group day;
model Bodyweight=dag dag*group/s ;
repeated day/subject=mouse type=un rcorr r;
run;
```

The line that starts with model defines how the fixed structure of the model looks like. We include a term that corresponds to the time (day) and we include the interaction term of time with treatment group (group) because we assume that the effect on the bodyweight may be different for each treatment group. Note that the main effect of group is not in the model anymore. This term appears to be not significant (p=0.125) which means that the bodyweight at day −1 is the same for each treatment group. The latter makes sense because at day −1 no treatment has been administered to the mouse yet. The intra mouse variation is covered by the repeated statement in the sas code above. For this variation we should find the most appropriate correlation structure for the different time point. By comparing the AIC criteria of several models with different correlation structures we obtained that the unstructured was the most appropriate correlation structure. This means that the correlation between all the different time points has been estimated, as well as the variance at each time point. The resulting correlation structure holds for every mouse and represents the intra mouse variation.

The residuals of the mixed model (see FIG. 36e) look normally distributed and homogeneous hence no violation of the assumptions is present. We agree that this model is a good model for the bodyweight levels.

From this model we can derive the p-values for the comparison between the different treatment groups. In Table B-31 we present the results of the statistical tests to compare bodyweight increase for different treatment groups.

TABLE B-31

Statistical tests to compare bodyweight increase for different treatment groups.
Table B-31 Estimates

| Label | Estimate | Standard Error | DF | t Value | Pr > \|t\| | Alpha | Lower | Upper |
|---|---|---|---|---|---|---|---|---|
| test i.t. 4.10-Alb1 vs IL6R202 | 0.07239 | 0.02090 | 39 | 3.46 | 0.0013 | 0.05 | 0.03010 | 0.1147 |
| test i.p. 4.10-Alb1 vs IL6R202 | 0.2364 | 0.02437 | 39 | 9.70 | <.0001 | 0.05 | 0.1871 | 0.2857 |
| test i.t. 4.10-Alb1 vs i.p. 4.10-Alb1 | −0.1482 | 0.02294 | 39 | −6.46 | <.0001 | 0.05 | −0.1946 | −0.1018 |

The first row in Table B-31 represents the test that compares the two i.t. treatment groups with respect to their bodyweight increase. From the p-value (0.0013) we may conclude that increase in bodyweight is significantly larger for the 4.10-Alb1 group compared to the control group (IL6R202). The estimated difference in bodyweight increase is 0.07239. The second row in Table B-31 represents the test that compares the two ip treatment groups with respect to their bodyweight increase. From the p-value (<0.0001) we may conclude that increase in bodyweight is significantly larger for the 4.10-Alb1 group compared to the control group (IL6R202). The estimated difference in bodyweight increase is 0.2364. The third row in Table B-31 represents the test that compares the 4.10-Alb1 i.t. treatment group with the 4.10-Alb1 i.p. treatment group with respect to their bodyweight increase. From the p-value (<0.0001) we may conclude that increase in bodyweight is significantly larger for the i.p. group compared to the i.t. group. The estimated difference in bodyweight increase is −0.1482. The predicted bodyweight model with corresponding confidence bands is presented in FIGS. 24f&g.

Preferred Aspects or Particular Embodiments of the Present Invention

Method Aspects of the Invention

1. Method of providing and/or delivering an effective amount of an immunoglobulin single variable domain and/or construct thereof to a mammal, e.g. human; wherein said immunoglobulin single variable domain and/or construct thereof is directed against at least one target; and wherein the method comprises the step of administering said immunoglobulin single variable domain and/or construct thereof to the pulmonary tissue.

2. Method of aspect 1, wherein the process of administering comprises the step of forming an aerosol comprising said immunoglobulin single variable domain and/or construct thereof by an appropriate inhaler device such as e.g. nebulizer, metered dose liquid inhalers and/or dry powder inhalers, preferably mesh nebulizer.

3. Method of aspect 1 or aspect 2, wherein an effective amount of an immunoglobulin single variable domain and/or construct thereof to the systemic circulation of said mammal, e.g. human, is provided.

4. Method of aspect 3, wherein the method is able to deliver said immunoglobulin single variable domain and/or construct thereof to the systemic circulation with a substantial absolute bioavailability, e.g. with an absolute bioavailability that is at least 10%, preferably 20%, more preferably 30%, more preferably 40%, more preferably 50% after administration of a single dose of said immunoglobulin single variable domain and/or construct thereof.

5. Method of aspect 3, wherein the half-life or terminal half-life of said immunoglobulin single variable domain and/or construct thereof in the systemic circulation is longer than 5 hours, preferably 6 hours or more, more preferably 7, 8 or 9 hours or more, even more preferably is 10 hours, 15 hours, or 20 hours or more, more preferred is 1, 2, 3, 4, 5, 6 or more days.

6. Method of any previous aspects, wherein said immunoglobulin single variable domain and/or construct thereof is a Nanobody and/or construct thereof.

7. Method of any previous aspects, wherein said immunoglobulin single variable domain and/or construct thereof is selected from the group consisting of a Nanobody, a construct comprising or essentially consisting of two Nanobodies directed against the same or different antigens optionally connected by a linker; and a construct comprising or essentially consisting of 3 Nanobodies directed against the same or different antigens optionally connected by a linker.

8. Method of any previous aspects, wherein said immunoglobulin single variable domain and/or construct thereof is selected from the group consisting of a Nanobody, and a construct comprising or essentially consisting of two Nanobodies directed against the same or different antigens optionally connected by a linker.

9. Method of any previous aspects, wherein said immunoglobulin single variable domain and/or construct thereof is selected from the group consisting of a construct comprising or essentially consisting of two Nanobodies directed against the same or different antigens optionally connected by a linker; and a construct comprising or essentially consisting of 3 Nanobodies directed against the same or different antigens optionally connected by a linker.

10. Method of any previous aspects, wherein said immunoglobulin single variable domain and/or construct thereof is selected from the group consisting of a construct comprising or essentially consisting of two Nanobodies directed against the same or different antigens optionally connected by a linker.

11. Method of aspect 1, wherein the method additionally comprises the step of using an intranasal delivery device in order to administer said immunoglobulin single variable domain and/or construct thereof to the pulmonary tissue of the mammal.

12. Method of any previous aspects, wherein the antigen is an antigen in the pulmonary tissue.

13. Method of any previous aspects, wherein the antigen is an antigen in the pulmonary tissue and is derived from a microorganism such as a virus, e.g. RSV such as e.g. RSV407 and variants thereof, e.g. functional variants of RSV407 that have up to 30, preferably 25, 20, 15, 10, or 5 mutated amino acid residues, or avian influenza virus, a fungi, a parasite or a bacterium and also allergic entities like house dust mite/protein.

14. Method of any previous aspects, wherein the antigen is a druggable antigen primarily expressed in the mammal but expressed also outside the pulmonary tissue of said mammal, e.g. is a) RANK-L, and the immunoglobulin single variable domain is e.g. RANKL008AA and variants thereof, e.g. functional variants of RANKL008AA that have up to 30, preferably 25, 20, 15, 10, or 5 mutated amino acid residues; or b) van Willebrand Factor and the immunoglobulin single variable domain is e.g. ALX-0081 and variants thereof, e.g. functional variants of ALX-0081 that have up to 30, preferably 25, 20, 15, 10, or 5 mutated amino acid residues; or c) leptin and the immunoglobulin single variable domain is 4.10-Alb1 and variants thereof, e.g. functional variants of 4.10-Alb1 that have up to 30, preferably 25, 20, 15, 10, or 5 mutated amino acid residues.

15. Method of any previous aspects, wherein an effective amount of said immunoglobulin single variable domain and/or construct thereof is administered once daily or once every 2 to 7 days, preferably once daily.

16. Method of any previous aspects, wherein an effective amount of said immunoglobulin single variable domain and/or construct thereof is administered once daily or once every 2 to 7 days, preferably once daily and wherein the construct is preferably administered locally.

17. Method of any previous aspects, wherein an effective amount of said immunoglobulin single variable domain and/or construct thereof is delivered to the systemic circulation when administered once daily or once every 2 to 7 days, preferably once daily, wherein none of said construct is directed against a serum protein.

18. Method of any previous aspects, wherein about 10, 20, 30, 40, 50, 60, 70, 80% or less of said immunoglobulin single variable domain and/or construct thereof is stable in the pulmonary tissue for at least 24 hours after administration of said construct.

19. Method of any previous aspects, wherein said construct comprises in addition an immunoglobulin single variable domain against a serum protein, e.g. human serum protein such as human serum albumin or human Fc-IgG1.

20. Method of aspect 16, wherein the systemic bioavailability of said construct is up to about 10 to 50%, preferably up to 20%, more preferably up to 30%, even more preferably up to 40%, most preferred up to 50%.

21. Method of any previous aspects, wherein the in vivo terminal half-life of the immunoglobulin single variable domain and/or construct thereof in the systemic circulation of e.g. rats and/or humans is at least 5 times higher compared to the in vivo half-life of the same immunoglobulin single variable domain and/or construct thereof when administered intravenously, more preferably 6 to 10 times, most preferred about 10 times higher.

22. Method of any previous aspects, wherein at least one of the antigen is involved or plays a part in respiratory diseases, e.g. COPD, asthma and respiratory viruses infection.

23. Method of any previous aspects wherein the mammal is a human, e.g. a human with a disease.

Use Aspect of the Invention

1. Use of an immunoglobulin single variable domain and/or construct thereof for delivering an effective amount of said immunoglobulin single variable domain and/or construct thereof to a mammal, e.g. human; wherein said immunoglobulin single variable domain and/or construct thereof is directed against at least one antigen; and wherein the said immunoglobulin single variable domain and/or construct thereof is administered to the pulmonary tissue.

2. Use of aspect A, wherein the process of administering comprises the step of forming an aerosol comprising said immunoglobulin single variable domain and/or construct thereof by an appropriate inhaler device such as e.g. nebulizer, metered dose liquid inhalers and/or dry powder inhalers.

3. Use of aspect A or aspect B, wherein an effective amount of an immunoglobulin single variable domain and/or construct thereof to the systemic circulation of said mammal, e.g. human, is provided.

4. Use of aspect C, wherein the delivery of said immunoglobulin single variable domain and/or construct thereof to the systemic circulation is achieved with a substantial absolute bioavailability, e.g. with an absolute bioavailability that is at least 10%, preferably 20%, more preferably 30%, more preferably 40%, more preferably 50% after administration of a single dose of said immunoglobulin single variable domain and/or construct thereof.

5. Use of aspect C, wherein the half-life or terminal half-life of said immunoglobulin single variable domain and/or construct thereof in the systemic circulation is longer than 5 hours, preferably 6 hours or more, more preferably 7, 8 or 9 hours or more, even more preferably is 10 hours, 15 hours, or 20 hours or more, more preferred is 1, 2, 3, 4, 5, 6 or more days.

6. Use of any previous aspects, wherein said immunoglobulin single variable domain and/or construct thereof is a Nanobody and/or construct thereof.

7. Use of any previous aspects, wherein said immunoglobulin single variable domain and/or construct thereof is selected from the group consisting of a Nanobody, a construct comprising or essentially consisting of two Nanobodies directed against the same or different antigens optionally connected by a linker; and a construct comprising or essentially consisting of 3 Nanobodies directed against the same or different antigens optionally connected by a linker.

8. Use of any previous aspects, wherein said immunoglobulin single variable domain and/or construct thereof is selected from the group consisting of a Nanobody, and a construct comprising or essentially consisting of two Nanobodies directed against the same or different antigens optionally connected by a linker.

9. Use of any previous aspects, wherein said immunoglobulin single variable domain and/or construct thereof is selected from the group consisting of a construct comprising or essentially consisting of two Nanobodies directed against the same or different antigens optionally connected by a linker; and a construct comprising or essentially consisting of 3 Nanobodies directed against the same or different antigens optionally connected by a linker.

10. Use of any previous aspects, wherein said immunoglobulin single variable domain and/or construct thereof is selected from the group consisting of a construct comprising or essentially consisting of two Nanobodies directed against the same or different antigens optionally connected by a linker.

11. Use of any previous aspects, wherein the immunoglobulin single variable domain and/or construct thereof is administered to the mammal, e.g. human, by using an intranasal delivery device.

12. Use of any previous aspects, wherein the antigen is an antigen in the pulmonary tissue.

13. Use of any previous aspects, wherein the antigen is not an antigen in the pulmonary tissue.

24. Use of any previous aspects, wherein the antigen is an antigen in the pulmonary tissue and is derived from a microorganism such as a virus, e.g. RSV such as e.g. RSV407 and variants thereof, e.g. variants of functional RSV407 that have up to 30, preferably 25, 20, 15, 10, or 5 mutated amino acid residues, or avian flu virus, a fungi, a parasite or a bacterium and also allergic entities like house dust mite/protein.

14. Use of any previous aspects, wherein the antigen is a druggable antigen primarily expressed in the mammal but expressed outside the pulmonary tissue of said mammal, e.g. RANK-L such as e.g. RANKL008AA and variants thereof, e.g. functional variants of RANKL008AA that have up to 30, preferably 25, 20, 15, 10, or 5 mutated amino acid residues, or van Willebrand Factor such as e.g. ALX-0081 and variants thereof, e.g. functional variants of RANKL008AA that have up to 30, preferably 25, 20, 15, 10, or 5 mutated amino acid residues.

15. Use of any previous aspects, wherein an effective amount of said immunoglobulin single variable domain and/or construct thereof is delivered to the systemic circulation when administered once daily or once every 2 to 7 days, preferably once daily.

16. Use of any previous aspects, wherein an effective amount of said immunoglobulin single variable domain and/or construct thereof is administered once daily or once every 2 to 7 days, preferably once daily and wherein the immunoglobulin single variable domain and/or construct thereof is preferably delivered in the pulmonary tissue.

17. Use of any previous aspects, wherein an effective amount of said immunoglobulin single variable domain and/or construct thereof is administered once daily or once every 2 to 7 days, preferably once daily, wherein none of said immunoglobulin single variable domain and/or construct thereof is directed against a serum protein.

18. Use of any previous aspects, wherein about 10, 20, 30, 40, 50, 60, 70, 80% or less of said immunoglobulin single variable domain and/or construct thereof is stable in the pulmonary tissue for at least 24 hours after administration of said immunoglobulin single variable domain and/or construct thereof.

19. Use of any previous aspects, wherein said immunoglobulin single variable domain and/or construct thereof comprises in addition an immunoglobulin single variable domain against a serum protein, e.g. human serum protein such as human serum albumin or human Fc-IgG1.

20. Use of aspect Q, wherein the systemic bioavailability of said immunoglobulin single variable domain and/or construct thereof is up to about 10 to 50%, preferably up to 50%.

21. Use of any previous aspects, wherein the in vivo terminal half-life of the immunoglobulin single variable domain and/or construct thereof in e.g. rats is at least 5 times higher compared to the in vivo half-life of the same immunoglobulin single variable domain and/or construct thereof when administered intravenously, more preferably 6 to 10 times, most preferred about 10 times higher.

22. Use of any previous aspects, wherein at least one of the antigen is involved or plays a part in respiratory diseases, e.g. COPD, asthma and respiratory viruses infection.

i. Pharmaceutical compositions and devices of the invention:
 ii. Pharmaceutical composition suitable for pulmonary administration according to a use or method as described in the above aspects.
 iii. Pharmaceutical composition of aspect i, wherein the composition comprises a) a construct comprising at least one immunoglobulin single variable domain and/or construct thereof directed against at least one antigen or essentially consisting of at least one immunoglobulin single variable domain and/or construct thereof directed against at least one antigen; and b) optionally comprising suitable excipients such as e.g. buffers, stabilizers and/or propellants.
 iv. Pharmaceutical composition of aspect I or ii that is administered once daily or once every 2 to 7 days, preferably once daily.
 v. Pharmaceutical composition of aspect I to iii that is a liquid.
 vi. Pharmaceutical composition of aspect i to iii that is a dry powder.
 vii. Pharmaceutical device suitable in the methods and/or uses as described above and/or suitable in the use with a pharmaceutical composition of aspects I to v.
 viii. Pharmaceutical device of claim vi that is an inhaler for liquids such as e.g. a suspension of fine solid particles or liquid droplets in a gas.
 ix. Pharmaceutical device of claim vi that is dry powder inhaler.

Dosing Interval:

a) Method of administering an immunoglobulin single variable domain and/or construct thereof, e.g. a Nanobody, to the pulmonary tissue as described above; wherein said administration is once a day, once every 2, 3, 4, 5, 6, or once every week, preferably once every day.

b) Method of aspect a); wherein said immunoglobulin single variable domain and/or construct thereof, e.g. a Nanobody, is delivered to the systemic circulation in an effective amount.

c) Use of an agent of the invention for administration once a day, once every 2, 3, 4, 5, 6, or once every week, preferably once every day.

d) Use of aspect c); wherein said immunoglobulin single variable domain and/or construct thereof, e.g. a Nanobody, is delivered to the systemic circulation in an effective amount.

Dosing interval for an anti-viral immunoglobulin single variable domain and/or construct thereof directed against said virus wherein said virus can cause respiratory tract infections:

e) Method of treating respiratory tract infections caused by a virus optionally after the therapeutic window for conventional anti-viral medications is closed with a single effective dose of a pharmaceutical composition comprising an immunoglobulin single variable domain and/or construct thereof; wherein said immunoglobulin single variable domain is directed against said virus.

f) Method of aspect e); wherein said treating is done after the therapeutic window for conventional anti-viral medications is closed.

g) Method of aspect e) or f); wherein said immunoglobulin single variable domain is a Nanobody.

h) Method of aspect e), f) or g); wherein said respiratory tract infections caused by a virus is selected from the group of influenza, viral bronchiolitis caused by respiratory syncytial virus (RSV), and respiratory diseases caused by an adenovirus.

i) Method of aspect e), f), g) or h); wherein said therapeutic window for conventional anti-viral medications is closed after 1 or more days after first infections, preferably 2 or more days after first infections, more preferably 3 or more days after first infections.

j) Method of aspect e), f), g), h) or i); wherein said therapeutic window for conventional anti-viral medications is closed after 1 or more days after first disease symptoms, preferably 2 or more days after first disease symptoms, more preferably 3 or more days after first disease symptoms.

k) Use of an agent of the invention for treating respiratory tract infections caused by a virus optionally after the therapeutic window for conventional anti-viral medications is closed with a single effective dose of a pharmaceutical composition comprising an immunoglobulin single variable domain and/or construct thereof; wherein said immunoglobulin single variable domain is directed against said virus.

l) of aspect k); wherein said treating is done after the therapeutic window for conventional anti-viral medications is closed.

m) Use of aspect k) or l); wherein said immunoglobulin single variable domain is a Nanobody.

n) Use of aspect k), l) or m); wherein said respiratory tract infections caused by a virus is selected from the group of influenza, viral bronchiolitis caused by respiratory syncytial virus (RSV), and respiratory diseases caused by an adenovirus.

o) Use of aspect k), l), m) or n); wherein said therapeutic window for conventional anti-viral medications is closed after 1 or more days after first infections, preferably 2 or more days after first infections, more preferably 3 or more days after first infections.

p) Use of aspect k), l), m), n) or o); wherein said therapeutic window for conventional anti-viral medications is closed after 1 or more days after first disease symptoms, preferably 2 or more days after first disease symptoms, more preferably 3 or more days after first disease symptoms.

Particularly Preferred Aspects:

1. Method of providing and/or delivering an effective amount of an immunoglobulin single variable domain and/or construct thereof to a mammal, e.g. human; wherein said immunoglobulin single variable domain and/or construct thereof is directed against at least one target; and wherein the method comprises the step of administering said immunoglobulin single variable domain and/or construct thereof to the pulmonary tissue; wherein the delivery of said immunoglobulin single variable domain and/or construct thereof to the systemic circulation is achieved with a substantial bioavailability, i.e.

a. in case the immunoglobulin single variable domain and/or construct thereof consists of essentially not more than 150, more preferably 140, even more preferably 130, most preferred not more than 120 amino acid residues (e.g. consists of a monovalent nanobody) the delivery of said immunoglobulin single variable domain and/or construct thereof to the systemic circulation is achieved with a bioavailability (compared to i.v. injection) that is at least 10%, preferably 15%, most preferably 20% after administration of a single dose of said immunoglobulin single variable domain and/or construct thereof; or b. in case the immunoglobulin single variable domain and/or construct thereof consists of essentially not more than 300, more preferably 280, even more preferably 260, most preferred not more than 240 amino acid residues (e.g. consists of two monovalent nanobodies and a linker) the delivery of said immunoglobulin single variable domain and/or construct thereof to the systemic circulation is achieved with a bioavailability (compared to i.v. injection) that is at least 5%, preferably 7.5%, most preferably 10% after administration of a single dose of said immunoglobulin single variable domain and/or construct thereof; or c. in case the immunoglobulin single variable domain and/or construct thereof consists of essentially not more than 450, more preferably 420, even more preferably 390, most preferred not more than 360 amino acid residues (e.g. consists of three monovalent nanobodies and two linkers) the delivery of said immunoglobulin single variable domain and/or construct thereof to the systemic circulation is achieved with a bioavailability (compared to i.v. injection) that is at least 5% after administration of a single dose of said immunoglobulin single variable domain and/or construct thereof.

2. Method of delivering an effective amount of an immunoglobulin single variable domain and/or construct thereof to a human; wherein said immunoglobulin single variable domain and/or construct thereof is directed against at least one antigen; and wherein the method comprises the step of administering said immunoglobulin single variable domain and/or construct thereof to the pulmonary tissue.

3. Method of aspects 1 or 2, wherein the process of administering comprises the step of forming an aerosol comprising said immunoglobulin single variable domain and/or construct thereof by an appropriate inhaler device such as e.g. a mesh nebulizer.

4. Method of previous aspects, wherein an effective amount of an immunoglobulin single variable domain and/or construct thereof to the systemic circulation of said human is provided.

5. Method of aspect 4, wherein the method is able to deliver said immunoglobulin single variable domain and/or construct thereof to the systemic circulation with an absolute bioavailability that is at least 10% after administration of a single dose administration of said immunoglobulin single variable domain and/or construct thereof.

6. Method of aspect 4, wherein the terminal half-life of said immunoglobulin single variable domain and/or construct thereof in the systemic circulation is longer than 5 hours.
7. Method of any previous aspects, wherein said immunoglobulin single variable domain and/or construct thereof is a Nanobody and/or construct thereof.
8. Method of any previous aspects, wherein said immunoglobulin single variable domain and/or construct thereof is selected from the group of a Nanobody, a construct essentially consisting of two Nanobodies directed against the same or different antigens optionally connected by a linker; and a construct essentially consisting of 3 Nanobodies directed against the same or different antigens optionally connected by a linker.
9. Method of administering an immunoglobulin single variable domain and/or construct thereof to the pulmonary tissue according to aspects 1 to 8; wherein said administration is once a day.

What is claimed is:

1. An inhaler device for use in delivery of a construct that consists essentially of one or more Nanobodies to the systemic circulation by passive absorption comprising an effective amount of a construct that consists essentially of one or more Nanobodies, wherein said construct is passively absorbed into the systemic circulation from the pulmonary tissue and specifically binds at least one druggable antigen expressed in a mammal but expressed outside the pulmonary tissue of said mammal.

2. The inhaler device of claim 1, wherein the inhaler device is an inhaler for liquids.

3. The inhaler device of claim 2, wherein the inhaler for liquids is a nebulizer or a metered dose inhaler.

4. The inhaler device of claim 3, wherein the nebulizer is an air-jet nebulizer, ultrasonic nebulizer or vibrating mesh nebulizer.

5. The inhaler device of claim 1, wherein the inhaler device is a dry powder inhaler.

6. The inhaler device of claim 1, wherein said construct is selected from the group consisting of a Nanobody, a construct comprising or essentially consisting of two Nanobodies directed against the same or different antigens, optionally connected by a linker, and a construct comprising or essentially consisting of three Nanobodies directed against the same or different antigens, optionally connected by a linker.

7. The inhaler device of claim 1, wherein the one or more Nanobodies is a VHH or a humanized VHH.

\* \* \* \* \*

SEQUENCE LISTING

```
<160> NUMBER OF SEQ ID NOS: 184

<210> SEQ ID NO 1
<211> LENGTH: 121
<212> TYPE: PRT
<213> ORGANISM: Lama glama

<400> SEQUENCE: 1

Gln Val Gln Leu Gln Asp Ser Gly Gly Gly Leu Val Gln Pro Gly Gly
1               5                   10                  15

Ser Leu Arg Leu Ser Cys Arg Ala Ser Gly Arg Ile Phe Arg Ile Asn
            20                  25                  30

Ala Met Gly Trp Tyr Arg Gln Ala Pro Gly Lys Gln Arg Glu Leu Val
        35                  40                  45

Ala Thr Ile Thr Ser Thr Gly Ser Thr Asn Phe Ala Asp Ser Val Lys
    50                  55                  60

Gly Arg Phe Thr Ile Tyr Arg Asp Gly Ala Lys Arg Thr Val Asp Leu
65                  70                  75                  80

Arg Leu Asn Ser Leu Lys Pro Glu Asp Thr Ala Val Tyr Phe Cys Asn
                85                  90                  95

Ala Asp Val Arg Glu Tyr Asp Leu Gly Pro Trp Arg Gln Tyr Trp Gly
            100                 105                 110

Gln Gly Thr Gln Val Thr Val Ser Ser
        115                 120

<210> SEQ ID NO 2
<211> LENGTH: 121
<212> TYPE: PRT
<213> ORGANISM: Lama glama

<400> SEQUENCE: 2

Gln Val Gln Leu Gln Glu Ser Gly Gly Gly Val Val Gln Pro Gly Gly
1               5                   10                  15

Ser Leu Arg Leu Ser Cys Ser Val Ser Gly Thr Ser Ile Ser Asn Arg
            20                  25                  30

Val Met Ala Trp Phe Arg Gln Ala Pro Gly Lys Gln Arg Asp Phe Val
        35                  40                  45

Ala Tyr Ile Thr Ser Ala Val Asn Thr Asp Tyr Ala Asp Phe Val Lys
    50                  55                  60

Gly Arg Phe Thr Ile Ser Arg Asp Asn Ala Gln Asn Met Val His Leu
65                  70                  75                  80

Gln Met Asn Ser Leu Lys Pro Glu Asp Thr Ala Val Tyr Tyr Cys Asn
                85                  90                  95

Val Leu Lys Asp Thr Trp Phe Arg Thr Pro Tyr Asp Tyr Tyr Trp Gly
            100                 105                 110

Gln Gly Thr Gln Val Thr Val Ser Ser
        115                 120
```

```
<210> SEQ ID NO 3
<211> LENGTH: 125
<212> TYPE: PRT
<213> ORGANISM: Lama glama

<400> SEQUENCE: 3

Gln Val Gln Leu Gln Glu Ser Gly Gly Gly Leu Val Gln Pro Gly Asp
1               5                   10                  15

Ser Leu Arg Leu Ser Cys Val Val Ser Gly Arg Thr Leu Ser Tyr Ser
            20                  25                  30

Ser Leu Ala Trp Phe Arg Gln Ala Pro Gly Lys Glu Arg Asp Phe Val
        35                  40                  45

Ala Ala Leu Ser Leu Thr Thr Tyr Tyr Ala Asp Ser Val Lys Gly Arg
    50                  55                  60

Phe Thr Ile Ser Arg Asp Asn Ala Lys Asn Thr Val Tyr Leu Gln Met
65                  70                  75                  80

Asn Ser Leu Lys Pro Asp Asp Thr Ala Asp Tyr Phe Cys Ala Thr Ala
                85                  90                  95

Arg Thr Arg Thr Asp Tyr Ala Pro Leu Leu Ser Ala Ala Ser Thr Tyr
            100                 105                 110

Asp Ala Trp Gly Gln Gly Thr Gln Val Thr Val Ser Leu
        115                 120                 125

<210> SEQ ID NO 4
<211> LENGTH: 124
<212> TYPE: PRT
<213> ORGANISM: Lama glama

<400> SEQUENCE: 4

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Ser Ser Arg Tyr Tyr
            20                  25                  30

Ala Met Gly Trp Phe Arg Gln Gly Pro Gly Lys Glu Arg Glu Phe Val
        35                  40                  45

Ala Ala Val Asn Trp Asn Gly Asp Ser Thr Tyr Tyr Ala Asp Ser Val
    50                  55                  60

Lys Gly Arg Phe Thr Ile Ser Arg Gly Asn Ala Glu Asn Thr Ala Tyr
65                  70                  75                  80

Leu Gln Met Asn Ser Leu Val Pro Glu Asp Thr Ala Val Tyr Tyr Cys
                85                  90                  95

Ala Met Arg Met Asn Ala Gly Leu Gly Tyr Ser Ala Ala Ser Tyr Gln
            100                 105                 110

Tyr Trp Gly Gln Gly Thr Gln Val Thr Val Ser Leu
        115                 120

<210> SEQ ID NO 5
<211> LENGTH: 122
<212> TYPE: PRT
<213> ORGANISM: Lama glama

<400> SEQUENCE: 5

Gln Val Gln Leu Gln Glu Ser Gly Gly Gly Leu Val Gln Ala Gly Asp
1               5                   10                  15

Ser Leu Arg Leu Ser Cys Ala Ala Ser Gly Leu Thr Phe Leu Glu His
            20                  25                  30

Val Met Ala Trp Phe Arg Gln Thr Pro Gly Lys Glu Arg Glu Phe Val
        35                  40                  45
```

Gly Ala Ile Asp Trp Ser Gly Arg Arg Ile Thr Tyr Thr Asp Ser Val
            50                  55                  60

Lys Gly Arg Phe Thr Ile Ser Arg Asp Asn Ala Lys Asn Thr Val Tyr
 65                  70                  75                  80

Leu Gln Met Asn Thr Leu Lys Pro Glu Asp Thr Ala Val Tyr Tyr Cys
                 85                  90                  95

Ala Ala Asp Arg Thr Tyr Ser Tyr Ser Ser Thr Gly Tyr Tyr Tyr Trp
                100                 105                 110

Gly Gln Gly Thr Gln Val Thr Val Ser Ser
                115                 120

<210> SEQ ID NO 6
<211> LENGTH: 122
<212> TYPE: PRT
<213> ORGANISM: Lama glama

<400> SEQUENCE: 6

Gln Val Gln Leu Gln Asp Ser Gly Gly Gly Leu Val Gln Ala Gly Asp
  1               5                  10                  15

Ser Leu Arg Leu Ser Cys Ala Ala Ser Gly Leu Thr Phe Leu Glu His
                 20                  25                  30

Val Met Ala Trp Phe Arg Gln Thr Pro Gly Lys Glu Arg Glu Phe Val
             35                  40                  45

Gly Ala Ile Asp Trp Ser Gly Arg Arg Ile Thr Tyr Thr Asp Ser Val
            50                  55                  60

Lys Gly Arg Phe Thr Ile Ser Arg Asp Asn Ala Lys Asn Thr Val Tyr
 65                  70                  75                  80

Leu Gln Met Asn Thr Leu Lys Pro Glu Asp Thr Ala Val Tyr Tyr Cys
                 85                  90                  95

Ala Ala Asp Arg Thr Tyr Ser Tyr Ser Ser Thr Gly Tyr Tyr Tyr Trp
                100                 105                 110

Gly Gln Gly Thr Gln Val Thr Val Ser Ser
                115                 120

<210> SEQ ID NO 7
<211> LENGTH: 126
<212> TYPE: PRT
<213> ORGANISM: Lama glama

<400> SEQUENCE: 7

Gln Val Gln Leu Gln Glu Ser Gly Gly Gly Leu Val Gln Ala Gly Gly
  1               5                  10                  15

Ser Leu Arg Leu Ser Cys Ala Ala Ser Gly Arg Thr Leu Ser Ser Tyr
                 20                  25                  30

Thr Met Ala Trp Phe Arg Gln Ala Pro Gly Lys Glu Arg Glu Phe Val
             35                  40                  45

Ala Ser Ile Ser Ser Ser Gly Ile Ser Thr Tyr Tyr Ala Asp Ser Val
            50                  55                  60

Lys Gly Arg Phe Thr Ile Ser Arg Asp Ile Ala Lys Asn Thr Val Tyr
 65                  70                  75                  80

Leu Gln Met Asn Ser Leu Lys Pro Glu Asp Thr Ala Val Tyr Tyr Cys
                 85                  90                  95

Ala Ala Lys Tyr Arg Tyr Tyr Ser Thr Leu Tyr Thr Lys Ser Gly Glu
                100                 105                 110

Tyr Asp Tyr Trp Gly Gln Gly Thr Gln Val Thr Val Ser Ser
                115                 120                 125

<210> SEQ ID NO 8
<211> LENGTH: 126
<212> TYPE: PRT
<213> ORGANISM: Lama glama

<400> SEQUENCE: 8

```
Gln Val Gln Leu Gln Asp Ser Gly Gly Gly Leu Val Gln Ala Gly Gly
1               5                   10                  15

Ser Leu Arg Leu Ser Cys Glu Ala Ser Gly Arg Thr Ile Ser Ser Tyr
            20                  25                  30

Ala Met Ala Trp Phe Arg Gln Ala Pro Gly Lys Glu Arg Glu Phe Val
        35                  40                  45

Ala Ser Ile Ser Ser Ser Gly Val Ser Lys His Tyr Ala Asp Ser Val
    50                  55                  60

Lys Gly Arg Phe Thr Ile Ser Asn Asp Lys Val Lys Asn Thr Val Tyr
65                  70                  75                  80

Leu Gln Met Asn Ser Leu Lys Pro Glu Asp Thr Ala Val Tyr Phe Cys
                85                  90                  95

Ala Ala Lys Tyr Arg Tyr Tyr Ser Ser Tyr Tyr Thr Lys Ser Gly Asp
            100                 105                 110

Tyr Asp Tyr Trp Gly Gln Gly Thr Gln Val Thr Val Ser Ser
        115                 120                 125
```

<210> SEQ ID NO 9
<211> LENGTH: 121
<212> TYPE: PRT
<213> ORGANISM: Lama glama

<400> SEQUENCE: 9

```
Gln Val Gln Leu Gln Glu Ser Gly Gly Gly Leu Val Gln Ala Gly Gly
1               5                   10                  15

Ser Leu Arg Leu Ser Cys Ala Ala Ser Gly Leu Thr Phe Ser Thr Tyr
            20                  25                  30

Ala Met Gly Trp Phe Arg Gln Ala Pro Gly Lys Glu Arg Glu Phe Val
        35                  40                  45

Ala Ala Val Ser Tyr Ser Gly Ser Tyr Tyr Ala Asp Ser Val Lys Gly
    50                  55                  60

Arg Phe Thr Ile Ser Arg Asp Asn Ala Lys Asn Thr Val Tyr Leu Gln
65                  70                  75                  80

Met Ala Ser Leu Lys Pro Glu Asp Thr Ala Val Tyr Tyr Cys Ala Ala
                85                  90                  95

Arg Asn Arg Gly Tyr Ser Thr Tyr Ala Gly Val Tyr Asp Tyr Trp Gly
            100                 105                 110

Gln Gly Thr Gln Val Thr Val Ser Ser
        115                 120
```

<210> SEQ ID NO 10
<211> LENGTH: 125
<212> TYPE: PRT
<213> ORGANISM: Lama glama

<400> SEQUENCE: 10

```
Gln Val Gln Leu Gln Asp Ser Gly Gly Gly Leu Val Gln Ala Gly Gly
1               5                   10                  15

Ser Leu Arg Leu Ser Cys Ala Ala Ser Gly Val Thr Phe Ser Ser Tyr
            20                  25                  30
```

```
Ala Met Gly Trp Phe Arg Gln Ala Pro Gly Lys Glu Arg Glu Phe Val
         35                  40                  45

Ala Ser Ile Thr Trp Ile Gly Gly Thr Tyr Tyr Ala Asp Ser Val
 50                  55                  60

Lys Gly Arg Phe Thr Ile Ser Arg Asp His Ala Gly Asn Thr Val Tyr
 65                  70                  75                  80

Leu Gln Met Asn Thr Leu Lys Pro Asp Asp Thr Ala Val Tyr Tyr Cys
                 85                  90                  95

Ala Leu Asp Arg Arg Ser Ser Thr Tyr Tyr Leu Met Lys Gly Glu Tyr
                100                 105                 110

Asp Tyr Arg Gly Arg Gly Thr Gln Val Thr Val Ser Ser
        115                 120                 125

<210> SEQ ID NO 11
<211> LENGTH: 125
<212> TYPE: PRT
<213> ORGANISM: Lama glama

<400> SEQUENCE: 11

Gln Val Gln Leu Gln Glu Ser Gly Gly Gly Leu Val Gln Ala Gly Gly
 1               5                  10                  15

Ser Leu Arg Leu Ser Cys Ala Ala Ser Gly Val Thr Phe Ser Ser Tyr
             20                  25                  30

Ala Met Gly Trp Phe Arg Gln Ala Pro Gly Lys Glu Arg Glu Phe Val
         35                  40                  45

Ala Ser Ile Thr Trp Thr Gly Thr Gly Thr Tyr Tyr Ala Asp Ser Val
 50                  55                  60

Lys Gly Arg Phe Thr Ile Ser Arg Asp His Ala Gly Thr Thr Val Tyr
 65                  70                  75                  80

Leu Gln Met Asn Ser Leu Lys Pro Glu Asp Thr Ala Val Tyr Tyr Cys
                 85                  90                  95

Ala Val Asp Arg Arg Ser Ser Thr Tyr Tyr Leu Met Lys Gly Glu Tyr
                100                 105                 110

Asp Tyr Arg Gly Arg Gly Thr Gln Val Thr Val Ser Ser
        115                 120                 125

<210> SEQ ID NO 12
<211> LENGTH: 151
<212> TYPE: PRT
<213> ORGANISM: Lama glama

<400> SEQUENCE: 12

Gln Val Gln Leu Gln Glu Ser Gly Gly Gly Leu Val Gln Pro Gly Gly
 1               5                  10                  15

Ser Leu Arg Leu Ser Cys Ala Ala Ser Gly Arg Thr Phe Ser Asp His
             20                  25                  30

Ser Gly Tyr Thr Tyr Thr Ile Gly Trp Phe Arg Gln Ala Pro Gly Lys Glu
         35                  40                  45

Arg Glu Phe Val Ala Arg Ile Tyr Trp Ser Ser Gly Asn Thr Tyr Tyr
 50                  55                  60

Ala Asp Ser Val Lys Gly Arg Phe Ala Ile Ser Arg Asp Ile Ala Lys
 65                  70                  75                  80

Asn Thr Val Asp Leu Thr Met Asn Asn Leu Glu Pro Glu Asp Thr Ala
                 85                  90                  95

Val Tyr Tyr Cys Ala Ala Arg Asp Gly Ile Pro Thr Ser Arg Ser Val
                100                 105                 110
```

Glu Ser Tyr Asn Tyr Trp Gly Gln Gly Thr Gln Val Thr Val Ser Ser
        115                 120                 125

Ala Ala Ala Glu Gln Lys Leu Ile Ser Glu Glu Asp Leu Asn Gly Ala
    130                 135                 140

Ala His His His His His His
145                 150

<210> SEQ ID NO 13
<211> LENGTH: 124
<212> TYPE: PRT
<213> ORGANISM: Lama glama

<400> SEQUENCE: 13

Gln Val Gln Leu Gln Asp Ser Gly Gly Gly Leu Val Gln Ala Gly Gly
1               5                   10                  15

Ser Leu Arg Leu Ser Cys Ala Ala Ser Gly Gly Thr Phe Ser Ser Ile
            20                  25                  30

Ile Met Ala Trp Phe Arg Gln Ala Pro Gly Lys Glu Arg Glu Phe Val
            35                  40                  45

Gly Ala Val Ser Trp Ser Gly Gly Thr Thr Val Tyr Ala Asp Ser Val
        50                  55                  60

Leu Gly Arg Phe Glu Ile Ser Arg Asp Ser Ala Arg Lys Ser Val Tyr
65                  70                  75                  80

Leu Gln Met Asn Ser Leu Lys Pro Glu Asp Thr Ala Val Tyr Tyr Cys
                85                  90                  95

Ala Ala Arg Pro Tyr Gln Lys Tyr Asn Trp Ala Ser Ala Ser Tyr Asn
            100                 105                 110

Val Trp Gly Gln Gly Thr Gln Val Thr Val Ser Ser
        115                 120

<210> SEQ ID NO 14
<211> LENGTH: 260
<212> TYPE: PRT
<213> ORGANISM: Lama glama

<400> SEQUENCE: 14

Gln Val Gln Leu Gln Asp Ser Gly Gly Gly Leu Val Gln Ala Gly Gly
1               5                   10                  15

Ser Leu Arg Leu Ser Cys Ala Ala Ser Gly Gly Thr Phe Ser Ser Ile
            20                  25                  30

Ile Met Ala Trp Phe Arg Gln Ala Pro Gly Lys Glu Arg Glu Phe Val
            35                  40                  45

Gly Ala Val Ser Trp Ser Gly Gly Thr Thr Val Tyr Ala Asp Ser Val
        50                  55                  60

Leu Gly Arg Phe Glu Ile Ser Arg Asp Ser Ala Arg Lys Ser Val Tyr
65                  70                  75                  80

Leu Gln Met Asn Ser Leu Lys Pro Glu Asp Thr Ala Val Tyr Tyr Cys
                85                  90                  95

Ala Ala Arg Pro Tyr Gln Lys Tyr Asn Trp Ala Ser Ala Ser Tyr Asn
            100                 105                 110

Val Trp Gly Gln Gly Thr Gln Val Thr Val Ser Ser Glu Pro Lys Thr
        115                 120                 125

Pro Lys Pro Gln Pro Ala Ala Ala Gln Val Gln Leu Gln Asp Ser Gly
    130                 135                 140

Gly Gly Leu Val Gln Ala Gly Gly Ser Leu Arg Leu Ser Cys Ala Ala
145                 150                 155                 160

```
Ser Gly Gly Thr Phe Ser Ser Ile Ile Met Ala Trp Phe Arg Gln Ala
            165                 170                 175

Pro Gly Lys Glu Arg Glu Phe Val Gly Ala Val Ser Trp Ser Gly Gly
        180                 185                 190

Thr Thr Val Tyr Ala Asp Ser Val Leu Gly Arg Phe Glu Ile Ser Arg
            195                 200                 205

Asp Ser Ala Arg Lys Ser Val Tyr Leu Gln Met Asn Ser Leu Lys Pro
        210                 215                 220

Glu Asp Thr Ala Val Tyr Tyr Cys Ala Ala Arg Pro Tyr Gln Lys Tyr
225                 230                 235                 240

Asn Trp Ala Ser Ala Ser Tyr Asn Val Trp Gly Gln Gly Thr Gln Val
            245                 250                 255

Thr Val Ser Ser
        260

<210> SEQ ID NO 15
<211> LENGTH: 118
<212> TYPE: PRT
<213> ORGANISM: Lama glama

<400> SEQUENCE: 15

Gln Val Gln Leu Gln Glu Ser Gly Gly Gly Leu Val Gln Pro Gly Gly
1               5                   10                  15

Ser Leu Arg Leu Ser Cys Val Ala Ser Gly Phe Thr Phe Ser Asp Tyr
            20                  25                  30

Pro Met Ala Trp Val Arg Gln Ala Pro Gly Lys Gly Leu Glu Trp Ile
        35                  40                  45

Ser Val Ile Asn Ser Gly Gly Val Asn Thr Ser Tyr Ala Ala Ser Val
    50                  55                  60

Lys Gly Arg Phe Thr Ile Ser Arg Asp Asn Ala Lys Asn Thr Leu Phe
65                  70                  75                  80

Leu Gln Met Asn Ser Leu Lys Pro Glu Asp Thr Ala Val Tyr Tyr Cys
                85                  90                  95

Ala Lys Tyr Ser Leu Lys Asn Glu Gln Tyr Trp Arg Gly Gln Gly Thr
            100                 105                 110

Gln Val Thr Val Ser Ser
        115

<210> SEQ ID NO 16
<211> LENGTH: 124
<212> TYPE: PRT
<213> ORGANISM: Lama glama

<400> SEQUENCE: 16

Gln Val Gln Leu Gln Glu Ser Gly Gly Gly Leu Val Gln Pro Gly Gly
1               5                   10                  15

Ser Leu Arg Leu Ser Cys Ala Ala Ser Gly Ser Ile Phe Ser Ile Asp
            20                  25                  30

Gly Met Gly Trp Tyr Arg Gln Ala Pro Gly Lys Gln Arg Glu Arg Lys
        35                  40                  45

Gln Arg Glu Leu Val Ala Ala Ile Thr Ser Gly Ser Thr Lys Tyr
    50                  55                  60

Ala Asp Ser Val Lys Gly Arg Phe Thr Ile Ser Arg Asp Asn Ala Asn
65                  70                  75                  80

Asp Thr Val Tyr Leu Gln Met Asn Thr Leu Lys Pro Glu Asp Thr Ala
                85                  90                  95
```

```
Val Tyr Tyr Cys Asn Ala Val Leu Leu Arg Arg Gly Ile Val Tyr Asp
                100                 105                 110

Tyr Trp Gly Gln Gly Lys Gln Val Thr Val Ser Ser
            115                 120

<210> SEQ ID NO 17
<211> LENGTH: 124
<212> TYPE: PRT
<213> ORGANISM: Lama glama

<400> SEQUENCE: 17

Gln Val Gln Leu Gln Glu Ser Gly Gly Gly Ser Val Lys Ala Gly Gly
1               5                   10                  15

Ser Leu Arg Leu Ser Cys Ala Ala Ser Gly Ser Ile Phe Ser Ile Asp
            20                  25                  30

Gly Met Gly Trp Tyr Arg Gln Ala Pro Gly Lys Gln Arg Glu Arg Lys
        35                  40                  45

Gln Arg Glu Leu Val Ala Ala Ile Thr Ser Gly Gly Ser Thr Lys Tyr
    50                  55                  60

Ala Asp Ser Val Lys Gly Arg Phe Thr Ile Ser Arg Asp Asn Ala Asn
65                  70                  75                  80

Asp Thr Val Tyr Leu Gln Met Asn Thr Leu Lys Pro Glu Asp Thr Ala
                85                  90                  95

Val Tyr Tyr Cys Asn Ala Val Leu Leu Arg Arg Gly Ile Val Tyr Asp
                100                 105                 110

Tyr Trp Gly Gln Gly Lys Gln Val Thr Val Ser Ser
            115                 120

<210> SEQ ID NO 18
<211> LENGTH: 121
<212> TYPE: PRT
<213> ORGANISM: Lama glama

<400> SEQUENCE: 18

Gln Val Gln Leu Gln Glu Ser Gly Gly Gly Leu Val Arg Ala Gly Gly
1               5                   10                  15

Ser Leu Arg Leu Ser Cys Val Ala Ser Gly Arg Thr Leu Ser Lys Tyr
            20                  25                  30

Arg Met Gly Trp Phe Arg Gln Phe Pro Gly Lys Glu Arg Glu Leu Val
        35                  40                  45

Ala Glu Ile Glu Trp Lys Ser Ser Thr Trp Tyr Arg Asp Ser Val
    50                  55                  60

Lys Gly Arg Phe Thr Ile Ser Arg Asp Asn Ala Lys Asn Thr Val Tyr
65                  70                  75                  80

Leu Arg Met Asn Ser Leu Lys Pro Glu Asp Thr Ala Val Tyr Tyr Cys
                85                  90                  95

Ala Ala Ala Thr Leu Gly Glu Pro Leu Val Lys Tyr Thr Tyr Trp Gly
                100                 105                 110

Gln Gly Thr Gln Val Thr Val Ser Ser
            115                 120

<210> SEQ ID NO 19
<211> LENGTH: 124
<212> TYPE: PRT
<213> ORGANISM: Lama glama

<400> SEQUENCE: 19

Gln Val Gln Leu Gln Glu Ser Gly Gly Gly Leu Val Gln Pro Gly Gly
```

```
               1               5                  10                 15
           Ser Leu Arg Leu Ser Cys Ala Ala Ser Gly Ser Ile Phe Ser Ile Asp
                          20                 25                 30

Gly Met Gly Trp Tyr Arg Gln Ala Pro Gly Lys Gln Arg Glu Arg Lys
                          35                 40                 45

Gln Arg Glu Leu Val Ala Ala Ile Thr Ser Gly Ser Thr Lys Tyr
                          50                 55                 60

Ala Asp Ser Val Lys Gly Arg Phe Thr Ile Ser Arg Asp Asn Ala Asn
           65                 70                 75                 80

Asp Thr Val Tyr Leu Gln Met Asn Thr Leu Lys Pro Glu Asp Thr Ala
                          85                 90                 95

Val Tyr Tyr Cys Asn Ala Val Leu Leu Arg Arg Gly Ile Val Tyr Asp
                          100                105                110

Tyr Trp Gly Gln Gly Lys Gln Val Thr Val Ser Ser
                          115                120
```

<210> SEQ ID NO 20
<211> LENGTH: 128
<212> TYPE: PRT
<213> ORGANISM: Lama glama

<400> SEQUENCE: 20

```
           Gln Val Gln Leu Gln Asp Ser Gly Gly Gly Leu Val Arg Thr Gly Asp
           1               5                  10                 15

Ser Leu Arg Leu Ser Cys Val Val Phe Gly Thr Ile Ser Thr Tyr
                          20                 25                 30

Ala Met Gly Trp Phe Arg Arg Ala Pro Gly Lys Glu Arg Glu Phe Val
                          35                 40                 45

Ala Ala Ile Asp Ala Ser Gly Gly Phe Thr Glu Tyr Ala Asp Ser Val
                          50                 55                 60

Arg Gly Arg Phe Arg Ile Ala Arg Asp Asn Pro Leu Ser Ala Val Tyr
           65                 70                 75                 80

Leu Gln Met Asn Ser Leu Lys Pro Glu Asp Thr Ala Phe Tyr Tyr Cys
                          85                 90                 95

Ala Ala Asp Lys Asp Arg Asp Thr Val Val Arg Phe Thr Thr Thr Pro
                          100                105                110

Asn Glu Tyr Asp Tyr Trp Gly Gln Gly Thr Gln Val Thr Val Ser Ser
                          115                120                125
```

<210> SEQ ID NO 21
<211> LENGTH: 121
<212> TYPE: PRT
<213> ORGANISM: Lama glama

<400> SEQUENCE: 21

```
           Gln Val Gln Leu Gln Glu Ser Gly Gly Gly Leu Val Gln Pro Gly Gly
           1               5                  10                 15

Ser Leu Arg Leu Ser Cys Ala Ala Ser Gly Phe Thr Phe Asn Asn His
                          20                 25                 30

Trp Leu Tyr Trp Val Arg Gln Ala Gln Gly Lys Gly Leu Glu Trp Val
                          35                 40                 45

Ser Ala Ile Asn Pro Gly Gly Ser Thr Val Tyr Leu Asp Ser Val Lys
                          50                 55                 60

Gly Arg Phe Thr Ile Ser Arg Gly Asn Thr Lys Asn Thr Leu Tyr Leu
           65                 70                 75                 80

Gln Met Asn Ser Leu Lys Ser Glu Asp Thr Ala Val Tyr Tyr Cys Thr
```

```
                    85                  90                  95
Lys Ala Met Ala Trp Ala Thr Asp Trp Asp Glu Tyr Asp Leu Trp Gly
                100                 105                 110

Gln Gly Thr Gln Val Thr Val Ser Ser
            115                 120

<210> SEQ ID NO 22
<211> LENGTH: 124
<212> TYPE: PRT
<213> ORGANISM: Lama glama

<400> SEQUENCE: 22

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Thr Phe Thr Val Tyr
            20                  25                  30

Thr Thr Gly Trp Phe Arg Gln Ala Pro Gly Lys Glu Arg Glu Phe Val
        35                  40                  45

Ala Ala Ile Asp Trp Ser Gly Ser Ser Thr Tyr Tyr Thr Asp Ser Val
    50                  55                  60

Lys Gly Arg Phe Thr Ile Ser Arg Asp Asn Thr Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Arg Asp Ala Ile Val Gly Val Thr Asp Thr Ser Gly Tyr Arg
                100                 105                 110

Tyr Trp Gly Gln Gly Thr Gln Val Thr Val Ser Ser
            115                 120

<210> SEQ ID NO 23
<211> LENGTH: 127
<212> TYPE: PRT
<213> ORGANISM: Lama glama

<400> SEQUENCE: 23

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Asn Tyr
            20                  25                  30

Val Met Gly Trp Phe Arg Gln Ala Pro Gly Lys Glu Arg Asp Phe Val
        35                  40                  45

Val Gly Ile Gly Arg Ser Gly Asp Asn Thr Tyr Tyr Ala Asp Ser
    50                  55                  60

Val Lys Gly Arg Phe Thr Ile Ser Trp Asp Asn Ala Lys Asn Thr Met
65                  70                  75                  80

Tyr Leu Gln Met Asn Ser Leu Lys Pro Glu Asp Thr Ala Val Tyr Tyr
                85                  90                  95

Cys Ala Ala Ser Thr Tyr Ser Arg Asp Thr Ile Phe Thr Lys Trp Ala
                100                 105                 110

Asn Tyr Asn Tyr Trp Gly Gln Gly Thr Gln Val Thr Val Ser Ser
            115                 120                 125

<210> SEQ ID NO 24
<211> LENGTH: 127
<212> TYPE: PRT
<213> ORGANISM: Lama glama

<400> SEQUENCE: 24
```

-continued

```
Gln Val Gln Leu Gln Glu Ser Gly Gly Gly Leu Val Lys Ala Gly Gly
1               5                   10                  15

Ser Leu Arg Leu Ser Cys Ala Ala Ser Gly Arg Thr Phe Ser Ser Tyr
            20                  25                  30

Val Met Gly Trp Phe Arg Gln Ala Pro Gly Lys Glu Arg Glu Phe Val
        35                  40                  45

Gly Ala Ile His Trp Ser Gly Arg Thr Tyr Tyr Ala Asp Ser Val
    50                  55                  60

Lys Gly Arg Phe Thr Ile Ser Ser Asp Asn Ala Lys Asn Thr Leu Tyr
65                  70                  75                  80

Leu Gln Met Asn Ser Leu Lys Pro Glu Asp Thr Ala Val Tyr Tyr Cys
                85                  90                  95

Ala Ala Ser Arg Ile Ile Tyr Ser Tyr Val Asn Tyr Val Asn Pro Gly
                100                 105                 110

Glu Tyr Asp Tyr Trp Gly Gln Gly Thr Gln Val Thr Val Ser Ser
            115                 120                 125
```

<210> SEQ ID NO 25
<211> LENGTH: 122
<212> TYPE: PRT
<213> ORGANISM: Lama glama

<400> SEQUENCE: 25

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser His
            20                  25                  30

Tyr Met Ser Trp Phe Arg Gln Ala Pro Gly Lys Glu Arg Glu Phe Val
        35                  40                  45

Ala Ala Ile Thr Ser Ser Ser Arg Thr Tyr Tyr Thr Glu Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Ser Glu Asp Thr Ala Val Tyr Tyr Cys Ala
                85                  90                  95

Ala Asp Arg Thr Phe Tyr Gly Ser Thr Trp Ser Lys Tyr Asp Tyr Arg
                100                 105                 110

Gly Gln Gly Thr Gln Val Thr Val Ser Ser
            115                 120
```

<210> SEQ ID NO 26
<211> LENGTH: 129
<212> TYPE: PRT
<213> ORGANISM: Lama glama

<400> SEQUENCE: 26

```
Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Thr Phe Ser Lys Tyr
            20                  25                  30

Ala Met Gly Trp Phe Arg Gln Ala Pro Gly Lys Glu Arg Glu Phe Val
        35                  40                  45

Ser Ala Ile Ser Trp Ser Asp Gly Ser Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80
```

```
Leu Gln Val Asn Ser Leu Lys Pro Glu Asp Thr Ala Val Tyr Tyr Cys
                85                  90                  95

Ala Ala Thr Tyr Leu Val Asp Val Trp Ala Val His Val Pro Ile Arg
            100                 105                 110

Pro Tyr Glu Tyr Asp Tyr Trp Gly Gln Gly Thr Gln Val Thr Val Ser
        115                 120                 125

Ser
```

<210> SEQ ID NO 27
<211> LENGTH: 125
<212> TYPE: PRT
<213> ORGANISM: Lama glama

<400> SEQUENCE: 27

```
Gln Val Gln Leu Gln Asp Ser Gly Gly Gly Leu Val Gln Ala Gly Asp
1               5                   10                  15

Ser Leu Arg Leu Ser Cys Ala Ala Ser Gly Arg Ser Phe Gly Gly Tyr
            20                  25                  30

Ala Met Gly Trp Phe Arg Gln Ala Pro Gly Lys Glu Arg Glu Phe Val
        35                  40                  45

Ala Ala Ile Ser Trp Ser Gly Ser Thr Tyr Tyr Ala Asp Ser Leu
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Leu Tyr Tyr Cys
                85                  90                  95

Ala Ala Gly Leu Arg Pro Ser Pro Asn Tyr Asn His Glu Arg Ser Tyr
            100                 105                 110

Asp Tyr Trp Gly Gln Gly Thr Gln Val Thr Val Ser Ser
        115                 120                 125
```

<210> SEQ ID NO 28
<211> LENGTH: 129
<212> TYPE: PRT
<213> ORGANISM: Lama glama

<400> SEQUENCE: 28

```
Gln Val Gln Leu Gln Glu Ser Gly Gly Gly Leu Val Gln Ala Gly Gly
1               5                   10                  15

Ser Leu Leu Leu Ser Cys Ala Ala Ser Gly Arg Thr Phe Ser Ser Tyr
            20                  25                  30

Ala Met Gly Trp Phe Arg Gln Ala Pro Gly Lys Glu Arg Glu Phe Val
        35                  40                  45

Ala Ala Ile Asn Trp Ser Gly Ser Thr Ser Tyr Ala Asp Ser Val
    50                  55                  60

Lys Gly Arg Phe Thr Ile Ser Arg Asp Asn Thr Lys Asn Thr Val Tyr
65                  70                  75                  80

Leu Gln Met Asn Ser Leu Lys Pro Glu Asp Thr Ala Ala Phe Tyr Cys
                85                  90                  95

Ala Ala Thr Tyr Asn Pro Tyr Ser Arg Asp His Tyr Phe Pro Arg Met
            100                 105                 110

Thr Thr Glu Tyr Asp Tyr Trp Gly Gln Gly Thr Gln Val Thr Val Ser
        115                 120                 125

Ser
```

```
<210> SEQ ID NO 29
<211> LENGTH: 122
<212> TYPE: PRT
<213> ORGANISM: Lama glama

<400> SEQUENCE: 29

Gln Val Gln Leu Gln Glu Ser Gly Gly Arg Leu Val Gln Thr Gly Gly
1               5                   10                  15

Ser Leu Arg Leu Ser Cys Ala Ala Ser Gly Gly Thr Phe Gly Thr Tyr
            20                  25                  30

Ala Leu Gly Trp Phe Arg Gln Ala Pro Gly Lys Glu Arg Glu Phe Val
        35                  40                  45

Ala Ala Ile Ser Arg Phe Gly Ser Thr Tyr Tyr Ala Asp Ser Val Lys
    50                  55                  60

Gly Arg Phe Thr Ile Ser Arg Asp Asn Ala Asn Asn Thr Val Tyr Leu
65                  70                  75                  80

Glu Met Asn Ser Leu Lys Pro Glu Asp Thr Ala Val Tyr Tyr Cys Ala
                85                  90                  95

Ala Arg Glu Gly Val Ala Leu Gly Leu Arg Asn Asp Ala Asn Tyr Trp
            100                 105                 110

Gly Gln Gly Thr Gln Val Thr Val Ser Ser
        115                 120

<210> SEQ ID NO 30
<211> LENGTH: 121
<212> TYPE: PRT
<213> ORGANISM: Lama glama

<400> SEQUENCE: 30

Gln Val Gln Leu Gln Asp Ser Gly Gly Gly Leu Val Gln Ala Gly Gly
1               5                   10                  15

Ser Leu Arg Leu Ser Cys Ala Ala Ser Gly Gly Thr Phe Ser Ser Tyr
            20                  25                  30

Ala Met Gly Trp Phe Arg Gln Ala Pro Gly Lys Glu Arg Glu Phe Val
        35                  40                  45

Ala Ala Ile Gly Leu Asn Thr Tyr Tyr Ala Asp Ser Val Lys Gly Arg
    50                  55                  60

Phe Thr Ile Ser Arg Asp Asn Ala Lys Asn Thr Val Tyr Leu Gln Met
65                  70                  75                  80

Asn Ser Leu Lys Pro Glu Asp Thr Ala Val Tyr Tyr Cys Ala Ala Arg
                85                  90                  95

Thr Ser Gly Val Val Gly Gly Pro Lys Arg Tyr Asp Tyr Trp Gly
            100                 105                 110

Gln Gly Thr Gln Val Thr Val Ser Ser
        115                 120

<210> SEQ ID NO 31
<211> LENGTH: 122
<212> TYPE: PRT
<213> ORGANISM: Lama glama

<400> SEQUENCE: 31

Glu Val Gln Leu Val Glu Ser Gly Gly Gly Ser Val Gln Ala Gly Gly
1               5                   10                  15

Ser Leu Lys Leu Ser Cys Ala Ala Ser Gly Arg Ser Phe Ser Thr Tyr
            20                  25                  30

Ala Met Gly Trp Phe Arg Gln Ala Pro Gly Gln Asp Arg Glu Phe Val
        35                  40                  45
```

```
Ala Thr Ile Ser Trp Thr Asp Ser Thr Asp Tyr Ala Asp Ser Val Lys
        50                  55                  60

Gly Arg Phe Thr Ile Ser Arg Asp Asn Ala Lys Asn Thr Gly Tyr Leu
 65              70                  75                  80

Gln Met Asn Ser Leu Lys Pro Glu Asp Thr Ala Val Tyr Tyr Cys Ala
                85                  90                  95

Ala Asp Arg Trp Ala Ser Ser Arg Arg Asn Val Asp Tyr Asp Tyr Trp
            100                 105                 110

Gly Gln Gly Thr Gln Val Thr Val Ser Ser
            115                 120
```

<210> SEQ ID NO 32
<211> LENGTH: 123
<212> TYPE: PRT
<213> ORGANISM: Lama glama

<400> SEQUENCE: 32

```
Gln Val Gln Leu Gln Glu Ser Gly Gly Gly Leu Val Gln Ala Gly Gly
 1               5                  10                  15

Ser Leu Arg Leu Ser Cys Ala Ala Ser Gly Arg Thr Phe Ser Asn Tyr
            20                  25                  30

Ala Met Gly Trp Phe Arg Gln Ala Pro Gly Lys Glu Arg Glu Phe Val
            35                  40                  45

Ala Ala Ile Asn Trp Gly Gly Asn Thr Tyr Tyr Ala Asp Ser Val
        50                  55                  60

Lys Gly Arg Phe Thr Ile Ser Arg Asp Asn Ala Lys Asn Thr Val Tyr
 65              70                  75                  80

Leu Gln Met Asn Ser Leu Lys Pro Glu Asp Thr Ala Val Tyr Tyr Cys
                85                  90                  95

Ala Ala Ser Glu Trp Gly Gly Ser Asp Tyr Asp His Asp Tyr Asp Tyr
            100                 105                 110

Trp Gly Gln Gly Thr Gln Val Thr Val Ser Ser
            115                 120
```

<210> SEQ ID NO 33
<211> LENGTH: 123
<212> TYPE: PRT
<213> ORGANISM: Lama glama

<400> SEQUENCE: 33

```
Glu Val Gln Leu Val Glu Ser Gly Gly Gly Leu Val Gln Ala Gly Gly
 1               5                  10                  15

Ser Leu Arg Leu Ser Cys Ala Ala Ser Gly Arg Ser Phe Ser Ser Tyr
            20                  25                  30

Ala Met Ala Trp Phe Arg Gln Ala Pro Gly Lys Glu Arg Glu Phe Val
            35                  40                  45

Ala Ala Ile Ser Trp Gly Gly Gly Ser Thr Tyr Tyr Ala Val Ser Val
        50                  55                  60

Lys Gly Arg Phe Thr Ile Ser Arg Asp Asn Ala Lys Asn Thr Val Tyr
 65              70                  75                  80

Leu Gln Met Asn Ser Leu Lys Pro Glu Asp Thr Ala Arg Tyr Tyr Cys
                85                  90                  95

Ala Ala Asp Glu Thr Phe His Ser Ser Ala Tyr Gly Glu Tyr Glu Tyr
            100                 105                 110

Trp Gly Gln Gly Thr Gln Val Thr Val Ser Ser
            115                 120
```

<210> SEQ ID NO 34
<211> LENGTH: 133
<212> TYPE: PRT
<213> ORGANISM: Lama glama

<400> SEQUENCE: 34

Glu Val Gln Leu Val Glu Ser Gly Gly Gly Leu Val Gln Ala Gly Gly
1               5                   10                  15

Ser Leu Arg Leu Ser Cys Thr Ala Ser Gly Arg Thr Phe Ser Ser Tyr
            20                  25                  30

Ala Met Gly Trp Phe Arg Gln Thr Pro Gly Lys Glu Arg Glu Phe Val
        35                  40                  45

Ala Ala Ile Thr Ser Ser Gly Gly Ser Thr Tyr Tyr Ala Asp Ser Val
    50                  55                  60

Lys Gly Arg Phe Thr Ile Ser Arg Asp Asn Ala Lys Ser Thr Met Tyr
65                  70                  75                  80

Leu Gln Met Asp Ser Leu Met Leu Asp Thr Ser Val Tyr Tyr Cys
                85                  90                  95

Ala Ala Asp Ser Ser Arg Pro Gln Tyr Ser Asp Ser Ala Leu Arg Arg
            100                 105                 110

Ile Leu Ser Leu Ser Asn Ser Tyr Pro Tyr Trp Gly Gln Gly Thr Gln
        115                 120                 125

Val Thr Val Ser Ser
    130

<210> SEQ ID NO 35
<211> LENGTH: 120
<212> TYPE: PRT
<213> ORGANISM: Lama glama

<400> SEQUENCE: 35

Glu Val Gln Leu Val Glu Ser Gly Gly Gly Leu Val Gln Pro Gly Gly
1               5                   10                  15

Ser Leu Arg Leu Ser Cys Val Ala Ser Gly Phe Thr Phe Ala Asp Tyr
            20                  25                  30

Ala Met Ser Trp Val Arg Gln Ala Pro Gly Lys Gly Leu Gln Trp Val
        35                  40                  45

Ser Ser Ile Ser Tyr Asn Gly Asp Thr Thr Tyr Tyr Ala Glu Ser Met
    50                  55                  60

Lys Asp Arg Phe Thr Ile Ser Arg Asp Asn Ala Lys Asn Thr Leu Tyr
65                  70                  75                  80

Leu Gln Met Asn Ser Leu Lys Ser Glu Asp Thr Ala Val Tyr Tyr Cys
                85                  90                  95

Ala Ser Ser Gly Ser Tyr Tyr Pro Gly His Phe Glu Ser Trp Gly Gln
            100                 105                 110

Gly Thr Gln Val Thr Val Ser Ser
        115                 120

<210> SEQ ID NO 36
<211> LENGTH: 121
<212> TYPE: PRT
<213> ORGANISM: Lama glama

<400> SEQUENCE: 36

Gln Val Gln Leu Gln Glu Ser Gly Gly Gly Leu Val Gln Ala Gly Gly
1               5                   10                  15

```
Ser Leu Arg Leu Ser Cys Ala Ala Ser Gly Arg Thr Phe Ser Gly Tyr
            20                  25                  30

Ala Met Gly Trp Phe Arg Gln Ala Pro Gly Glu Glu Arg Glu Phe Val
        35                  40                  45

Ala Ala Ile Ser Trp Arg Gly Thr Ser Thr Tyr Tyr Gly Asp Ser Ala
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
            85                  90                  95

Ala Ala Gly Ser His Ser Asp Tyr Ala Pro Asp Tyr Asp Trp Gly
            100                 105                 110

Gln Gly Thr Gln Val Thr Val Ser Ser
        115                 120

<210> SEQ ID NO 37
<211> LENGTH: 123
<212> TYPE: PRT
<213> ORGANISM: Lama glama

<400> SEQUENCE: 37

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Thr Phe Ser Ser Tyr
            20                  25                  30

Ala Ile Gly Trp Phe Arg Gln Ala Pro Gly Lys Glu Arg Glu Phe Val
        35                  40                  45

Ala Ala Ile Ser Trp Gly Gly Ser Asn Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
            85                  90                  95

Ala Ala Gly Glu Val Ser Asn Ser Asp Tyr Ala Tyr Glu Tyr Asp Tyr
            100                 105                 110

Trp Gly Gln Gly Thr Gln Val Thr Val Ser Ser
        115                 120

<210> SEQ ID NO 38
<211> LENGTH: 122
<212> TYPE: PRT
<213> ORGANISM: Lama glama

<400> SEQUENCE: 38

Gln Val Gln Leu Gln Glu Ser Gly Gly Gly Leu Val Gln Thr Gly Gly
1               5                   10                  15

Ser Leu Arg Leu Ser Cys Ala Ala Ser Gly Arg Tyr Ile Met Gly Trp
            20                  25                  30

Phe Arg Gln Ala Pro Gly Lys Glu Arg Glu Phe Val Ala Gly Ile Ser
        35                  40                  45

Arg Ser Gly Ala Ser Thr Ala Tyr Ala Asp Ser Val Lys Asp Arg Phe
    50                  55                  60

Thr Ile Ser Arg Asp Ser Ala Leu Asn Thr Val Tyr Leu Gln Met Asn
65                  70                  75                  80

Ser Leu Lys Ala Glu Asp Thr Ala Val Tyr Phe Cys Ala Ala Ala Leu
            85                  90                  95
```

-continued

Ala Ile Arg Leu Gly Ile Pro Arg Gly Glu Thr Glu Tyr Glu Tyr Trp
                100                 105                 110

Gly Gln Gly Thr Gln Val Thr Val Ser Ser
            115                 120

<210> SEQ ID NO 39
<211> LENGTH: 121
<212> TYPE: PRT
<213> ORGANISM: Lama glama

<400> SEQUENCE: 39

Gln Val Lys Leu Glu Glu Ser Gly Gly Gly Leu Val Gln Ala Gly Gly
1               5                   10                  15

Ser Leu Arg Leu Ser Cys Ser Ala Ser Gly Leu Thr Phe Ser Asn Tyr
            20                  25                  30

Ala Met Ala Trp Phe Arg Gln Ala Pro Gly Lys Glu Arg Glu Phe Val
        35                  40                  45

Ala Thr Ile Ser Gln Arg Gly Gly Met Arg His Tyr Leu Asp Ser Val
    50                  55                  60

Lys Asp Arg Phe Thr Ile Ser Arg Asp Asn Ala Lys Asn Thr Val Tyr
65                  70                  75                  80

Leu Gln Met Asn Ser Leu Lys Pro Asp Asp Thr Ala Val Tyr Tyr Cys
                85                  90                  95

Ala Ala Asp Leu Met Tyr Gly Val Asp Arg Arg Tyr Tyr Trp Gly
                100                 105                 110

Arg Gly Thr Gln Val Thr Val Ser Ser
            115                 120

<210> SEQ ID NO 40
<211> LENGTH: 127
<212> TYPE: PRT
<213> ORGANISM: Lama glama

<400> SEQUENCE: 40

Gln Val Lys Leu Glu Glu Ser Gly Gly Gly Leu Val Gln Ala Gly Asp
1               5                   10                  15

Ser Leu Arg Leu Ser Cys Ala Ala Ser Gly Arg Ser Phe Ser Ser Ile
            20                  25                  30

Thr Met Gly Trp Phe Arg Gln Ala Pro Gly Lys Glu Arg Gln Phe Val
        35                  40                  45

Ser Ala Ile Asn Ser Asn Gly Asn Arg Tyr Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ala
                85                  90                  95

Ala Val Gln Ala Tyr Ser Ser Ser Asp Tyr Tyr Ser Gln Glu Gly
                100                 105                 110

Ala Tyr Asp Tyr Trp Gly Gln Gly Thr Gln Val Thr Val Ser Ser
            115                 120                 125

<210> SEQ ID NO 41
<211> LENGTH: 126
<212> TYPE: PRT
<213> ORGANISM: Lama glama

<400> SEQUENCE: 41

Glu Val Gln Leu Val Glu Ser Gly Gly Gly Leu Val Gln Ala Gly Gly

-continued

```
                1               5                   10                  15
            Ser Leu Arg Leu Ser Cys Ala Val Ser Gly Arg Thr Phe Ser Ser Met
                            20                  25                  30

Gly Trp Phe Arg Gln Ala Pro Gly Lys Glu Arg Glu Phe Val Ala Thr
                        35                  40                  45

Ile Asn Leu Ser Gly Asp Arg Thr Asp Tyr Ala Asp Ser Val Lys Gly
                50                  55                  60

Arg Phe Thr Ile Ser Arg Asp Asn Pro Lys Asn Thr Val Tyr Leu Gln
             65                 70                  75                  80

Met Asp Ser Leu Glu Pro Glu Asp Ser Ala Val Tyr Tyr Cys Ala Gly
                            85                  90                  95

Thr Ser Leu Tyr Pro Ser Asn Leu Arg Tyr Tyr Thr Leu Pro Gly Thr
                        100                 105                 110

Tyr Ala Asp Trp Gly Gln Gly Thr Gln Val Thr Val Ser Ser
                        115                 120                 125

<210> SEQ ID NO 42
<211> LENGTH: 126
<212> TYPE: PRT
<213> ORGANISM: Lama glama

<400> SEQUENCE: 42

Gln Val Lys Leu Glu Glu Ser Gly Gly Gly Leu Val Gln Ala Gly Gly
             1               5                   10                  15

Ser Leu Arg Leu Ser Cys Ala Ala Ser Gly Ser Ile Phe Ser Ile Asn
                            20                  25                  30

Ala Met Gly Trp Tyr Arg Gln Ala Pro Gly Lys Gln Arg Glu Leu Val
                        35                  40                  45

Ala Arg Ile Thr Gly Thr Gly Thr Ile Gly Ala Val Ser Thr
                50                  55                  60

Asn Tyr Ala Asp Ser Val Lys Gly Arg Phe Thr Ile Ser Arg Asp Asn
             65                 70                  75                  80

Ala Arg Asn Thr Val Tyr Leu Gln Met Asn Ser Leu Lys Pro Glu Asp
                            85                  90                  95

Thr Ala Val Tyr Tyr Cys Ala Ala Asp Arg Ser Arg Thr Ile Val Val
                        100                 105                 110

Pro Asp Tyr Trp Gly Gln Gly Thr Gln Val Thr Val Ser Ser
                        115                 120                 125

<210> SEQ ID NO 43
<211> LENGTH: 126
<212> TYPE: PRT
<213> ORGANISM: Lama glama

<400> SEQUENCE: 43

Gln Val Gln Leu Gln Asp Ser Gly Gly Gly Leu Val Gln Ala Gly Gly
             1               5                   10                  15

Ser Leu Arg Leu Ser Cys Ala Ser Arg Phe Ser Ser Ala Gln Tyr
                            20                  25                  30

Ala Ile Gly Trp Phe Arg Gln Ala Pro Gly Lys Glu Arg Glu Gly Val
                        35                  40                  45

Ser Tyr Ile Thr Phe Ser Gly Gly Pro Thr Gly Tyr Ala Asp Ser Val
                        50                  55                  60

Lys Gly Arg Phe Thr Val Ser Arg Asp Asn Ala Lys Asn Thr Val Tyr
             65                 70                  75                  80

Leu Gln Met Asn Ser Leu Lys Pro Glu Asp Thr Ala Val Tyr Tyr Cys
```

-continued

```
                 85                  90                  95
Ala Ala Arg Pro Tyr Thr Arg Pro Gly Ser Met Trp Val Ser Ser Leu
                100                 105                 110

Tyr Asp Asn Trp Gly Gln Gly Thr Gln Val Thr Val Ser Ser
            115                 120                 125

<210> SEQ ID NO 44
<211> LENGTH: 123
<212> TYPE: PRT
<213> ORGANISM: Lama glama

<400> SEQUENCE: 44

Gln Val Gln Leu Gln Glu Ser Gly Gly Arg Leu Val Gln Ala Gly Gly
1               5                   10                  15

Ser Leu Arg Leu Ser Cys Ala Ala Ser Glu His Thr Phe Arg Gly Tyr
            20                  25                  30

Ala Ile Gly Trp Phe Arg Gln Ala Pro Gly Lys Glu Arg Glu Phe Val
        35                  40                  45

Ser Ser Ile Thr Tyr Asp Gly Thr Leu Thr Asn Tyr Ala Asp Ser Val
    50                  55                  60

Thr Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Val Cys
                85                  90                  95

Ala Ala Gly Tyr Ser Tyr Arg Tyr Thr Thr Leu Asn Gln Tyr Asp Ser
            100                 105                 110

Trp Gly Gln Gly Thr Gln Val Thr Val Ser Ser
        115                 120

<210> SEQ ID NO 45
<211> LENGTH: 124
<212> TYPE: PRT
<213> ORGANISM: Lama glama

<400> SEQUENCE: 45

Gln Val Gln Leu Gln Asp Ser Gly Gly Gly Thr Val Gln Ala Gly Gly
1               5                   10                  15

Ser Leu Arg Leu Ser Cys Ala Ala Ser Gly Arg Thr Phe Ser Asp Tyr
            20                  25                  30

Ala Val Gly Trp Phe Arg Gln Ala Pro Gly Lys Glu Arg Glu Phe Val
        35                  40                  45

Ala Arg Ile Leu Trp Thr Gly Ala Ser Arg Ser Tyr Ala Asn Ser Val
    50                  55                  60

Asp Gly Arg Phe Thr Val Ser Thr Asp Asn Ala Lys Asn Thr Val Tyr
65                  70                  75                  80

Leu Gln Met Asn Ser Leu Lys Pro Glu Asp Thr Ala Ile Tyr Tyr Cys
                85                  90                  95

Ala Ala Leu Pro Ser Asn Ile Ile Thr Thr Asp Tyr Leu Arg Val Tyr
            100                 105                 110

Tyr Trp Gly Gln Gly Thr Gln Val Thr Val Ser Ser
        115                 120

<210> SEQ ID NO 46
<211> LENGTH: 123
<212> TYPE: PRT
<213> ORGANISM: Lama glama

<400> SEQUENCE: 46
```

```
Gln Val Gln Leu Gln Asp Ser Gly Gly Gly Thr Val Gln Ala Gly Gly
1               5                   10                  15

Ser Leu Arg Leu Ser Cys Ala Ala Ser Gly Arg Thr Phe Ser Asn Tyr
            20                  25                  30

Ala Val Gly Trp Phe Arg Gln Ala Pro Gly Lys Glu Arg Glu Phe Val
        35                  40                  45

Ala Arg Ile Lys Trp Ser Gly Gly Ser Arg Ser Tyr Ala Asn Ser Val
50                  55                  60

Asp Gly Arg Phe Thr Val Ser Thr Asp Asn Ala Lys Asn Thr Val Tyr
65                  70                  75                  80

Leu Gln Met Asn Ser Leu Lys Pro Glu Asp Thr Ala Ile Tyr Tyr Cys
                85                  90                  95

Ala Leu Pro Ser Asn Ile Ile Thr Thr Asp Tyr Leu Arg Val Tyr Tyr
            100                 105                 110

Trp Gly Gln Gly Thr Gln Val Thr Val Ser Ser
        115                 120
```

<210> SEQ ID NO 47
<211> LENGTH: 118
<212> TYPE: PRT
<213> ORGANISM: Lama glama

<400> SEQUENCE: 47

```
Gln Val Gln Leu Gln Glu Ser Gly Gly Gly Leu Val Gln Ala Gly Gly
1               5                   10                  15

Ser Leu Arg Leu Ser Cys Ala Ala Ala Gly Ile Ser Gly Ser Val Phe
            20                  25                  30

Ser Arg Thr Pro Met Gly Trp Tyr Arg Gln Ala Pro Gly Lys Gln Arg
        35                  40                  45

Glu Leu Val Ala Gly Ile Leu Thr Ser Gly Ala Thr Ser Tyr Ala Glu
50                  55                  60

Ser Val Lys Gly Arg Phe Thr Ile Ser Arg Asp Asn Ala Lys Asn Thr
65                  70                  75                  80

Val Tyr Leu Gln Met Asn Ser Leu Ser Pro Glu Asp Thr Ala Glu Tyr
                85                  90                  95

Tyr Cys Asn Thr Tyr Pro Thr Trp Val Leu Ser Trp Gly Gln Gly Thr
            100                 105                 110

Gln Val Thr Val Ser Ser
        115
```

<210> SEQ ID NO 48
<211> LENGTH: 118
<212> TYPE: PRT
<213> ORGANISM: Lama glama

<400> SEQUENCE: 48

```
Gln Val Gln Leu Gln Asp Ser Gly Gly Gly Leu Val Gln Ala Gly Gly
1               5                   10                  15

Ser Leu Arg Leu Ser Cys Ala Ala Ala Gly Ile Ser Gly Ser Val Phe
            20                  25                  30

Ser Arg Thr Pro Met Gly Trp Tyr Arg Gln Ala Pro Gly Lys Gln Arg
        35                  40                  45

Glu Leu Val Ala Gly Ile Leu Ser Ser Gly Ala Thr Val Tyr Ala Glu
50                  55                  60

Ser Val Lys Gly Arg Phe Thr Ile Ser Arg Asp Asn Ala Lys Asn Thr
65                  70                  75                  80
```

```
Val Tyr Leu Gln Met Asn Ser Leu Ser Pro Glu Asp Thr Ala Glu Tyr
                85                  90                  95

Tyr Cys Asn Thr Tyr Pro Thr Trp Val Leu Ser Trp Gly Gln Gly Thr
            100                 105                 110

Gln Val Thr Val Ser Ser
        115

<210> SEQ ID NO 49
<211> LENGTH: 118
<212> TYPE: PRT
<213> ORGANISM: Lama glama

<400> SEQUENCE: 49

Gln Val Gln Leu Gln Glu Ser Gly Gly Gly Leu Val Gln Ala Gly Gly
1               5                   10                  15

Ser Leu Arg Leu Ser Cys Ala Ala Gly Ile Ser Gly Ser Val Phe
            20                  25                  30

Ser Arg Thr Pro Met Gly Trp Tyr Arg Gln Ala Pro Lys Gln Arg
        35                  40                  45

Glu Leu Val Ala Gly Ile Leu Ser Ser Gly Ala Thr Ala Tyr Ala Glu
50                  55                  60

Ser Val Lys Gly Arg Phe Thr Ile Ser Arg Asp Asn Ala Lys Asn Thr
65                  70                  75                  80

Val Tyr Leu Gln Met Asn Ser Leu Ser Pro Glu Asp Thr Ala Glu Tyr
                85                  90                  95

Tyr Cys Asn Thr Tyr Pro Thr Trp Val Leu Ser Trp Gly Gln Gly Thr
            100                 105                 110

Gln Val Thr Val Ser Ser
        115

<210> SEQ ID NO 50
<211> LENGTH: 113
<212> TYPE: PRT
<213> ORGANISM: Lama glama

<400> SEQUENCE: 50

Gln Val Gln Leu Gln Glu Ser Gly Gly Gly Leu Val Gln Pro Gly Glu
1               5                   10                  15

Ser Leu Arg Leu Ser Cys Ala Ala Ser Arg Gly Ile Phe Arg Phe Asn
            20                  25                  30

Ala Gly Gly Trp Tyr Arg Gln Ala Pro Gly Lys Gln Arg Glu Leu Val
        35                  40                  45

Ala Phe Ile Gly Val Asp Asn Thr Thr Arg Tyr Ile Asp Ser Val Lys
50                  55                  60

Gly Arg Phe Thr Ile Ser Arg Asp Asn Ala Lys Thr Thr Val Tyr Leu
65                  70                  75                  80

Gln Met Asn Ser Leu Gln Pro Glu Asp Thr Ala Val Tyr Tyr Cys Asn
                85                  90                  95

Lys Val Pro Tyr Ile Asp Trp Gly Gln Gly Thr Gln Val Thr Val Ser
            100                 105                 110

Ser

<210> SEQ ID NO 51
<211> LENGTH: 126
<212> TYPE: PRT
<213> ORGANISM: Lama glama
```

<400> SEQUENCE: 51

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Thr Phe Ser Thr Tyr
            20                  25                  30

Asn Met Gly Trp Phe Arg Gln Ala Pro Gly Lys Glu Arg Glu Phe Val
        35                  40                  45

Ala Gly Ile Ser Trp Asn Gly Gly Ser Ile Tyr Tyr Thr Ser Ser Val
    50                  55                  60

Glu Gly Arg Phe Thr Ile Ser Arg Asp Asn Ala Glu Asn Thr Val Tyr
65                  70                  75                  80

Leu Gln Met Asn Ser Leu Lys Pro Glu Asp Thr Gly Val Tyr Tyr Cys
                85                  90                  95

Ala Ser Lys Gly Arg Pro Tyr Gly Val Pro Ser Pro Arg Gln Gly Asp
            100                 105                 110

Tyr Asp Tyr Trp Gly Gln Gly Thr Gln Val Thr Val Ser Ser
        115                 120                 125

<210> SEQ ID NO 52
<211> LENGTH: 126
<212> TYPE: PRT
<213> ORGANISM: Lama glama

<400> SEQUENCE: 52

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Thr Phe Ser Thr Tyr
            20                  25                  30

Asn Met Gly Trp Phe Arg Gln Ala Pro Gly Lys Glu Arg Glu Phe Val
        35                  40                  45

Ala Gly Ile Ser Trp Asn Gly Gly Ser Ile Tyr Tyr Thr Ser Ser Val
    50                  55                  60

Glu Gly Arg Phe Thr Ile Ser Arg Asp Asn Ala Glu Asn Thr Val Tyr
65                  70                  75                  80

Leu Gln Met Asn Ser Leu Lys Pro Glu Asp Thr Gly Val Tyr Tyr Cys
                85                  90                  95

Ala Ser Lys Gly Arg Pro Tyr Gly Val Pro Ser Pro Arg Gln Gly Asp
            100                 105                 110

Tyr Asp Tyr Trp Gly Gln Gly Thr Gln Val Thr Val Ser Ser
        115                 120                 125

<210> SEQ ID NO 53
<211> LENGTH: 126
<212> TYPE: PRT
<213> ORGANISM: Lama glama

<400> SEQUENCE: 53

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Thr Phe Ser Ile Tyr
            20                  25                  30

Asn Met Gly Trp Phe Arg Gln Ala Pro Gly Lys Glu Arg Glu Phe Val
        35                  40                  45

Ala Ala Ile Ser Trp Asn Gly Gly Ser Ile Tyr Tyr Thr Ser Ser Val
    50                  55                  60

Glu Gly Arg Phe Thr Ile Ser Arg Asp Asn Ala Ile Asn Thr Val Tyr

```
                65                  70                  75                  80
Leu Gln Met Asn Ser Leu Lys Pro Glu Asp Thr Gly Val Tyr Tyr Cys
                    85                  90                  95

Ala Ser Lys Gly Arg Pro Tyr Gly Val Pro Ser Pro Arg Gln Gly Glu
                100                 105                 110

Tyr Asp Tyr Trp Gly Gln Gly Thr Gln Val Thr Val Ser Ser
                115                 120                 125

<210> SEQ ID NO 54
<211> LENGTH: 126
<212> TYPE: PRT
<213> ORGANISM: Lama glama

<400> SEQUENCE: 54

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Thr Phe Asn Ile Tyr
                20                  25                  30

Asn Met Gly Trp Phe Arg Gln Ala Pro Gly Lys Glu Arg Asp Phe Val
                35                  40                  45

Ala Ala Ile Ser Trp Asn Gly Ser Ile Tyr Tyr Thr Ser Ser Val
    50                  55                  60

Glu Gly Arg Phe Thr Ile Ser Arg Asp Asn Ala Glu Asn Thr Val Tyr
65                  70                  75                  80

Leu Gln Met Asn Ser Leu Lys Pro Glu Asp Thr Gly Val Tyr Tyr Cys
                    85                  90                  95

Ala Ser Lys Gly Arg Pro Tyr Gly Val Pro Ser Pro Arg Gln Gly Asp
                100                 105                 110

Tyr Asp Tyr Trp Gly Gln Gly Thr Gln Val Thr Val Ser Ser
                115                 120                 125

<210> SEQ ID NO 55
<211> LENGTH: 126
<212> TYPE: PRT
<213> ORGANISM: Lama glama

<400> SEQUENCE: 55

Gln Val Lys Leu Glu Glu Ser Gly Gly Gly Leu Val Gln Ala Gly Gly
1               5                   10                  15

Ser Leu Arg Leu Ser Cys Ala Ala Ser Gly Arg Thr Phe Asn Asn Tyr
                20                  25                  30

Asn Met Gly Trp Phe Arg Gln Ala Pro Gly Lys Glu Arg Glu Phe Val
                35                  40                  45

Ala Ala Ile Ser Trp Asn Gly Ser Thr Tyr Tyr Asp Asp Ser Val
    50                  55                  60

Lys Gly Arg Phe Thr Ile Ser Arg Asp Asn Ala Asn Asn Leu Val Tyr
65                  70                  75                  80

Leu Gln Met Asn Ser Leu Asn Phe Glu Asp Thr Ala Val Tyr Tyr Cys
                    85                  90                  95

Ala Cys Ala Ala Asn Pro Tyr Gly Ile Pro Gln Tyr Arg Glu Asn Arg
                100                 105                 110

Tyr Asp Phe Trp Gly Gln Gly Thr Gln Val Thr Val Ser Ser
                115                 120                 125

<210> SEQ ID NO 56
<211> LENGTH: 126
<212> TYPE: PRT
```

```
<213> ORGANISM: Lama glama

<400> SEQUENCE: 56

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Thr Phe Asp Asn Tyr
            20                  25                  30

Asn Met Gly Trp Phe Arg Gln Ala Pro Gly Lys Glu Arg Glu Phe Val
        35                  40                  45

Ala Ala Ile Ser Trp Asn Gly Gly Ser Thr Tyr Tyr Asp Asp Ser Val
    50                  55                  60

Lys Gly Arg Phe Thr Ile Ser Arg Asp Asn Phe Gln Lys Leu Val Tyr
65                  70                  75                  80

Leu Gln Met Asn Ser Leu Lys Leu Glu Asp Thr Ala Val Tyr Tyr Cys
                85                  90                  95

Ala Cys Ala Ala Asn Pro Tyr Gly Ile Pro Gln Tyr Arg Glu Asn Arg
            100                 105                 110

Tyr Asp Phe Trp Gly Gln Gly Thr Gln Val Thr Val Ser Ser
        115                 120                 125

<210> SEQ ID NO 57
<211> LENGTH: 128
<212> TYPE: PRT
<213> ORGANISM: Lama glama

<400> SEQUENCE: 57

Gln Val Gln Leu Val Glu Ser Gly Gly Arg Leu Val Gln Ala Gly Gly
1               5                   10                  15

Ser Leu Arg Leu Ser Cys Ile Ala Ser Gly Arg Thr Ile Ser Asp Tyr
            20                  25                  30

Ala Ala Gly Trp Phe Arg Gln Ala Pro Gly Lys Glu Arg Glu Phe Leu
        35                  40                  45

Ala Ser Val Thr Trp Gly Phe Gly Ser Thr Ser Tyr Ala Asp Ser Val
    50                  55                  60

Lys Gly Arg Phe Thr Ile Ser Arg Asp Lys Ala Lys Asp Thr Val Tyr
65                  70                  75                  80

Leu Gln Met Asn Thr Leu Glu Pro Asp Asp Thr Ser Val Tyr Tyr Cys
                85                  90                  95

Ala Ser Ser Pro Arg Tyr Cys Ala Gly Tyr Arg Cys Tyr Val Thr Ala
            100                 105                 110

Ser Glu Phe Asp Ser Trp Gly Gln Gly Thr Gln Val Thr Val Ser Ser
        115                 120                 125

<210> SEQ ID NO 58
<211> LENGTH: 128
<212> TYPE: PRT
<213> ORGANISM: Lama glama

<400> SEQUENCE: 58

Gln Val Lys Leu Glu Glu Ser Gly Gly Arg Leu Val Gln Ala Gly Gly
1               5                   10                  15

Ser Leu Arg Leu Ser Cys Ile Ala Ser Gly Arg Thr Ile Ser Asp Tyr
            20                  25                  30

Ala Ala Gly Trp Phe Arg Gln Ala Pro Gly Lys Glu Arg Glu Phe Leu
        35                  40                  45

Ala Ser Val Ser Trp Gly Phe Gly Ser Thr Tyr Tyr Ala Asp Ser Val
    50                  55                  60
```

```
Lys Gly Arg Phe Thr Ile Ser Arg Asp Thr Ala Lys Asp Thr Val Tyr
 65                  70                  75                  80

Leu Gln Met Asn Thr Leu Glu Pro Asp Asp Thr Ser Val Tyr Tyr Cys
                 85                  90                  95

Ala Ser Ser Pro Arg Tyr Cys Ala Gly Tyr Arg Cys Tyr Ala Thr Ala
            100                 105                 110

Ser Glu Phe Asp Ser Trp Gly Gln Gly Thr Gln Val Thr Val Ser Ser
        115                 120                 125
```

<210> SEQ ID NO 59
<211> LENGTH: 128
<212> TYPE: PRT
<213> ORGANISM: Lama glama

<400> SEQUENCE: 59

```
Gln Val Gln Leu Gln Glu Ser Gly Gly Arg Leu Val Gln Ala Gly Gly
  1               5                  10                  15

Ser Leu Arg Leu Ser Cys Ile Ala Ser Gly Arg Thr Ile Ser Asp Tyr
             20                  25                  30

Ala Ala Gly Trp Phe Arg Gln Ala Pro Gly Lys Glu Arg Glu Phe Leu
         35                  40                  45

Ala Ser Val Thr Trp Gly Phe Gly Ser Thr Tyr Tyr Ala Asp Ser Val
     50                  55                  60

Lys Gly Arg Phe Thr Ile Ser Arg Asp Lys Ala Lys Asp Thr Val Tyr
 65                  70                  75                  80

Leu Gln Met Asn Thr Leu Glu Pro Asp Asp Thr Ser Ala Tyr Tyr Cys
                 85                  90                  95

Ala Ser Ser Pro Arg Tyr Cys Ala Gly Tyr Arg Cys Tyr Val Thr Ala
            100                 105                 110

Ser Glu Phe Asp Ser Trp Gly Pro Gly Thr Gln Val Thr Val Ser Ser
        115                 120                 125
```

<210> SEQ ID NO 60
<211> LENGTH: 126
<212> TYPE: PRT
<213> ORGANISM: Lama glama

<400> SEQUENCE: 60

```
Gln Val Gln Leu Gln Asp Ser Gly Gly Gly Leu Val Gln Ala Gly Asp
  1               5                  10                  15

Ser Leu Arg Leu Ser Cys Ala Ala Ser Gly Arg Ser Phe Ser Ser Tyr
             20                  25                  30

Gly Met Gly Trp Phe Arg Gln Ala Pro Gly Lys Glu His Glu Phe Val
         35                  40                  45

Ala Gly Ile Trp Arg Ser Gly Val Ser Leu Tyr Tyr Thr Asp Ser Val
     50                  55                  60

Lys Gly Arg Phe Thr Ile Ser Arg Asp Asp Ala Lys Met Thr Val Ser
 65                  70                  75                  80

Leu Gln Met Asn Ser Leu Lys Pro Glu Asp Thr Ala Val Tyr Tyr Cys
                 85                  90                  95

Ala Ala Glu Ala Thr Phe Pro Thr Trp Ser Arg Gly Arg Phe Ala Asp
            100                 105                 110

Tyr Asp Tyr Arg Gly Gln Gly Thr Gln Val Thr Val Ser Ser
        115                 120                 125
```

<210> SEQ ID NO 61

<211> LENGTH: 126
<212> TYPE: PRT
<213> ORGANISM: Lama glama

<400> SEQUENCE: 61

```
Gln Val Gln Leu Gln Glu Ser Gly Gly Gly Leu Val Gln Ala Gly Asp
1               5                   10                  15

Ser Leu Arg Leu Ser Cys Thr Ala Ser Gly Arg Ser Phe Ser Ser Tyr
            20                  25                  30

Gly Met Gly Trp Phe Arg Gln Ala Pro Gly Lys Asp His Glu Phe Val
        35                  40                  45

Ala Gly Ile Trp Arg Ser Gly Val Ser Leu Tyr Tyr Ala Asp Ser Val
    50                  55                  60

Lys Gly Arg Phe Thr Ile Ser Arg Asp Asp Ala Lys Met Thr Val Ser
65                  70                  75                  80

Leu Gln Met Asn Gly Leu Lys Pro Glu Asp Thr Ala Val Tyr Tyr Cys
                85                  90                  95

Ala Ala Glu Ala Thr Phe Pro Thr Trp Asn Arg Gly Thr Phe Ala Asp
            100                 105                 110

Tyr Asp Tyr Arg Gly Gln Gly Thr Gln Val Thr Val Ser Ser
        115                 120                 125
```

<210> SEQ ID NO 62
<211> LENGTH: 126
<212> TYPE: PRT
<213> ORGANISM: Lama glama

<400> SEQUENCE: 62

```
Gln Val Gln Leu Gln Glu Ser Gly Gly Gly Leu Val Gln Ala Gly Asp
1               5                   10                  15

Ser Leu Arg Leu Ser Cys Ala Ala Ser Gly Arg Ser Phe Ser Ser Tyr
            20                  25                  30

Gly Met Gly Trp Phe Arg Gln Ala Pro Gly Lys Glu His Glu Phe Val
        35                  40                  45

Ala Gly Ile Trp Arg Ser Gly Val Ser Leu Tyr Tyr Ala Asp Ser Val
    50                  55                  60

Lys Gly Arg Phe Thr Ile Ser Arg Asp Asp Ala Lys Met Thr Val Ser
65                  70                  75                  80

Leu Gln Met Asn Gly Leu Lys Pro Glu Asp Thr Ala Val Tyr Tyr Cys
                85                  90                  95

Ala Ala Glu Ala Thr Phe Pro Thr Trp Asn Arg Gly Ser Phe Ala Asp
            100                 105                 110

Tyr Asp Tyr Arg Gly Gln Gly Thr Gln Val Thr Val Ser Ser
        115                 120                 125
```

<210> SEQ ID NO 63
<211> LENGTH: 126
<212> TYPE: PRT
<213> ORGANISM: Lama glama

<400> SEQUENCE: 63

```
Gln Val Gln Leu Gln Glu Ser Gly Gly Gly Leu Val Gln Ala Gly Asp
1               5                   10                  15

Ser Leu Arg Leu Ser Cys Ala Ala Ser Gly Arg Ser Phe Ser Ser Tyr
            20                  25                  30

Gly Met Gly Trp Phe Arg Gln Ala Pro Gly Lys Glu His Glu Phe Val
        35                  40                  45
```

```
Ala Gly Ile Trp Arg Ser Gly Val Ser Leu Tyr Tyr Ala Asp Ser Val
 50                  55                  60

Lys Gly Arg Phe Thr Ile Ser Arg Asp Asp Ala Lys Met Thr Val Ser
 65                  70                  75                  80

Leu Gln Met Asn Ser Leu Lys Pro Glu Asp Thr Ala Val Tyr Tyr Cys
                 85                  90                  95

Ala Ala Glu Ala Thr Phe Pro Thr Trp Asn Arg Gly Arg Phe Ala Asp
            100                 105                 110

Tyr Asp Tyr Ser Gly Gln Gly Thr Gln Val Thr Val Ser Ser
            115                 120                 125
```

<210> SEQ ID NO 64
<211> LENGTH: 120
<212> TYPE: PRT
<213> ORGANISM: Lama glama

<400> SEQUENCE: 64

```
Ala Val Gln Leu Val Glu Ser Gly Gly Gly Leu Val Gln Thr Gly Asp
 1               5                  10                  15

Ser Leu Arg Leu Ser Cys Val Ala Ser Gly Gly Thr Phe Ser Arg Tyr
                 20                  25                  30

Ala Met Gly Trp Phe Arg Gln Ala Pro Gly Lys Glu Arg Glu Phe Val
             35                  40                  45

Ala Arg Ile Gly Tyr Ser Gly Arg Ser Ile Ser Tyr Ala Thr Ser Val
 50                  55                  60

Glu Gly Arg Phe Ala Ile Ser Arg Asp Asn Ala Lys Asn Thr Val Tyr
 65                  70                  75                  80

Leu Gln Met Asn Ser Leu Lys Pro Glu Asp Thr Ala Val Tyr Tyr Cys
                 85                  90                  95

Ala Ser Leu Val Ser Gly Thr Leu Tyr Gln Ala Asp Tyr Trp Gly Gln
            100                 105                 110

Gly Thr Gln Val Thr Val Ser Ser
            115                 120
```

<210> SEQ ID NO 65
<211> LENGTH: 120
<212> TYPE: PRT
<213> ORGANISM: Lama glama

<400> SEQUENCE: 65

```
Gln Val Gln Leu Val Glu Ser Gly Gly Gly Leu Val Gln Thr Gly Asp
 1               5                  10                  15

Ser Leu Arg Leu Ser Cys Val Ala Ser Gly Gly Thr Phe Ser Arg Tyr
                 20                  25                  30

Ala Met Gly Trp Phe Arg Gln Pro Pro Gly Lys Glu Arg Asp Phe Val
             35                  40                  45

Ala Arg Ile Gly Tyr Ser Gly Gln Ser Ile Ser Tyr Ala Thr Ser Val
 50                  55                  60

Glu Gly Arg Phe Ala Ile Ser Arg Asp Asn Ala Lys Asn Thr Val Tyr
 65                  70                  75                  80

Leu Gln Met Asn Ser Leu Lys Pro Glu Asp Thr Ala Val Tyr Tyr Cys
                 85                  90                  95

Ala Ser Leu Val Ser Gly Thr Leu Tyr Lys Pro Asn Tyr Trp Gly Gln
            100                 105                 110

Gly Thr Gln Val Thr Val Ser Ser
            115                 120
```

<210> SEQ ID NO 66
<211> LENGTH: 121
<212> TYPE: PRT
<213> ORGANISM: Lama glama

<400> SEQUENCE: 66

Gln Val Lys Leu Glu Glu Ser Gly Gly Gly Leu Val Gln Ala Gly Gly
1               5                   10                  15

Ser Leu Arg Leu Ser Cys Ala Ala Ser Gly Leu Thr Tyr Thr Val Gly
            20                  25                  30

Trp Phe Arg Gln Ala Pro Gly Lys Glu Arg Glu Phe Val Ala Ala Ile
        35                  40                  45

Ser Trp Ser Gly Gly Ser Ala Leu Tyr Ala Asp Ser Val Lys Gly Arg
    50                  55                  60

Phe Thr Ile Ser Arg Asp Asn Ala Lys Asn Thr Val Tyr Leu Gln Met
65                  70                  75                  80

Gly Ser Leu Glu Pro Glu Asp Thr Ala Tyr Tyr Ser Cys Ala Ala Pro
                85                  90                  95

Gly Thr Arg Tyr Tyr Gly Ser Asn Gln Val Asn Tyr Asn Tyr Trp Gly
            100                 105                 110

Gln Gly Thr Gln Val Thr Val Ser Ser
            115                 120

<210> SEQ ID NO 67
<211> LENGTH: 121
<212> TYPE: PRT
<213> ORGANISM: Lama glama

<400> SEQUENCE: 67

Gln Val Lys Leu Glu Glu Ser Gly Gly Gly Leu Val Gln Ala Gly Asp
1               5                   10                  15

Ser Leu Arg Leu Ser Cys Ala Ala Ser Gly Leu Thr Tyr Thr Val Gly
            20                  25                  30

Trp Phe Arg Gln Ala Pro Gly Lys Glu Arg Glu Phe Val Ala Ala Ile
        35                  40                  45

Asp Trp Ser Gly Ser Ala Leu Tyr Ala Asp Ser Val Lys Gly Arg
    50                  55                  60

Phe Thr Ile Ser Arg Asp Asn Thr Lys Asn Thr Val Tyr Leu Gln Met
65                  70                  75                  80

Gly Ser Leu Glu Pro Glu Asp Thr Ala Val Tyr Trp Cys Ala Ala Pro
                85                  90                  95

Gly Thr Arg Tyr His Gly Arg Asn Gln Val Asn Tyr Asn Tyr Trp Gly
            100                 105                 110

Gln Gly Thr Gln Val Thr Val Ser Ser
            115                 120

<210> SEQ ID NO 68
<211> LENGTH: 116
<212> TYPE: PRT
<213> ORGANISM: Lama glama

<400> SEQUENCE: 68

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Ser Ser Asn Tyr
            20                  25                  30

Ala Met Ser Trp Val Arg Gln Ala Pro Gly Lys Gly Leu Glu Trp Val

```
            35                  40                  45
Ser Ser Ile Asn Ser Arg Thr Gly Ser Ile Thr Tyr Ala Asp Ser Val
    50                  55                  60
Lys Gly Arg Phe Thr Ile Thr Leu Asp Asn Ala Lys Asn Thr Leu Tyr
65                  70                  75                  80
Leu Gln Met Asn Ser Leu Lys Pro Glu Asp Thr Ala Val Tyr Tyr Cys
                85                  90                  95
Ala Ser Arg Val Asp Asp Arg Val Ser Arg Gly Gln Gly Thr Gln Val
            100                 105                 110
Thr Val Ser Ser
        115

<210> SEQ ID NO 69
<211> LENGTH: 120
<212> TYPE: PRT
<213> ORGANISM: Lama glama

<400> SEQUENCE: 69

Gln Val Gln Leu Val Glu Ser Gly Gly Gly Leu Val Gln Ala Gly Gly
1               5                   10                  15
Ser Leu Arg Leu Ser Cys Ala Ala Ser Gly Arg Thr Ile Ser Ser Phe
            20                  25                  30
Arg Met Gly Trp Phe Arg Arg Ala Pro Gly Glu Glu Arg Glu Phe Val
        35                  40                  45
Ala Phe Val Arg Ser Asn Gly Thr Ser Thr Tyr Tyr Ala Asp Ser Val
    50                  55                  60
Glu Gly Arg Phe Thr Ile Thr Arg Asp Asn Ala Lys Asn Thr Val Tyr
65                  70                  75                  80
Leu Arg Met Asp Ser Leu Lys Pro Glu Asp Thr Ala Val Tyr Tyr Cys
                85                  90                  95
Ala Ala Ala Thr Arg Asp Tyr Gly Gly Ser Phe Asp Tyr Trp Gly Gln
            100                 105                 110
Gly Thr Gln Val Thr Val Ser Ser
        115                 120

<210> SEQ ID NO 70
<211> LENGTH: 120
<212> TYPE: PRT
<213> ORGANISM: Lama glama

<400> SEQUENCE: 70

Gln Val Gln Leu Gln Asp Ser Gly Gly Gly Leu Val Gln Ala Gly Gly
1               5                   10                  15
Ser Leu Arg Leu Ser Cys Ala Ala Ser Gly Arg Thr Phe Ser Ser Phe
            20                  25                  30
Arg Met Gly Trp Phe Arg Arg Ala Pro Gly Glu Glu Arg Glu Phe Val
        35                  40                  45
Ala Phe Val Arg Ser Asn Gly Thr Ser Thr Tyr Tyr Ala Asp Ser Val
    50                  55                  60
Glu Gly Arg Phe Thr Ile Thr Arg Asp Asn Ala Lys Asn Thr Val Tyr
65                  70                  75                  80
Leu Arg Met Asp Ser Leu Lys Pro Glu Asp Thr Ala Val Tyr Tyr Cys
                85                  90                  95
Ala Ala Ala Thr Arg Asp Tyr Gly Gly Ser Phe Asp Tyr Trp Gly Gln
            100                 105                 110
Gly Thr Gln Val Ile Val Ser Ser
```

```
                115                 120

<210> SEQ ID NO 71
<211> LENGTH: 115
<212> TYPE: PRT
<213> ORGANISM: Lama glama

<400> SEQUENCE: 71

Gln Val Gln Leu Gln Glu Ser Gly Gly Gly Leu Val Gln Pro Gly Gly
1               5                   10                  15

Ser Leu Arg Leu Ser Cys Glu Ala Ser Gly Phe Thr Phe Ser Arg Phe
            20                  25                  30

Gly Met Thr Trp Val Arg Gln Ala Pro Gly Lys Gly Val Glu Trp Val
        35                  40                  45

Ser Gly Ile Ser Ser Leu Gly Asp Ser Thr Leu Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Asp Thr Ala Val Tyr Tyr Cys
                85                  90                  95

Thr Ile Gly Gly Ser Leu Asn Pro Gly Gly Gln Gly Thr Gln Val Thr
            100                 105                 110

Val Ser Ser
        115

<210> SEQ ID NO 72
<211> LENGTH: 128
<212> TYPE: PRT
<213> ORGANISM: Lama glama

<400> SEQUENCE: 72

Ala Val Gln Leu Val Glu Ser Gly Gly Gly Leu Val Gln Ala Gly Asp
1               5                   10                  15

Ser Leu Arg Leu Ser Cys Val Val Ser Gly Thr Thr Phe Ser Ser Ala
            20                  25                  30

Ala Met Gly Trp Phe Arg Gln Ala Pro Gly Lys Glu Arg Glu Phe Val
        35                  40                  45

Gly Ala Ile Lys Trp Ser Gly Thr Ser Thr Tyr Tyr Thr Asp Ser Val
    50                  55                  60

Lys Gly Arg Phe Thr Ile Ser Arg Asp Asn Val Lys Asn Thr Val Tyr
65                  70                  75                  80

Leu Gln Met Asn Asn Leu Lys Pro Glu Asp Thr Gly Val Tyr Thr Cys
                85                  90                  95

Ala Ala Asp Arg Asp Arg Tyr Arg Asp Arg Met Gly Pro Met Thr Thr
            100                 105                 110

Thr Asp Phe Arg Phe Trp Gly Gln Gly Thr Gln Val Thr Val Ser Ser
        115                 120                 125

<210> SEQ ID NO 73
<211> LENGTH: 124
<212> TYPE: PRT
<213> ORGANISM: Lama glama

<400> SEQUENCE: 73

Gln Val Lys Leu Glu Glu Ser Gly Gly Gly Leu Val Gln Thr Gly Gly
1               5                   10                  15

Ser Leu Arg Leu Ser Cys Ala Ala Ser Gly Arg Thr Phe Ser Ser Phe
            20                  25                  30
```

```
Ala Met Gly Trp Phe Arg Gln Ala Pro Gly Arg Glu Arg Glu Phe Val
            35                  40                  45

Ala Ser Ile Gly Ser Ser Gly Ile Thr Thr Asn Tyr Ala Asp Ser Val
        50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Gly Leu Cys Tyr Cys
                85                  90                  95

Ala Val Asn Arg Tyr Gly Ile Pro Tyr Arg Ser Gly Thr Gln Tyr Gln
            100                 105                 110

Asn Trp Gly Gln Gly Thr Gln Val Thr Val Ser Ser
            115                 120

<210> SEQ ID NO 74
<211> LENGTH: 120
<212> TYPE: PRT
<213> ORGANISM: Lama glama

<400> SEQUENCE: 74

Glu Val Gln Leu Glu Glu Ser Gly Gly Leu Val Gln Pro Gly Gly
1               5                   10                  15

Ser Leu Arg Leu Ser Cys Ala Ala Ser Gly Leu Thr Phe Asn Asp Tyr
            20                  25                  30

Ala Met Gly Trp Tyr Arg Gln Ala Pro Gly Lys Glu Arg Asp Met Val
            35                  40                  45

Ala Thr Ile Ser Ile Gly Gly Arg Thr Tyr Tyr Ala Asp Ser Val Lys
        50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Ile Tyr Tyr Cys Val
                85                  90                  95

Ala His Arg Gln Thr Val Val Arg Gly Pro Tyr Leu Leu Trp Gly Gln
            100                 105                 110

Gly Thr Gln Val Thr Val Ser Ser
            115                 120

<210> SEQ ID NO 75
<211> LENGTH: 123
<212> TYPE: PRT
<213> ORGANISM: Lama glama

<400> SEQUENCE: 75

Gln Val Gln Leu Val Glu Ser Gly Gly Lys Leu Val Gln Ala Gly Gly
1               5                   10                  15

Ser Leu Arg Leu Ser Cys Ala Ala Ser Gly Arg Thr Phe Ser Asn Tyr
            20                  25                  30

Ala Met Gly Trp Phe Arg Gln Ala Pro Gly Lys Glu Arg Glu Phe Val
            35                  40                  45

Ala Gly Ser Gly Arg Ser Asn Ser Tyr Asn Tyr Tyr Ser Asp Ser Val
        50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Ser Thr Asn Leu Trp Pro Arg Asp Arg Asn Leu Tyr Ala Tyr
            100                 105                 110
```

```
Trp Gly Gln Gly Thr Gln Val Thr Val Ser Ser
        115                 120
```

<210> SEQ ID NO 76
<211> LENGTH: 125
<212> TYPE: PRT
<213> ORGANISM: Lama glama

<400> SEQUENCE: 76

```
Glu Val Gln Leu Val Glu Ser Gly Gly Gly Leu Val Gln Ala Gly Asp
1               5                   10                  15

Ser Leu Arg Leu Ser Cys Ala Ala Ser Gly Arg Ser Leu Gly Ile Tyr
            20                  25                  30

Arg Met Gly Trp Phe Arg Gln Val Pro Gly Lys Glu Arg Glu Phe Val
        35                  40                  45

Ala Ala Ile Ser Trp Ser Gly Gly Thr Thr Arg Tyr Leu Asp Ser Val
    50                  55                  60

Lys Gly Arg Phe Thr Ile Ser Arg Asp Ser Thr Lys Asn Ala Val Tyr
65                  70                  75                  80

Leu Gln Met Asn Ser Leu Lys Pro Glu Asp Thr Ala Val Tyr Tyr Cys
                85                  90                  95

Ala Val Asp Ser Ser Gly Arg Leu Tyr Trp Thr Leu Ser Thr Ser Tyr
            100                 105                 110

Asp Tyr Trp Gly Gln Gly Thr Gln Val Thr Val Ser Ser
        115                 120                 125
```

<210> SEQ ID NO 77
<211> LENGTH: 125
<212> TYPE: PRT
<213> ORGANISM: Lama glama

<400> SEQUENCE: 77

```
Gln Val Gln Leu Val Glu Phe Gly Gly Gly Leu Val Gln Ala Gly Asp
1               5                   10                  15

Ser Leu Arg Leu Ser Cys Ala Ala Ser Gly Arg Ser Leu Gly Ile Tyr
            20                  25                  30

Lys Met Ala Trp Phe Arg Gln Val Pro Gly Lys Glu Arg Glu Phe Val
        35                  40                  45

Ala Ala Ile Ser Trp Ser Gly Gly Thr Thr Arg Tyr Ile Asp Ser Val
    50                  55                  60

Lys Gly Arg Phe Thr Leu Ser Arg Asp Asn Thr Lys Asn Met Val Tyr
65                  70                  75                  80

Leu Gln Met Asn Ser Leu Lys Pro Asp Asp Thr Ala Val Tyr Tyr Cys
                85                  90                  95

Ala Val Asp Ser Ser Gly Arg Leu Tyr Trp Thr Leu Ser Thr Ser Tyr
            100                 105                 110

Asp Tyr Trp Gly Gln Gly Thr Gln Val Thr Val Ser Ser
        115                 120                 125
```

<210> SEQ ID NO 78
<211> LENGTH: 124
<212> TYPE: PRT
<213> ORGANISM: Lama glama

<400> SEQUENCE: 78

```
Glu Val Gln Leu Val Glu Ser Gly Gly Gly Leu Val Gln Ala Gly Gly
1               5                   10                  15
```

```
Ser Leu Ser Leu Ser Cys Ala Ala Ser Gly Arg Thr Phe Ser Pro Tyr
            20                  25                  30

Thr Met Gly Trp Phe Arg Gln Ala Pro Gly Lys Glu Arg Glu Phe Leu
        35                  40                  45

Ala Gly Val Thr Trp Ser Gly Ser Ser Thr Tyr Gly Asp Ser Val
    50                  55                  60

Lys Gly Arg Phe Thr Ala Ser Arg Asp Ser Ala Lys Asn Thr Val Thr
 65                  70                  75                  80

Leu Glu Met Asn Ser Leu Asn Pro Glu Asp Thr Ala Val Tyr Tyr Cys
                85                  90                  95

Ala Ala Ala Tyr Gly Gly Gly Leu Tyr Arg Asp Pro Arg Ser Tyr Asp
            100                 105                 110

Tyr Trp Gly Arg Gly Thr Gln Val Thr Val Ser Ser
        115                 120
```

<210> SEQ ID NO 79
<211> LENGTH: 131
<212> TYPE: PRT
<213> ORGANISM: Lama glama

<400> SEQUENCE: 79

```
Ala Val Gln Leu Val Glu Ser Gly Gly Gly Leu Val Gln Ala Gly Gly
 1               5                  10                  15

Ser Leu Arg Leu Ser Cys Ala Ala Ser Gly Phe Thr Leu Asp Ala Trp
            20                  25                  30

Pro Ile Ala Trp Phe Arg Gln Ala Pro Gly Lys Glu Arg Glu Gly Val
        35                  40                  45

Ser Cys Ile Arg Asp Gly Thr Thr Tyr Tyr Ala Asp Ser Val Lys Gly
    50                  55                  60

Arg Phe Thr Ile Ser Ser Asp Asn Ala Asn Asn Thr Val Tyr Leu Gln
 65                  70                  75                  80

Thr Asn Ser Leu Lys Pro Glu Asp Thr Ala Val Tyr Tyr Cys Ala Ala
                85                  90                  95

Pro Ser Gly Pro Ala Thr Gly Ser Ser His Thr Phe Gly Ile Tyr Trp
            100                 105                 110

Asn Leu Arg Asp Asp Tyr Asp Asn Trp Gly Gln Gly Thr Gln Val Thr
        115                 120                 125

Val Ser Ser
    130
```

<210> SEQ ID NO 80
<211> LENGTH: 126
<212> TYPE: PRT
<213> ORGANISM: Lama glama

<400> SEQUENCE: 80

```
Glu Val Gln Leu Val Glu Ser Gly Gly Gly Leu Val Gln Ala Gly Gly
 1               5                  10                  15

Ser Leu Arg Leu Ser Cys Ala Ala Ser Gly Phe Thr Phe Asp His Tyr
            20                  25                  30

Thr Ile Gly Trp Phe Arg Gln Val Pro Gly Lys Glu Arg Glu Gly Val
        35                  40                  45

Ser Cys Ile Ser Ser Ser Asp Gly Ser Thr Tyr Tyr Ala Asp Ser Val
    50                  55                  60

Lys Gly Arg Phe Thr Ile Ser Asp Asn Ala Lys Asn Thr Val Tyr
 65                  70                  75                  80
```

```
Leu Gln Met Asn Thr Leu Glu Pro Asp Asp Thr Ala Val Tyr Tyr Cys
                85                  90                  95

Ala Ala Gly Gly Leu Leu Arg Val Glu Leu Gln Ala Ser Asp
            100                 105                 110

Tyr Asp Tyr Trp Gly Gln Gly Ile Gln Val Thr Val Ser Ser
        115                 120                 125
```

<210> SEQ ID NO 81
<211> LENGTH: 128
<212> TYPE: PRT
<213> ORGANISM: Lama glama

<400> SEQUENCE: 81

```
Ala Val Gln Leu Val Asp Ser Gly Gly Gly Leu Val Gln Pro Gly Gly
1               5                   10                  15

Ser Leu Arg Leu Ser Cys Thr Ala Ser Gly Phe Thr Leu Asp Tyr Tyr
            20                  25                  30

Ala Ile Gly Trp Phe Arg Gln Ala Pro Gly Lys Glu Arg Glu Gly Val
        35                  40                  45

Ala Cys Ile Ser Asn Ser Asp Gly Ser Thr Tyr Tyr Gly Asp Ser Val
    50                  55                  60

Lys Gly Arg Phe Thr Ile Ser Arg Asp Asn Ala Lys Thr Thr Val Tyr
65                  70                  75                  80

Leu Gln Met Asn Ser Leu Lys Pro Glu Asp Thr Ala Val Tyr Tyr Cys
                85                  90                  95

Ala Thr Ala Asp Arg His Tyr Ser Ala Ser His His Pro Phe Ala Asp
            100                 105                 110

Phe Ala Phe Asn Ser Trp Gly Gln Gly Thr Gln Val Thr Val Ser Ser
        115                 120                 125
```

<210> SEQ ID NO 82
<211> LENGTH: 120
<212> TYPE: PRT
<213> ORGANISM: Lama glama

<400> SEQUENCE: 82

```
Glu Val Gln Leu Val Glu Ser Gly Gly Gly Leu Val Gln Ala Gly Gly
1               5                   10                  15

Ser Leu Arg Leu Ser Cys Ala Ala Tyr Gly Leu Thr Phe Trp Arg Ala
            20                  25                  30

Ala Met Ala Trp Phe Arg Arg Ala Pro Gly Lys Glu Arg Glu Leu Val
        35                  40                  45

Val Ala Arg Asn Trp Gly Asp Gly Ser Thr Arg Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Val Arg Thr Tyr Gly Ser Ala Thr Tyr Asp Ile Trp Gly Gln
            100                 105                 110

Gly Thr Gln Val Thr Val Ser Ser
        115                 120
```

<210> SEQ ID NO 83
<211> LENGTH: 123
<212> TYPE: PRT
<213> ORGANISM: Lama glama

<400> SEQUENCE: 83

Glu Val Gln Leu Val Glu Ser Gly Gly Gly Leu Val Gln Asp Gly Gly
1               5                   10                  15

Ser Leu Arg Leu Ser Cys Ile Phe Ser Gly Arg Thr Phe Ala Asn Tyr
            20                  25                  30

Ala Met Gly Trp Phe Arg Gln Ala Pro Gly Lys Glu Arg Glu Phe Val
        35                  40                  45

Ala Ala Ile Asn Arg Asn Gly Gly Thr Thr Asn Tyr Ala Asp Ala Leu
    50                  55                  60

Lys Gly Arg Phe Thr Ile Ser Arg Asp Asn Thr Lys Asn Thr Ala Phe
65                  70                  75                  80

Leu Gln Met Asn Ser Leu Lys Pro Asp Asp Thr Ala Val Tyr Tyr Cys
                85                  90                  95

Ala Ala Arg Glu Trp Pro Phe Ser Thr Ile Pro Ser Gly Trp Arg Tyr
            100                 105                 110

Trp Gly Gln Gly Thr Gln Val Thr Val Ser Ser
            115                 120

<210> SEQ ID NO 84
<211> LENGTH: 125
<212> TYPE: PRT
<213> ORGANISM: Lama glama

<400> SEQUENCE: 84

Asp Val Gln Leu Val Glu Ser Gly Gly Gly Trp Val Gln Pro Gly Gly
1               5                   10                  15

Ser Leu Arg Leu Ser Cys Ala Ala Ser Gly Pro Thr Ala Ser Ser His
            20                  25                  30

Ala Ile Gly Trp Phe Arg Gln Ala Pro Gly Lys Glu Arg Glu Phe Val
        35                  40                  45

Val Gly Ile Asn Arg Gly Gly Val Thr Arg Asp Tyr Ala Asp Ser Val
    50                  55                  60

Lys Gly Arg Phe Ala Val Ser Arg Asp Asn Val Lys Asn Thr Val Tyr
65                  70                  75                  80

Leu Gln Met Asn Arg Leu Lys Pro Glu Asp Ser Ala Ile Tyr Ile Cys
                85                  90                  95

Ala Ala Arg Pro Glu Tyr Ser Phe Thr Ala Met Ser Lys Gly Asp Met
            100                 105                 110

Asp Tyr Trp Gly Lys Gly Thr Leu Val Thr Val Ser Ser
        115                 120                 125

<210> SEQ ID NO 85
<211> LENGTH: 23
<212> TYPE: DNA
<213> ORGANISM: Lama glama

<400> SEQUENCE: 85
ggctgagctc ggtggtcctg gct                                    23

<210> SEQ ID NO 86
<211> LENGTH: 45
<212> TYPE: DNA
<213> ORGANISM: Lama glama

<400> SEQUENCE: 86
aactggaaga attcgcggcc gcaggaattt tttttttttt tttt             45

```
<210> SEQ ID NO 87
<211> LENGTH: 23
<212> TYPE: DNA
<213> ORGANISM: Lama glama

<400> SEQUENCE: 87
ggctgagctc ggtggtcctg gct                                       23

<210> SEQ ID NO 88
<211> LENGTH: 45
<212> TYPE: DNA
<213> ORGANISM: Lama glama

<400> SEQUENCE: 88
aactggaaga attcgcggcc gcaggaattt ttttttttt ttttt                45

<210> SEQ ID NO 89
<211> LENGTH: 23
<212> TYPE: DNA
<213> ORGANISM: Lama glama

<400> SEQUENCE: 89
ggctgagctc ggtggtcctg gct                                       23

<210> SEQ ID NO 90
<211> LENGTH: 45
<212> TYPE: DNA
<213> ORGANISM: Lama glama

<400> SEQUENCE: 90
aactggaaga attcgcggcc gcaggaattt ttttttttt ttttt                45

<210> SEQ ID NO 91
<211> LENGTH: 23
<212> TYPE: DNA
<213> ORGANISM: Lama glama

<400> SEQUENCE: 91
cccctggccc cagtagttat acg                                       23

<210> SEQ ID NO 92
<211> LENGTH: 17
<212> TYPE: DNA
<213> ORGANISM: Lama glama

<400> SEQUENCE: 92
tgtgcagcaa gagacgg                                              17

<210> SEQ ID NO 93
<211> LENGTH: 44
<212> TYPE: DNA
<213> ORGANISM: Lama glama

<400> SEQUENCE: 93
gtcctcgcaa ctgcggccca gccggcctgt gcagcaagag acgg                44

<210> SEQ ID NO 94
<211> LENGTH: 45
<212> TYPE: DNA
<213> ORGANISM: Lama glama

<400> SEQUENCE: 94
gtcctcgcaa ctgcgcggcc gccccctggc cccagtagtt atacg                45
```

<210> SEQ ID NO 95
<211> LENGTH: 53
<212> TYPE: DNA
<213> ORGANISM: Lama glama

<400> SEQUENCE: 95
aacagttaag cttccgcttg cggccgcgga gctggggtct tcgctgtggt gcg        53

<210> SEQ ID NO 96
<211> LENGTH: 23
<212> TYPE: DNA
<213> ORGANISM: Lama glama

<400> SEQUENCE: 96
gaggtbcarc tgcaggastc ygg        23

<210> SEQ ID NO 97
<211> LENGTH: 20
<212> TYPE: DNA
<213> ORGANISM: Lama glama

<400> SEQUENCE: 97
ctggccccag aagtcatacc        20

<210> SEQ ID NO 98
<211> LENGTH: 19
<212> TYPE: DNA
<213> ORGANISM: Lama glama

<400> SEQUENCE: 98
tgtgcatgtg cagcaaacc        19

<210> SEQ ID NO 99
<211> LENGTH: 46
<212> TYPE: DNA
<213> ORGANISM: Lama glama

<400> SEQUENCE: 99
gtcctcgcaa ctgcggccca gccggcctgt gcatgtgcag caaacc        46

<210> SEQ ID NO 100
<211> LENGTH: 42
<212> TYPE: DNA
<213> ORGANISM: Lama glama

<400> SEQUENCE: 100
gtcctcgcaa ctgcgcggcc gcctggcccc agaagtcata cc        42

<210> SEQ ID NO 101
<211> LENGTH: 23
<212> TYPE: DNA
<213> ORGANISM: Lama glama

<400> SEQUENCE: 101
ggctgagctc ggtggtcctg gct        23

<210> SEQ ID NO 102
<211> LENGTH: 45
<212> TYPE: DNA
<213> ORGANISM: Lama glama

<400> SEQUENCE: 102
aactggaaga attcgcggcc gcaggaattt tttttttttt ttttt        45

<210> SEQ ID NO 103
<211> LENGTH: 57
<212> TYPE: DNA
<213> ORGANISM: Lama glama

<400> SEQUENCE: 103
catgccatga ctcgcggccc agccggccat ggccgaggtg cagctggtgg agtctgg        57

<210> SEQ ID NO 104
<211> LENGTH: 57
<212> TYPE: DNA
<213> ORGANISM: Lama glama

<400> SEQUENCE: 104
catgccatga ctcgcggccc agccggccat ggccgatgtg cagctggtgg agtctgg        57

<210> SEQ ID NO 105
<211> LENGTH: 57
<212> TYPE: DNA
<213> ORGANISM: Lama glama

<400> SEQUENCE: 105
catgccatga ctcgcggccc agccggccat ggccgcggtg cagctggtgg agtctgg        57

<210> SEQ ID NO 106
<211> LENGTH: 57
<212> TYPE: DNA
<213> ORGANISM: Lama glama

<400> SEQUENCE: 106
catgccatga ctcgcggccc agccggccat ggccgccgtg cagctggtgg attctgg        57

<210> SEQ ID NO 107
<211> LENGTH: 57
<212> TYPE: DNA
<213> ORGANISM: Lama glama

<400> SEQUENCE: 107
catgccatga ctcgcggccc agccggccat ggcccaggtg cagctggtgg agtctgg        57

<210> SEQ ID NO 108
<211> LENGTH: 57
<212> TYPE: DNA
<213> ORGANISM: Lama glama

<400> SEQUENCE: 108
catgccatga ctcgcggccc agccggccat ggcccaggta cagctggtgg agtctgg        57

<210> SEQ ID NO 109
<211> LENGTH: 57
<212> TYPE: DNA
<213> ORGANISM: Lama glama

<400> SEQUENCE: 109
catgccatga ctcgcggccc agccggccat ggcccaggta aagctggagg agtctgg        57

<210> SEQ ID NO 110
<211> LENGTH: 19
<212> TYPE: DNA
<213> ORGANISM: Lama glama

<400> SEQUENCE: 110
ccacagacag ccctcatag                                                      19

<210> SEQ ID NO 111
<211> LENGTH: 20
<212> TYPE: DNA
<213> ORGANISM: Lama glama

<400> SEQUENCE: 111
ggataacaat ttcacacagg                                                     20

<210> SEQ ID NO 112
<211> LENGTH: 122
<212> TYPE: PRT
<213> ORGANISM: Lama glama

<400> SEQUENCE: 112

Ala Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser His
            20                  25                  30

Tyr Met Ser Trp Phe Arg Gln Ala Pro Gly Lys Glu Arg Glu Phe Val
        35                  40                  45

Ala Ala Ile Thr Ser Ser Ser Arg Thr Tyr Tyr Thr Glu Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Ser Glu Asp Thr Ala Val Tyr Tyr Cys Ala
                85                  90                  95

Ala Asp Arg Thr Phe Tyr Gly Ser Thr Trp Ser Lys Tyr Asp Tyr Arg
            100                 105                 110

Gly Gln Gly Thr Gln Val Thr Val Ser Ser
        115                 120

<210> SEQ ID NO 113
<211> LENGTH: 122
<212> TYPE: PRT
<213> ORGANISM: Lama glama

<400> SEQUENCE: 113

Gln Val Lys Leu Glu Glu Ser Gly Gly Gly Leu Val Gln Pro Gly Asp
1               5                   10                  15

Ser Leu Arg Leu Ser Cys Ala Ala Ser Gly Phe Thr Phe Ser Ser His
            20                  25                  30

Tyr Met Ser Trp Phe Arg Gln Ala Pro Gly Lys Glu Arg Glu Phe Val
        35                  40                  45

Ala Ala Ile Thr Ser Ser Ser Arg Thr Tyr Tyr Thr Glu Ser Val Lys
    50                  55                  60

Gly Arg Phe Thr Ile Ser Arg Asp Asn Ala Lys Asn Thr Val Tyr Leu
65                  70                  75                  80

Gln Met Asp Ser Leu Lys Ser Glu Asp Thr Ala Val Tyr Tyr Cys Ala
                85                  90                  95

Ala Asp Arg Thr Phe Tyr Gly Ser Thr Trp Ser Lys Tyr Asp Tyr Arg
            100                 105                 110

Gly Gln Gly Thr Gln Val Thr Val Ser Ser
        115                 120

<210> SEQ ID NO 114
<211> LENGTH: 127

```
<212> TYPE: PRT
<213> ORGANISM: Lama glama

<400> SEQUENCE: 114

Gln Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Asn Tyr
            20                  25                  30

Val Met Gly Trp Phe Arg Gln Ala Pro Gly Lys Glu Arg Asp Phe Val
        35                  40                  45

Val Gly Ile Gly Arg Ser Gly Gly Asp Asn Thr Tyr Tyr Ala Asp Ser
    50                  55                  60

Val Lys Gly Arg Phe Thr Ile Ser Trp Asp Asn Ala Lys Asn Thr Met
65                  70                  75                  80

Tyr Leu Gln Met Asn Ser Leu Lys Pro Glu Asp Thr Ala Val Tyr Tyr
                85                  90                  95

Cys Ala Ala Ser Thr Tyr Ser Arg Asp Thr Ile Phe Thr Lys Trp Ala
            100                 105                 110

Asn Tyr Asn Tyr Trp Gly Gln Gly Thr Gln Val Thr Val Ser Ser
        115                 120                 125

<210> SEQ ID NO 115
<211> LENGTH: 122
<212> TYPE: PRT
<213> ORGANISM: Lama glama

<400> SEQUENCE: 115

Gln Val Gln Leu Gln Glu Ser Gly Gly Gly Ser Val Gln Ala Gly Gly
1               5                   10                  15

Ser Leu Lys Leu Ser Cys Ala Ala Ser Gly Arg Gly Phe Ser Arg Tyr
            20                  25                  30

Ala Met Gly Trp Phe Arg Gln Ala Pro Gly Gln Asp Arg Glu Phe Val
        35                  40                  45

Ala Thr Ile Ser Trp Thr Asn Ser Thr Asp Tyr Ala Asp Ser Val Lys
    50                  55                  60

Gly Arg Phe Ala Ile Ser Arg Asp Asn Ala Lys Asn Thr Ala Tyr Leu
65                  70                  75                  80

Gln Met Asn Ser Leu Lys Pro Glu Asp Thr Ala Val Tyr Tyr Cys Ala
                85                  90                  95

Ala Asp Lys Trp Ala Ser Ser Thr Arg Ser Ile Asp Tyr Asp Tyr Trp
            100                 105                 110

Gly Gln Gly Ile Gln Val Thr Val Ser Ser
        115                 120

<210> SEQ ID NO 116
<211> LENGTH: 122
<212> TYPE: PRT
<213> ORGANISM: Lama glama

<400> SEQUENCE: 116

Gln Val Gln Leu Gln Glu Ser Gly Gly Gly Ser Val Gln Ala Gly Gly
1               5                   10                  15

Ser Leu Lys Leu Ser Cys Thr Ala Ser Gly Arg Arg Phe Ser Thr Tyr
            20                  25                  30

Ala Val Gly Trp Phe Arg Gln Ala Pro Gly Gln Asp Arg Glu Phe Val
        35                  40                  45

Ala Thr Ile Ser Trp Thr Asn Ser Thr Asp Tyr Ala Asp Ser Val Lys
```

```
                    50                  55                  60
Gly Arg Phe Thr Ile Ser Arg Asp Asn Ala Lys Asn Thr Gly Tyr Leu
 65                  70                  75                  80

Gln Met Asn Ser Leu Lys Pro Glu Asp Thr Ser Val Tyr Val Cys Ala
                    85                  90                  95

Ala Asp Lys Trp Ser Ser Arg Arg Ser Val Asp Tyr Asp Tyr Trp
                100                 105                 110

Gly Gln Gly Thr Gln Val Thr Val Ser Ser
            115                 120
```

<210> SEQ ID NO 117
<211> LENGTH: 122
<212> TYPE: PRT
<213> ORGANISM: Lama glama

<400> SEQUENCE: 117

```
Glu Val Gln Leu Val Glu Ser Gly Gly Gly Val Gln Ala Gly Gly
 1               5                  10                  15

Ser Leu Lys Leu Ser Cys Thr Ala Ser Gly Arg Arg Phe Ser Thr Tyr
                 20                  25                  30

Ala Val Gly Trp Phe Arg Gln Ala Pro Gly Gln Asp Arg Glu Phe Val
                35                  40                  45

Ala Thr Ile Ser Trp Thr Asn Ser Thr Asp Tyr Ala Asp Ser Val Lys
                50                  55                  60

Gly Arg Phe Thr Ile Ser Arg Asp Asn Ala Lys Asn Thr Gly Tyr Leu
 65                  70                  75                  80

Gln Met Asn Ser Leu Lys Pro Glu Asp Thr Ser Val Tyr Val Cys Ala
                    85                  90                  95

Ala Asp Lys Trp Ser Ser Arg Arg Ser Val Asp Tyr Asp Tyr Trp
                100                 105                 110

Gly Gln Gly Thr Gln Val Thr Val Ser Ser
            115                 120
```

<210> SEQ ID NO 118
<211> LENGTH: 129
<212> TYPE: PRT
<213> ORGANISM: Lama glama

<400> SEQUENCE: 118

```
Gln Val Gln Leu Gln Glu Ser Gly Gly Gly Leu Val Gln Ala Gly Gly
 1               5                  10                  15

Ser Leu Leu Leu Ser Cys Ala Ala Ser Gly Arg Thr Phe Ser Ser Tyr
                 20                  25                  30

Ala Met Gly Trp Phe Arg Gln Ala Pro Gly Lys Glu Arg Glu Phe Val
                35                  40                  45

Ala Ala Ile Asn Trp Ser Gly Gly Ser Thr Ser Tyr Ala Asp Ser Val
                50                  55                  60

Lys Gly Arg Phe Thr Ile Ser Lys Asp Asn Thr Lys Asn Thr Val Tyr
 65                  70                  75                  80

Leu Gln Met Asn Ser Leu Lys Pro Glu Asp Thr Ala Ala Phe Tyr Cys
                    85                  90                  95

Ala Ala Thr Tyr Asn Pro Tyr Ser Arg Asp His Tyr Phe Pro Arg Met
                100                 105                 110

Thr Thr Glu Tyr Asp Tyr Trp Gly Gln Gly Thr Gln Val Thr Val Ser
                115                 120                 125

Ser
```

```
<210> SEQ ID NO 119
<211> LENGTH: 129
<212> TYPE: PRT
<213> ORGANISM: Lama glama

<400> SEQUENCE: 119

Gln Val Gln Leu Gln Glu Ser Gly Gly Gly Leu Val Gln Ala Gly Gly
1               5                   10                  15

Ser Leu Leu Leu Ser Cys Ala Ala Ser Gly Arg Thr Phe Ser Ser Tyr
            20                  25                  30

Ala Met Gly Trp Phe Arg Gln Ala Pro Gly Lys Glu Arg Glu Phe Val
        35                  40                  45

Ala Ala Ile Asn Trp Ser Gly Ser Thr Ser Tyr Ala Asp Ser Val
    50                  55                  60

Lys Gly Arg Phe Thr Ile Ser Arg Asp Asn Thr Lys Asn Thr Val Tyr
65                  70                  75                  80

Leu Gln Met Asn Ser Leu Lys Pro Glu Asp Thr Ala Ala Phe Tyr Cys
                85                  90                  95

Ala Ala Thr Tyr Asn Pro Tyr Ser Arg Asp His Tyr Phe Pro Arg Met
            100                 105                 110

Thr Thr Glu Tyr Asp Tyr Trp Gly Gln Gly Thr Gln Val Thr Val Ser
        115                 120                 125

Ser

<210> SEQ ID NO 120
<211> LENGTH: 72
<212> TYPE: PRT
<213> ORGANISM: Lama glama

<400> SEQUENCE: 120

Gln Val Lys Leu Glu Glu Ser Gly Gly Gly Leu Val Gln Ala Gly Gly
1               5                   10                  15

Ser Leu Arg Leu Ser Cys Ala Ala Ser Gly Ser Ile Phe Ser Ile Asn
            20                  25                  30

Ala Met Gly Trp Tyr Arg Gln Ala Pro Gly Lys Gln Arg Glu Leu Val
        35                  40                  45

Ala Arg Ile Thr Gly Thr Gly Thr Ile Thr Gly Ala Val Ser Thr
    50                  55                  60

Asn Tyr Ala Asp Ser Val Lys Gly
65                  70

<210> SEQ ID NO 121
<211> LENGTH: 65
<212> TYPE: PRT
<213> ORGANISM: Lama glama

<400> SEQUENCE: 121

Gln Val Lys Leu Glu Glu Ser Gly Gly Gly Leu Val Gln Ala Gly Asp
1               5                   10                  15

Ser Leu Arg Leu Ser Cys Ala Ala Ser Gly Arg Ser Phe Ser Ser Ile
            20                  25                  30

Thr Met Gly Trp Phe Arg Gln Ala Pro Gly Lys Glu Arg Gln Phe Val
        35                  40                  45

Ser Ala Ile Asn Ser Asn Gly Asn Arg Tyr Tyr Ala Asp Ser Val Lys
    50                  55                  60

Gly
```

<210> SEQ ID NO 122
<211> LENGTH: 64
<212> TYPE: PRT
<213> ORGANISM: Lama glama

<400> SEQUENCE: 122

Glu Val Gln Leu Val Glu Ser Gly Gly Gly Leu Val Gln Ala Gly Gly
1               5                   10                  15

Ser Leu Arg Leu Ser Cys Ala Val Ser Gly Arg Thr Phe Ser Ser Met
            20                  25                  30

Gly Trp Phe Arg Gln Ala Pro Gly Lys Glu Arg Glu Phe Val Ala Thr
        35                  40                  45

Ile Asn Leu Ser Gly Asp Arg Thr Asp Tyr Ala Asp Ser Val Lys Gly
    50                  55                  60

<210> SEQ ID NO 123
<211> LENGTH: 66
<212> TYPE: PRT
<213> ORGANISM: Lama glama

<400> SEQUENCE: 123

Glu Val Gln Leu Val Glu Ser Gly Gly Gly Leu Val Gln Ala Gly Gly
1               5                   10                  15

Ser Leu Arg Leu Ser Cys Thr Ala Ser Gly Arg Thr Phe Ser Ser Tyr
            20                  25                  30

Ala Met Gly Trp Phe Arg Gln Thr Pro Gly Lys Glu Arg Glu Phe Val
        35                  40                  45

Ala Ala Ile Thr Ser Ser Gly Gly Ser Thr Tyr Tyr Ala Asp Ser Val
    50                  55                  60

Lys Gly
65

<210> SEQ ID NO 124
<211> LENGTH: 66
<212> TYPE: PRT
<213> ORGANISM: Lama glama

<400> SEQUENCE: 124

Glu Val Gln Leu Val Glu Ser Gly Gly Gly Leu Val Gln Pro Gly Gly
1               5                   10                  15

Ser Leu Arg Leu Ser Cys Val Ala Ser Gly Phe Thr Phe Ala Asp Tyr
            20                  25                  30

Ala Met Ser Trp Val Arg Gln Ala Pro Gly Lys Gly Leu Gln Trp Val
        35                  40                  45

Ser Ser Ile Ser Tyr Asn Gly Asp Thr Thr Tyr Tyr Ala Glu Ser Met
    50                  55                  60

Lys Asp
65

<210> SEQ ID NO 125
<211> LENGTH: 53
<212> TYPE: DNA
<213> ORGANISM: Lama glama

<400> SEQUENCE: 125
aacagttaag cttccgcttg cggccgctgg ttgtggtttt ggtgtcttgg gtt        53

```
<210> SEQ ID NO 126
<211> LENGTH: 122
<212> TYPE: PRT
<213> ORGANISM: Lama glama

<400> SEQUENCE: 126

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser His
            20                  25                  30

Tyr Met Ser Trp Phe Arg Gln Ala Pro Gly Lys Glu Arg Glu Phe Val
        35                  40                  45

Ala Ala Ile Thr Ser Ser Arg Thr Tyr Tyr Thr Glu Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Ser Glu Asp Thr Ala Val Tyr Tyr Cys Ala
                85                  90                  95

Ala Asp Arg Thr Phe Tyr Gly Ser Thr Trp Ser Lys Tyr Asp Tyr Arg
            100                 105                 110

Gly Gln Gly Thr Gln Val Thr Val Ser Ser
        115                 120

<210> SEQ ID NO 127
<211> LENGTH: 127
<212> TYPE: PRT
<213> ORGANISM: Lama glama

<400> SEQUENCE: 127

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Asn Tyr
            20                  25                  30

Val Met Gly Trp Phe Arg Gln Ala Pro Gly Lys Glu Arg Asp Phe Val
        35                  40                  45

Val Gly Ile Gly Arg Ser Gly Gly Asp Asn Thr Tyr Tyr Ala Asp Ser
    50                  55                  60

Val Lys Gly Arg Phe Thr Ile Ser Trp Asp Asn Ala Lys Asn Thr Met
65                  70                  75                  80

Tyr Leu Gln Met Asn Ser Leu Lys Pro Glu Asp Thr Ala Val Tyr Tyr
                85                  90                  95

Cys Ala Ala Ser Thr Tyr Ser Arg Asp Thr Ile Phe Thr Lys Trp Ala
            100                 105                 110

Asn Tyr Asn Tyr Trp Gly Gln Gly Thr Gln Val Thr Val Ser Ser
        115                 120                 125

<210> SEQ ID NO 128
<211> LENGTH: 123
<212> TYPE: PRT
<213> ORGANISM: Lama glama

<400> SEQUENCE: 128

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Ser Phe Ser Ser Tyr
            20                  25                  30

Ala Met Ala Trp Phe Arg Gln Ala Pro Gly Lys Glu Arg Glu Phe Val
        35                  40                  45
```

```
Ala Ala Ile Ser Trp Gly Gly Ser Thr Tyr Tyr Ala Val Ser Val
        50                  55                  60

Lys Gly Arg Phe Thr Ile Ser Arg Asp Asn Ala Lys Asn Thr Val Tyr
 65                  70                  75                  80

Leu Gln Met Asn Ser Leu Lys Pro Glu Asp Thr Ala Arg Tyr Tyr Cys
                85                  90                  95

Ala Ala Asp Glu Thr Phe His Ser Ser Ala Tyr Gly Glu Tyr Glu Tyr
            100                 105                 110

Trp Gly Gln Gly Thr Gln Val Thr Val Ser Ser
            115                 120

<210> SEQ ID NO 129
<211> LENGTH: 123
<212> TYPE: PRT
<213> ORGANISM: Lama glama

<400> SEQUENCE: 129

Glu Val Gln Leu Val Glu Ser Gly Gly Gly Leu Val Gln Ala Gly Gly
  1               5                  10                  15

Ser Leu Arg Leu Ser Cys Ala Ala Ser Gly Arg Ser Phe Ser Ser Tyr
                 20                  25                  30

Ala Met Ala Trp Phe Arg Gln Ala Pro Gly Lys Glu Arg Glu Phe Val
             35                  40                  45

Ala Ala Ile Ser Trp Gly Gly Ser Thr Tyr Tyr Ala Val Ser Val
        50                  55                  60

Lys Gly Arg Phe Thr Ile Ser Arg Asp Asn Ala Lys Asn Thr Val Tyr
 65                  70                  75                  80

Leu Gln Met Asn Ser Leu Lys Pro Glu Asp Thr Ala Arg Tyr Tyr Cys
                85                  90                  95

Ala Ala Asp Glu Thr Phe His Ser Ser Ala Tyr Gly Glu Tyr Glu Tyr
            100                 105                 110

Trp Gly Gln Gly Thr Gln Val Thr Val Ser Ser
            115                 120

<210> SEQ ID NO 130
<211> LENGTH: 122
<212> TYPE: PRT
<213> ORGANISM: Lama glama

<400> SEQUENCE: 130

Glu Val Gln Leu Val Glu Ser Gly Gly Gly Ser Val Gln Ala Gly Gly
  1               5                  10                  15

Ser Leu Lys Leu Ser Cys Ala Ala Ser Gly Arg Ser Phe Ser Thr Tyr
                 20                  25                  30

Ala Met Gly Trp Phe Arg Gln Ala Pro Gly Gln Asp Arg Glu Phe Val
             35                  40                  45

Ala Thr Ile Ser Trp Thr Asp Ser Thr Asp Tyr Ala Asp Ser Val Lys
        50                  55                  60

Gly Arg Phe Thr Ile Ser Arg Asp Asn Ala Lys Asn Thr Gly Tyr Leu
 65                  70                  75                  80

Gln Met Asn Ser Leu Lys Pro Glu Asp Thr Ala Val Tyr Tyr Cys Ala
                85                  90                  95

Ala Asp Arg Trp Ala Ser Ser Arg Arg Asn Val Asp Tyr Asp Tyr Trp
            100                 105                 110

Gly Gln Gly Thr Gln Val Thr Val Ser Ser
            115                 120
```

<210> SEQ ID NO 131
<211> LENGTH: 129
<212> TYPE: PRT
<213> ORGANISM: Lama glama

<400> SEQUENCE: 131

Gln Val Gln Leu Gln Glu Ser Gly Gly Gly Leu Val Gln Ala Gly Gly
1               5                   10                  15

Ser Leu Leu Leu Ser Cys Ala Ala Ser Gly Arg Thr Phe Ser Ser Tyr
            20                  25                  30

Ala Met Gly Trp Phe Arg Gln Ala Pro Gly Lys Glu Arg Glu Phe Val
        35                  40                  45

Ala Ala Ile Asn Trp Ser Gly Ser Thr Ser Tyr Ala Asp Ser Val
    50                  55                  60

Lys Gly Arg Phe Thr Ile Ser Arg Asp Asn Thr Lys Asn Thr Val Tyr
65                  70                  75                  80

Leu Gln Met Asn Ser Leu Lys Pro Glu Asp Thr Ala Ala Phe Tyr Cys
                85                  90                  95

Ala Ala Thr Tyr Asn Pro Tyr Ser Arg Asp His Tyr Phe Pro Arg Met
            100                 105                 110

Thr Thr Glu Tyr Asp Tyr Trp Gly Gln Gly Thr Gln Val Thr Val Ser
        115                 120                 125

Ser

<210> SEQ ID NO 132
<211> LENGTH: 127
<212> TYPE: PRT
<213> ORGANISM: Lama glama

<400> SEQUENCE: 132

Gln Val Gln Leu Gln Glu Ser Gly Gly Gly Leu Val Lys Ala Gly Gly
1               5                   10                  15

Ser Leu Arg Leu Ser Cys Ala Ala Ser Gly Arg Thr Phe Ser Ser Tyr
            20                  25                  30

Val Met Gly Trp Phe Arg Gln Ala Pro Gly Lys Glu Arg Glu Phe Val
        35                  40                  45

Gly Ala Ile His Trp Ser Gly Arg Thr Tyr Tyr Ala Asp Ser Val
    50                  55                  60

Lys Gly Arg Phe Thr Ile Ser Asp Asn Ala Lys Asn Thr Leu Tyr
65                  70                  75                  80

Leu Gln Met Asn Ser Leu Lys Pro Glu Asp Thr Ala Val Tyr Tyr Cys
                85                  90                  95

Ala Ala Ser Arg Ile Ile Tyr Ser Tyr Val Asn Tyr Val Asn Pro Gly
            100                 105                 110

Glu Tyr Asp Tyr Trp Gly Gln Gly Thr Gln Val Thr Val Ser Ser
        115                 120                 125

<210> SEQ ID NO 133
<211> LENGTH: 129
<212> TYPE: PRT
<213> ORGANISM: Lama glama

<400> SEQUENCE: 133

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Thr Phe Ser Lys Tyr

```
                20                  25                  30
Ala Met Gly Trp Phe Arg Gln Ala Pro Gly Lys Glu Arg Glu Phe Val
            35                  40                  45
Ser Ala Ile Ser Trp Ser Asp Gly Ser Thr Tyr Tyr Ala Asp Ser Val
     50                  55                  60
Lys Gly Arg Phe Thr Ile Ser Arg Asp Asn Ala Lys Asn Thr Val Tyr
 65                  70                  75                  80
Leu Gln Val Asn Ser Leu Lys Pro Glu Asp Thr Ala Val Tyr Tyr Cys
                 85                  90                  95
Ala Ala Thr Tyr Leu Val Asp Val Trp Ala Val His Val Pro Ile Arg
            100                 105                 110
Pro Tyr Glu Tyr Asp Tyr Trp Gly Gln Gly Thr Gln Val Thr Val Ser
            115                 120                 125
Ser

<210> SEQ ID NO 134
<211> LENGTH: 129
<212> TYPE: PRT
<213> ORGANISM: Lama glama

<400> SEQUENCE: 134

Gln Val Gln Leu Gln Glu Ser Gly Gly Gly Leu Val Gln Ala Gly Gly
 1               5                  10                  15
Ser Leu Arg Leu Ser Cys Ala Ala Ser Gly Arg Thr Phe Ser Lys Tyr
             20                  25                  30
Ala Met Gly Trp Phe Arg Gln Ala Pro Gly Lys Glu Arg Glu Phe Val
            35                  40                  45
Ser Ala Ile Ser Trp Ser Asp Gly Ser Thr Tyr Tyr Ala Asp Ser Val
     50                  55                  60
Lys Gly Arg Phe Thr Ile Ser Arg Asp Asn Ala Lys Asn Thr Val Tyr
 65                  70                  75                  80
Leu Gln Val Asn Ser Leu Lys Pro Glu Asp Thr Ala Val Tyr Tyr Cys
                 85                  90                  95
Ala Ala Thr Tyr Leu Val Asp Val Trp Ala Val His Val Pro Ile Arg
            100                 105                 110
Pro Tyr Glu Tyr Asp Tyr Trp Gly Gln Gly Thr Gln Val Thr Val Ser
            115                 120                 125
Ser

<210> SEQ ID NO 135
<211> LENGTH: 123
<212> TYPE: PRT
<213> ORGANISM: Lama glama

<400> SEQUENCE: 135

Gln Val Gln Leu Gln Glu Ser Gly Gly Gly Leu Val Gln Ala Gly Gly
 1               5                  10                  15
Ser Leu Arg Leu Ser Cys Ala Ala Ser Gly Arg Thr Phe Ser Asn Tyr
             20                  25                  30
Ala Met Gly Trp Phe Arg Gln Ala Pro Gly Lys Glu Arg Glu Phe Val
            35                  40                  45
Ala Ala Ile Asn Trp Gly Gly Gly Asn Thr Tyr Tyr Ala Asp Ser Val
     50                  55                  60
Lys Gly Arg Phe Thr Ile Ser Arg Asp Asn Ala Lys Asn Thr Val Tyr
 65                  70                  75                  80
```

Leu Gln Met Asn Ser Leu Lys Pro Glu Asp Thr Ala Val Tyr Tyr Cys
                    85                  90                  95

Ala Ala Ser Glu Trp Gly Gly Ser Asp Tyr Asp His Asp Tyr Asp Tyr
            100                 105                 110

Trp Gly Gln Gly Thr Gln Val Thr Val Ser Ser
            115                 120

<210> SEQ ID NO 136
<211> LENGTH: 123
<212> TYPE: PRT
<213> ORGANISM: Lama glama

<400> SEQUENCE: 136

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Thr Phe Ser Ser Tyr
            20                  25                  30

Ala Ile Gly Trp Phe Arg Gln Ala Pro Gly Lys Glu Arg Glu Phe Val
            35                  40                  45

Ala Ala Ile Ser Trp Gly Gly Ser Asn Thr Tyr Tyr Ala Asp Ser Val
        50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                    85                  90                  95

Ala Ala Gly Glu Val Ser Asn Ser Asp Tyr Ala Tyr Glu Tyr Asp Tyr
            100                 105                 110

Trp Gly Gln Gly Thr Gln Val Thr Val Ser Ser
            115                 120

<210> SEQ ID NO 137
<211> LENGTH: 125
<212> TYPE: PRT
<213> ORGANISM: Lama glama

<400> SEQUENCE: 137

Gln Val Gln Leu Gln Asp Ser Gly Gly Gly Leu Val Gln Ala Gly Asp
1               5                   10                  15

Ser Leu Arg Leu Ser Cys Ala Ala Ser Gly Arg Ser Phe Gly Gly Tyr
            20                  25                  30

Ala Met Gly Trp Phe Arg Gln Ala Pro Gly Lys Glu Arg Glu Phe Val
            35                  40                  45

Ala Ala Ile Ser Trp Ser Gly Ser Thr Tyr Tyr Ala Asp Ser Leu
        50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Leu Tyr Tyr Cys
                    85                  90                  95

Ala Ala Gly Leu Arg Pro Ser Pro Asn Tyr Asn His Glu Arg Ser Tyr
            100                 105                 110

Asp Tyr Trp Gly Gln Gly Thr Gln Val Thr Val Ser Ser
            115                 120                 125

<210> SEQ ID NO 138
<211> LENGTH: 121
<212> TYPE: PRT
<213> ORGANISM: Lama glama -continued

```
<400> SEQUENCE: 138

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Thr Phe Ser Gly Tyr
            20                  25                  30

Ala Met Gly Trp Phe Arg Gln Ala Pro Gly Glu Glu Arg Glu Phe Val
        35                  40                  45

Ala Ala Ile Ser Trp Arg Gly Thr Ser Thr Tyr Tyr Gly Asp Ser Ala
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Gly Ser His Ser Asp Tyr Ala Pro Tyr Asp Tyr Trp Gly
            100                 105                 110

Gln Gly Thr Gln Val Thr Val Ser Ser
        115                 120

<210> SEQ ID NO 139
<211> LENGTH: 121
<212> TYPE: PRT
<213> ORGANISM: Lama glama

<400> SEQUENCE: 139

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Thr Phe Ser Gly Tyr
            20                  25                  30

Ala Met Gly Trp Phe Arg Gln Ala Pro Gly Glu Glu Arg Glu Phe Val
        35                  40                  45

Ala Ala Ile Ser Trp Arg Gly Thr Ser Thr Tyr Tyr Gly Asp Ser Ala
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Gly Ser His Ser Asp Tyr Ala Pro Tyr Asp Tyr Trp Gly
            100                 105                 110

Gln Gly Thr Gln Val Thr Val Ser Ser
        115                 120

<210> SEQ ID NO 140
<211> LENGTH: 121
<212> TYPE: PRT
<213> ORGANISM: Lama glama

<400> SEQUENCE: 140

Gln Val Gln Leu Gln Asp Ser Gly Gly Gly Leu Val Gln Ala Gly Gly
1               5                   10                  15

Ser Leu Arg Leu Ser Cys Ala Ala Ser Gly Gly Thr Phe Ser Ser Tyr
            20                  25                  30

Ala Met Gly Trp Phe Arg Gln Ala Pro Gly Lys Glu Arg Glu Phe Val
        35                  40                  45

Ala Ala Ile Gly Leu Asn Thr Tyr Tyr Ala Asp Ser Val Lys Gly Arg
    50                  55                  60

Phe Thr Ile Ser Arg Asp Asn Ala Lys Asn Thr Val Tyr Leu Gln Met
```

```
                65                  70                  75                  80
Asn Ser Leu Lys Pro Glu Asp Thr Ala Val Tyr Tyr Cys Ala Ala Arg
                    85                  90                  95
Thr Ser Gly Val Val Gly Gly Thr Pro Lys Arg Tyr Asp Tyr Trp Gly
                    100                 105                 110
Gln Gly Thr Gln Val Thr Val Ser Ser
                115                 120
```

```
<210> SEQ ID NO 141
<211> LENGTH: 122
<212> TYPE: PRT
<213> ORGANISM: Lama glama

<400> SEQUENCE: 141

Gln Val Gln Leu Gln Glu Ser Gly Gly Arg Leu Val Gln Thr Gly Gly
1               5                   10                  15
Ser Leu Arg Leu Ser Cys Ala Ala Ser Gly Gly Thr Phe Gly Thr Tyr
                20                  25                  30
Ala Leu Gly Trp Phe Arg Gln Ala Pro Gly Lys Glu Arg Glu Phe Val
                35                  40                  45
Ala Ala Ile Ser Arg Phe Gly Ser Thr Tyr Tyr Ala Asp Ser Val Lys
                50                  55                  60
Gly Arg Phe Thr Ile Ser Arg Asp Asn Ala Asn Asn Thr Val Tyr Leu
65                  70                  75                  80
Glu Met Asn Ser Leu Lys Pro Glu Asp Thr Ala Val Tyr Tyr Cys Ala
                85                  90                  95
Ala Arg Glu Gly Val Ala Leu Gly Leu Arg Asn Asp Ala Asn Tyr Trp
                100                 105                 110
Gly Gln Gly Thr Gln Val Thr Val Ser Ser
                115                 120
```

```
<210> SEQ ID NO 142
<211> LENGTH: 122
<212> TYPE: PRT
<213> ORGANISM: Lama glama

<400> SEQUENCE: 142

Gln Val Gln Leu Gln Glu Ser Gly Gly Gly Leu Val Gln Thr Gly Gly
1               5                   10                  15
Ser Leu Arg Leu Ser Cys Ala Ala Ser Gly Arg Tyr Ile Met Gly Trp
                20                  25                  30
Phe Arg Gln Ala Pro Gly Lys Glu Arg Glu Phe Val Ala Gly Ile Ser
        35                  40                  45
Arg Ser Gly Ala Ser Thr Ala Tyr Ala Asp Ser Val Lys Asp Arg Phe
        50                  55                  60
Thr Ile Ser Arg Asp Ser Ala Leu Asn Thr Val Tyr Leu Gln Met Asn
65                  70                  75                  80
Ser Leu Lys Ala Glu Asp Thr Ala Val Tyr Phe Cys Ala Ala Ala Leu
                85                  90                  95
Ala Ile Arg Leu Gly Ile Pro Arg Gly Glu Thr Glu Tyr Glu Tyr Trp
                100                 105                 110
Gly Gln Gly Thr Gln Val Thr Val Ser Ser
                115                 120
```

```
<210> SEQ ID NO 143
<211> LENGTH: 121
<212> TYPE: PRT
```

<213> ORGANISM: Lama glama

<400> SEQUENCE: 143

Gln Val Lys Leu Glu Glu Ser Gly Gly Gly Leu Val Gln Ala Gly Gly
1               5                   10                  15

Ser Leu Arg Leu Ser Cys Ser Ala Ser Gly Leu Thr Phe Ser Asn Tyr
            20                  25                  30

Ala Met Ala Trp Phe Arg Gln Ala Pro Gly Lys Glu Arg Glu Phe Val
        35                  40                  45

Ala Thr Ile Ser Gln Arg Gly Gly Met Arg His Tyr Leu Asp Ser Val
    50                  55                  60

Lys Asp Arg Phe Thr Ile Ser Arg Asp Asn Ala Lys Asn Thr Val Tyr
65                  70                  75                  80

Leu Gln Met Asn Ser Leu Lys Pro Asp Asp Thr Ala Val Tyr Tyr Cys
                85                  90                  95

Ala Ala Asp Leu Met Tyr Gly Val Asp Arg Arg Tyr Asp Tyr Trp Gly
            100                 105                 110

Arg Gly Thr Gln Val Thr Val Ser Ser
        115                 120

<210> SEQ ID NO 144
<211> LENGTH: 128
<212> TYPE: PRT
<213> ORGANISM: Artificial
<220> FEATURE:
<223> OTHER INFORMATION: Nanobody or nanobody construct

<400> SEQUENCE: 144

Glu Val Gln Leu Val Glu Ser Gly Gly Gly Leu Val Gln Ala Gly Gly
1               5                   10                  15

Ser Leu Arg Leu Ser Cys Glu Ala Ser Gly Arg Thr Tyr Ser Arg Tyr
            20                  25                  30

Gly Met Gly Trp Phe Arg Gln Ala Pro Gly Lys Glu Arg Glu Phe Val
        35                  40                  45

Ala Ala Val Ser Arg Leu Ser Gly Pro Arg Thr Val Tyr Ala Asp Ser
    50                  55                  60

Val Lys Gly Arg Phe Thr Ile Ser Arg Asp Asn Ala Glu Asn Thr Val
65                  70                  75                  80

Tyr Leu Gln Met Asn Ser Leu Lys Pro Glu Asp Thr Ala Val Tyr Thr
                85                  90                  95

Cys Ala Ala Glu Leu Thr Asn Arg Asn Ser Gly Ala Tyr Tyr Tyr Ala
            100                 105                 110

Trp Ala Tyr Asp Tyr Trp Gly Gln Gly Thr Gln Val Thr Val Ser Ser
        115                 120                 125

<210> SEQ ID NO 145
<211> LENGTH: 259
<212> TYPE: PRT
<213> ORGANISM: Artificial
<220> FEATURE:
<223> OTHER INFORMATION: Nanobody or nanobody construct

<400> SEQUENCE: 145

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Tyr Asn
            20                  25                  30

Pro Met Gly Trp Phe Arg Gln Ala Pro Gly Lys Gly Arg Glu Leu Val

```
                35                  40                  45
Ala Ala Ile Ser Arg Thr Gly Gly Ser Thr Tyr Tyr Pro Asp Ser Val
 50                  55                  60

Glu Gly Arg Phe Thr Ile Ser Arg Asp Asn Ala Lys Arg Met Val Tyr
 65                  70                  75                  80

Leu Gln Met Asn Ser Leu Arg Ala Glu Asp Thr Ala Val Tyr Tyr Cys
                 85                  90                  95

Ala Ala Ala Gly Val Arg Ala Glu Asp Gly Arg Val Arg Thr Leu Pro
            100                 105                 110

Ser Glu Tyr Thr Phe Trp Gly Gln Gly Thr Gln Val Thr Val Ser Ser
            115                 120                 125

Ala Ala Ala Glu Val Gln Leu Val Glu Ser Gly Gly Gly Leu Val Gln
            130                 135                 140

Pro Gly Gly Ser Leu Arg Leu Ser Cys Ala Ala Ser Gly Arg Thr Phe
145                 150                 155                 160

Ser Tyr Asn Pro Met Gly Trp Phe Arg Gln Ala Pro Gly Lys Gly Arg
                165                 170                 175

Glu Leu Val Ala Ala Ile Ser Arg Thr Gly Gly Ser Thr Tyr Tyr Pro
            180                 185                 190

Asp Ser Val Glu Gly Arg Phe Thr Ile Ser Arg Asp Asn Ala Lys Arg
            195                 200                 205

Met Val Tyr Leu Gln Met Asn Ser Leu Arg Ala Glu Asp Thr Ala Val
            210                 215                 220

Tyr Tyr Cys Ala Ala Ala Gly Val Arg Ala Glu Asp Gly Arg Val Arg
225                 230                 235                 240

Thr Leu Pro Ser Glu Tyr Thr Phe Trp Gly Gln Gly Thr Gln Val Thr
                245                 250                 255

Val Ser Ser
```

<210> SEQ ID NO 146
<211> LENGTH: 385
<212> TYPE: PRT
<213> ORGANISM: Artificial
<220> FEATURE:
<223> OTHER INFORMATION: Nanobody or nanobody construct

<400> SEQUENCE: 146

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                20                  25                  30

Pro Met Gly Trp Phe Arg Gln Ala Pro Gly Lys Gly Arg Glu Phe Val
             35                  40                  45

Ser Ser Ile Thr Gly Ser Gly Ser Thr Tyr Tyr Ala Asp Ser Val
 50                  55                  60

Lys Gly Arg Phe Thr Ile Ser Arg Asp Asn Ala Lys Asn Thr Leu Tyr
 65                  70                  75                  80

Leu Gln Met Asn Ser Leu Arg Pro Glu Asp Thr Ala Val Tyr Tyr Cys
                 85                  90                  95

Ala Ala Tyr Ile Arg Pro Asp Tyr Leu Ser Arg Asp Tyr Arg Lys
            100                 105                 110

Tyr Asp Tyr Trp Gly Gln Gly Thr Leu Val Thr Val Ser Ser Gly Gly
            115                 120                 125

Gly Gly Ser Gly Gly Gly Ser Glu Val Gln Leu Val Glu Ser Gly Gly
            130                 135                 140
```

```
Gly Leu Val Gln Pro Gly Asn Ser Leu Arg Leu Ser Cys Ala Ala Ser
145                 150                 155                 160

Gly Phe Thr Phe Ser Ser Phe Gly Met Ser Trp Val Arg Gln Ala Pro
                165                 170                 175

Gly Lys Gly Leu Glu Trp Val Ser Ser Ile Ser Gly Ser Gly Ser Asp
            180                 185                 190

Thr Leu Tyr Ala Asp Ser Val Lys Gly Arg Phe Thr Ile Ser Arg Asp
            195                 200                 205

Asn Ala Lys Thr Thr Leu Tyr Leu Gln Met Asn Ser Leu Arg Pro Glu
210                 215                 220

Asp Thr Ala Val Tyr Tyr Cys Thr Ile Gly Ser Leu Ser Arg Ser
225                 230                 235                 240

Ser Gln Gly Thr Leu Val Thr Val Ser Ser Gly Gly Gly Ser Gly
                245                 250                 255

Gly Gly Ser Glu Val Gln Leu Val Glu Ser Gly Gly Gly Leu Val Gln
            260                 265                 270

Pro Gly Gly Ser Leu Arg Leu Ser Cys Ala Ala Ser Gly Phe Thr Phe
                275                 280                 285

Ser Ser Tyr Pro Met Gly Trp Phe Arg Gln Ala Pro Gly Lys Gly Arg
290                 295                 300

Glu Phe Val Ser Ser Ile Thr Gly Ser Gly Gly Ser Thr Tyr Tyr Ala
305                 310                 315                 320

Asp Ser Val Lys Gly Arg Phe Thr Ile Ser Arg Asp Asn Ala Lys Asn
                325                 330                 335

Thr Leu Tyr Leu Gln Met Asn Ser Leu Arg Pro Glu Asp Thr Ala Val
            340                 345                 350

Tyr Tyr Cys Ala Ala Tyr Ile Arg Pro Asp Thr Tyr Leu Ser Arg Asp
            355                 360                 365

Tyr Arg Lys Tyr Asp Tyr Trp Gly Gln Gly Thr Leu Val Thr Val Ser
    370                 375                 380

Ser
385

<210> SEQ ID NO 147
<211> LENGTH: 294
<212> TYPE: PRT
<213> ORGANISM: Artificial
<220> FEATURE:
<223> OTHER INFORMATION: Nanobody or nanobody construct

<400> SEQUENCE: 147

Glu Val Gln Leu Val Glu Ser Gly Gly Gly Leu Val Gln Ala Gly Gly
1               5                   10                  15

Ser Leu Arg Leu Ser Cys Glu Ala Ser Gly Arg Thr Tyr Ser Arg Tyr
            20                  25                  30

Gly Met Gly Trp Phe Arg Gln Ala Pro Gly Lys Glu Arg Glu Phe Val
        35                  40                  45

Ala Ala Val Ser Arg Leu Ser Gly Pro Arg Thr Val Tyr Ala Asp Ser
    50                  55                  60

Val Lys Gly Arg Phe Thr Ile Ser Arg Asp Asn Ala Glu Asn Thr Val
65                  70                  75                  80

Tyr Leu Gln Met Asn Ser Leu Lys Pro Glu Asp Thr Ala Val Tyr Thr
                85                  90                  95

Cys Ala Ala Glu Leu Thr Asn Arg Asn Ser Gly Ala Tyr Tyr Tyr Ala
            100                 105                 110
```

Trp Ala Tyr Asp Tyr Trp Gly Gln Gly Thr Gln Val Thr Val Ser Ser
            115                 120                 125

Gly Gly Gly Gly Ser Gly Gly Gly Ser Gly Gly Gly Ser Glu
130                 135                 140

Val Gln Leu Val Glu Ser Gly Gly Gly Leu Val Gln Ala Gly Gly Ser
145                 150                 155                 160

Leu Arg Leu Ser Cys Glu Ala Ser Gly Arg Thr Tyr Ser Arg Tyr Gly
            165                 170                 175

Met Gly Trp Phe Arg Gln Ala Pro Gly Lys Glu Arg Glu Phe Val Ala
            180                 185                 190

Ala Val Ser Arg Leu Ser Gly Pro Arg Thr Val Tyr Ala Asp Ser Val
            195                 200                 205

Lys Gly Arg Phe Thr Ile Ser Arg Asp Asn Ala Glu Asn Thr Val Tyr
            210                 215                 220

Leu Gln Met Asn Ser Leu Lys Pro Glu Asp Thr Ala Val Tyr Thr Cys
225                 230                 235                 240

Ala Ala Glu Leu Thr Asn Arg Asn Ser Gly Ala Tyr Tyr Tyr Ala Trp
            245                 250                 255

Ala Tyr Asp Tyr Trp Gly Gln Gly Thr Gln Val Thr Val Ser Ser Ala
            260                 265                 270

Ala Ala Glu Gln Lys Leu Ile Ser Glu Glu Asp Leu Asn Gly Ala Ala
            275                 280                 285

His His His His His His
            290

<210> SEQ ID NO 148
<211> LENGTH: 386
<212> TYPE: PRT
<213> ORGANISM: Artificial
<220> FEATURE:
<223> OTHER INFORMATION: Nanobody or nanobody construct

<400> SEQUENCE: 148

Glu Val Gln Leu Leu Glu Ser Gly Gly Gly Leu Val Gln Pro Gly Gly
1               5                   10                  15

Ser Leu Arg Leu Ser Cys Ala Ala Ser Gly Arg Ile Phe Ser Leu Pro
            20                  25                  30

Ala Ser Gly Asn Ile Phe Asn Leu Leu Thr Ile Ala Trp Tyr Arg Gln
        35                  40                  45

Ala Pro Gly Lys Gly Arg Glu Leu Val Ala Thr Ile Asn Ser Gly Ser
    50                  55                  60

Arg Thr Tyr Tyr Ala Asp Ser Val Lys Gly Arg Phe Thr Ile Ser Arg
65                  70                  75                  80

Asp Asn Ser Lys Lys Thr Leu Tyr Leu Gln Met Asn Ser Leu Arg Pro
                85                  90                  95

Glu Asp Thr Ala Val Tyr Tyr Cys Gln Thr Gly Ser Gly Ser Pro
            100                 105                 110

Asn Phe Trp Gly Gln Gly Thr Leu Val Thr Val Ser Ser Gly Gly Gly
        115                 120                 125

Gly Ser Gly Gly Gly Ser Glu Val Gln Leu Val Glu Ser Gly Gly Gly
    130                 135                 140

Leu Val Gln Pro Gly Asn Ser Leu Arg Leu Ser Cys Ala Ala Ser Gly
145                 150                 155                 160

Phe Thr Phe Ser Ser Phe Gly Met Ser Trp Val Arg Gln Ala Pro Gly
            165                 170                 175

```
Lys Gly Leu Glu Trp Val Ser Ser Ile Ser Gly Ser Gly Ser Asp Thr
            180                 185                 190

Leu Tyr Ala Asp Ser Val Lys Gly Arg Phe Thr Ile Ser Arg Asp Asn
        195                 200                 205

Ala Lys Thr Thr Leu Tyr Leu Gln Met Asn Ser Leu Arg Pro Glu Asp
    210                 215                 220

Thr Ala Val Tyr Tyr Cys Thr Ile Gly Gly Ser Leu Ser Arg Ser Ser
225                 230                 235                 240

Gln Gly Thr Leu Val Thr Val Ser Ser Gly Gly Gly Ser Gly Gly
            245                 250                 255

Gly Ser Glu Val Gln Leu Leu Glu Ser Gly Gly Gly Leu Val Gln Pro
            260                 265                 270

Gly Gly Ser Leu Arg Leu Ser Cys Ala Ala Ser Gly Arg Thr Leu Ser
            275                 280                 285

Ser Tyr Ala Met Gly Trp Phe Arg Gln Ala Pro Gly Lys Gly Arg Glu
            290                 295                 300

Phe Val Ala Arg Ile Ser Gln Gly Gly Thr Ala Ile Tyr Tyr Ala Asp
305                 310                 315                 320

Ser Val Lys Gly Arg Phe Thr Ile Ser Arg Asp Asn Ser Lys Asn Thr
                325                 330                 335

Leu Tyr Leu Gln Met Asn Ser Leu Arg Pro Glu Asp Thr Ala Val Tyr
            340                 345                 350

Tyr Cys Ala Lys Asp Pro Ser Pro Tyr Tyr Arg Gly Ser Ala Tyr Leu
            355                 360                 365

Leu Ser Gly Ser Tyr Asp Ser Trp Gly Gln Gly Thr Leu Val Thr Val
    370                 375                 380

Ser Ser
385

<210> SEQ ID NO 149
<211> LENGTH: 120
<212> TYPE: PRT
<213> ORGANISM: Artificial
<220> FEATURE:
<223> OTHER INFORMATION: Nanobody or nanobody construct

<400> SEQUENCE: 149

Glu Val Gln Leu Val Glu Ser Gly Gly Asp Leu Val Gln Pro Gly Gly
1               5                   10                  15

Ser Leu Arg Leu Ser Cys Ala Ala Ser Gly Phe Thr Phe Arg Gly Tyr
            20                  25                  30

Trp Met Thr Trp Val Arg Gln Ala Pro Gly Lys Gly Leu Glu Trp Val
        35                  40                  45

Ser Ser Ile Asn Asn Ile Gly Glu Glu Ala Tyr Tyr Val Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Ser Glu Asp Thr Ala Val Tyr Tyr Cys
                85                  90                  95

Val Lys Asp Trp Ala Ser Asp Tyr Ala Gly Tyr Ser Pro Asn Ser Gln
            100                 105                 110

Gly Thr Gln Val Thr Val Ser Ser
        115                 120

<210> SEQ ID NO 150
```

<211> LENGTH: 124
<212> TYPE: PRT
<213> ORGANISM: Artificial
<220> FEATURE:
<223> OTHER INFORMATION: Nanobody or nanobody construct

<400> SEQUENCE: 150

Glu Val Gln Leu Val Glu Ser Gly Gly Gly Leu Val Gln Ala Gly Asp
1               5                   10                  15

Ser Leu Arg Leu Ser Cys Ile Asp Ser Gly Arg Thr Phe Ser Asp Tyr
            20                  25                  30

Pro Ile Gly Trp Phe Arg Gln Ala Pro Gly Lys Glu Arg Glu Phe Val
        35                  40                  45

Ala Ala Ile Tyr Ala Ile Gly Gly Asp Val Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Ser Ser Leu Lys Pro Glu Asp Thr Ala Ile Tyr Ser Cys
                85                  90                  95

Ala Val Ala Ser Gly Gly Gly Ser Ile Arg Ser Ala Arg Arg Tyr Asp
            100                 105                 110

Tyr Trp Gly Arg Gly Thr Gln Val Thr Val Ser Ser
        115                 120

<210> SEQ ID NO 151
<211> LENGTH: 126
<212> TYPE: PRT
<213> ORGANISM: Artificial
<220> FEATURE:
<223> OTHER INFORMATION: Nanobody or nanobody construct

<400> SEQUENCE: 151

Glu Val Gln Leu Val Glu Ser Gly Gly Gly Leu Val Gln Ala Gly Gly
1               5                   10                  15

Ser Leu Arg Leu Ser Cys Ala Ala Ser Gly Gly Thr Phe Ser Ser Tyr
            20                  25                  30

Ala Met Gly Trp Phe Arg Gln Ala Pro Gly Lys Glu Arg Asp Phe Val
        35                  40                  45

Ser Ala Ile Thr Trp Ser Gly Gly Ser Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Asp Asp Gln Lys Tyr Asp Tyr Ile Ala Tyr Ala Glu Tyr Glu
            100                 105                 110

Tyr Asp Tyr Trp Gly Gln Gly Thr Gln Val Thr Val Ser Ser
        115                 120                 125

<210> SEQ ID NO 152
<211> LENGTH: 120
<212> TYPE: PRT
<213> ORGANISM: Artificial
<220> FEATURE:
<223> OTHER INFORMATION: Nanobody or nanobody construct

<400> SEQUENCE: 152

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Gly Tyr
            20                  25                  30

Trp Met Ser Trp Val Arg Gln Ala Pro Gly Lys Gly Leu Glu Trp Val
        35                  40                  45

Ser Ala Ile Asn Asn Val Gly Asp Glu Val Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Ser Glu Asp Thr Ala Val Tyr Tyr Cys
                85                  90                  95

Thr Arg Asp Trp Phe Asp Asp Pro Asn Lys Asn Glu Tyr Lys Gly Gln
            100                 105                 110

Gly Thr Gln Val Thr Val Ser Ser
        115                 120

<210> SEQ ID NO 153
<211> LENGTH: 120
<212> TYPE: PRT
<213> ORGANISM: Artificial
<220> FEATURE:
<223> OTHER INFORMATION: Nanobody or nanobody construct

<400> SEQUENCE: 153

Glu Val Gln Leu Val Glu Ser Gly Gly Leu Val Gln Pro Gly Gly
1               5                   10                  15

Ser Leu Arg Leu Ser Cys Ala Ala Ser Gly Phe Thr Phe Arg Gly Tyr
            20                  25                  30

Trp Met Ser Trp Val Arg Gln Ala Pro Gly Lys Gly Leu Glu Trp Val
        35                  40                  45

Ser Ala Ile Asn Asn Val Gly Asp Glu Val Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Ser Glu Asp Thr Ala Val Tyr Tyr Cys
                85                  90                  95

Thr Arg Asp Trp Tyr Asn Asp Pro Asn Lys Asn Glu Tyr Lys Gly Gln
            100                 105                 110

Gly Thr Gln Val Thr Val Ser Ser
        115                 120

<210> SEQ ID NO 154
<211> LENGTH: 120
<212> TYPE: PRT
<213> ORGANISM: Artificial
<220> FEATURE:
<223> OTHER INFORMATION: Nanobody or nanobody construct

<400> SEQUENCE: 154

Lys Val Gln Leu Val Glu Ser Gly Gly Asp Leu Val Gln Pro Gly Gly
1               5                   10                  15

Ser Leu Arg Leu Ser Cys Ala Ala Ser Gly Phe Thr Phe Arg Gly Tyr
            20                  25                  30

Trp Met Thr Trp Val Arg Gln Ala Pro Gly Lys Gly Leu Glu Trp Val
        35                  40                  45

Ser Ser Ile Asn Asn Ile Gly Glu Glu Ala Tyr Tyr Val Asp Ser Val
    50                  55                  60

Lys Gly Arg Phe Thr Ile Ser Arg Asp Asn Ala Lys Asn Thr Leu Tyr
65                  70                  75                  80

```
Leu Gln Met Asn Ser Leu Lys Ser Glu Asp Thr Ala Val Tyr Tyr Cys
                85                  90                  95

Val Lys Asp Trp Ala Ser Asp Tyr Ala Gly Tyr Ser Pro Asn Ser Gln
            100                 105                 110

Gly Thr Gln Val Thr Val Ser Ser
        115                 120

<210> SEQ ID NO 155
<211> LENGTH: 120
<212> TYPE: PRT
<213> ORGANISM: Artificial
<220> FEATURE:
<223> OTHER INFORMATION: Nanobody or nanobody construct

<400> SEQUENCE: 155

Glu Val Gln Leu Val Glu Ser Gly Gly Asp Leu Val Gln Pro Gly Gly
1               5                   10                  15

Ser Leu Arg Leu Ser Cys Ala Ala Ser Gly Phe Thr Phe Arg Gly Tyr
            20                  25                  30

Trp Met Thr Trp Val Arg Gln Ala Pro Gly Lys Gly Leu Glu Trp Val
        35                  40                  45

Ser Ser Ile Asn Asn Ile Gly Glu Glu Ala Tyr Tyr Val Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Ser Glu Asp Thr Ala Val Tyr Tyr Cys
                85                  90                  95

Val Lys Asp Trp Ala Ser Asp Tyr Ala Gly Tyr Ser Pro Asn Ser Gln
            100                 105                 110

Gly Thr Gln Val Thr Val Ser Ser
        115                 120

<210> SEQ ID NO 156
<211> LENGTH: 119
<212> TYPE: PRT
<213> ORGANISM: Artificial
<220> FEATURE:
<223> OTHER INFORMATION: Nanobody or nanobody construct

<400> SEQUENCE: 156

Glu Val Gln Leu Val Glu Ser Gly Gly Gly Leu Val Gln Pro Gly Gly
1               5                   10                  15

Ser Leu Arg Leu Ser Cys Thr Gly Ser Gly Phe Thr Phe Ser Ser Tyr
            20                  25                  30

Trp Met Asp Trp Val Arg Gln Thr Pro Gly Lys Asp Leu Glu Tyr Val
        35                  40                  45

Ser Gly Ile Ser Pro Ser Gly Ser Asn Thr Asp Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Asp Thr Ala Leu Tyr Tyr Cys
                85                  90                  95

Arg Arg Ser Leu Thr Leu Thr Asp Ser Pro Asp Leu Arg Ser Gln Gly
            100                 105                 110

Thr Gln Val Thr Val Ser Ser
        115
```

```
<210> SEQ ID NO 157
<211> LENGTH: 120
<212> TYPE: PRT
<213> ORGANISM: Artificial
<220> FEATURE:
<223> OTHER INFORMATION: Nanobody or nanobody construct

<400> SEQUENCE: 157

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Gly Tyr
            20                  25                  30

Trp Met Ser Trp Val Arg Gln Ala Pro Gly Lys Gly Leu Glu Trp Val
        35                  40                  45

Ser Ala Ile Asn Asn Val Gly Gly Glu Thr Tyr Tyr Ala Asp Ser Val
    50                  55                  60

Lys Gly Arg Phe Thr Ile Ser Arg Asp Asn Ala Lys Asn Ala Leu Tyr
65                  70                  75                  80

Leu Gln Met Asn Ser Leu Lys Ser Glu Asp Thr Ala Val Tyr Tyr Cys
                85                  90                  95

Ala Arg Asp Trp Tyr Asn Asp Pro Asn Lys Asn Glu Tyr Lys Gly Gln
            100                 105                 110

Gly Thr Gln Val Thr Val Ser Ser
        115                 120

<210> SEQ ID NO 158
<211> LENGTH: 115
<212> TYPE: PRT
<213> ORGANISM: Artificial
<220> FEATURE:
<223> OTHER INFORMATION: Nanobody or nanobody construct

<400> SEQUENCE: 158

Glu Val Gln Leu Val Glu Ser Gly Gly Gly Leu Val Gln Ala Gly Gly
1               5                   10                  15

Ser Leu Arg Leu Ser Cys Ala Ala Ser Gly Ser Thr Gly Ser Ser Thr
            20                  25                  30

Ala Met Gly Trp Ser Arg Gln Ala Pro Gly Lys Gln Arg Glu Trp Val
        35                  40                  45

Ala Ser Ile Ser Ser Ala Gly Thr Ile Arg Tyr Val Asp Ser Val Lys
    50                  55                  60

Gly Arg Phe Thr Ile Ser Arg Asp Asn Ala Lys Asn Thr Gly Tyr Leu
65                  70                  75                  80

Gln Met Asn Ser Leu Lys Pro Glu Asp Thr Ala Val Tyr Tyr Cys Tyr
                85                  90                  95

Val Val Gly Asn Phe Thr Thr Tyr Trp Gly Arg Gly Thr Gln Val Thr
            100                 105                 110

Val Ser Ser
    115

<210> SEQ ID NO 159
<211> LENGTH: 120
<212> TYPE: PRT
<213> ORGANISM: Artificial
<220> FEATURE:
<223> OTHER INFORMATION: Nanobody or nanobody construct

<400> SEQUENCE: 159

Glu Val Gln Leu Val Glu Ser Gly Gly Gly Leu Val Gln Pro Gly Gly
1               5                   10                  15
```

Ser Leu Arg Leu Ser Cys Ala Ala Ser Gly Phe Thr Phe Arg Gly Tyr
            20                  25                  30

Trp Met Ser Trp Val Arg Gln Ala Pro Gly Lys Gly Leu Glu Trp Val
        35                  40                  45

Ser Ala Ile Asn Asn Val Gly Asp Glu Val Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Ser Glu Asp Thr Ala Val Tyr Tyr Cys
                85                  90                  95

Thr Arg Asp Trp Tyr Asn Asp Pro Asn Lys Asn Glu Tyr Lys Gly Gln
                100                 105                 110

Gly Thr Gln Val Thr Val Ser Ser
            115                 120

<210> SEQ ID NO 160
<211> LENGTH: 113
<212> TYPE: PRT
<213> ORGANISM: Artificial
<220> FEATURE:
<223> OTHER INFORMATION: Nanobody or nanobody construct

<400> SEQUENCE: 160

Glu Val Gln Leu Val Glu Ser Gly Gly Gly Leu Val Gln Ala Gly Gly
1               5                   10                  15

Ser Leu Arg Leu Ser Cys Ala Ala Ser Val Ser Ala Phe Ser Glu Tyr
            20                  25                  30

Ala Met Gly Trp Tyr Arg Gln Ala Pro Gly Lys Gln Arg Glu Phe Val
        35                  40                  45

Ala Thr Ile Asn Ser Leu Gly Gly Thr Ser Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Thr
                85                  90                  95

Leu Tyr Arg Ala Asn Leu Trp Gly Gln Gly Thr Gln Val Thr Val Ser
                100                 105                 110

Ser

<210> SEQ ID NO 161
<211> LENGTH: 120
<212> TYPE: PRT
<213> ORGANISM: Artificial
<220> FEATURE:
<223> OTHER INFORMATION: Nanobody or nanobody construct

<400> SEQUENCE: 161

Glu Val Gln Leu Val Glu Ser Gly Gly Asp Leu Val Gln Pro Gly Gly
1               5                   10                  15

Ser Leu Arg Leu Ser Cys Ala Ala Ser Gly Phe Thr Phe Arg Gly Tyr
            20                  25                  30

Trp Met Thr Trp Val Arg Gln Ala Pro Gly Lys Gly Leu Glu Trp Val
        35                  40                  45

Ser Ser Ile Asn Asn Ile Gly Glu Glu Thr Tyr Tyr Val Asp Ser Val
    50                  55                  60

Lys Gly Arg Phe Thr Ile Ser Arg Asp Asn Ala Lys Asn Thr Leu Tyr
65                  70                  75                  80

```
Leu Gln Met Asn Ser Leu Lys Ser Glu Asp Thr Ala Val Tyr Tyr Cys
                85                  90                  95

Val Lys Asp Trp Ala Ser Asp Tyr Ala Gly Tyr Ser Pro Asn Ser Gln
            100                 105                 110

Gly Thr Gln Val Thr Val Ser Ser
        115                 120

<210> SEQ ID NO 162
<211> LENGTH: 127
<212> TYPE: PRT
<213> ORGANISM: Artificial
<220> FEATURE:
<223> OTHER INFORMATION: Nanobody or nanobody construct

<400> SEQUENCE: 162

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Ser Tyr
            20                  25                  30

Ala Met Gly Trp Phe Arg Gln Ala Pro Gly Lys Glu Arg Glu Phe Val
        35                  40                  45

Ala Ala Ile Ser Trp Ser Gly Arg Thr Thr Tyr Tyr Ala Asp Phe Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Asp Leu Ser Pro Gly Asn Glu Tyr Gly Glu Met Met Glu Tyr
            100                 105                 110

Glu Tyr Asp Tyr Trp Gly Glu Gly Thr Gln Val Thr Val Ser Ser
        115                 120                 125

<210> SEQ ID NO 163
<211> LENGTH: 120
<212> TYPE: PRT
<213> ORGANISM: Artificial
<220> FEATURE:
<223> OTHER INFORMATION: Nanobody or nanobody construct

<400> SEQUENCE: 163

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Gly Tyr
            20                  25                  30

Trp Met Ser Trp Val Arg Gln Ala Pro Gly Lys Gly Leu Glu Trp Val
        35                  40                  45

Ser Ala Ile Asn Asn Val Gly Gly Glu Thr Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Ser Glu Asp Thr Ala Ala Tyr Tyr Cys
                85                  90                  95

Ala Arg Asp Trp Tyr Asn Asp Pro Asn Lys Asn Glu Tyr Lys Gly Gln
            100                 105                 110

Gly Thr Gln Val Thr Val Ser Ser
        115                 120
```

```
<210> SEQ ID NO 164
<211> LENGTH: 120
<212> TYPE: PRT
<213> ORGANISM: Artificial
<220> FEATURE:
<223> OTHER INFORMATION: Nanobody or nanobody construct

<400> SEQUENCE: 164

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Gly Tyr
            20                  25                  30

Trp Met Ser Trp Val Arg Gln Ala Pro Gly Lys Gly Leu Glu Trp Val
        35                  40                  45

Ser Ala Ile Asn Asn Val Gly Asp Glu Val Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Ser Glu Asp Thr Ala Val Tyr Tyr Cys
                85                  90                  95

Thr Arg Asp Trp Tyr Asn Asp Pro Asn Lys Asn Glu Tyr Lys Gly Gln
            100                 105                 110

Gly Thr Gln Val Thr Val Ser Ser
        115                 120

<210> SEQ ID NO 165
<211> LENGTH: 120
<212> TYPE: PRT
<213> ORGANISM: Artificial
<220> FEATURE:
<223> OTHER INFORMATION: Nanobody or nanobody construct

<400> SEQUENCE: 165

Glu Val Gln Leu Val Glu Ser Gly Gly Asp Leu Val Gln Pro Gly Gly
1               5                   10                  15

Ser Leu Arg Leu Ser Cys Ala Ala Ser Gly Phe Thr Phe Arg Gly Tyr
            20                  25                  30

Trp Met Thr Trp Val Arg Gln Ala Pro Gly Lys Gly Leu Glu Trp Val
        35                  40                  45

Ser Ser Ile Asn Asn Ile Gly Glu Glu Ala Tyr Tyr Val Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Ser Glu Asp Thr Ala Val Tyr Tyr Cys
                85                  90                  95

Val Lys Asp Trp Ala Ser Asp Tyr Ala Gly Tyr Ser Pro Asn Ser Gln
            100                 105                 110

Gly Thr Gln Val Thr Val Ser Ser
        115                 120

<210> SEQ ID NO 166
<211> LENGTH: 120
<212> TYPE: PRT
<213> ORGANISM: Artificial
<220> FEATURE:
<223> OTHER INFORMATION: Nanobody or nanobody construct

<400> SEQUENCE: 166

Glu Val Gln Leu Val Glu Ser Gly Gly Asp Leu Val Gln Pro Gly Gly
1               5                   10                  15
```

Ser Leu Arg Leu Ser Cys Ala Ala Ser Gly Phe Thr Phe Arg Gly Tyr
            20                  25                  30

Trp Met Thr Trp Val Arg Gln Ala Pro Gly Lys Gly Leu Glu Trp Val
                35                  40                  45

Ser Ser Ile Asn Asn Ile Gly Glu Glu Ala Tyr Tyr Val Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Ser Glu Asp Thr Ala Val Tyr Tyr Cys
                85                  90                  95

Val Lys Asp Trp Ala Ser Asp Tyr Ala Gly Tyr Ser Pro Asn Ser Gln
            100                 105                 110

Gly Thr Gln Val Thr Val Ser Ser
            115                 120

<210> SEQ ID NO 167
<211> LENGTH: 122
<212> TYPE: PRT
<213> ORGANISM: Artificial
<220> FEATURE:
<223> OTHER INFORMATION: Nanobody or nanobody construct

<400> SEQUENCE: 167

Glu Val Gln Leu Val Glu Ser Gly Gly Gly Leu Val Gln Pro Gly Gly
1               5                   10                  15

Ser Leu Arg Leu Ser Cys Ala Ala Ser Gly Leu Ile Phe Ser Ser Tyr
            20                  25                  30

Asp Met Gly Trp Phe Arg Gln Ala Pro Gly Glu Glu Arg Ala Phe Val
                35                  40                  45

Gly Ala Ile Ser Arg Ser Gly Asp Val Arg Tyr Val Asp Pro Val Lys
    50                  55                  60

Gly Arg Phe Thr Ile Thr Arg Asp Asn Ala Lys Asn Thr Val Tyr Leu
65                  70                  75                  80

Gln Met Asn Ser Leu Lys Pro Glu Asp Thr Ala Val Tyr Tyr Cys Ala
                85                  90                  95

Ala Asp Ala Asp Gly Trp Trp His Arg Gly Gln Ala Tyr His Trp Trp
            100                 105                 110

Gly Gln Gly Thr Gln Val Thr Val Ser Ser
            115                 120

<210> SEQ ID NO 168
<211> LENGTH: 124
<212> TYPE: PRT
<213> ORGANISM: Artificial
<220> FEATURE:
<223> OTHER INFORMATION: Nanobody or nanobody construct

<400> SEQUENCE: 168

Glu Val Gln Leu Met Glu Ser Gly Gly Gly Leu Val Gln Ala Gly Gly
1               5                   10                  15

Ser Leu Arg Leu Ser Cys Ala Ala Ser Gly Arg Thr Phe Ser Gly Tyr
            20                  25                  30

Thr Met Gly Trp Phe Arg Gln Ala Pro Gly Lys Gly Arg Glu Trp Val
                35                  40                  45

Ala Gly Ile Ser Trp Ser Gly Asp Ser Thr Tyr Tyr Ala Asp Ser Val
    50                  55                  60

Lys Gly Arg Phe Thr Ile Ser Arg Glu Asp Ala Lys Asn Thr Val Tyr

```
                65                  70                  75                  80
Leu Gln Met Asn Ser Leu Lys Pro Gly Asp Thr Ala Asp Tyr Tyr Cys
                    85                  90                  95

Ala Ala Glu Cys Ala Met Tyr Gly Ser Ser Trp Pro Pro Cys Met
                100                 105                 110

Asp Trp Gly Gln Gly Thr Gln Val Thr Val Ser Ser
            115                 120
```

<210> SEQ ID NO 169
<211> LENGTH: 120
<212> TYPE: PRT
<213> ORGANISM: Artificial
<220> FEATURE:
<223> OTHER INFORMATION: Nanobody or nanobody construct

<400> SEQUENCE: 169

```
Glu Val Gln Leu Val Glu Ser Gly Gly Gly Ser Val Gln Pro Gly Gly
1               5                   10                  15

Ser Leu Arg Leu Ser Cys Ala Ala Ser Gly Phe Thr Phe Arg Gly Tyr
                20                  25                  30

Trp Met Ser Trp Val Arg Gln Ala Pro Gly Lys Gly Leu Glu Trp Val
            35                  40                  45

Ser Ala Ile Asn Asn Leu Gly Gly Asp Thr Tyr Tyr Ala Asp Ser Val
        50                  55                  60

Lys Gly Arg Phe Thr Ile Ser Arg Asp Asn Ala Lys Asn Met Leu Tyr
65                  70                  75                  80

Leu Gln Met Asn Ser Leu Lys Ala Glu Asp Thr Ala Val Tyr Tyr Cys
                85                  90                  95

Ala Arg Asp Trp Tyr Asp Asp Pro Asn Lys Asn Glu Tyr Lys Gly Gln
                100                 105                 110

Gly Thr Gln Val Thr Val Ser Ser
            115                 120
```

<210> SEQ ID NO 170
<211> LENGTH: 120
<212> TYPE: PRT
<213> ORGANISM: Artificial
<220> FEATURE:
<223> OTHER INFORMATION: Nanobody or nanobody construct

<400> SEQUENCE: 170

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Gly Tyr
                20                  25                  30

Trp Met Ser Trp Val Arg Gln Ala Pro Gly Lys Gly Leu Glu Trp Val
            35                  40                  45

Ser Ala Ile Asn Asn Val Gly Gly Glu Thr Tyr Tyr Ala Asp Ser Val
        50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Ser Glu Asp Thr Ala Ala Tyr Tyr Cys
                85                  90                  95

Ala Arg Asp Trp Tyr Asn Asp Pro Asn Lys Asn Glu Tyr Lys Gly Gln
                100                 105                 110

Gly Thr Gln Val Thr Val Ser Ser
            115                 120
```

-continued

<210> SEQ ID NO 171
<211> LENGTH: 120
<212> TYPE: PRT
<213> ORGANISM: Artificial
<220> FEATURE:
<223> OTHER INFORMATION: Nanobody or nanobody construct

<400> SEQUENCE: 171

```
Glu Val Gln Leu Val Glu Ser Gly Gly Asp Leu Val Gln Pro Gly Gly
1               5                   10                  15

Ser Leu Arg Leu Ser Cys Ala Ala Ser Gly Phe Thr Phe Arg Gly Tyr
            20                  25                  30

Trp Met Thr Trp Val Arg Gln Ala Pro Gly Lys Gly Leu Glu Trp Val
        35                  40                  45

Ser Ser Ile Asn Asn Val Gly Glu Glu Thr Tyr Tyr Val Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Ser Glu Asp Thr Ala Val Tyr Tyr Cys
                85                  90                  95

Val Lys Asp Trp Glu Ser Ser Tyr Ala Gly Tyr Ser Pro Asn Ser Gln
            100                 105                 110

Gly Thr Gln Val Thr Val Ser Ser
        115                 120
```

<210> SEQ ID NO 172
<211> LENGTH: 124
<212> TYPE: PRT
<213> ORGANISM: Artificial
<220> FEATURE:
<223> OTHER INFORMATION: Nanobody or nanobody construct

<400> SEQUENCE: 172

```
Glu Val Gln Leu Val Glu Ser Gly Gly Gly Val Val Gln Ala Gly Gly
1               5                   10                  15

Ser Leu Arg Leu Ser Cys Ala Ala Ser Gly Leu Thr Phe Asp Ile Tyr
            20                  25                  30

Ser Met Gly Trp Phe Arg Gln Pro Gly Lys Glu Arg Glu Phe Val
        35                  40                  45

Ala Ser Ile Gly Arg Ser Gly Asn Ser Thr Asn Tyr Ala Ser Ser Val
    50                  55                  60

Lys Asp Arg Phe Thr Ile Ser Arg Asp Asn Ala Lys Lys Leu Val Tyr
65                  70                  75                  80

Leu Glu Met Asn Ser Leu Thr Val Glu Asp Ala Ala Val Tyr Val Cys
                85                  90                  95

Ala Ala Lys Asp Gly Pro Leu Ile Thr His Tyr Ser Thr Ser Met
            100                 105                 110

Tyr Trp Gly Gln Gly Thr Gln Val Thr Val Ser Ser
        115                 120
```

<210> SEQ ID NO 173
<211> LENGTH: 120
<212> TYPE: PRT
<213> ORGANISM: Artificial
<220> FEATURE:
<223> OTHER INFORMATION: Nanobody or nanobody construct

<400> SEQUENCE: 173

```
Glu Val Gln Leu Val Glu Ser Gly Gly Gly Leu Val Gln Pro Gly Gly
```

```
            1               5                  10                 15
        Ser Leu Arg Leu Ser Cys Ala Ala Ser Gly Phe Thr Phe Arg Gly Tyr
                    20                  25                  30

Trp Met Ser Trp Val Arg Gln Ala Pro Gly Lys Gly Leu Glu Trp Val
                    35                  40                  45

Ser Ala Ile Asn Asn Val Gly Asp Glu Val Tyr Tyr Ala Asp Ser Val
                    50                  55                  60

Lys Gly Arg Phe Thr Ile Ser Arg Asp Asn Ala Lys Asn Thr Leu Tyr
         65                  70                  75                  80

Leu Gln Met Asn Ser Leu Lys Ser Glu Asp Thr Ala Val Tyr Tyr Cys
                    85                  90                  95

Thr Arg Asp Trp Tyr Asn Asp Pro Asn Lys Asn Glu Tyr Lys Gly Gln
                    100                 105                 110

Gly Thr Gln Val Thr Val Ser Ser
                    115                 120

<210> SEQ ID NO 174
<211> LENGTH: 119
<212> TYPE: PRT
<213> ORGANISM: Artificial
<220> FEATURE:
<223> OTHER INFORMATION: Nanobody or nanobody construct

<400> SEQUENCE: 174

Glu Val Gln Leu Val Glu Ser Gly Gly Gly Leu Val Gln Pro Gly Gly
         1               5                  10                 15

Ser Leu Arg Leu Ser Cys Thr Val Ser Gly Phe Thr Phe Ser Ser Tyr
                    20                  25                  30

Trp Met Asp Trp Val Arg Gln Thr Pro Gly Lys Asp Leu Glu Tyr Val
                    35                  40                  45

Ser Gly Ile Ser Pro Ser Gly Gly Asn Thr Asp Tyr Ala Asp Ser Val
                    50                  55                  60

Lys Gly Arg Phe Thr Ile Ser Arg Asp Asn Ala Lys Asn Thr Leu Tyr
         65                  70                  75                  80

Leu Gln Met Asn Ser Leu Gln Pro Glu Asp Thr Ala Leu Tyr Tyr Cys
                    85                  90                  95

Arg Arg Ser Leu Thr Leu Thr Asp Ser Pro Asp Leu Arg Ser Gln Gly
                    100                 105                 110

Thr Gln Val Thr Val Ser Ser
                    115

<210> SEQ ID NO 175
<211> LENGTH: 121
<212> TYPE: PRT
<213> ORGANISM: Artificial
<220> FEATURE:
<223> OTHER INFORMATION: Nanobody or nanobody construct

<400> SEQUENCE: 175

Glu Val Gln Leu Val Glu Ser Gly Gly Gly Leu Val Gln Pro Gly Gly
         1               5                  10                 15

Ser Leu Arg Leu Ser Cys Ala Ala Ser Gly Phe Thr Phe Ser Ser Tyr
                    20                  25                  30

Ala Met Gly Trp Val Arg Arg Ala Pro Gly Glu Gly Leu Glu Trp Val
                    35                  40                  45

Ser Ser Ile Ser Ser Gly Gly Ala Leu Pro Thr Tyr Ala Asp Ser Val
                    50                  55                  60
```

```
Lys Gly Arg Phe Thr Ile Ser Arg Asp Asn Val Lys Asn Thr Leu Tyr
 65                  70                  75                  80

Leu Gln Met Asn Ser Leu Lys Pro Glu Asp Thr Ala Val Tyr Ser Cys
                 85                  90                  95

Glu Lys Tyr Ala Gly Ser Met Trp Thr Ser Glu Arg Asp Ala Trp Gly
            100                 105                 110

Gln Gly Thr Gln Val Thr Val Ser Ser
        115                 120
```

<210> SEQ ID NO 176
<211> LENGTH: 129
<212> TYPE: PRT
<213> ORGANISM: Artificial
<220> FEATURE:
<223> OTHER INFORMATION: Nanobody or nanobody construct

<400> SEQUENCE: 176

```
Glu Val Gln Leu Val Glu Ser Gly Gly Gly Leu Val Gln Ala Gly Asp
 1               5                  10                  15

Ser Leu Arg Leu Ser Cys Ile Asp Ser Gly Arg Thr Phe Ser Asp Tyr
            20                  25                  30

Pro Ile Gly Trp Phe Arg Gln Ala Pro Gly Lys Glu Arg Glu Phe Val
        35                  40                  45

Ala Ala Ile Tyr Pro Thr Asp Asp Asn Pro Thr Gly Pro Asn Ala Tyr
 50                  55                  60

Tyr Ala Asp Ser Val Lys Gly Arg Phe Thr Ile Ser Arg Asp Asn Ala
 65                  70                  75                  80

Lys Asn Thr Val Tyr Leu Gln Met Ser Ser Leu Lys Pro Glu Asp Thr
                 85                  90                  95

Ala Ile Tyr Ser Cys Ala Val Ala Ser Gly Gly Gly Ser Ile Ile Ser
            100                 105                 110

Ala Arg Arg Tyr Asp Tyr Trp Gly Gln Gly Thr Gln Val Thr Val Ser
        115                 120                 125

Ser
```

<210> SEQ ID NO 177
<211> LENGTH: 126
<212> TYPE: PRT
<213> ORGANISM: Artificial
<220> FEATURE:
<223> OTHER INFORMATION: Nanobody or nanobody construct

<400> SEQUENCE: 177

```
Glu Val Gln Leu Val Glu Ser Gly Gly Gly Trp Val Gln Ala Gly Asp
 1               5                  10                  15

Ser Leu Arg Leu Ser Cys Ala Ser Gly Arg Thr Leu Ser Ser Tyr
            20                  25                  30

Ala Met Ala Trp Phe Arg Gln Ala Pro Gly Lys Glu Arg Asp Phe Val
        35                  40                  45

Thr Gly Ile Thr Trp Asn Gly Gly Ser Thr Tyr Tyr Ala Asp Ser Val
 50                  55                  60

Lys Gly Arg Phe Thr Ile Ser Arg Asp Asn Ala Lys Asn Thr Val Tyr
 65                  70                  75                  80

Leu Gln Met Asn Ser Leu Lys Pro Glu Asp Thr Ala Val Tyr Tyr Cys
                 85                  90                  95

Ala Ala Asx Gln Asn Thr Tyr Gly Tyr Met Asp Arg Ser Asp Tyr Glu
            100                 105                 110
```

Tyr Asp Tyr Trp Gly Gln Gly Thr Gln Val Thr Val Ser Ser
            115                 120                 125

<210> SEQ ID NO 178
<211> LENGTH: 119
<212> TYPE: PRT
<213> ORGANISM: Artificial
<220> FEATURE:
<223> OTHER INFORMATION: Nanobody or nanobody construct

<400> SEQUENCE: 178

Lys Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Ser Ile Asn
            20                  25                  30

Ala Met Gly Trp Tyr Arg Gln Ala Pro Gly Lys Gln Arg Glu Leu Val
        35                  40                  45

Ala His Ile Ala Ser Ser Gly Ser Thr Ile Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Thr Arg Gly Pro Ala Ala His Glu Val Arg Asp Tyr Trp Gly Gln Gly
            100                 105                 110

Thr Gln Val Thr Val Ser Ser
            115

<210> SEQ ID NO 179
<211> LENGTH: 431
<212> TYPE: PRT
<213> ORGANISM: Artificial
<220> FEATURE:
<223> OTHER INFORMATION: Nanobody or nanobody construct

<400> SEQUENCE: 179

Glu Val Gln Leu Val Glu Ser Gly Gly Gly Leu Val Gln Ala Gly Gly
1               5                   10                  15

Ser Leu Ser Ile Ser Cys Ala Ala Ser Gly Gly Ser Leu Ser Asn Tyr
            20                  25                  30

Val Leu Gly Trp Phe Arg Gln Ala Pro Gly Lys Glu Arg Glu Phe Val
        35                  40                  45

Ala Ala Ile Asn Trp Arg Gly Asp Ile Thr Ile Gly Pro Pro Asn Val
    50                  55                  60

Glu Gly Arg Phe Thr Ile Ser Arg Asp Asn Ala Lys Asn Thr Gly Tyr
65                  70                  75                  80

Leu Gln Met Asn Ser Leu Ala Pro Asp Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Arg Gly Thr Gln Val Thr Val Ser Ser Gly Gly
            115                 120                 125

Gly Gly Ser Gly Gly Gly Ser Gly Gly Gly Ser Glu Val Gln
        130                 135                 140

Leu Val Glu Ser Gly Gly Gly Leu Val Gln Ala Gly Gly Ser Leu Ser
145                 150                 155                 160

Ile Ser Cys Ala Ala Ser Gly Gly Ser Leu Ser Asn Tyr Val Leu Gly
                165                 170                 175

Trp Phe Arg Gln Ala Pro Gly Lys Glu Arg Glu Phe Val Ala Ala Ile
            180                 185                 190

Asn Trp Arg Gly Asp Ile Thr Ile Gly Pro Pro Asn Val Glu Gly Arg
        195                 200                 205

Phe Thr Ile Ser Arg Asp Asn Ala Lys Asn Thr Gly Tyr Leu Gln Met
    210                 215                 220

Asn Ser Leu Ala Pro Asp Asp Thr Ala Val Tyr Tyr Cys Gly Ala Gly
225                 230                 235                 240

Thr Pro Leu Asn Pro Gly Ala Tyr Ile Tyr Asp Trp Ser Tyr Asp Tyr
                245                 250                 255

Trp Gly Arg Gly Thr Gln Val Thr Val Ser Ser Gly Gly Gly Gly Ser
            260                 265                 270

Gly Gly Gly Gly Ser Gly Gly Gly Ser Glu Val Gln Leu Val Glu
        275                 280                 285

Ser Gly Gly Gly Leu Val Gln Ala Gly Gly Ser Leu Ser Ile Ser Cys
    290                 295                 300

Ala Ala Ser Gly Gly Ser Leu Ser Asn Tyr Val Leu Gly Trp Phe Arg
305                 310                 315                 320

Gln Ala Pro Gly Lys Glu Arg Glu Phe Val Ala Ala Ile Asn Trp Arg
                325                 330                 335

Gly Asp Ile Thr Ile Gly Pro Pro Asn Val Glu Gly Arg Phe Thr Ile
            340                 345                 350

Ser Arg Asp Asn Ala Lys Asn Thr Gly Tyr Leu Gln Met Asn Ser Leu
        355                 360                 365

Ala Pro Asp Asp Thr Ala Val Tyr Tyr Cys Gly Ala Gly Thr Pro Leu
    370                 375                 380

Asn Pro Gly Ala Tyr Ile Tyr Asp Trp Ser Tyr Asp Tyr Trp Gly Arg
385                 390                 395                 400

Gly Thr Gln Val Thr Val Ser Ser Ala Ala Ala Glu Gln Lys Leu Ile
                405                 410                 415

Ser Glu Glu Asp Leu Asn Gly Ala Ala His His His His His His
            420                 425                 430

<210> SEQ ID NO 180
<211> LENGTH: 247
<212> TYPE: PRT
<213> ORGANISM: Artificial
<220> FEATURE:
<223> OTHER INFORMATION: Nanobody or nanobody construct

<400> SEQUENCE: 180

Glu Val Gln Leu Val Glu Ser Gly Gly Gly Leu Val Gln Pro Gly Gly
1               5                   10                  15

Ser Leu Arg Leu Ser Cys Thr Gly Ser Gly Phe Thr Phe Ser Ser Tyr
            20                  25                  30

Trp Met Asp Trp Val Arg Gln Thr Pro Gly Lys Asp Leu Glu Tyr Val
        35                  40                  45

Ser Gly Ile Ser Pro Ser Gly Ser Asn Thr Asp Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Asp Thr Ala Leu Tyr Tyr Cys
                85                  90                  95

Arg Arg Ser Leu Thr Leu Thr Asp Ser Pro Asp Leu Arg Ser Gln Gly
            100                 105                 110

```
Thr Gln Val Thr Val Ser Ser Gly Gly Gly Gly Gly Ser
            115                 120                 125

Glu Val Gln Leu Val Glu Ser Gly Gly Leu Val Gln Pro Gly Gly
            130                 135                 140

Ser Leu Arg Leu Ser Cys Thr Gly Ser Gly Phe Thr Phe Ser Ser Tyr
145                 150                 155                 160

Trp Met Asp Trp Val Arg Gln Thr Pro Gly Lys Asp Leu Glu Tyr Val
            165                 170                 175

Ser Gly Ile Ser Pro Ser Gly Ser Asn Thr Asp Tyr Ala Asp Ser Val
            180                 185                 190

Lys Gly Arg Phe Thr Ile Ser Arg Asp Asn Ala Lys Asn Thr Leu Tyr
            195                 200                 205

Leu Gln Met Asn Ser Leu Lys Pro Glu Asp Thr Ala Leu Tyr Tyr Cys
            210                 215                 220

Arg Arg Ser Leu Thr Leu Thr Asp Ser Pro Asp Leu Arg Ser Gln Gly
225                 230                 235                 240

Thr Gln Val Thr Val Ser Ser
            245

<210> SEQ ID NO 181
<211> LENGTH: 294
<212> TYPE: PRT
<213> ORGANISM: Artificial
<220> FEATURE:
<223> OTHER INFORMATION: Nanobody or nanobody construct

<400> SEQUENCE: 181

Glu Val Gln Leu Val Glu Ser Gly Gly Gly Leu Val Gln Ala Gly Gly
1               5                   10                  15

Ser Leu Arg Leu Ser Cys Glu Ala Ser Gly Arg Thr Tyr Ser Arg Tyr
                20                  25                  30

Gly Met Gly Trp Phe Arg Gln Ala Pro Gly Lys Glu Arg Glu Phe Val
            35                  40                  45

Ala Ala Val Ser Arg Leu Ser Gly Pro Arg Thr Val Tyr Ala Asp Ser
    50                  55                  60

Val Lys Gly Arg Phe Thr Ile Ser Arg Asp Asn Ala Glu Asn Thr Val
65                  70                  75                  80

Tyr Leu Gln Met Asn Ser Leu Lys Pro Glu Asp Thr Ala Val Tyr Thr
                85                  90                  95

Cys Ala Ala Glu Leu Thr Asn Arg Asn Ser Gly Ala Tyr Tyr Tyr Ala
                100                 105                 110

Trp Ala Tyr Asp Tyr Trp Gly Gln Gly Thr Gln Val Thr Val Ser Ser
            115                 120                 125

Gly Gly Gly Gly Ser Gly Gly Gly Ser Gly Gly Gly Gly Ser Glu
            130                 135                 140

Val Gln Leu Val Glu Ser Gly Gly Gly Leu Val Gln Ala Gly Gly Ser
145                 150                 155                 160

Leu Arg Leu Ser Cys Glu Ala Ser Gly Arg Thr Tyr Ser Arg Tyr Gly
                165                 170                 175

Met Gly Trp Phe Arg Gln Ala Pro Gly Lys Glu Arg Glu Phe Val Ala
            180                 185                 190

Ala Val Ser Arg Leu Ser Gly Pro Arg Thr Val Tyr Ala Asp Ser Val
        195                 200                 205

Lys Gly Arg Phe Thr Ile Ser Arg Asp Asn Ala Glu Asn Thr Val Tyr
            210                 215                 220
```

```
Leu Gln Met Asn Ser Leu Lys Pro Glu Asp Thr Ala Val Tyr Thr Cys
225                 230                 235                 240

Ala Ala Glu Leu Thr Asn Arg Asn Ser Gly Ala Tyr Tyr Ala Trp
            245                 250                 255

Ala Tyr Asp Tyr Trp Gly Gln Gly Thr Gln Val Thr Val Ser Ser Ala
        260                 265                 270

Ala Ala Glu Gln Lys Leu Ile Ser Glu Glu Asp Leu Asn Gly Ala Ala
        275                 280                 285

His His His His His His
    290

<210> SEQ ID NO 182
<211> LENGTH: 276
<212> TYPE: PRT
<213> ORGANISM: Artificial
<220> FEATURE:
<223> OTHER INFORMATION: Nanobody or nanobody construct

<400> SEQUENCE: 182

Met Ala Gln Val Gln Leu Gln Glu Ser Gly Gly Gly Leu Val Gln Ala
1               5                   10                  15

Gly Gly Ser Leu Arg Leu Ser Cys Ala Ala Ser Gly Phe Thr Leu Gly
            20                  25                  30

Tyr Tyr Ala Ile Gly Trp Phe Arg Gln Ala Pro Gly Asn Glu Arg Glu
        35                  40                  45

Gly Leu Ser Val Ile Thr Ser Gly Gly Ala Ile Tyr Tyr Ala Asp
    50                  55                  60

Ser Val Lys Gly Arg Phe Thr Ile Ser Arg Asp Asn Val Lys Asn Thr
65                  70                  75                  80

Val Ser Leu Gln Met Asn Ser Leu Lys Pro Glu Asp Thr Ala Val Tyr
                85                  90                  95

Tyr Cys Ala Arg Val Arg Ala Ala Phe Thr Ser Thr Thr Trp Thr Ser
            100                 105                 110

Pro Lys Trp Tyr Asp Tyr Trp Gly Gln Gly Thr Gln Val Thr Val Ser
        115                 120                 125

Ser Gly Gly Gly Gly Ser Gly Gly Ser Glu Val Gln Leu Val Glu
    130                 135                 140

Ser Gly Gly Gly Leu Val Gln Pro Gly Asn Ser Leu Arg Leu Ser Cys
145                 150                 155                 160

Ala Ala Ser Gly Phe Thr Phe Arg Ser Phe Gly Met Ser Trp Val Arg
            165                 170                 175

Gln Ala Pro Gly Lys Glu Pro Glu Trp Val Ser Ser Ile Ser Gly Ser
        180                 185                 190

Gly Ser Asp Thr Leu Tyr Ala Asp Ser Val Lys Gly Arg Phe Thr Ile
    195                 200                 205

Ser Arg Asp Asn Ala Lys Thr Thr Leu Tyr Leu Gln Met Asn Ser Leu
        210                 215                 220

Lys Pro Glu Asp Thr Ala Val Tyr Tyr Cys Thr Ile Gly Gly Ser Leu
225                 230                 235                 240

Ser Arg Ser Ser Gln Gly Thr Gln Val Thr Val Ser Ser Ala Ala Ala
            245                 250                 255

Glu Gln Lys Leu Ile Ser Glu Glu Asp Leu Asn Gly Ala Ala His His
        260                 265                 270

His His His His
    275
```

```
<210> SEQ ID NO 183
<211> LENGTH: 251
<212> TYPE: PRT
<213> ORGANISM: Artificial
<220> FEATURE:
<223> OTHER INFORMATION: Nanobody or nanobody construct

<400> SEQUENCE: 183
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Asp Ile Gly Trp Phe Arg Gln Ala Pro Gly Lys Gly Arg Glu Gly Val
        35                  40                  45

Ser Gly Ile Ser Ser Ser Asp Gly Asn Thr Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Ala Glu Pro Pro Asp Ser Ser Trp Tyr Leu Asp Gly Ser Pro Glu
            100                 105                 110

Phe Phe Lys Tyr Trp Gly Gln Gly Thr Leu Val Thr Val Ser Ser Gly
        115                 120                 125

Gly Gly Gly Ser Gly Gly Ser Glu Val Gln Leu Val Glu Ser Gly
    130                 135                 140

Gly Gly Leu Val Gln Pro Gly Asn Ser Leu Arg Leu Ser Cys Ala Ala
145                 150                 155                 160

Ser Gly Phe Thr Phe Ser Ser Phe Gly Met Ser Trp Val Arg Gln Ala
                165                 170                 175

Pro Gly Lys Gly Leu Glu Trp Val Ser Ser Ile Ser Gly Ser Gly Ser
            180                 185                 190

Asp Thr Leu Tyr Ala Asp Ser Val Lys Gly Arg Phe Thr Ile Ser Arg
        195                 200                 205

Asp Asn Ala Lys Thr Thr Leu Tyr Leu Gln Met Asn Ser Leu Arg Pro
    210                 215                 220

Glu Asp Thr Ala Val Tyr Tyr Cys Thr Ile Gly Gly Ser Leu Ser Arg
225                 230                 235                 240

Ser Ser Gln Gly Thr Leu Val Thr Val Ser Ser
                245                 250

```
<210> SEQ ID NO 184
<211> LENGTH: 128
<212> TYPE: PRT
<213> ORGANISM: Artificial
<220> FEATURE:
<223> OTHER INFORMATION: Nanobody or nanobody construct

<400> SEQUENCE: 184
```

Glu Val Gln Leu Val Glu Ser Gly Gly Gly Leu Val Gln Ala Gly Gly
1               5                   10                  15

Ser Leu Arg Leu Ser Cys Glu Ala Ser Gly Arg Thr Tyr Ser Arg Tyr
            20                  25                  30

Gly Met Gly Trp Phe Arg Gln Ala Pro Gly Lys Glu Arg Glu Phe Val
        35                  40                  45

Ala Ala Val Ser Arg Leu Ser Gly Pro Arg Thr Val Tyr Ala Asp Ser
    50                  55                  60

-continued

```
Val Lys Gly Arg Phe Thr Ile Ser Arg Asp Asn Ala Glu Asn Thr Val
 65              70                  75                  80

Tyr Leu Gln Met Asn Ser Leu Lys Pro Glu Asp Thr Ala Val Tyr Thr
             85              90                  95

Cys Ala Ala Glu Leu Thr Asn Arg Asn Ser Gly Ala Tyr Tyr Tyr Ala
            100             105                 110

Trp Ala Tyr Asp Tyr Trp Gly Gln Gly Thr Gln Val Thr Val Ser Ser
        115             120                 125
```